(12) United States Patent
Mitchell et al.

(10) Patent No.: US 9,163,029 B2
(45) Date of Patent: Oct. 20, 2015

(54) SUBSTITUTED IMIDAZO[1,2-A]PYRROLO[1,2-D]PYRAZINES FOR TREATING RESPIRATORY SYNCYTIAL VIRUS INFECTIONS

(71) Applicant: Biota Scientific Management Pty Ltd., Notting Hill (AU)

(72) Inventors: Jeffrey Peter Mitchell, Notting Hill (AU); Gary Pitt, Notting Hill (AU); Alistair George Draffan, Notting Hill (AU); Penelope Anne Mayes, Notting Hill (AU); Laura Andrau, Notting Hill (AU); Kelly Helen Anderson, Notting Hill (AU)

(73) Assignee: BIOTA SCIENTIFIC MANAGEMENT PTY LTD., Notting Hill (AU)

( * ) Notice: Subject to any disclaimer, the term of this patent is extended or adjusted under 35 U.S.C. 154(b) by 0 days.

(21) Appl. No.: 14/061,616

(22) Filed: Oct. 23, 2013

(65) Prior Publication Data
US 2014/0051697 A1 Feb. 20, 2014

Related U.S. Application Data

(62) Division of application No. 13/023,473, filed on Feb. 8, 2011, now Pat. No. 8,604,034.

(60) Provisional application No. 61/391,491, filed on Oct. 8, 2010.

(30) Foreign Application Priority Data

Feb. 8, 2010 (AU) ................................ 2010900494

(51) Int. Cl.
| | | |
|---|---|---|
| *C07D 487/14* | (2006.01) | |
| *A61K 31/407* | (2006.01) | |
| *A61K 31/4162* | (2006.01) | |
| *A61K 31/4188* | (2006.01) | |
| *A61K 31/4985* | (2006.01) | |
| *A61K 31/506* | (2006.01) | |
| *A61K 31/5377* | (2006.01) | |
| *A61K 45/06* | (2006.01) | |
| *C07D 207/333* | (2006.01) | |
| *C07D 213/79* | (2006.01) | |

(52) U.S. Cl.
CPC ............ *C07D 487/14* (2013.01); *A61K 31/407* (2013.01); *A61K 31/4162* (2013.01); *A61K 31/4188* (2013.01); *A61K 31/4985* (2013.01); *A61K 31/506* (2013.01); *A61K 31/5377* (2013.01); *A61K 45/06* (2013.01); *C07D 207/333* (2013.01); *C07D 213/79* (2013.01)

(58) Field of Classification Search
CPC ..................................................... C07D 487/14
USPC ........................................................ 544/346
See application file for complete search history.

(56) References Cited

U.S. PATENT DOCUMENTS

| | | | |
|---|---|---|---|
| 3,311,629 A | 3/1967 | Sulkowski | |
| 3,379,733 A | 4/1968 | Houlinhan | |
| 3,507,863 A | 4/1970 | Houlinhan | |
| 3,590,043 A | 6/1971 | Graf | |
| 3,624,101 A | 11/1971 | Sulkowski et al. | |
| 3,657,221 A | 4/1972 | Sulkowski et al. | |
| 3,770,766 A | 11/1973 | Sulkowski et al. | |
| 3,885,037 A | 5/1975 | Sulkowski et al. | |
| 3,935,218 A | 1/1976 | Sulkowski | |
| 3,966,955 A | 6/1976 | Shriver et al. | |
| 4,056,536 A | 11/1977 | Atkinson et al. | |
| 4,058,529 A | 11/1977 | Graf et al. | |
| 4,565,566 A | 1/1986 | Draber et al. | |
| 4,701,208 A | 10/1987 | Los | |
| 4,717,414 A | 1/1988 | Hunt | |
| 4,726,838 A | 2/1988 | Durr et al. | |
| 4,741,767 A | 5/1988 | Obrecht | |

(Continued)

FOREIGN PATENT DOCUMENTS

| | | |
|---|---|---|
| BE | 687161 | 3/1967 |
| CA | 2104963 | 2/1992 |

(Continued)

OTHER PUBLICATIONS

Aeberli et al., "5-Aryl-2,3-dihydro-5H-imidazo[2,1-a]isoindol-5-ols. Novel class of anorectic agents," *J Med. Chem.* 18:177-182, 1975.

(Continued)

*Primary Examiner* — Douglas M Willis
(74) *Attorney, Agent, or Firm* — B. Aaron Schulman, Esq.; Stites & Harbison, PLLC.

(57) ABSTRACT

The present invention relates to compounds of formula (I)

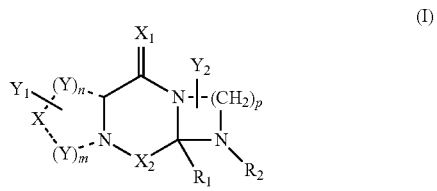

its salts, isomers or prodrugs thereof useful in the treatment of viral infections, in particular respiratory syncytial virus (RSV) infections. The present invention also relates to processes for preparing the compounds and intermediates used in their preparation.

9 Claims, No Drawings

(56) References Cited

U.S. PATENT DOCUMENTS

| | | | |
|---|---|---|---|
| 4,785,002 | A | 11/1988 | Draber et al. |
| 4,846,876 | A | 7/1989 | Draber et al. |
| 5,329,006 | A | 7/1994 | Baumann et al. |
| 5,426,192 | A | 6/1995 | Baumann et al. |
| 5,512,564 | A | 4/1996 | Zilch et al. |
| 2006/0293320 | A1 | 12/2006 | Schmitz et al. |
| 2007/0287700 | A1 | 12/2007 | Bond et al. |
| 2008/0021030 | A1 | 1/2008 | Faucher et al. |
| 2010/0021458 | A1 | 1/2010 | Mitchell et al. |
| 2010/0286191 | A1 | 11/2010 | Samuel et al. |

FOREIGN PATENT DOCUMENTS

| | | |
|---|---|---|
| CA | 2108899 | 3/1992 |
| CH | 481124 | 9/1966 |
| CH | 482697 | 3/1967 |
| EP | 183993 | 6/1986 |
| EP | 0475908 | 3/1992 |
| EP | 1207161 | 5/2002 |
| GB | 1038735 | 8/1966 |
| GB | 1105219 | 9/1966 |
| GB | 1059175 | 2/1967 |
| GB | 1229651 | 4/1971 |
| GB | 1322339 | 7/1973 |
| JP | S-6345220 | 2/1988 |
| WO | WO 92/13863 | 8/1992 |
| WO | WO 92/16207 | 10/1992 |
| WO | WO 01/95910 | 12/2001 |
| WO | WO 02/26228 | 4/2002 |
| WO | WO 02/42326 | 5/2002 |
| WO | WO 02/066479 | 8/2002 |
| WO | WO 03/040178 | 5/2003 |
| WO | WO 2005/061513 | 7/2005 |
| WO | WO 2006/116764 | 11/2006 |
| WO | WO 2008/037011 | 4/2008 |
| WO | WO-2009/130232 | 10/2009 |
| WO | WO 2011/094823 | 11/2011 |

OTHER PUBLICATIONS

Aeberli et all, "Anorectic agents. 2. Structural analogs of 5-(p-chlorophenyl)-2,3-dihydro-5H-imidazo[2,1-a]isoindol-5-ol,"*J.Med. Chem.* 18:182-185, 1975.

Aeberli et al., "Lithium aluminum hydride reduction products from heterocycles containing an isoindolone nucleus," *J. Org. Chem* 34:1720-1726, 1969.

Ames et al., "Heterocyclic synthesis from o-halogeno-acids. Part III. Synthesis of 2-methylindole-4-carboxylic acid and related compounds and of some derivatives of 3-pheylisoquinolin-1(2H)-one," *J. Chem. Soc. Perkin Trans. 1* 1073-1078, 1976.

Black, "Systemaatic review of the biology and medical management of respiratory syncytial virus infection," *Respir. Care.* 48:209-233, 2003.

Bruggink et al., "A study of the copper-catalysed direct arylation of β-dicarbonyl compounds with 2-bromobenzoic acids," *Tetrahedron* 31:2607-2619, 1975.

Cianci et al., "Orally Active Fusion Inhibitor of Respiratory Syncytial Virus," *Antimicrob. Agents Chemother* 48:413-422, 2004.

Epsztajn et al., "Application of Organolithium and Related Reagents in Synthesis. Part II. Metallation of 2-Methyl- and 4-Methylnicotinic Acids. A Useful Method for Preparation of Aza-Isocoumarins," *Synthetic Compounds* 22(9):1239-1247, 1992.

Evans et al., "Viral Infections of Humans," *Epidemiology and Control*, 3rd Edition, Plenum Medical Book, New York, pp. 525-544, 1989.

Falsey, "Noninfluenza Respiratory Virus Infection in Long-Term Care Facilities," *Infection Control and Hospital Epidemiology* 12:602-608, 1991.

Garvie et al., "Outbreak of respiratory syncytial virus infection in the elderly," *Br. Med. J.* 281:1253-1254, 1980.

Guion et al., "The Preparation of 2-(2-OXO-2-Phenylethyl)Benzoic Acids From Dilithiated Ortho-Toluic Acid," *Synthetic Compounds* 26(9):1753-1762, 1996.

Hackam et al., "Translation of Research Evidence From Animals to Humans," *JAMA* 296(14): 1731-1732, 2006.

Hall et al., "Aerosolized ribavirin treatment of infants with respiratory syncytial viral infection. A randomized double-blind study," *N. Engl. J Med.* 308:1443-1447, 1983.

Hall et al., "Ribavirin treatment of respiratory syncytial viral infection in infants with underlying cardiopulmonary disease," *JAMA* 254:3047-3051, 1985.

Hertz et al., "Respiratory Syncytial Virus-Induced Acute Lung Injury in Adult Patients with Bone Marrow Transplants: A Clinical Approach and Review of the Literature," *Medicine* 68(5):269-281, 1989.

Jordan, V.C., "Tamoxifen: A Most Unlikely Pioneering Medicine," *Nature Reviews: Drug Discovery*, 2:205-213, 2003.

Katritzky et al., "Convenient syntheses of dihydropyrrolo[2',1':3,4]pyrazino- and dihydropyrrolo[2',1':3,4][1,4]diazepino-[2,1-a]isoindolones," *Tretrahedron Let.* 43:2831-2833, 2002.

Katritzky et al., "Stereoselective syntheses of chiral (3S,9bS)-1,2,3,9b-tetrahydro-5H-imidazo[2,1-a]isoindol-5-ones," *Tretrahedron Asymmetry* 13:933-938, 2002.

Kruse et al., "Some Benzyl-Substituted Imidazoles, Triazoles, Tetrazoles, Pyridinethiones, and Structural Relatives as Multisubstrate Inhibitors of Dopamine β-Hydroxylase. 4. Structure-Activity Relationships at the Copper Binding Site," *J. Med. Chem.* 33:781-789, 1990.

Metlesics et al., "Structure of the reaction product of o-benzoyl-benzoic acid with ethylenediamine," *J. Org. Chem.* 32:2185-2187, 1967.

Morton et al., "Structural characterization of respiratory syncytial virus fusion inhibitor escape mutants: homology model of the F protein and a syncytium formation assay," *Virology* 311:275-288, 2003.

Mufson et al., "Two distinct subtypes of human respiratory syncytial virus," *J. Gen. Virol* 66:2111-2124, 1985.

Natsugari et al., "Novel, Potent, and Orally Active Substance P Antagonists: Synthesis and Antagonist Activity of N-Benzylcarboxamide Derivatives of Pyrido[3,4-b]pyridine," *J. Med. Chem.* 38:3106-3120, 1995.

Prasad et al., "18-Crown-6 as a Catalyst in the Dialkylation of o-Nitrophenacyl Derivatives," *J. Org. Chem.* 56:7188-7190, 1991.

Stephenson, "New HIV prevention strategies urged," *JAMA* 292(10):1163-1164, 2004.

Sulkowski et al., "2,5-Benzodiazocines and intermediates," *J. Org. Chem.* 32:2180-2184, 1967.

van den Hoogen et al., "A newly discovered human pneumovirus isolated from young children with respiratory tract disease," *Nat. Med.* 7(6):719-724, Jun. 2001.

van den Hoogen et al., "Analysis of the Genomic Sequence of a Human Metapneumovirus," *Virology* 295:119-132, 2002.

van den Hoogen et al., "Prevalence and Clinical Symptoms of Human Metapneumovirus Infection in Hospitalized Patients," *J. Infect. Dis.* 188:1571-1577, 2003.

van den Hoogen et al., "Clinical impact and diagnosis of human metapneumovirus infection," *Pediatr. Infect. Dis. J.* 23:S25-32, 2004.

Watanabe et al., "MTT colorimetric assay system for the screening of anti-orthomyxo- and anti-paramyxoviral agents," *J. Virological Methods* 48:257-265, 1994.

Wyde et al., "Short duration aerosols of JNJ 2408068 (R170591) administered prophylactically or therapeutically protect cotton rats from experimental respiratory syncytial virus infection," *Antiviral Res.* 60:221-231, 2003.

Yamaguchi et al., "Novel Antiasthmatic Agents with Dual Activities of Thromboxane $A_2$ Synthetase Inhibition and Bronchodilation. 1. 2-[2-(1-Imidazolyl)alkyl]-1(2H)-phthalazinones," *J. Med. Chem.* 36:4052-4060, 1993.

Non-Final Office Action dated May 26, 2010, from U.S. Appl. No. 10/585,230.

Final Office Action dated Dec. 8, 2010, from U.S. Appl. No. 10/585,230.

(56) References Cited

OTHER PUBLICATIONS

Non-Final Office Action dated Apr. 20, 2011, from U.S. Appl. No. 12/443,177.

Final Office Action dated Nov. 8, 2011, from U.S. Appl. No. 12/443,177.

Non-Final Office Action dated Oct. 29, 2012, from U.S. Appl. No. 12/443,177.

Japanese Office Action dated Nov. 12, 2014 in corresponding Japanese Application No. 2012-551449.

SUBSTITUTED IMIDAZO[1,2-A]PYRROLO[1,2-D]PYRAZINES FOR TREATING RESPIRATORY SYNCYTIAL VIRUS INFECTIONS

CROSS REFERENCE TO RELATED APPLICATIONS

This application is a Divisional of U.S. patent application Ser. No. 13/023,473, filed Feb. 8, 2011, which claims the benefit under 35 U.S.C. §119(a) of Australia Application No. 2010900494, filed Feb. 8, 2010; and under 35 U.S.C. §119(e) of U.S. Provisional Application No. 61/391,491, filed Oct. 8, 2010; the disclosure of each of which is incorporated herein by reference in its entirety.

TECHNICAL FIELD

The present invention relates to compounds useful in the treatment of viral infections, in particular respiratory syncytial viral (RSV) infections. The present invention also relates to processes for preparing the compounds and intermediates used in their preparation.

BACKGROUND

RSV is the leading cause of acute upper and lower respiratory tract infections (LRI) in adults, young children and infants. Serological evidence indicates that in the western world approximately 95% of all children have been infected with RSV by the age of two and 100% of children have been exposed by the time they reach adulthood (see Black, C. P., 2003, Resp. Care 48:209-31 for a review of the biology and management of RSV). In most cases the RSV infections will only cause minor upper respiratory illness with symptoms resembling that of the common cold. However, severe infection with the virus may result in bronchiolitis or pneumonia which may result in hospitalization or death. In a given year, around 91,000 infants are hospitalized with RSV infections in the United States. Infants who have been born prematurely or have a pre-existing lung disease are a high risk of severe infection and complications. These infections are responsible for 40 to 50% of hospitalizations for paediatric bronchiolitis and 25% of hospitalizations for paediatric pneumonia. Since the immune response to RSV infection is not protective, RSV infections reoccur throughout adulthood. In adults and older children, RSV infection has been associated with upper respiratory infection, tracheobronchitis, and otitis media. However, RSV in the institutionalized elderly can be more serious and is characterized by severe pneumonia and mortality rates of up to 20 and 78%, respectively. Adults with a previous history of heart or lung conditions are at a high risk for RSV infection.

RSV is a member of the order Mononegavirales, which consists of the non-segmented negative strand RNA viruses in the Families Paramyxoviridae, Rhabdoviridae and Filoviridae. RSV of humans (often also termed RSV or HRSV) is a member of the *Pneumovirus* genus of the sub-family Pneumovirinae within the Family Paramyxoviridae. Based on genetic and antigenic variations in the structural proteins, RSV is classified into two subgroups, A and B (Mufson, M. et al., J. Gen. Virol. 66:2111-2124). Other members of the *Pneumovirus* genus include viruses such as bovine RSV (BRSV), ovine RSV (ORSV) and pneumonia virus of mice (PVM) amongst others.

In addition to the genome features described above, family characteristics include a lipid envelope containing one or more glycoprotein species considered to be associated with attachment and entry of the host cell. Entry is considered to require a process by which the viral envelope fuses with the membrane of the host cell. Fusion of infected cells with, for example, their neighbours, can also result in the formation of fused multinucleate cells known as syncytial in some cases. The fusion process is believed to be glycoprotein mediated and is a feature shared with diverse enveloped viruses in other taxonomic groups. In the case of the Paramyxoviridae viruses of all genera characteristically express a fusion glycoprotein (F) which mediates membrane fusion.

While a RSV licensed vaccine is not yet available, some success has been achieved in the area of prevention for infants at high risk of serious lower respiratory tract disease caused by RSV, as well as a reduction of LRI. In particular, there are two immunoglobulin-based therapies approved to protect high-risk infants from serious LRI: RSV-IGIV (RSV-immunoglobulin intravenous, also known as RespiGamn™) and palivizumab) (SYNAGIS®). RSV-IGIV (RespiGam, Massachusetts Public Health Biological Laboratories and MedImmune Inc, Gaithersburg, Md.) was licensed by the Food and Drug Administration in January 1996 for prevention of severe RSV lower respiratory tract disease in infants and children younger than 24 months with chronic lung disease (CLD) or a history of preterm birth (≤35 weeks' gestation). In June 1998, the Food and Drug Administration licensed Palivizumab (MedImmune, Gaithersburg, Md.) for administration as a monthly intramuscular injection for the prevention of serious respiratory disease caused by RSV in infants and children with a history of preterm birth (≤35 weeks' gestation) or CLD.

The only drug currently approved for the treatment of severe RSV is the antiviral medication, Virazole, also known as Ribavirin currently licensed for therapy of RSV pneumonia and bronchiolitis (Hall et al, 1983, N. Engl. J. Med., 308: 1443; Hall et al., 1985, JAMA, 254:3047. This agent has a broad spectrum antiviral with virustatic effects, and acts by inhibiting RSV replication. Unfortunately, the agent is toxic so that administration of the agent is confined to a hospital setting (Black, C. P., 2003, Resp. Care 48(3):209-31). Its administration is further complicated by the need to follow a strict procedural process when administering the agent in order to minimise the likelihood of certain adverse affects. The agent has a number of adverse effects including sudden deterioration of respiratory function (bronchiospasm). The efficacy of Virazole has remained controversial.

Accordingly, there remains an ongoing need for new compounds that are useful in the treatment of RSV infections.

SUMMARY

In a first aspect there is provided a compound of formula (I):

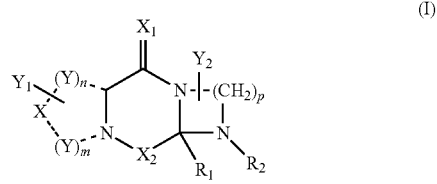

wherein
-------- represents single or double bonds depending on the required valencies of the ring atoms;

each Y is independently selected from $CH_2$, CH, NH and N;

X is selected from CH, $CH_2$, N, NH and C=O;

$X_1$ is selected from O, S, $NR_6$, and $C(R_6)_2$ wherein each $R_6$ is independently selected from H, optionally substituted $C_{1-6}$alkyl, optionally substituted $C_{2-6}$alkenyl, optionally substituted $C_{2-6}$alkynyl, optionally substituted $C_{3-8}$cycloalkyl, optionally substituted heterocyclyl and optionally substituted aryl;

$X_2$ is $C(R_3R_4)$ or $C(R_3R_4)$—$C(R_{3'}R_{4'})$ wherein $R_3$, $R_{3'}$, $R_4$ and $R_{4'}$ are each independently selected from H, optionally substituted $C_{1-6}$alkyl, optionally substituted $C_{2-6}$alkenyl, optionally substituted $C_{2-6}$alkynyl, optionally substituted $C_{3-8}$cycloalkyl, optionally substituted heterocyclyl and optionally substituted aryl or any two of $R_3$, $R_{3'}$, $R_4$ and $R_{4'}$ together with the carbon atom(s) to which they are attached join to form an optionally substituted $C_{3-8}$ cycloalkyl;

$R_1$ is optionally substituted $C_{1-6}$alkyl, optionally substituted $C_{2-6}$alkenyl, optionally substituted $C_{2-6}$alkynyl, optionally substituted $C_{3-8}$cycloalkyl, optionally substituted heterocyclyl or optionally substituted aryl;

$R_2$ is H, $R_8$, $C(=O)R_8$, $C(=S)R_8$ or $S(O)_2R_8$ wherein $R_8$ is selected from optionally substituted $C_{1-6}$alkyl, optionally substituted $C_{2-6}$alkenyl, optionally substituted $C_{2-6}$alkynyl, optionally substituted $C_{3-8}$cycloalkyl, optionally substituted heterocyclyl, optionally substituted aryl, $N(R_6)_2$, optionally substituted —$(NR_6)_q(R_7)_q$cycloalkyl, optionally substituted —$(NR_6)_q(R_7)_q$heterocyclyl and optionally substituted —$(NR_6)_q(R_7)_q$aryl wherein each $R_7$ is independently selected from optionally substituted $C_{1-6}$alkyl, optionally substituted $C_{2-6}$alkenyl, optionally substituted $C_{2-6}$alkynyl, optionally substituted $C_{3-8}$cycloalkyl, optionally substituted heterocyclyl and optionally substituted aryl and q is 0 or 1;

$Y_1$ is one or more optional substituents;

$Y_2$ is H or one or more optionally substituted $R_7$;

m and n are integers independently selected from 0, 1, 2 and 3 wherein m and n together at least equal 2;

p is an integer selected from 1, 2, 3 and 4; and wherein the optional substituents are independently selected from $R_7$, $R_7$-$R_7$, $(R_7)_q$halo, $(R_7)_q$CN, =O, $(R_7)_qOR_6$, $(R_7)_qOCHF_2$, $(R_7)_qOCF_3$, $(R_7)_qCHF_2$, $(R_7)_qCF_3$, =S, $(R_7)_qSR_6$, $(R_7)_qSO_3H$, $(R_7)_qSO_2$—$R_7$, $(R_7)_qSO_2N(R_6)_2$, $(R_7)_qNO_2$, $(R_7)_qN(R_6)_2$, $(R_7)_qOC(=O)$—$R_7$, $(R_7)_qC(=O)OR_6$, $(R_7)_qC(=O)R_6$, $(R_7)_qC(=O)N(R_6)_2$, $(R_7)_qNR_6C(=O)$—$R_7$, $(R_7)_qNR_6SO_2R_7$, $(R_7)_qSi(R_7)_3$ and $(R_7)_qO$—$Si(R_7)_3$ wherein each optional substituent may be further optionally substituted;

or salts, isomers and/or prodrugs thereof.

Preferably m and n together equal 2 or 3.

Preferably p is 2 or 3, more preferably 2.

Preferably aryl is a 6-membered aryl.

Preferably heterocyclyl is a 5-membered or 6-membered mono-cyclic heterocyclyl or a 5-membered or 6-membered heterocyclyl fused to a carbocyclic aromatic ring. 5-membered or 6-membered mono-cyclic heterocyclyls are preferred.

In one embodiment X is CH or $CH_2$, preferably CH.

In another embodiment X is N or NH, preferably N.

In still another embodiment X is C=O.

In one embodiment Y in each occurrence of $(Y)_n$ and $(Y)_m$, is $CH_2$ or CH, preferably CH.

In another embodiment Y in one occurrence of $(Y)_n$ or $(Y)_m$, is N or NH, preferably N.

In yet another embodiment, the compounds of formula (I) are in a single stereoisomeric form.

The compounds of formula (I) are RSV antiviral agents and are useful in the treatment of RSV infections. Accordingly, the compounds of the invention are useful in the treatment of RSV disease, such as bronchiolitis or pneumonia, or in reducing exacerbation of underlying or pre-existing respiratory diseases or conditions wherein RSV infection is a cause of said exacerbation. The underlying or pre-existing respiratory diseases or conditions may include asthma, chronic obstructive pulmonary disease (COPD) and immunosuppression such as immunosuppression experienced by bone marrow transplant recipients.

In a second aspect there is provided an RSV antiviral agent comprising the compound of formula (I) defined above or its salts, isomers or prodrugs thereof.

There is also provided use of the compound of formula (I) defined above as a RSV antiviral agent or its salts, isomers or prodrugs thereof.

There is further provided the compound of formula (I) defined above for use as an RSV antiviral agent or its salts, isomers or prodrugs thereof.

The compound of formula (I) may also be administered in the form of a pharmaceutical composition together with a pharmaceutically acceptable carrier.

In a third aspect there is provided a composition comprising the compound of formula (I) defined above or its salts, isomers or prodrugs thereof and a carrier.

In one embodiment, the composition is a pharmaceutical composition and the carrier is a pharmaceutically acceptable carrier.

In one embodiment, the pharmaceutical agent or composition also comprises one or more other RSV antiviral agents.

In a fourth aspect there is provided a method of treating an RSV infection comprising the step of administering the compound of formula (I) defined above or its salts, isomers or prodrugs thereof or the pharmaceutical composition defined above to a subject in need thereof.

In a fifth aspect there is provided a method of treating an RSV disease comprising the step of administering the compound of formula (I) defined above or its salts, isomers or prodrugs thereof or the pharmaceutical composition defined above to a subject in need thereof. There is also provided a method of reducing exacerbation of an underlying or pre-existing respiratory disease wherein RSV infection is a cause of said exacerbation comprising the step of administering the compound of formula (I) defined above or its salts, isomers or prodrugs thereof or the pharmaceutical composition defined above to a subject in need thereof.

There is also provided use of the compound of formula (I) defined above or its salts, isomers or prodrugs thereof or the pharmaceutical composition defined above in the manufacture of a medicament for treating an RSV infection or an RSV disease or reducing exacerbation of an underlying or pre-existing respiratory disease wherein RSV infection is a cause of said exacerbation.

There is further provided use of the compound of formula (I) or its salts, isomers or prodrugs thereof or the pharmaceutical composition defined above for treating an RSV infection or an RSV disease or reducing exacerbation of an underlying or pre-existing respiratory disease wherein RSV infection is a cause of said exacerbation.

There is still further provided the compound of formula (I) defined above or its salts, isomers or prodrugs thereof or the pharmaceutical composition defined above for use in treating an RSV infection or RSV disease or reducing exacerbation of an underlying or pre-existing respiratory disease wherein RSV infection is a cause of said exacerbation.

In a sixth aspect, there is provided a process for preparing the compound of formula (I) defined above comprising the step of reacting a compound of formula (II)

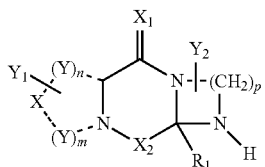

(II)

with a compound of general formula selected from R—$R_8$, R—C(=O)$R_8$, R—C(=S)$R_8$ and R—S(O)$_2$$R_8$;

wherein ------, X, $X_1$, $X_2$, $R_1$, Y, $Y_1$, $Y_2$, m, n, p and $R_8$ are as defined in formula (I) above and wherein R is a leaving group or an activated ester group and wherein the obtained compound of formula (I) is optionally converted into a salt or prodrug thereof.

The intermediate compounds of formula (II) are novel. Accordingly, in a seventh aspect there is provided the compound of formula (II) defined above.

In one embodiment, the compounds of formula (II) are in a single stereoisomeric form.

In one embodiment, the compound of formula (II) is prepared via cyclisation of a precursor compound of formula (III) or formula (IV)

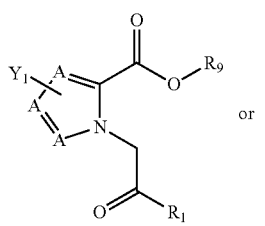

(III)

or

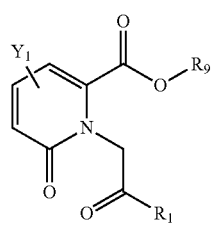

(IV)

wherein each A is independently CH or N, $R_9$ is H or $C_{1-3}$alkyl and $R_1$ and $Y_1$ are as defined in Formula (I) above.

There is also provided a compound of formula (III) defined above wherein $R_1$ is optionally substituted $C_{3-8}$cycloalkyl, optionally substituted heterocyclyl or optionally substituted aryl and $R_9$ is H provided that the compound is not 5-(4-tert-butylphenyl)-2-phenacyl-pyrazole-3-carboxylic acid.

There is still further provided a compound of formula (IV) defined above wherein $R_1$ is optionally substituted $C_{3-8}$cycloalkyl, optionally substituted heterocyclyl or optionally substituted aryl and $R_9$ is H or $C_{1-3}$alkyl.

DETAILED DESCRIPTION

The present invention relates to compounds of formula (I) as defined above which are RSV antiviral agents and are useful in treating RSV infections or an RSV disease or reducing exacerbation of an underlying or pre-existing respiratory disease wherein RSV infection is a cause of said exacerbation.

Without wishing to be bound by theory the bridgehead nitrogen is believed to provide access to a novel class of RSV inhibitors by facilitating the introduction of, for example, optionally substituted fused 5-membered heteroaromatic ring systems and fused 6-membered rings such as pyridinone.

Compounds

In one embodiment there is provided a compound of formula (Ia):

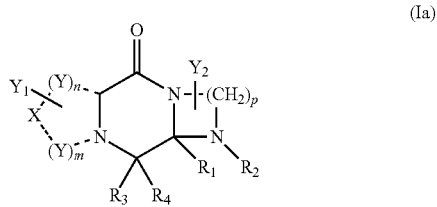

(Ia)

wherein ------, X, $R_1$, $R_2$, $R_3$, $R_4$, Y, $Y_1$, $Y_2$, m, n and p are as defined in formula (I) above or its salts, isomers or prodrugs thereof.

Preferably m and n together equal 2 or 3.

Preferably p is 2 or 3.

In one embodiment m and n together equal 2 and p is 2.

In another embodiment m and n together equal 2 and p is 3.

In still another embodiment m and n together equal 3 and p is 2.

In yet another embodiment m and n together equal 3 and p is 3.

In one embodiment, Y in each occurrence of $(Y)_n$ and $(Y)_m$, is $CH_2$ or CH preferably CH.

In another embodiment, Y in one occurrence of $(Y)_n$ or $(Y)_m$, is N or NH, preferably N.

In one embodiment X is CH or $CH_2$, preferably CH.

In another embodiment X is N or NH, preferably N.

In still another embodiment X is C=O.

The compound of formula (Ia) may be selected from the compounds of any one of formulae (Ia-i) to (Ia-vii) set out below:

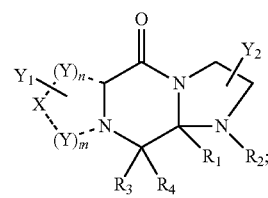

(Ia-i)

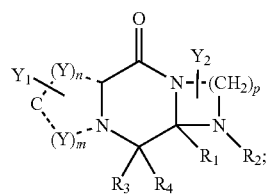

(Ia-ii)

(Ia-iii)
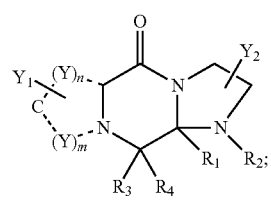

(Ia-iv)
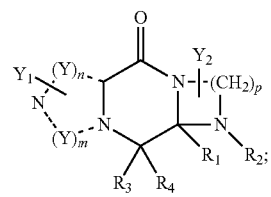

(Ia-v)
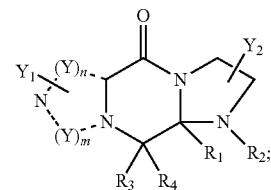

(Ia-vi)
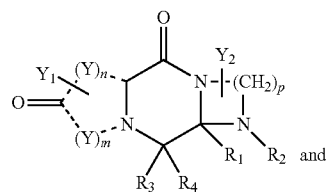

(Ia-vii)
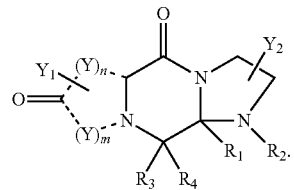

wherein ------ X, $R_1$, $R_2$, $R_3$, $R_4$, Y, $Y_1$, $Y_2$, m, n and p are as defined in formula (I) above.

In one embodiment when p is 2, the compound of formula (Ia) is selected from the group consisting of a compound of formulae (Ia-iii), (Ia-v) and (Ia-vii), its salts, isomers and prodrugs thereof:

(Ia-iii)
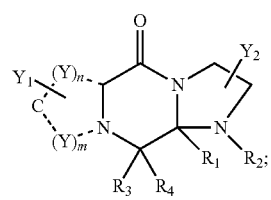

(Ia-v)
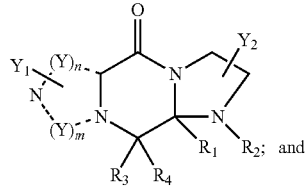

(Ia-vii)
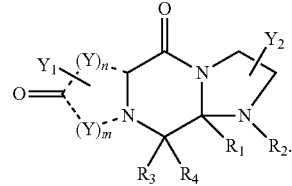

In one embodiment, the compound of formula (Ia) may be selected from the compounds represented by any one of the following formulae wherein $R_1$, $R_2$, $R_3$, $R_4$, $Y_1$ and $Y_2$ are as defined in formula (I) above and Y in each occurrence of $(Y)_m$ and $(Y)_n$ (where present) is CH.

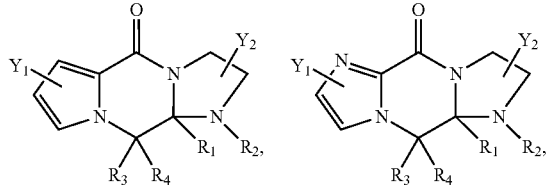

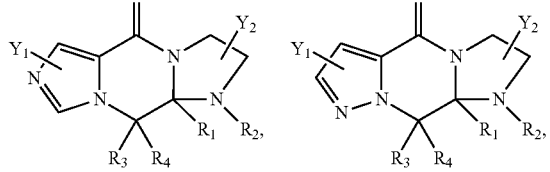

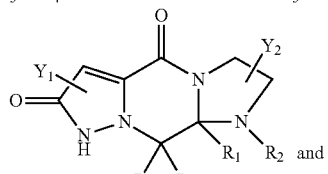

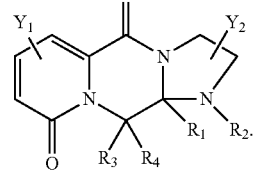

In another embodiment, the compound of formula (Ia) may be selected from the compounds represented by any one of the following formulae wherein $R_1$, $R_2$, $R_3$, $R_4$, $Y_1$ and $Y_2$ are as defined in formula (I) above and Y in one occurrence of $(Y)_m$ or $(Y)_n$ (where present) is N:

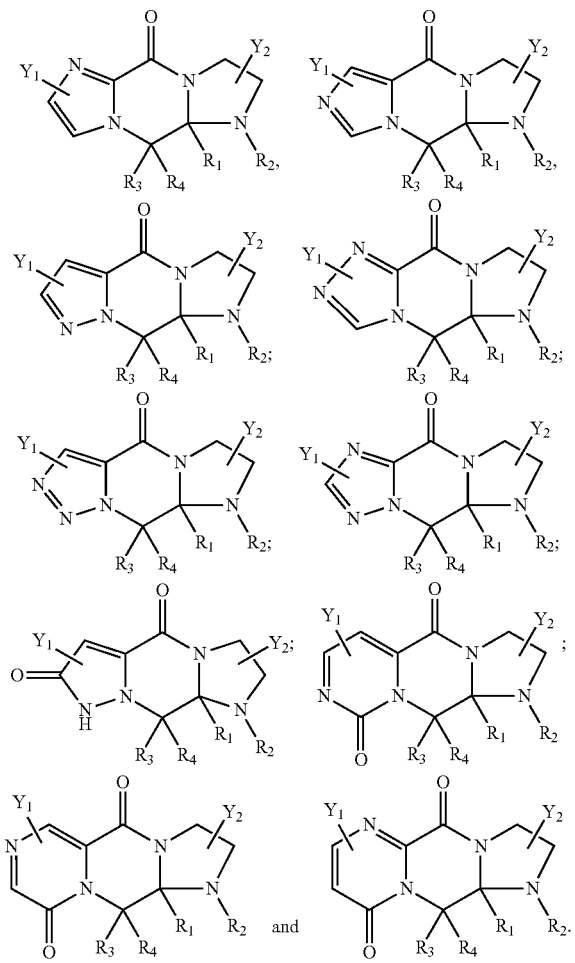

In still another embodiment, the compound of formula (Ia) may be a compound represented by the following formula wherein $R_1$, $R_2$, $R_3$, $R_4$, $Y_1$ and $Y_2$ are as defined in formula (I) above and Y in two occurrences of $(Y)_m$ or $(Y)_n$ (where present) is N:

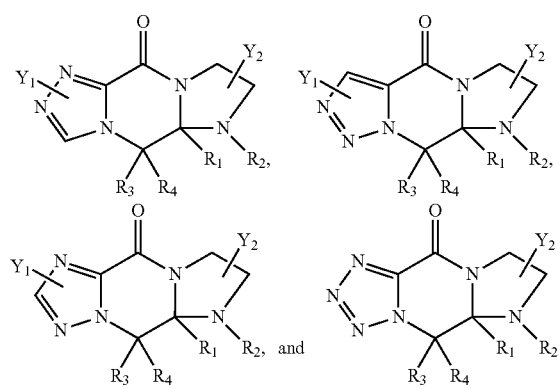

In another embodiment, there is provided a compound of formula (Ib) or its salts, isomers or prodrugs thereof:

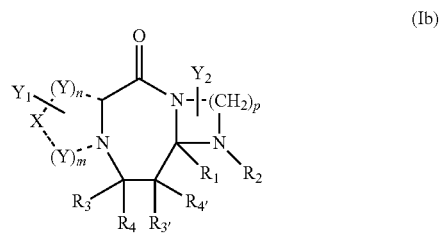

wherein ------, X, $R_1$, $R_2$, $R_3$, $R_4$, $R_{3'}$, $R_{4'}$, Y, $Y_1$, $Y_2$, m, n and p are as defined in formula (I) above or its salts, isomers or prodrugs thereof.

The compound of formula (Ib) may be selected from the compounds of any one of formulae (Ib-i) to (Ib-iii) set out below:

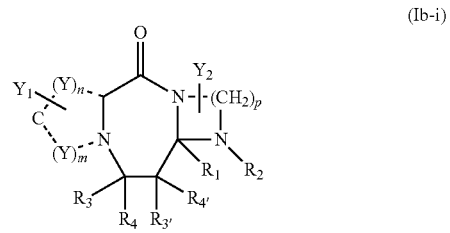

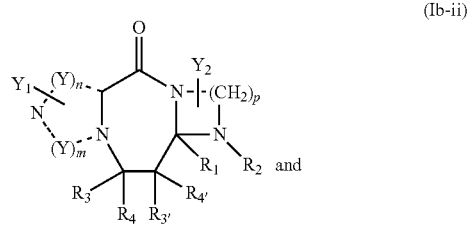

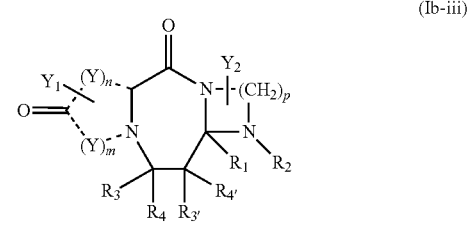

wherein ------, X, $R_1$, $R_2$, $R_3$, $R_4$, $R_{3'}$, $R_{4'}$, Y, $Y_1$, $Y_2$, m, n, and p are as defined in formula (I) above.

In one embodiment the compound of formula (I) is in a single stereoisomeric form. In a preferred embodiment, the single isomeric form is represented by

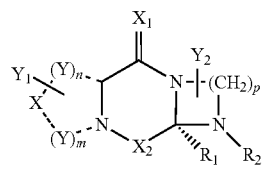

wherein ------, X, $X_1$, $X_2$, $R_1$, $R_2$, $Y_1$, $Y_2$, m, n, and p are as previously defined.

In one embodiment of the compounds of formula (I) and sub-formulae (Ia) or (Ib), $R_1$ is optionally substituted $C_{0-3}$alkylene$C_{3-8}$cycloalkyl, optionally substituted $C_{0-3}$alkyleneheterocyclyl or optionally substituted $C_{0-3}$alkylenearyl. More preferably, $R_1$ is optionally substituted and is selected from $C_{3-8}$cycloalkyl, 5- or 6-membered heterocycle, 9- or 10-membered heterocycle and $C_6$aryl. Examples of preferred $C_{3-8}$cycloalkyls include $C_{3-6}$cycloalkyls such as cyclopropyl, cyclobutyl, cyclopentyl and cyclohexyl, with cyclohexyl being particularly preferred. Examples of preferred 6-membered aryl groups include phenyl. Examples of preferred 5-membered heterocyclyls containing N and/or O and/or S include thienyl, thiazolyl, isothiazolyl, thiadiazolyl, furanyl, pyrrolyl, pyrazolyl, triazolyl, tetrazolyl, imidazolyl, pyrrolidinyl, oxazolyl, oxadiazolyl and isoxazolyl. Examples of preferred 6-membered heterocyclyls containing N and/or O include pyridinyl, pyridazinyl, pyrimidinyl, pyrazinyl, pyridinone, morpholinyl and tetrahydropyran. Examples of preferred 9-10 membered heterocycles include fused bicyclic heterocyclyls such as benzofuranyl or dihydrobenzofuranyl. Examples of suitable optional substituents for $R_1$ include $C_{1-3}$alkyl particularly methyl, $C_{2-3}$alkenyl, $C_{2-3}$alkynyl, $C_{3-6}$cycloalkyl, 5- or 6-membered heterocyclyl and $C_6$aryl, $(R_7)_q$halo particularly F, Cl and Br, $(R_7)_q$OCHF$_2$ particularly OCHF$_2$, $(R_7)_q$CN particularly CN, $(R_7)_q$OR$_6$ particularly OH, $C_{1-3}$alkylOH such as CH$_2$OH, $C_{1-3}$alkoxy such as methoxy and CH$_2$OCH$_3$ and optionally substituted $C_{1-3}$alkoxy such as OCH$_2$CH$_2$OH and OCH$_2$CH$_2$-5- or 6-membered heterocyclyl, $(R_7)_q$OCF$_3$ particularly OCF$_3$, $(R_7)_q$CHF$_2$ particularly CHF$_2$, $(R_7)_q$CF$_3$ particularly CF$_3$, $(R_7)_q$SR$_6$ particularly SH or SC$_{1-3}$alkyl such as SCH$_3$, $(R_7)_q$SO$_3$H, $(R_7)_q$SO$_2$—R$_7$ particularly SO$_2$(C$_{1-3}$alkyl), $(R_7)_q$SO$_2$N(R$_6$)$_2$ particularly SO$_2$N(C$_{1-3}$alkyl)$_2$ such as SO$_2$N(Et)$_2$, $(R_7)_q$NO$_2$ particularly NO$_2$, $(R_7)_q$N(R$_6$)$_2$ particularly NH$_2$, NH(C$_{1-3}$alkyl) and N(C$_{1-3}$alkyl)$_2$, $(R_7)_q$OC(=O)—R$_7$ including C$_{1-3}$alkylOC(=O)-5- or 6-membered heterocyclyl, $(R_7)_q$C(=O)OR$_6$ particularly CO$_2$H and CO$_2$C$_{1-3}$alkyl such as CO$_2$CH$_2$, $(R_7)_q$C(=O)R$_6$ particularly C(=O)H and C(=O)C$_{1-3}$alkyl, $(R_7)_q$C(=O)N(R$_6$)$_2$ particularly C(=O)NH$_2$, C(=O)NH(C$_{1-3}$alkyl) and C(=O)N(C$_{1-3}$alkyl)$_2$, $(R_7)_q$NR$_6$C(=O)—R$_7$, $(R_7)_q$NR$_6$SO$_2$R$_7$, wherein each optional substituent may be further optionally substituted and wherein R$_7$ is selected from $C_{1-3}$alkyl, $C_{2-3}$alkenyl, $C_{2-3}$alkynyl, $C_{3-6}$cycloalkyl, 5- or 6-membered-heterocyclyl and $C_6$aryl and R$_6$ is preferably H or $C_{1-3}$alkyl. Particularly preferred optional substituents for $R_1$ include halo such as Br, F and Cl; CN; OH; CF$_3$; OCHF$_2$; optionally substituted $C_{1-3}$alkyl including methyl, CH$_2$OH and CH$_2$OCH$_3$; SO$_2$N(Et)$_2$, optionally substituted 5- or 6-membered heterocyclyl; optionally substituted $C_{1-3}$alkylOC(=O)-5- or 6-membered heterocyclyl; and optionally substituted $C_{1-3}$alkoxy including OCH$_3$, OCH$_2$CH$_2$OH and OCH$_2$CH$_2$-5- or 6-membered heterocyclyl. Particularly preferred optional substituents in the case of 5- or 6-membered heterocycles containing N include $C_{1-3}$alkyl, particularly methyl.

In a particular embodiment, $R_1$ is an optionally substituted $C_{0-3}$alkylenearyl, more preferably $C_6$aryl which when substituted may preferably be para and/or meta substituted, more preferably para-substituted. Phenyl is particularly preferred. In a preferred embodiment $R_1$ is a para-substituted phenyl. Suitable optional substituents on the phenyl include, but are not limited to, $(R_7)_q$OC(=O)—R$_7$ such as C$_{1-3}$alkylOC(=O)-5- or 6-membered heterocyclyl; OCHF$_2$; halo preferably fluoro, chloro or bromo; OH; OC$_{1-6}$alkyl preferably OCH$_3$ or OCH$_2$CH$_3$ which may be optionally substituted with substituents including, but not limited to, OH or morpholinyl; $C_{1-4}$alkyl preferably $C_{1-3}$alkyl, more preferably methyl which may be optionally substituted with substituents including, but not limited to, OH, OCH$_3$ or halo where in the case of $C_{1-3}$alkyl substituted with halo includes CF$_3$; SO$_2$N(C$_{1-3}$alkyl)$_2$; CN; and 5-membered heterocyclyls containing N such as pyrrolidinyl.

In another particular embodiment $R_1$ is an optionally substituted $C_{0-3}$alkyleneheterocyclyl more preferably a 5- or 6-membered heterocyclyl or a 9- or 10-membered heterocyclyl. In a preferred embodiment the optionally substituted heterocyclyl of the $C_{0-3}$alkyleneheterocyclyl may be selected from fused bicyclic heterocyclyls such as benzofuranyl or dihydrobenzofuranyl, 6-membered non-aromatic heterocyclyls such as tetrahydropyran, six-membered aromatic heterocyclyls such as pyridinyl, pyridinonyl, or pyrazinyl or five-membered aromatic heterocyclyls such as furanyl, thiophenyl or pyrazolyl. Pyridyl is particularly preferred. Suitable optional substituents on the heterocyclyl include, but are not limited to, OH, haloalkyl such as CF$_3$; $C_{1-4}$alkyl preferably methyl; OC$_{1-6}$alkyl preferably OCH$_3$, and, in the case of N containing heterocyclyls for $R_1$, may be an N-oxide derivative thereof.

In another embodiment of the compounds of formula (I) and sub-formulae (Ia) or (Ib), $R_2$ is C(=O)R$_8$ wherein R$_8$ is optionally substituted and is selected from —(NR$_6$)$_q$(C$_{1-6}$alkylene)$_q$-C$_{3-8}$cycloalkyl, —(NR$_6$)$_q$(C$_{1-6}$alkylene)$_q$heterocyclyl and —(NR$_6$)$_q$(C$_{1-6}$alkylene)$_q$-aryl. R$_6$ is preferably H. In a further preferred embodiment R$_8$ is optionally substituted and is selected from $C_{3-6}$cycloalkyl, 5- or 6-membered heterocyclyl, $C_6$aryl, NH—$C_{1-3}$alkylene-$C_{3-6}$cycloalkyl, NH—$C_{1-3}$alkylene-5- or 6-membered heterocyclyl, NH—$C_{1-3}$alkylene-$C_6$aryl. Examples of preferred $C_{3-8}$cycloalkyls include $C_{3-6}$cycloalkyls such as cyclopropyl, cyclobutyl, cyclopentyl and cyclohexyl with cyclopropyl being particularly preferred. Examples of preferred 6-membered aryl groups include phenyl. Optionally substituted 5- or 6-membered heterocyclyls containing N and/or O and/or S are particularly preferred. Examples of preferred 6-membered heterocyclyls containing N and/or O include pyridinyl, pyridazinyl, pyrimidinyl, pyrazinyl, morpholinyl and tetrahydropyran with pyridyl being particularly preferred. Examples of preferred 5-membered heterocyclyls containing N and/or O and/or S include thienyl, thiazolyl, isothiazolyl, thiadiazolyl, furanyl, pyrrolyl, pyrazolyl, triazoyl, tetrazoyl, imidazolyl, pyrrolidinyl, oxazolyl, oxadiazolyl and isoxazolyl with optionally substituted oxazolyl and isoxazolyl being particularly preferred. Suitable optional substituents on R$_8$ include, but are not limited to, $C_{1-3}$alkyl such as methyl, ethyl, propyl and iso-propyl, cyclopropyl, $(R_7)_q$halo such as Cl, Br and F and $(R_7)_q$CF$_3$. Particularly preferred optional substituents include methyl, CF$_3$ and halo, preferably F. Methyl substituted isoxazolyls are particularly preferred.

In one embodiment $Y_1$ in each occurrence is independently selected from R$_7$, R$_7$-R$_7$, $(R_7)_q$halo particularly F, Cl and Br, $(R_7)_q$CN particularly CN, =O, $(R_7)_q$OR$_6$ particularly OH, $C_{1-3}$alkylOH and $C_{1-3}$alkoxy such as methoxy, $(R_7)_q$OCHF$_2$ particularly OCHF$_2$, $(R_7)_q$OCF$_3$ particularly OCF$_3$, $(R_7)_q$CHF$_2$ particularly CHF$_2$, $(R_7)_q$CF$_3$ particularly CF$_3$, =S, $(R_7)_q$SR$_6$ particularly SH or SC$_{1-3}$alkyl such as SCH$_3$, $(R_7)_q$SO$_3$H, $(R_7)_q$SO$_2$—R$_7$ particularly SO$_2$(C$_{1-3}$alkyl), $(R_7)_q$SO$_2$N(R$_6$)$_2$ particularly SO$_2$N(C$_{1-3}$alkyl)$_2$, $(R_7)_q$NO$_2$ particularly NO$_2$, $(R_7)_q$N(R$_6$)$_2$ particularly $C_{1-3}$alkylNH$_2$, NH$_2$, NH(C$_{1-3}$alkyl), NH(C$_{3-6}$cycloalkyl) and N(C$_{1-3}$alkyl)$_2$, $(R_7)_q$OC(=O)—R$_7$, $(R_7)_q$C(=O)OR$_6$ particularly CO$_2$H and CO$_2$C$_{1-3}$alkyl, $(R_7)_q$C(=O)R$_6$ particularly C(=O)H and C(=O)C$_{1-3}$alkyl, $(R_7)_q$C(=O)N(R$_6$)$_2$ particularly C(=O)NH$_2$, C(=O)NH(C$_{1-3}$alkyl) and C(=O)N(C$_{1-3}$alkyl)$_2$, $(R_7)_q$NR$_6$C(=O)—R$_7$, $(R_7)_q$NR$_6$SO$_2$R$_7$, $(R_7)_q$Si(R$_7$)$_3$ and $(R_7)_q$O—Si(R$_7$)$_3$ wherein each optional substituent may be further optionally substituted and wherein R$_7$ is selected from $C_{1-3}$alkyl, $C_{2-3}$alkenyl, $C_{2-3}$alkynyl, $C_{3-6}$cycloalkyl, 5- or 6-membered heterocyclyl and $C_6$aryl. In a preferred embodiment $Y_1$ in each occurrence is independently selected from an optionally substituted $C_{1-3}$alkyl, $C_{2-3}$alkenyl, $C_{2-3}$alkynyl, $C_{3-6}$cycloalkyl, 5- or 6-membered heterocyclyl, $C_6$aryl, $C_{1-3}$alkyl-$C_{3-6}$cycloalkyl, $C_{1-3}$alkyl-5- or 6-membered heterocyclyl, $C_{1-3}$alkyl-$C_6$aryl, =O, $(R_7)_q$halo, $(R_7)_qC(=O)R_6$, $(R_7)_qN(R_6)_2$, $(R_7)_qOR_6$, $(R_7)_qC(=O)N(R_6)_2$, $(R_7)_qCN$, $(R_7)_qNO_2$, $(R_7)_qC(=O)OR_6$. Particularly preferred $R_7$ is $C_{1-3}$alkyl. Particularly preferred $R_6$ include H, $C_{1-3}$alkyl, $C_{2-3}$alkenyl, $C_{2-3}$alkynyl, $C_{3-6}$cycloalkyl, 5- or 6-membered heterocyclyl, $C_6$aryl with H and $C_{1-3}$alkyl being most preferred. Optionally substituted phenyl is a particularly preferred aryl. Particularly preferred optionally substituted 5- or 6-membered heterocyclyl include non-aromatic heterocyclyls such as morpholinlyl, S containing aromatic heterocyclyls such as thienyl and additionally containing N such as thiazolyl and thiadiazolyl, O containing aromatic heterocyclyls such as furanyl and additionally containing N such as oxazolyl, isoxazolyl and oxadiazolyl and N containing aromatic heterocyclyls such as pyridyl, pyrazolyl, imidazolyl, triazoyl, tetrazoyl, pyrrolyl, pyridazinyl and pyrimidinyl and may be further optionally substituted with one or two $C_{1-3}$alkyl.

In a further embodiment of $Y_1$ q is 0. In an alternative further embodiment of $Y_1$ q is 1.

In another embodiment of the compounds of formula (I) and sub-formulae (Ia) or (Ib), the optional substituent $Y_1$ is present and represents one or more substituents, preferably 1, 2 or 3, more preferably 1 or 2 substituents independently selected from halo including Cl, Fl and Br; CN, OH, $C_{1-3}$alkylOH, $C_{1-3}$alkylN$(R_6)_2$ particularly $C_{1-3}$alkylNH$_2$, N$(R_6)_2$ particularly NH$_2$, NH($C_{1-3}$alkyl), NH($C_{3-6}$cyloalkyl) and N($C_{1-3}$alkyl)$_2$; NO$_2$, =O, C(=O)N$(R_6)_2$ particularly C(=O)N($C_{1-3}$alkyl)$_2$; C(=O)R$_6$ particularly C(=O)($C_{1-3}$alkyl), optionally substituted aryl preferably phenyl including phenyl optionally substituted with C(=O)OR$_6$ particularly CO$_2$H; optionally substituted heterocyclyls preferably 5-membered or 6-membered heterocyclyls containing at least one heteroatom selected from N, O and S wherein optionally substituted 5-membered or 6-membered aromatic heterocyclyls are particularly preferred and suitable aromatic heterocyclyls include, but are not limited to, thienyl, pyridyl, furanyl, pyrazolyl, pyrrolyl, pyrimidinyl, triazolyl and tetrazolyl and suitable optional substituents on the aromatic heterocyclyl when the heterocyclyl contains a N heteroatom include, but are not limited to, $C_{1-4}$alkyl preferably $C_{1-3}$alkyl most preferably methyl for example N-methyl; optionally substituted $C_{2-3}$alkenyl, optionally substituted $C_{2-3}$alkynyl and optionally substituted $C_{1-4}$alkyl preferably $C_{1-3}$alkyl most preferably methyl which may be optionally substituted with substituents including, but not limited to, morpholinyl, N$(R_6)_2$ including NH$_2$ and N(CH$_3$)$_2$ and OH.

In a particular embodiment, X is substituted with $Y_1$ wherein X is selected from CH, CH$_2$ and NH and Y in each occurrence of $(Y)_m$ or $(Y)_n$ (where present) may independently be further optionally substituted with $Y_1$ and wherein m and n together preferably equal 2, most preferably m and n are each independently 1. In another embodiment, m is 2 and n is 0. In yet another embodiment, m is 0 and n is 2.

In another particular embodiment, X is C=O or an unsubstituted CH, CH$_2$, N or NH and Y in each occurrence of $(Y)_m$ or $(Y)_n$ (where present) may independently be further optionally substituted with Y, and wherein m and n together preferably equal 2 or 3. In one embodiment when m an n together equal 2, m and n are each independently 1. In another embodiment, m is 2 and n is 0. In yet another embodiment, m is 0 and n is 2. In still another embodiment when m and n together equal 3, m is 3 and n is 0. In another embodiment, m is 2 and n is 1. In yet another embodiment m is 1 and n is 2. In yet another embodiment, m is 0 and n is 3.

In an alternative embodiment of the compounds of formula (I) and sub-formulae (Ia) or (Ib), the optional substituent $Y_1$ is absent.

In one embodiment $Y_2$ is H.

In one embodiment $R_3$, $R_4$, $R_{3'}$ and $R_{4'}$ are each independently selected from H or $C_{1-3}$alkyl with H being particularly preferred.

Unless otherwise defined, the term "optionally substituted" as used herein means that a group may include one or more optional substituents, preferably 1, 2 or 3 more preferably 1 or 2 optional substituents selected from $R_7$, $R_7$-$R_7$, $(R_7)_q$halo, $(R_7)_q$CN, =O, $(R_7)_qOR_6$, $(R_7)_qOCHF_2$, $(R_7)_qCF_3$, $(R_7)_qCHF_2$, $(R_7)_qCF_3$, =S, $(R_7)_qSR_6$, $(R_7)_qSO_3H$, $(R_7)_qSO_2$—$R_7$, $(R_7)_qSO_2N(R_6)_2$, $(R_7)_qNO_2$, $(R_7)_qN(R_6)_2$, $(R_7)_qOC(=O)$—$R_7$, $(R_7)_qC(=O)OR_6$, $(R_7)_qC(=O)R_6$, $(R_7)_qC(=O)N(R_6)_2$, $(R_7)_qNR_6C(=O)$—$R_7$, $(R_7)_qNR_6SO_2R_7$, $(R_7)_qSi(R_7)_3$ and $(R_7)O$—$Si(R_7)_3$ where $R_6$ and $R_7$ are as defined above and where q is 0 or 1 and wherein each optional substituent may be further optionally substituted.

It will be understood that reference to an isomer includes structural isomers, such as tautomers. The term "tautomer" is used herein in its broadest sense to include compounds of formula (I) which are in a state of rapid equilibrium between two isomeric forms. Such compounds may differ in the nature of the bond connecting two atoms or groups and the position of these atoms or groups in the compound.

A representative tautomeric form of a compound of formula (I) may include but is not limited to the following general formulae:

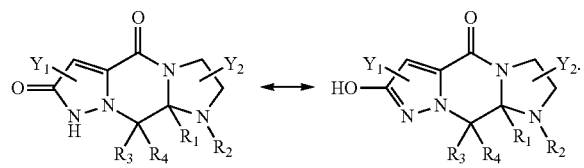

It will also be understood that, if it is appropriate in the context, a reference to a compound of formula (I) could refer to a compound of formula (I) per se or a salt, isomer or prodrug thereof.

The term "$C_{1-6}$alkyl" encompasses optionally substituted straight chain or branched chain hydrocarbon groups having from 1 to 6 carbon atoms and encompasses groups of the formula —$C_xH_{2x+1}$, where x is an integer of 1 to 6. Examples include methyl, ethyl, propyl, isopropyl, butyl, isobutyl, sec-butyl, tert-butyl, pentyl, neopentyl hexyl, and so forth. Unless the context requires otherwise, the term "$C_{1-6}$alkyl" also encompasses alkyl groups containing one less hydrogen atom such that the group is attached via two positions. Such groups are also referred to as "$C_{1-6}$alkylene" groups.

The term "$C_{2-6}$alkenyl" refers to optionally substituted straight chain or branched chain hydrocarbon groups having at least one double bond of either E or Z stereochemistry where applicable and 2 to 6 carbon atoms. Examples include vinyl, 1-propenyl, 1- and 2-butenyl, 2-methyl-2-propenyl hexenyl, butadienyl, hexadienyl, hexatrienyl and so forth. Unless the context requires otherwise, the term "$C_{1-6}$alkenyl" also encompasses alkenyl groups containing one less hydrogen atom such that the group is attached via two positions. Such groups are also referred to as "$C_{2-6}$alkenylene" groups.

The term "$C_{2-6}$alkynyl" refers to optionally substituted straight chain or branched chain hydrocarbon groups having at least one triple bond and 2 to 6 carbon atoms. Examples include ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl, 5-hexynyl and so forth. Unless the context indicates otherwise, the term "$C_{2-6}$alkynyl" also encompasses alkynyl groups containing one less hydrogen atom such that the group is attached via two positions. Such groups are also referred to as "$C_{2-6}$alkynylene" groups.

The term "$C_{3-43}$cycloalky" refers to non-aromatic cyclic hydrocarbon groups having from 3 to 8 carbon atoms, including cyclopropyl, cyclobutyl, cyclopentyl, cyclohexyl, cyclohexenyl, cycloheptyl and so forth. $C_{3-6}$cycloalkyl groups are preferred. It will be understood that cycloalkyl groups may be saturated such as cyclohexyl or unsaturated such as cyclohexenyl.

The term "$C_{1-6}$alkoxy" refers to the group —$OC_xH_{2x+1}$, where x is an integer of 1 to 6. Examples include methoxy, ethoxy, propoxy, isoproxy, butoxy, tert-butoxy, pentoxy and so forth. The oxygen atom may be located along the hydrocarbon chain, and need not be the atom linking the group to the remainder of the compound.

The term "aryl" refers to any group containing a carbocyclic (non-heterocyclic) aromatic ring and may be a mono-, bi- or tri-cyclic ring system. The aromatic ring or ring system is generally composed of 6 to 10 carbon atoms. Such groups may contain fused ring systems (such as napthyl, tetrahydronapthyl, fluorenyl, indenyl, azulenyl, anthracenyl and the like), linked ring systems (such as biphenyl groups), and may be substituted or unsubstituted. Examples of aryl groups include, but are not limited to, phenyl, biphenyl, naphthyl and tetrahydronaphthyl. Phenyl is preferred.

The term "heterocyclyl" encompasses aromatic heterocyclyls and non-aromatic heterocyclyls.

The term "aromatic heterocyclyl" may be used interchangeably with the term "heteroaromatic" or the term "heteroaryl". The term "aromatic heterocyclyl" also encompasses pseudoaromatic heterocyclyls. The term "pseudoaromatic" refers to a ring system which is not strictly aromatic, but which is stabilized by means of delocalization of electrons and behaves in a similar manner to aromatic rings.

The heteroatoms in the aromatic heterocyclyl group may be selected from N, S and O. Such groups may be substituted or unsubstituted.

Aromatic heterocyclyl groups may be 5-membered or 6-membered mono-cyclic aromatic ring systems.

Examples of 5-membered mono-cyclic aromatic ring systems include furanyl, thienyl, pyrrolyl, oxazolyl, oxadiazolyl (including 1,2,3 and 1,2,4 oxadiazolyls and furazanyl i.e. 1,2,5-oxadiazolyl), thiazolyl, isoxazolyl, isothiazolyl, pyrazolyl, imidazolyl, triazolyl (including 1,2,3, 1,2,4 and 1,3,4 triazolyls), tetrazolyl, thiadiazolyl (including 1,2,3 and 1,3,4 thiadiazolyls) and so forth.

Examples of 6-membered mono-cyclic aromatic ring systems include pyridinyl, pyrimidinyl, pyridazinyl, pyrazinyl, triazinyl and so forth.

Aromatic heterocyclyl groups may also be bicyclic or polycyclic heteroaromatic ring systems such as fused ring systems (including purine, pteridinyl, napthyridinyl, 1H thieno[2,3-c]pyrazolyl, thieno[2,3-b]furyl and the like) or linked ring systems (such as oligothiophene, polypyrrole and so forth). Fused ring systems may also include aromatic 5-membered or 6-membered heterocyclyls fused to carbocyclic aromatic rings such as phenyl, napthyl, indenyl, azulenyl, fluorenyl, anthracenyl and the like.

Examples of aromatic heterocyclyls fused to carbocyclic aromatic rings include benzothiophenyl, indolyl, isoindolyl, benzofuranyl, isobenzofuranyl, benzimidazolyl, indazolyl, benzoxazolyl, benzisoxazolyl, benzothiazolyl, benzisothiazolyl, benzimidazolyl, indazolyl, quinolinyl, isoquinolinyl, quinoxalinyl, quinazolinyl, cinnolinyl, benzotriazinyl, phthalazinyl, carbolinyl and so forth. Particularly preferred are 5-membered aromatic heterocyclyls containing O and/or N heteroatoms. Particularly preferred are 6-membered aromatic heterocyclyls containing N heteroatoms.

The term "non-aromatic heterocyclyl" encompasses optionally substituted saturated and unsaturated rings which contain at least one heteroatom selected from the group consisting of O, N and S.

Non-aromatic heterocyclyls may be 5-membered, 6-membered or 7-membered mono-cyclic rings.

Examples of 5-membered non-aromatic heterocyclyl rings include 2H-pyrrolyl, 1-pyrrolinyl, 2-pyrrolinyl, 3-pyrrolinyl, pyrrolidinyl, 1-pyrrolidinyl, 2-pyrrolidinyl, 3-pyrrolidinyl, tetrahydrofuranyl, tetrahydrothiophenyl, pyrazolinyl, 2-pyrazolinyl, 3-pyrazolinyl, pyrazolidinyl, 2-pyrazolidinyl, 3-pyrazolidinyl, imidazolidinyl, 3-dioxalanyl, thiazolidinyl, isoxazolidinyl, 2-imidazolinyl and the like. Particularly preferred are 5-membered non-aromatic heterocyclyls containing N and/or O.

Examples of 6-membered non-aromatic heterocyclyls include piperidinyl, pyranyl, dihyrdopyranyl, tetrahydropyranyl, 2H pyranyl, 4H pyranyl, piperazinyl, diozanyl, 1,4-dioxinyl, 1,4-dithianyl, 1,3,5-triozalanyl, 1,3,5-trithianyl, 1,4-morpholinyl, thiomorpholinyl, 1,4-oxathianyl, triazinyl, 1,4-thiazinyl and the like. Particularly preferred are 6-membered heterocyclyls containing N and/or O.

Examples of 7-membered non-aromatic heterocyclyls include azepanyl, oxepanyl, thiepanyl and the like.

Non-aromatic heterocyclyl rings may also be bicyclic heterocyclyl rings such as linked ring systems (for example uridinyl and so forth) or fused ring systems. Fused ring systems include non-aromatic 5-membered, 6-membered or 7-membered heterocyclyls fused to carbocyclic aromatic rings such as phenyl, napthyl, indenyl, azulenyl, fluorenyl, anthracenyl and the like. Examples of non-aromatic 5-membered, 6-membered or 7-membered heterocyclyls fused to carbocyclic aromatic rings include indolinyl, benzodiazepinyl, benzazepinyl, dihydrobenzofuranyl and the like.

The term "halo" refers to fluoro, chloro, bromo or iodo.

The compounds of the invention may also be prepared as salts which are pharmaceutically acceptable. It will be appreciated that non-pharmaceutically acceptable salts also fall within the scope of the present invention, since these are useful as intermediates in the preparation of pharmaceutically acceptable salts. Examples of pharmaceutically acceptable salts include salts of pharmaceutically acceptable cations such as sodium, potassium, lithium, calcium, magnesium, ammonium, alkylammonium and the like; acid addition salts of pharmaceutically acceptable inorganic acids such as hydrochloric, orthophosphoric, sulfuric, phosphoric, nitric, carbonic, boric, sulfamic, hydrobromic acids and the like; and salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulfonic, trihalomethanesulfonic, toluenesulfonic, benzenesulfonic, isethionic, salicylic, sulphanilic, aspartic, glutamic, edetic, stearic, palmitic, oleic, lauric, pantothenic, tannic, ascorbic, valeric, orotic acids and the like. Salts of amine groups may also comprise quaternary ammonium salts in which the amino nitrogen atom carries a suitable organic group such as an alkyl, alkenyl, alkynyl, aralkyl moiety and so forth.

The salts may be formed by conventional means, such as by reacting the free base form of the compound with one or more equivalents of the appropriate acid.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, alcohols such as methanol, ethanol or isopropyl alcohol, DMSO, acetonitrile, dimethyl formamide (DMF) and the like with the solvate forming part of the crystal lattice by either non-covalent binding or by occupying a hole in the crystal lattice. Hydrates are formed when the solvent is water; alcoholates are formed when the solvent is alcohol. Solvates of the compounds of the present invention can be conveniently prepared or formed during the processes described herein. In addition, the compounds of the present invention can exist in unsolvated as well as solvated forms. In general, the solvated forms are considered equivalent to the unsolvated forms for the purposes of the compounds and methods provided herein.

Additionally, the compounds of the present invention can exist in unsolvated as well as solvated forms with pharmaceutically acceptable solvents such as water, ethanol, and the like. The solvated forms of the compounds of the present invention are also considered to be disclosed herein.

It will be understood that compounds of formula (I) possess a chiral centre and may therefore exist as a racemate or an R- or S-enantiomer. The compounds may therefore be used as a purified enantiomer or diastereomer, or as a mixture of any ratio thereof. In one embodiment there is provided a compound of formula (I) as defined above or a compound of formula (II) as defined above in a single stereoisomeric form. The isomers may be separated conventionally by chromatographic methods or using a resolving agent. Alternatively the individual isomers may be prepared by asymmetric synthesis using chiral intermediates. Where the compound has at least one carbon-carbon double bond, it may occur in Z- and E-forms and all isomeric forms of the compounds being included in the present invention.

This invention also encompasses prodrugs of the compounds of formula (I).

The term "pro-drug" is used herein in its broadest sense to include those compounds which are converted in vivo to the compound of formula (I). Use of the prodrug strategy optimises the delivery of the drug to its site of action, for example, the brain. In one embodiment, compounds of formula (I) having free amino, amido, hydroxyl, or carboxylic acid groups can be converted into prodrugs. Prodrugs include compounds wherein carbonates, carbamates, amides and alkyl esters are covalently bonded to the above substituents of compounds of the present invention through the carbonyl carbon prodrug sidechain. Prodrugs also include phosphate derivatives of compounds (such as acids, salts of acids, or esters) joined through a phosphorus-oxygen bond to a free hydroxyl of compounds of formula I. Prodrugs may also include N-oxides, and S-oxides of appropriate nitrogen atoms in formula (I).

Pharmaceutical Compositions

The invention also provides a pharmaceutical composition comprising a compound of formula (I) and a pharmaceutically acceptable carrier.

The pharmaceutical composition may further comprise or be administered in combination with one or more other RSV antiviral agents such as Virazole®.

The term "composition" is intended to include the formulation of an active ingredient with conventional carriers and excipients, and also with encapsulating materials as the carrier, to give a capsule in which the active ingredient (with or without other carriers) is surrounded by the encapsulation carrier. Any carrier must be "pharmaceutically acceptable" meaning that it is compatible with the other ingredients of the composition and is not deleterious to a subject. The compositions of the present invention may contain other therapeutic agents as described above, and may be formulated, for example, by employing conventional solid or liquid vehicles or diluents, as well as pharmaceutical additives of a type appropriate to the mode of desired administration (for example, excipients, binders, preservatives, stabilizers, flavours and so forth) according to techniques such as those well known in the art of pharmaceutical formulation (See, for example, Remington: *The Science and Practice of Pharmacy*, 21st Ed., 2005, Lippincott Williams & Wilkins).

The pharmaceutical composition includes those suitable for oral, rectal, nasal, topical (including buccal and sub-lingual), vaginal or parenteral (including intramuscular, subcutaneous and intravenous) administration or in a form suitable for administration by inhalation or insufflation.

The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use.

Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

For preparing pharmaceutical compositions from the compounds of the present invention, pharmaceutically acceptable carriers can be either solid or liquid. Solid form preparations include powders, tablets, pills, capsules, cachets, suppositories, and dispensable granules. A solid carrier can be one or more substances which may also act as diluents, flavouring agents, solubilisers, lubricants, suspending agents, binders, preservatives, tablet disintegrating agents, or an encapsulating material.

Suitable carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with an encapsulating material as the carrier by providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

Liquid form preparations include solutions, suspensions, and emulsions, for example, water or water-propylene glycol solutions. For example, parenteral injection liquid preparations can be formulated as solutions in aqueous polyethylene glycol solution.

Sterile liquid form compositions include sterile solutions, suspensions, emulsions, syrups and elixirs. The active ingredient can be dissolved or suspended in a pharmaceutically acceptable carrier, such as sterile water, sterile organic solvent or a mixture of both.

The compositions according to the present invention may thus be formulated for parenteral administration (for example, by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilisation from solution, for constitution with a suitable vehicle, for example, sterile, pyrogen-free water, before use.

Pharmaceutical forms suitable for injectable use include sterile injectable solutions or dispersions, and sterile powders for the extemporaneous preparation of sterile injectable solutions. They should be stable under the conditions of manufacture and storage and may be preserved against oxidation and the contaminating action of microorganisms such as bacteria or fungi.

The solvent or dispersion medium for the injectable solution or dispersion may contain any of the conventional solvent or carrier systems for the compounds, and may contain, for example, water, ethanol, polyol (for example, glycerol, propylene glycol and liquid polyethylene glycol, and the like), suitable mixtures thereof, and vegetable oils.

Pharmaceutical forms suitable for injectable use may be delivered by any appropriate route including intravenous, intramuscular, intracerebral, intrathecal, epidural injection or infusion.

Sterile injectable solutions are prepared by incorporating the active compounds in the required amount in the appropriate solvent with various other ingredients such as these enumerated above, as required, followed by filtered sterilization. Generally, dispersions are prepared by incorporating the various sterilised active ingredient into a sterile vehicle which contains the basic dispersion medium and the required other ingredients from those enumerated above. In the case of sterile powders for the preparation of sterile injectable solutions, preferred methods of preparation are vacuum drying or freeze-drying of a previously sterile-filtered solution of the active ingredient plus any additional desired ingredients.

When the active ingredients are suitably protected they may be orally administered, for example, with an inert diluent or with an assimilable edible carrier, or they may be enclosed in hard or soft shell gelatin capsule, or they may be compressed into tablets, or they may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like.

The amount of active compound in therapeutically useful compositions should be sufficient that a suitable dosage will be obtained.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin; or a flavouring agent such as peppermint, oil of wintergreen, or cherry flavouring. When the dosage unit form is a capsule, it may contain, in addition to materials of the above type, a liquid carrier.

Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations, including those that allow specific delivery of the active peptide to specific regions of the gut.

Aqueous solutions suitable for oral use can be prepared by dissolving the active component in water and adding suitable colorants, flavours, stabilising and thickening agents, as desired. Aqueous suspensions suitable for oral use can be made by dispersing the finely divided active component in water with viscous material, such as natural or synthetic gums, resins, methylcellulose, sodium carboxymethylcellulose, or other well known suspending agents.

Pharmaceutically acceptable carriers and/or diluents include any and all solvents, dispersion media, coatings, antibacterial and antifungal agents, isotonic and absorption delaying agents and the like.

Also included are solid form preparations that are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilising agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension.

In the case of a spray, this may be achieved for example by means of a metering atomising spray pump. To improve nasal delivery and retention the compounds according to the invention may be encapsulated with cyclodextrins, or formulated with other agents expected to enhance delivery and retention in the nasal mucosa.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas.

The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, for example gelatin, or blister packs from which the powder may be administered by means of an inhaler.

In formulations intended for administration to the respiratory tract, including intranasal formulations, the compound will generally have a small particle size for example of the order of 5 to 10 microns or less. Such a particle size may be obtained by means known in the art, for example by micronisation.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of viral infection in living subjects having a diseased condition in which bodily health is impaired as herein disclosed in detail.

The invention also includes the compounds in the absence of carrier where the compounds are in unit dosage form.

Liquids or powders for intranasal administration, tablets or capsules for oral administration and liquids for intravenous administration are the preferred compositions.

Methods of Treatment

The compounds of formula (I) have demonstrated submolar potency as inhibitors of RSV and therefore offer a method of treating an RSV infection. The compounds of formula (I) can also be used to treat an RSV disease or reduce exacerbation of an underlying or pre-existing respiratory disease wherein RSV infection is a cause of said exacerbation. The RSV disease may include brochiolitis or pneumonia. The underlying or pre-existing respiratory diseases or conditions may include asthma, chronic obstructive pulmonary disease (COPD) and immunosuppression such as immunosuppression experienced by bone marrow transplant recipients.

Generally, the term "treating" means affecting a subject, tissue or cell to obtain a desired pharmacological and/or physiological effect and includes: (a) inhibiting the viral infection or RSV disease, such as by arresting its development or further development; (b) relieving or ameliorating the effects of the viral infection or RSV disease, such as by causing regression of the effects of the viral infection or RSV disease; (c) reducing the incidence of the viral infection or RSV disease or (d) preventing the infection or disease from occurring in a subject, tissue or cell predisposed to the viral infection or RSV disease or at risk thereof, but has not yet been diagnosed with a protective pharmacological and/or physiological effect so that the viral infection or RSV disease does not develop or occur in the subject, tissue or cell.

The term "subject" refers to any animal, in particular mammals such as humans, having a disease which requires treatment with the compound of formula (I).

The term "administering" should be understood to mean providing a compound or pharmaceutical composition of the invention to a subject suffering from or at risk of the disease or condition to be treated or prevented.

Although the invention has been described with reference to treating RSV infections or diseases, more particularly human and animal RSV infections or diseases, it will be appreciated that the invention may also be useful in the treatment of other viruses of the sub-family Pneumovirinae, more particularly, the genera *Pneumovirus* and *Metapneumovirus*.

Dosages

The term "therapeutically effective amount" refers to the amount of the compound of formula (I) that will elicit the biological or medical response of a subject, tissue or cell that is being sought by the researcher, veterinarian, medical doctor or other clinician.

In the prevention or treatment of RSV infections or diseases, an appropriate dosage level will generally be about 0.01 to about 500 mg per kg subject body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to about 250 mg/kg per day, about 0.05 to about 100 mg/kg per day, or about 0.1 to about 50 mg/kg per day. Within this range the dosage may be 0.05 to 0.5, 0.5 to 5 or 5 to 50 mg/kg per day. The dosage may be selected, for example to any dose within any of these ranges, for therapeutic efficacy and/or symptomatic adjustment of the dosage to the subject to be treated.

It will be understood that the specific dose level and frequency of dosage for any particular subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the subject undergoing therapy.

Method of Preparation

The compounds of the invention may be provided by one of the methods generally described as follows. Unless otherwise defined in the general schemes, the variable R' represents an optional substituent in any position and R" represents variable $R_8$ as defined in accordance with the compounds of formula (I).

General Method A
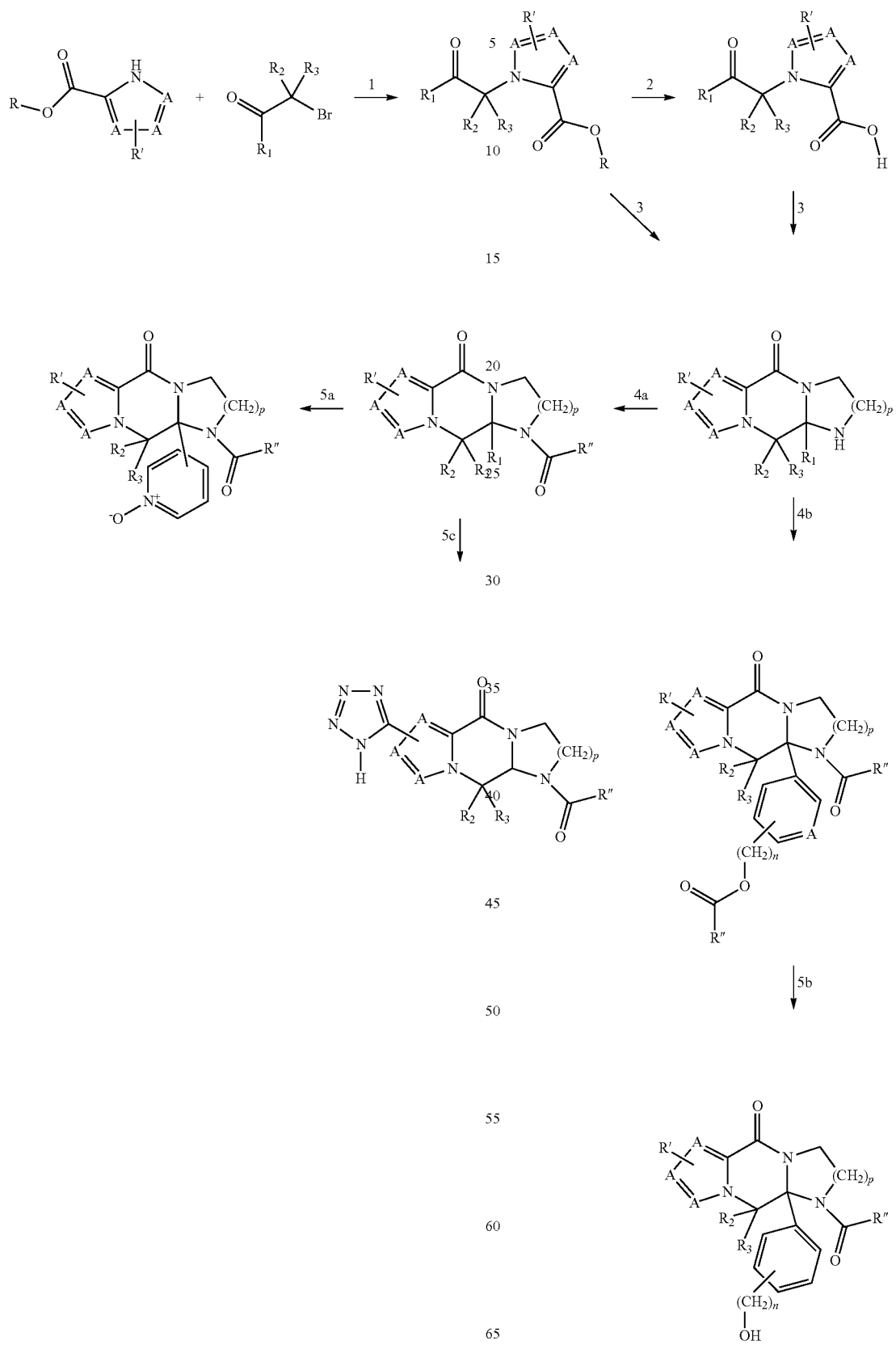

where each A is independently C or N and $R_1$ may be an optionally substituted alkyl, cycloalkyl, aryl, heterocyclyl or heteroaryl including but not limited to:

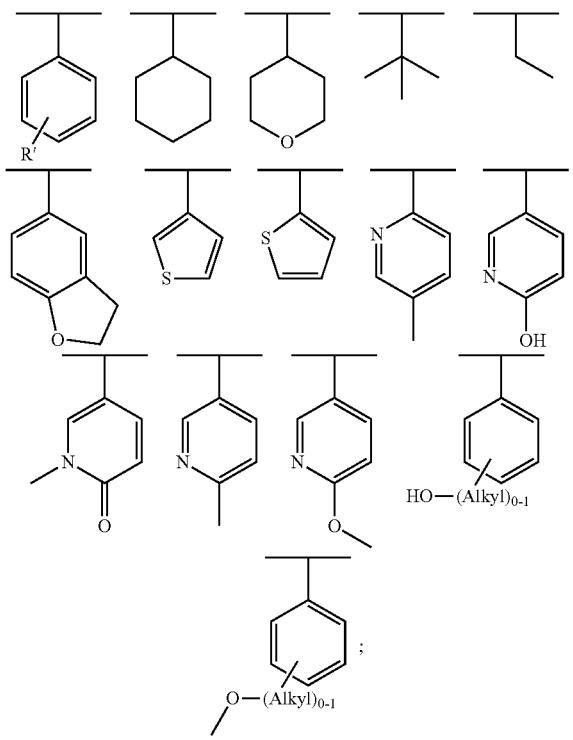

and optional substituents R' may include but are not limited to $C_{1-6}$alkyl such as methyl, $C_{1-6}$alkoxyl such as methoxy, halo such as fluoro, chloro and bromo, halo$C_{1-6}$alkoxyl such as $OCHF_2$, N-oxides, CN, $SO_2N(R_6)_2$, OH, $C_{1-6}$alkylOH, optionally substituted phenyl and optionally substituted heterocyclyls such as 5- or 6-membered heteroaryls.

Step 1

One equivalent of the appropriate ester, such as methylpyrrole-2-carboxylate is reacted with 1 to 1.5 equivalent of an appropriate bromo-ketone in the presence of 1 to 2 equivalents of base, such as potassium carbonate, potassium tert-butoxide, cesium carbonate or NaH at low temperature in a suitable organic solvent, such as ACN or DMF at temperatures ranging between −20° C. and 0° C. The reaction mixture is then stirred at the appropriate temperature and time ranging from 0° C. to 75° C. for 20 min to 48 h. Water or a saturated aqueous solution of ammonium chloride is then added until precipitation. The solid obtained is then collected by filtration and used such as in the next step. If no precipitate forms the mixture is extracted with the appropriate organic solvent, such as EtOAc or $CH_2Cl_2$. The organic layers are washed with NaCl, dried ($MgSO_4$ or $Na_2SO_4$) and concentrated in vacuo. The residue is then purified by flash chromatography or crystallisation. Alternatively, product may be purchased commercially.

Step 2

An appropriate pyrrole, imidazole or pyridinone carboxylate derivative in an organic solvent, such as THF, 1,4-dioxane or MeOH is treated with 1.5 to 10 equivalents of aqueous lithium hydroxide or aqueous NaOH. The mixture is then stirred at the appropriate temperature ranging from room temperature to 70° C. After completion of the reaction (1-48 h) the mixture is acidified (pH 2-4) with 1M HCl and then extracted with $CH_2Cl_2$, EtOAc or $CH_2Cl_2$ containing 20-25% of isopropyl alcohol. If necessary the mixture is first basified with a base, such as 1 M NaOH and then washed with an organic solvent such as EtOAc to remove the remaining ester starting material. The organic layers are dried ($MgSO_4$ or $Na_2SO_4$), filtrated and concentrated in vacuo. In cases where a precipitate forms after acidification the solid is filtrated and collected. The residue obtained from the work up or by filtration can be used without purification in the next step. Alternatively the residue may be purified by crystallization or by trituration with an appropriate solvent Step 3

In general, one equivalent of an appropriate keto-acid or keto-ester is reacted with 7 to 40 equivalents of ethane-1,2-diamine or propane-1,3-diamine. The mixture is heated conventionally or in a microwave reactor at the appropriate temperature and time ranging from 100-180° C. for 4-84 hours in an appropriate solvent, such as 1,4-dioxane, xylenes or 1,2-dichloroethane. After this time the reaction is concentrated in vacuo. In some cases water is added and the mixture extracted with an organic solvent, such as EtOAc or $CH_2Cl_2$. The organic layers are then dried ($MgSO_4$ or $Na_2SO_4$), filtrated and concentrated in vacuo. The residue obtained is either purified by flash chromatography or by triturating the residue with an appropriate solvent.
Route (a)

Step 4a

One equivalent of an appropriate cyclic amine in a base such as pyridine or in a mixture of $CH_2Cl_2$/pyridine is added to an appropriate acid chloride, sulfonyl chloride or isocyanate derivative (3 to 10 equivalents) in a base such as pyridine or in a mixture of pyridine or triethylamine in $CH_2Cl_2$ at 0° C. The acid chloride used is commercially available or initially prepared in situ by reacting the corresponding acid with thionyl chloride or oxalyl chloride in an organic solvent such as $CH_2Cl_2$. The acid chloride in some examples may be prepared in situ with cyanuric chloride and triethylamine in $CH_2Cl_2$. The acylation reaction is monitored by LCMS. When complete the reaction mixture is quenched with water and extracted with an organic solvent, such as EtOAc, $CH_2Cl_2$ or $CH_2Cl_2$ containing propan-2-ol. The organic layers are subsequently washed with a saturated aqueous solution of NaCl, dried ($Na_2SO_4$ or $MgSO_4$), filtrated and concentrated in vacuo to give a residue that is purified by flash chromatography.

Step 5a

To one equivalent of an appropriate pyridine derivative in $CH_2Cl_2$ is added methyltrioxorhenium (0.1 equivalents) and hydrogen peroxide (30% aq. sol., 15 equivalents). The mixture is stirred vigorously at room temperature until completion (monitored by LCMS). Water is added and the mixture extracted with an organic solvent, such as $CH_2Cl_2$. The organic layers are dried ($MgSO_4$), filtrated and concentrated in vacuo to give a residue that is purified by flash chromatography.
Route (b)

Step 4b

Refer to step 4a general method A.

Step 5b

To one equivalent of an appropriate bis-acylated compound in an appropriate organic solvent, such as THF is added a base such as aqueous lithium hydroxide (1-2 equivalents) and stirred at room temperature. After completion (monitored by LCMS) water is added and the mixture extracted with an organic solvent, such as $CH_2Cl_2$. The organic layers are dried ($MgSO_4$), filtrated and concentrated in vacuo to give a residue that is purified by flash chromatography.
Route (c)

Step 5c

To a solution of one equivalent of an appropriate nitrile derivative in an appropriate organic solvent, such as DMF is added sodium azide (1.2 equivalents), ammonium chloride (1.2 equivalents) and the reaction mixture is heated in a sealed tube at 120° C. until completion. The reaction is then purified by flash chromatography.
General Method B where $R_1$ may be an optionally substituted aryl or heterocyclyl including, but not limited to

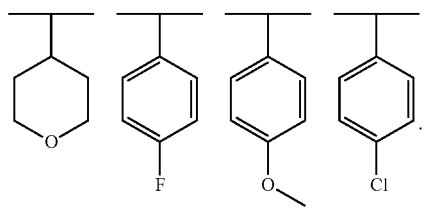

Steps 1, 2 and 3

Refer to steps 1, 2 and 3 in general method A.

Step 4a and Step 5b

To a solution of an appropriate tricyclic compound is added N-chlorosuccinimide (1 equivalent) in an appropriate organic solvent, such as THF. The reaction mixture is stirred at the appropriate temperature ranging from 50-60° C. After completion (monitored by LCMS) the mixture is concentrated in vacuo and purified by flash chromatography.

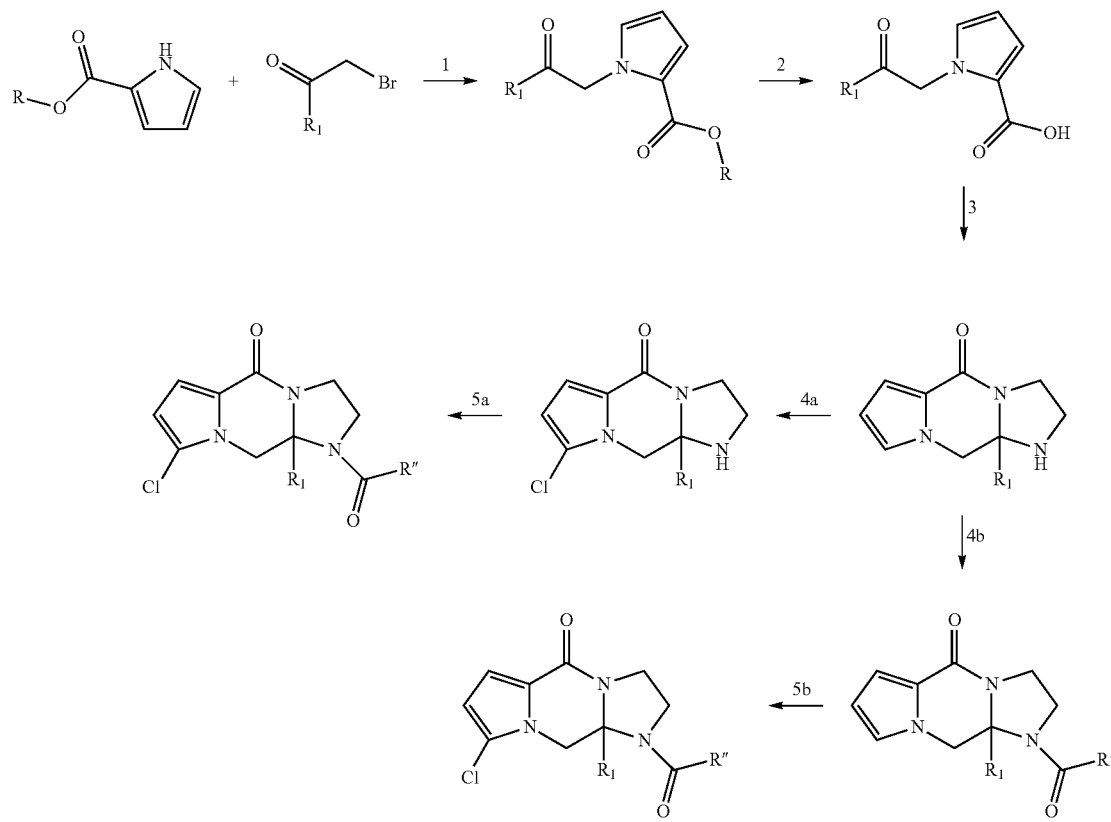

Step 4b and 5a

Refer to step 4a in general method A.
General Method C

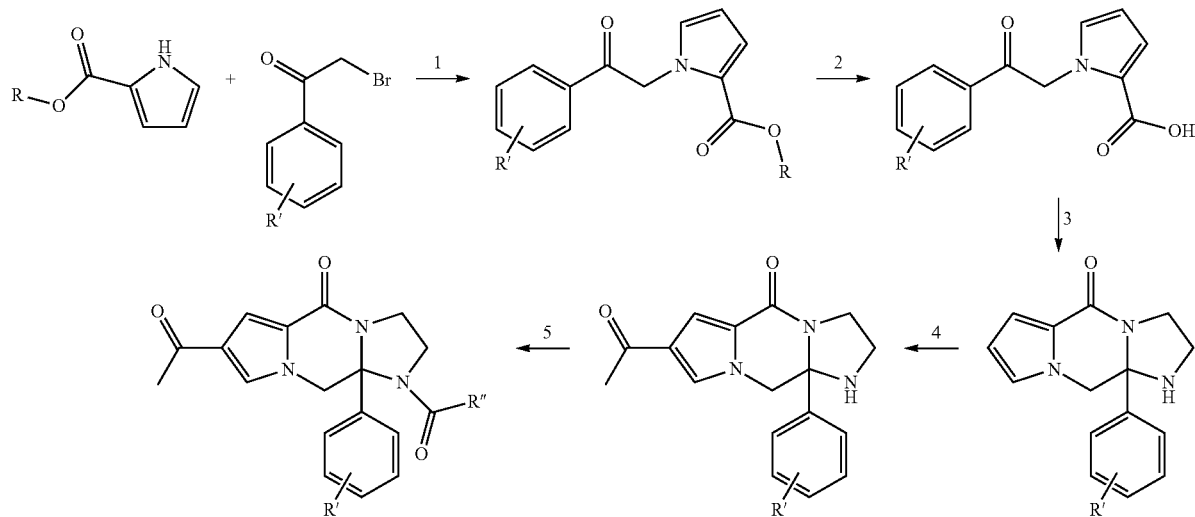

Steps 1, 2 and 3

Refer to steps 1, 2 and 3 in general method A.

Step 4

To a suspension of appropriate tricyclic compound and aluminium chloride in an appropriate organic solvent, such as $CH_2Cl_2$ is added acetyl chloride (1.2 equivalents) in $CH_2Cl_2$ and the mixture heated at reflux. The outcome of the reaction is monitored by LCMS and as required more acetyl chloride is added (2-3 equivalents) to the mixture. After 18-20 h the mixture is quenched with a saturated aqueous solution of $NaHCO_3$ and extracted with an appropriate organic solvent, such as $CH_2Cl_2$ containing 20% of propan-2-ol. The organic layers are dried, filtrated and concentrated in vacuo to give a residue that is purified by flash chromatography.

Step 5

Refer to step 4a in general method A.
General Method D

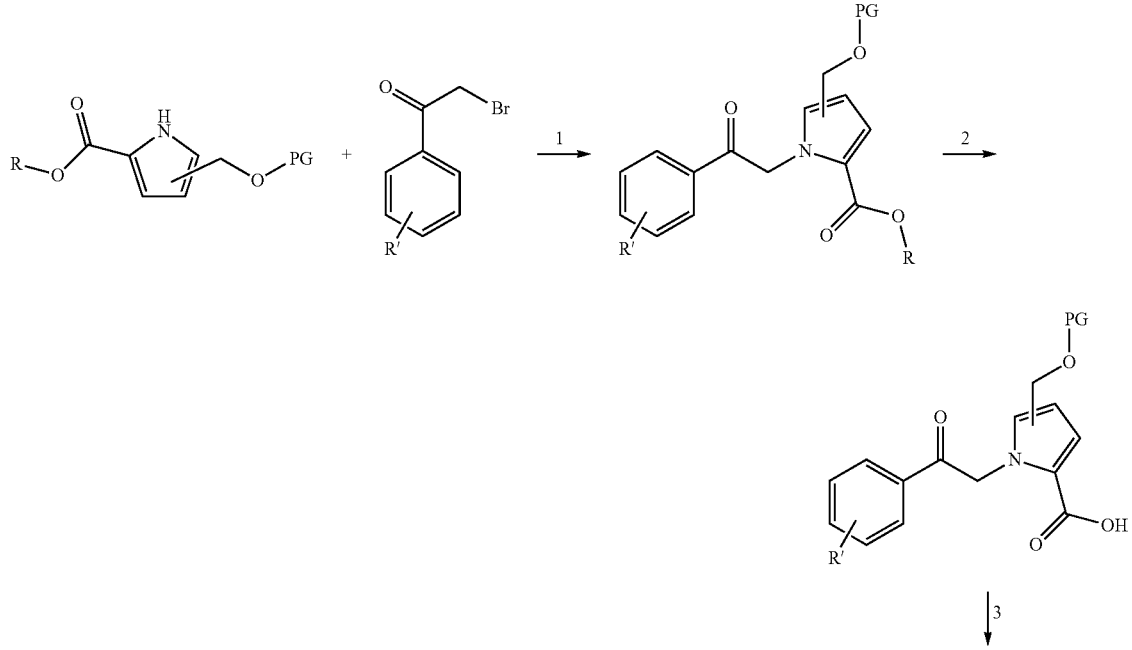

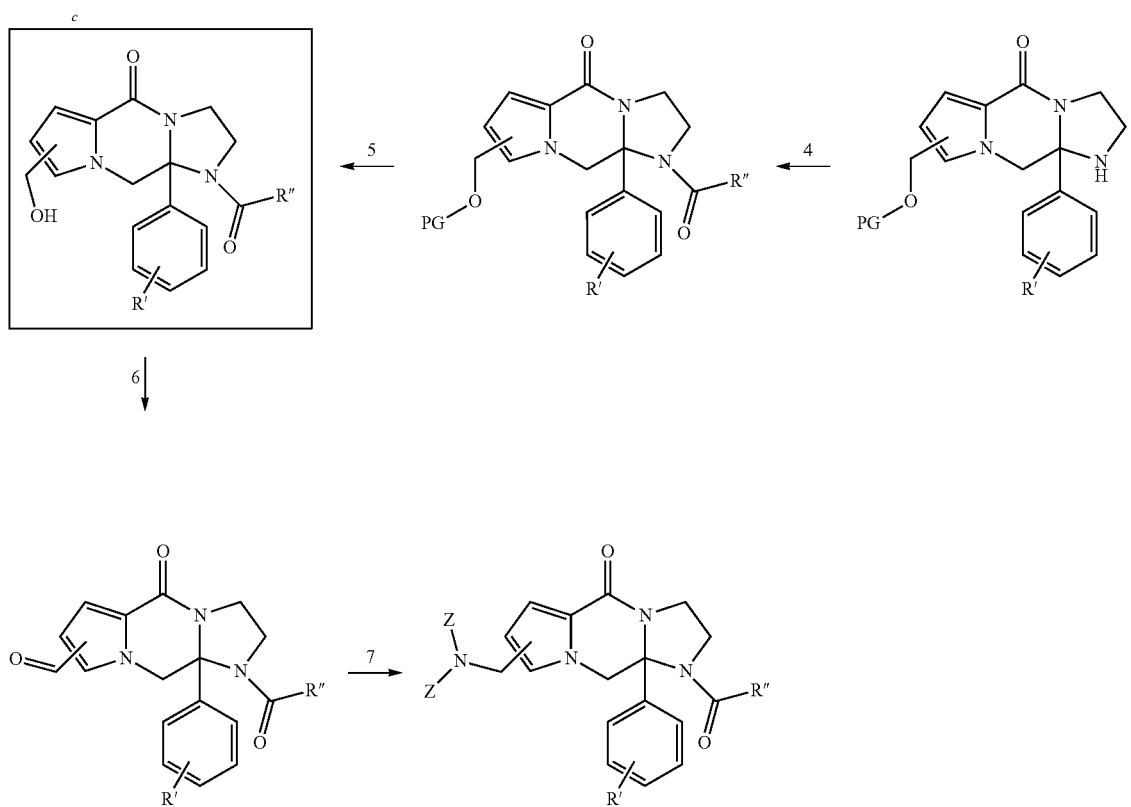

where PG is an optional protecting group and N(Z)$_2$ represents an amino moiety such as N(R$_6$)$_2$ or a heterocyclyl containing nitrogen such as morpholinyl or piperidinyl.

Steps 1, 2, 3 and 4

Refer to steps 1, 2, 3 and 4a in general method A.

Step 5

An O-protected pyrrole derivative, such as a silane derivative is dissolved in an acidic mixture of solvents such as acetic acid/THF/water. The mixture is stirred at room temperature. After completion (3-6 h) the mixture is extracted with a solvent such as CH$_2$Cl$_2$ or the volume is half concentrated in vacuo and then extracted. The organic layers are directly concentrated in vacuo or washed with a saturated aqueous solution of NaHCO$_3$, dried (MgSO$_4$), filtrated and concentrated in vacuo and purified by flash chromatography.

Step 6

To an appropriate alcohol in an appropriate organic solvent, such as CH$_2$Cl$_2$ is added an appropriate oxidant, such as manganese (IV) oxide and heated at 50° C. until completion of the reaction. The reaction mixture is filtrated and the filtrate concentrated in vacuo to give the corresponding aldehyde that is used in the next step without purification.

Step 7

To an appropriate solution of aldehyde in an organic solvent, such as CH$_2$Cl$_2$ is added the amine derivative (2 equivalents) at room temperature. Sodium triacetoxyborohydride (2 equivalents) is added and the resulting mixture is stirred at room temperature for 18 h, quenched with saturated aqueous solution of NaHCO$_3$ and extracted with an organic solvent, such as CH$_2$Cl$_2$. The organic layer is washed with brine, dried (MgSO$_4$), filtrated and concentrated in vacuo to give a residue that is purified by flash chromatography.

General Method E

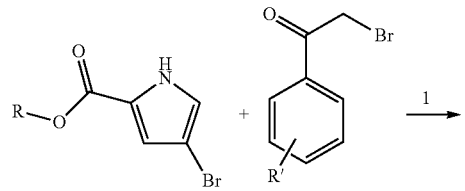

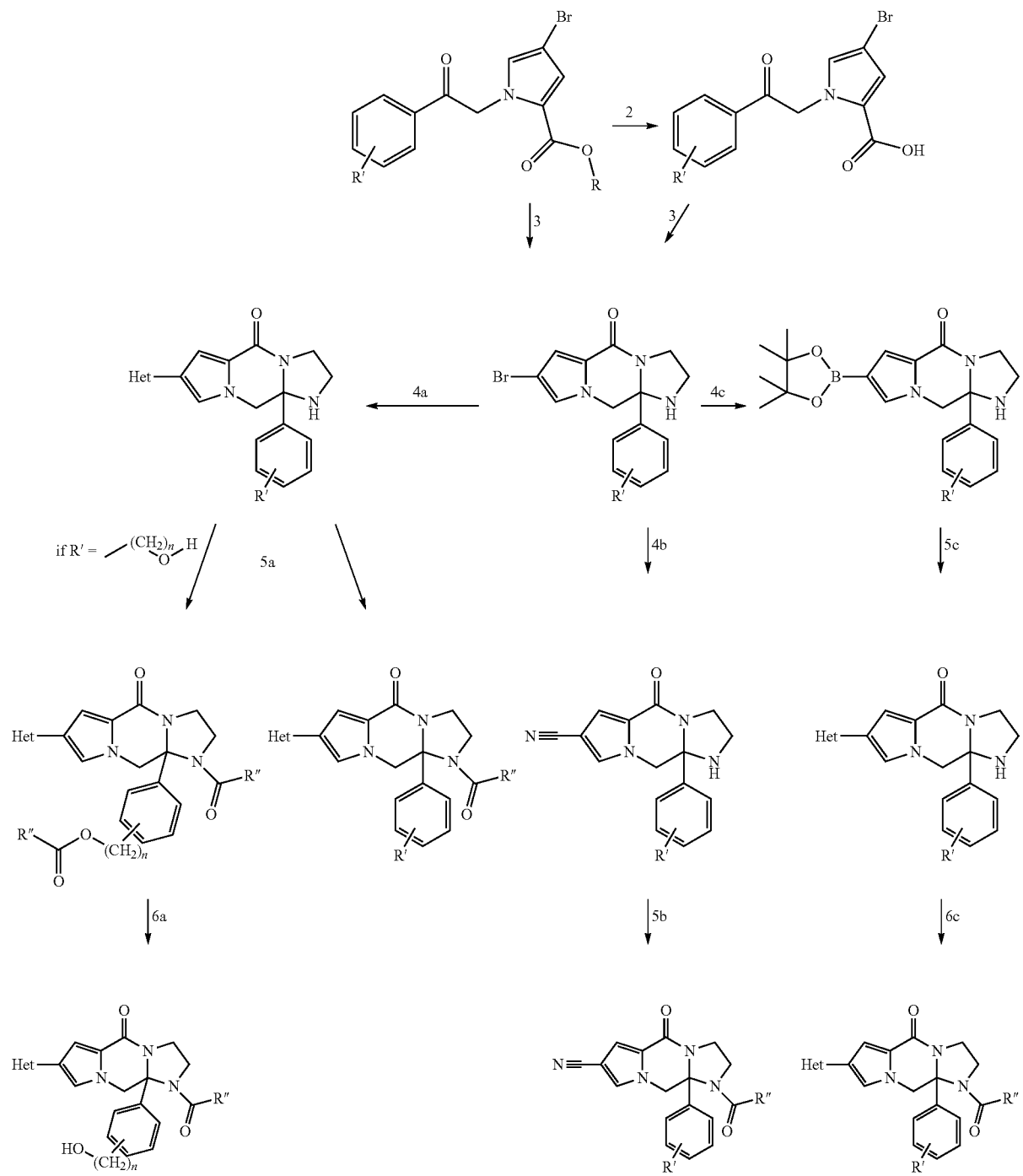

where Het is an optionally substituted heterocyclyl including but not limited to 5-membered heteroaryls such as pyrazolyl, imidazolyl, triazolyl and tetrazolyl and 6-membered heteroaryls such as pyridinyl, pyridazinyl, pyrazinyl and pyrimidinyl wherein optional substituents may include but are not limited to $C_{1-6}$alkyl including methyl, ethyl, propyl and isopropyl; halo; $C_{1-3}$alkylOH; $C_{1-3}$alkoxyl such as methoxy; and $C_{1-3}$alkylamino.

Step 1, 2 and 3

Refer to steps 1, 2 and 3 in general method A.

Route (a)

Step 4a

The appropriate bromo-pyrrole derivative (1 equivalent) is added to a mixture of the appropriate boronic acid ester (1.1 equivalents) or boronic acid (1.1 equivalents) in an appropriate organic solvent, such as 1,2-dimethoxyethane, ethanol and water (14:2:3). An appropriate cross coupling catalyst, such as dichlorobis(triphenylphosphine)palladium(II) (0.02 equivalents) and a base, such as $Na_2CO_3$ (1.5 equivalents) are suspended in the above mixture under argon and heated conventionally or in a microwave reactor at the appropriate temperature and time. If required more boronic acid ester or boronic acid or catalyst and base are added. After completion the reaction is quenched with water and extracted with an organic solvent, such as $CH_2Cl_2$. The organic layers are dried ($MgSO_4$), filtrated, concentrated in vacuo and purified by flash chromatography.

Step 5a

Refer to step 4a in general method A.

Step 6a

To an appropriate bis-acylated compound in an appropriate organic solvent, such as MeOH/CN (1:1) is added a base, such as lithium hydroxide (1 M, 1.1 eq.) and stirred at room temperature. After completion (monitored by LCMS) brine is added and the mixture extracted with an organic solvent, such as EtOAc. The organic layers are dried ($MgSO_4$), filtrated and concentrated in vacuo and purified by flash chromatography.
Route (b)

Step 4b

Refer to step 3a in general method M.

Step 5b

Refer to step 4a in general method A.
Route (c)

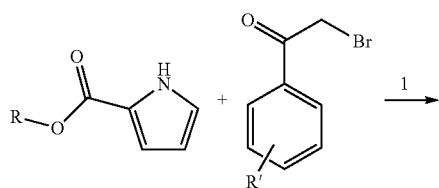

Step 4c

An appropriate bromo-pyrrole derivative (1 equivalent) is mixed with potassium acetate (3 equivalents), 4,4,4',4',5,5,5',5'-octamethyl-2,2'-bi-1,3,2-dioxaborolane (2 equivalent) in a solvent, such as DMF. The mixture is purged with argon and an appropriate palladium catalyst, such as catalyst [1,1'-bis(diphenylphosphino)ferrocene]dichloropalladium(II) (0.07 equivalents) is added and heated conventionally or in a microwave reactor at the appropriate temperature and time. Water is then poured onto the mixture that is then washed with an organic solvent, such as $CH_2Cl_2$. The aqueous layer is then filtrated and concentrated in vacuo to give the target product that is used in the next step without further purification.

Step 5c

To a degassed solution of an appropriate boronic ester pyrrole derivative in an organic solvent such as 1,4-dioxane is added a base, such as cesium carbonate (2 equivalents), water and an appropriate halo-aryl, halo-heteroaryl, aryltriflate or heteroaryltriflate derivative. The mixture is further flushed with argon and an appropriate palladium catalyst, such as bis(diphenylphosphino)ferrocene]dichloropalladium(II) (0.08 eq.) is added and heated conventionally or in a microwave reactor at the appropriate temperature and time. Water is added and the mixture extracted with an organic solvent, such as $CH_2Cl_2$. The organic layer is concentrated in vacuo to give the target product used in the next step without purification.

6c

Refer to step 4a in general method A.
General Method F

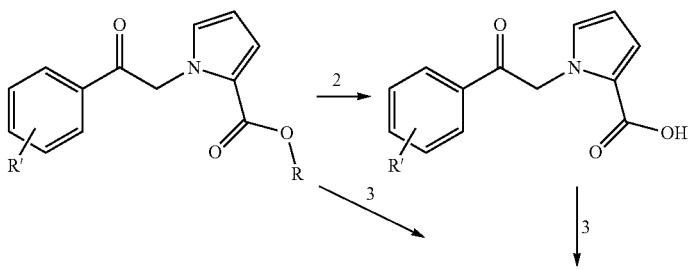

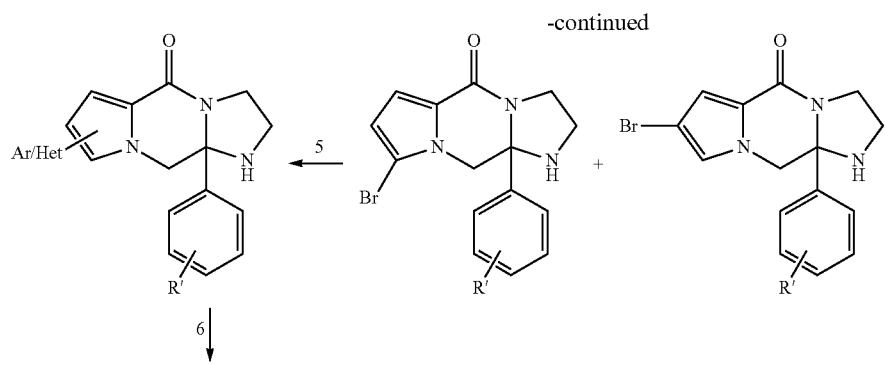

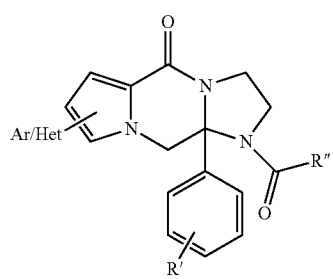

where Ar is an optionally substituted aryl including but not limited to phenyl and Het is an optionally substituted heterocyclyl including but not limited to 5-membered heteroaryls such as pyrazolyl, imidazolyl, triazolyl and tetrazolyl and 6-membered heteroaryls such as pyridinyl, pyridazinyl, pyrazinyl and pyrimidinyl wherein optional substituents may include but are not limited to $C_{1-6}$alkyl, halo, $C_{1-3}$alkoxyl such as methoxy and $CO_2H_6$ such as $CO_2H$.

Steps 1, 2 and 3

Refer to steps 1, 2 and 3 in general method A.

Step 4

To an appropriate unsubstituted pyrrole derivative in an organic solvent, such as THF is added N-bromosuccinimide (1 equivalent). The reaction is stirred at room temperature until complete. Water is added and the mixture is extracted with an organic solvent, such as $CH_2Cl_2$. The organic layer is then concentrated in vacuo to give a residue that is purified by flash chromatography to give a mixture of both regioisomers 4- and 5-bromo substituted pyrrole derivatives.

Step 5

The appropriate mixture of regioisomer bromo-pyrrole derivatives is added to an appropriate pyridine boronic acid derivative (1.5-2 equivalents) in a mixture of solvents, such as 1,2-dimethoxyethane, ethanol and water (14:2:3). A appropriate palladium catalyst, such as dichlorobis(triphenylphosphine)palladium(II) (0.03 equivalents) and a base, such as $Na_2CO_3$ (2.3-2.5 equivalents) are suspended in the mixture. The reaction vessel is flushed with argon, and heated conventionally or in a microwave reactor at the appropriate temperature and time. The outcome of the reaction is monitored by LCMS. When completed water is added and the mixture is extracted with a solvent, such as $CH_2Cl_2$ containing propan-2-ol. The organic layers are dried, filtrated, concentrated in vacuo to give a residue that is purified by flash chromatography.

Step 6

Refer to step 4a in general method A (the separation of both regioisomers occurs at that stage).

General Method G

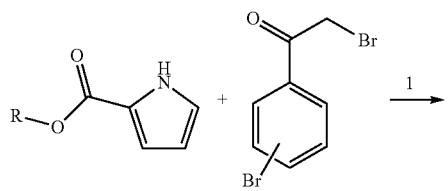

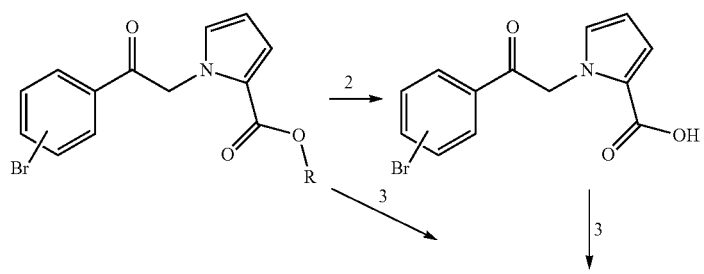

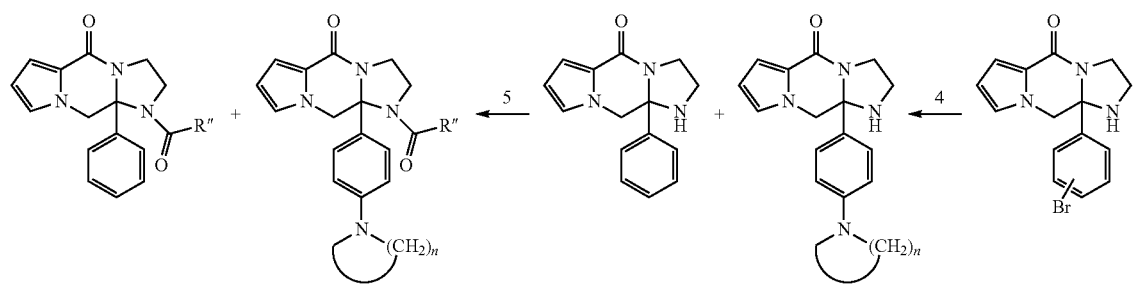

Steps 1, 2 and 3

Refer to steps 1, 2 and 3 in general method A.

Step 4

An appropriate bromo-aryl derivative is mixed with an appropriate cyclic amine, such as pyrrolidine (4 equivalents), an appropriate palladium catalyst, such as Pd(OAc)$_2$ (0.1 equivalents), an appropriate ligand, such as racemic-BINAP (0.2 equivalent) and a base, such as Cs$_2$CO$_3$ (4 equivalent). The mixture is suspended in organic solvent, such as toluene and heated conventionally or in a microwave reactor at the appropriate temperature and time. After completion the reaction mixture is filtered and the filtrate concentrated in vacuo to give a residue that is purified by flash chromatography.

Step 5

To the appropriate mixture of aryl (debrominated product) and aryl amine derivative in an organic solvent, such as pyridine is added the appropriate acid chloride (generated in situ by reacting the corresponding acid with oxalyl chloride) in an organic solvent, such as pyridine/CH$_2$Cl$_2$. The reaction is stirred at room temperature. After completion a saturated aqueous solution of NaHCO$_3$ is added and the mixture is extracted with an organic solvent, such as CH$_2$Cl$_2$. The organic layers are dried (MgSO$_4$), filtrated and concentrated in vacuo to give a residue that is purified by flash chromatography.

General Method H

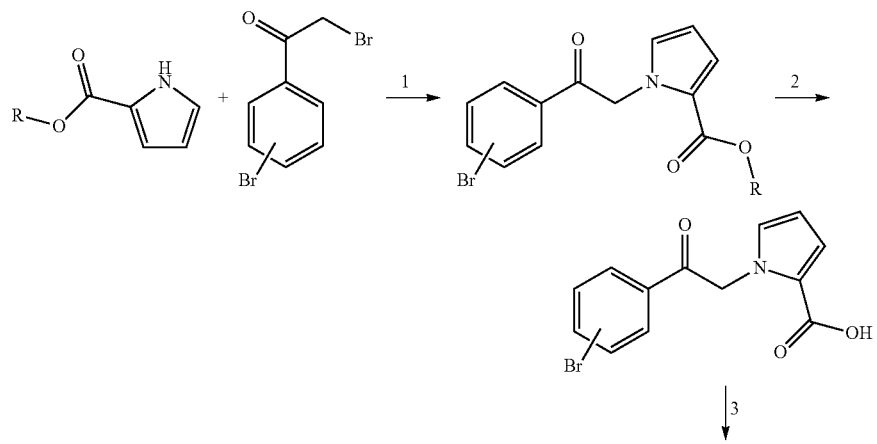

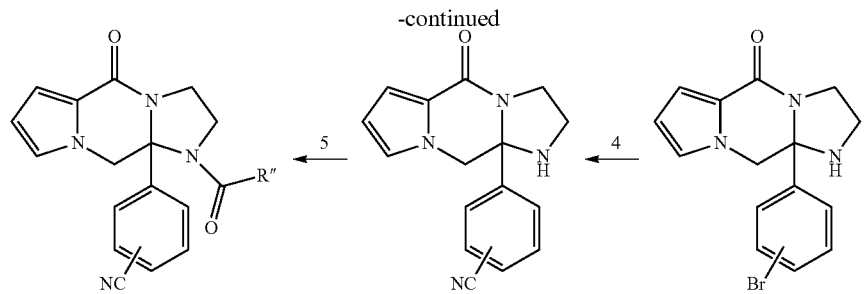

Steps 1, 2 and 3

Refer to steps 1, 2 and 3 in general method A.

Step 4

An appropriate mixture of bromo-aryl derivative, appropriate palladium catalyst, such as tetrakis(triphenylphosphine)-palladium(0) (0.1 equivalents) and cyanide source such as $Zn(CN)_2$ (1.5 equivalents) in appropriate solvent, such as DMF is sealed under Argon and heated and heated conventionally or in a microwave reactor at the appropriate temperature and time. The outcome of the reaction is monitored by LCMS. Further tetrakis(triphenylphosphine)-palladium(0) and $Zn(CN)_2$ is added if required. A saturated aqueous solution of $NaHCO_3$ is added and the mixture is extracted with an organic solvent, such as $CH_2Cl_2$ containing 20% of propan-2-ol. The organic layer is dried, filtrated and concentrated in vacuo to give a residue that is purified by flash chromatography.

Step 5

Refer to step 4a in general method A.

General Method I

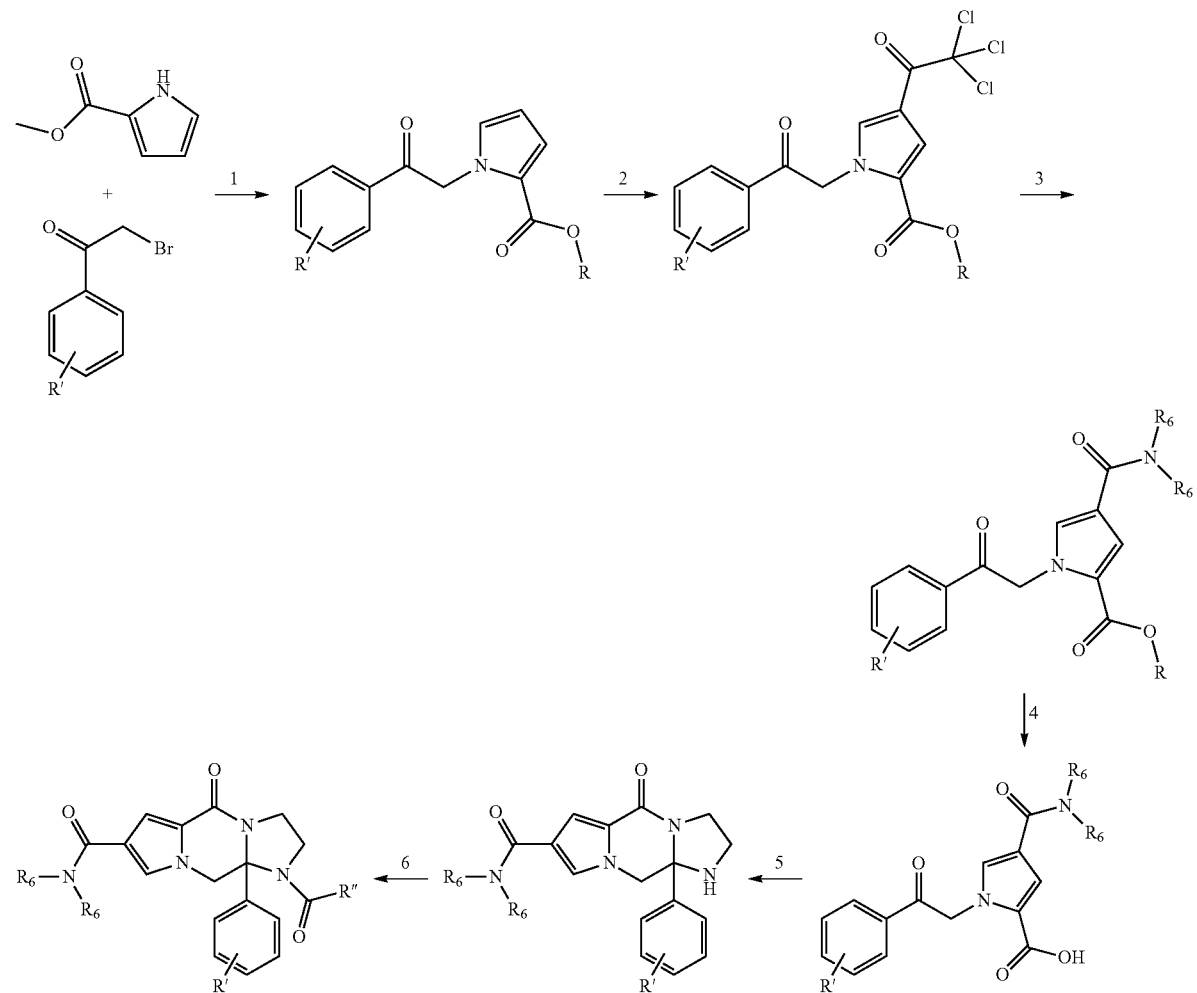

Step 1

Refer to step 1 in general method A.

Step 2

To an appropriate pyrrole carboxylate an organic solvent, such as $CH_2Cl_2$ is added trichloroacetyl chloride (2 equivalents) and aluminium chloride (4 equivalents). The mixture is stirred at room temperature for 18 h and quenched with a saturated aqueous solution of $NaHCO_3$. The mixture is then extracted with an organic solvent, such as $CH_2Cl_2$. The organic layers are dried, concentrated in vacuo to give a residue that is purified by flash chromatography.

Step 3

To an appropriate trichloroacethyl carboxylate derivate is added an appropriate amine, such as dimethylamine (3.3 equivalents) in an organic solvent, such as THF. The reaction is monitored by LCMS. After two days at room temperature a saturated solution of ammonium chloride is added and the mixture is extracted with an organic solvent, such as $CH_2Cl_2$ containing 20% propan-2-ol. The organic layer is dried, filtrated and concentrated in vacuo to give a residue that is purified by flash chromatography.

Steps 4, 5 and 6

Refer to steps 2, 3 and 4a in general method A.
General Method J

Step 1

To an appropriate hydroxypyridine carboxylate (1 equivalent) in a solvent, such as THF/water (100:1) is added an appropriate base, such as potassium carbonate (2 equivalents) and an appropriate phase transfer reagent, such as lithium bromide (2.5 equivalents), tertrabutylammonium bromide (0.1 equivalents) and an appropriate bromo ketone (1.5 equivalents). The suspension is heated at 80° C. until completion (around 40 minutes). Alternatively, the reaction can be performed in a solvent such as dry acetone at 0° C. to room temperature for around 16 hours. The mixture is diluted with an organic solvent, such as $CH_2Cl_2$ and filtrated through a Filter Aid that is then thoroughly rinsed with $CH_2Cl_2$. The organic layers are concentrated in vacuo. The residue obtained is purified by flash chromatography.

Steps 2, 3 and 4

Refer to steps 2, 3 and 4a in general method A.
General Method K

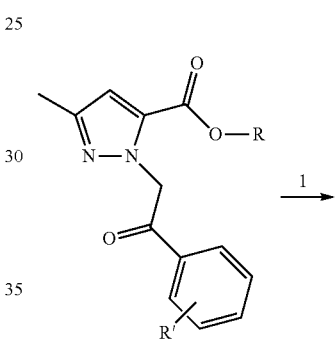

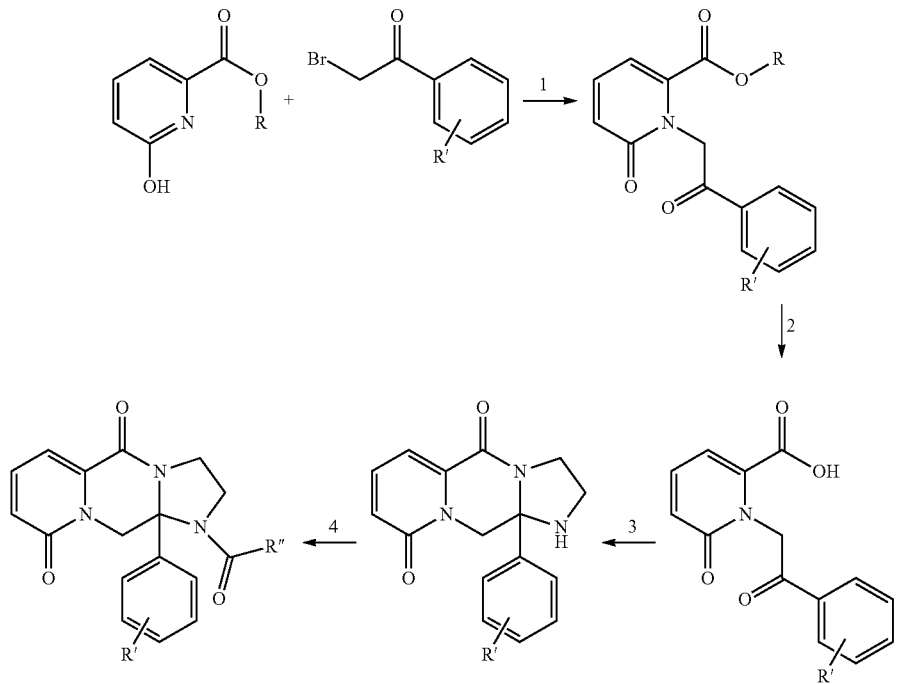

-continued

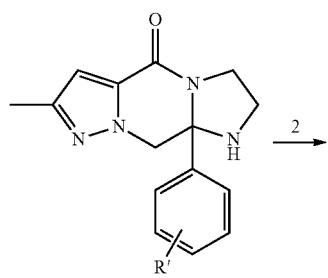

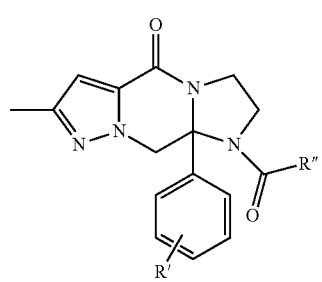

Step 1

To an appropriate pyrazole carboxylate derivative is added an appropriate amine, such as ethane-1,2-diamine (50 equivalents) and a catalytic amount of toluenesulfonic acid monohydrate in a solvent, such as xylenes and the mixture heated under reflux with a Dean-Stark trap. After completion (around 24 h) the mixture is concentrated in vacuo, dissolved in water and extracted with a solvent, such as EtOAc. The organic layers are dried ($MgSO_4$), filtrated and concentrated in vacuo to give a residue that is purified by flash chromatography.

Step 2

Refer to step 2 in general method A.
General Method L wherein $R_1$ is an optionally substituted aryl or an optionally substituted heterocyclyl including pyridinyl.

Step 1

To a refluxing solution of an appropriate glycine ester (1 equivalent) and sodium acetate (1.7 equivalents) in an appropriate solvent, such as mixture water/acetic acid (1:2) is added 2,5-dimethoxytetrahydrofuran (1 equivalent). The solution is refluxed for 4 hours, diluted with water, washed with a saturated aqueous solution of $NaHCO_3$ and extracted with a solvent, such as $CH_2Cl_2$. The organic layers are dried ($MgSO_4$), filtrated and concentrated in vacuo to give an oil that is purified by flash chromatography.

Step 2

To a solution of an appropriate haloaryl or haloheteroaryl (1 equivalent) such as a 3-bromopyridine an appropriate solvent, such as THF is added a base, such as n-BuLi (1 equivalent) at −78° C. A solution of an appropriate pyrrole acetic acid ester derivative (1.2 equivalents) in THF is then added and the mixture stirred at room temperature, quenched with a saturated aqueous solution of $NH_4Cl$ and extracted with an organic solvent, such as EtOAc. The organic layers are dried ($MgSO_4$), filtrated and concentrated in vacuo to give a residue that is purified by flash chromatography.

Step 3

To a solution of an appropriate pyrrole derivative (1 equivalent) in an appropriate solvent, such as $CH_2Cl_2$ is added trichloroacetyl chloride (2 equivalents) at 0° C. The reaction mixture is allowed to warm to room temperature and stirred for 18 h. Additional trichloroacetyl chloride is added if required. The reaction mixture is then quenched with a chilled saturated aqueous solution of $NaHCO_3$ at 0° C. The aqueous layers are extracted with an organic solvent, such as $CH_2Cl_2$, dried ($MgSO_4$), filtrated and concentrated in vacuo to give a residue that is purified by flash chromatography.

Step 4

To an appropriate solution of trichloroacetyl pyrrole derivative (1 equivalent) appropriate solvent, such as 1,4-

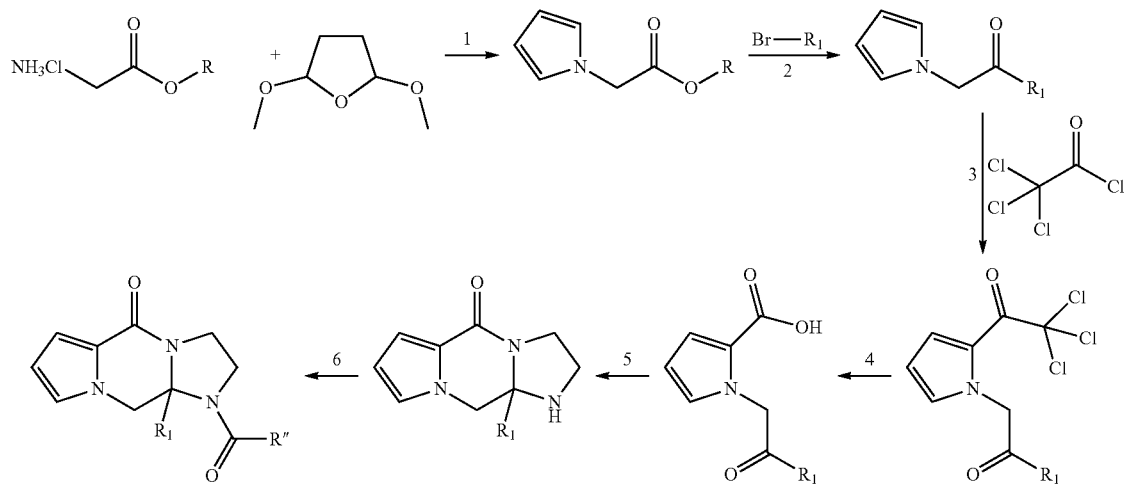

dioxane is added a base such as sodium hydroxide (1 M, 2 equivalents) and the mixture is allowed at room temperature. When complete the reaction is diluted with water and acidified with an aqueous solution of HCl (1 M). The mixture is then extracted with an organic solvent, such as EtOAc. The organic layer is dried ($Na_2SO_4$), filtrated and concentrated in vacuo to yield the desired acid derivative.

Steps 5 and 6

Refer to step 3 and 4 in general method A.
General Method M where PG is an optional protecting group.

Step 1

To a solution of an appropriate bromo pyrrole derivative (1 equivalent) in a solvent, such as DMF is added a base such as sodium hydride (60% dispersion in mineral oil, 1.1 equivalents) portionwise at 0° C. After one hour at that temperature a solution of an appropriate bromo-ketone in the above solvent is added and the reaction mixture stirred at room temperature until completion. A saturated aqueous solution of $NH_4Cl$ is added and the mixture extracted with a solvent, such as EtOAc. The organic layer is washed with brine, dried

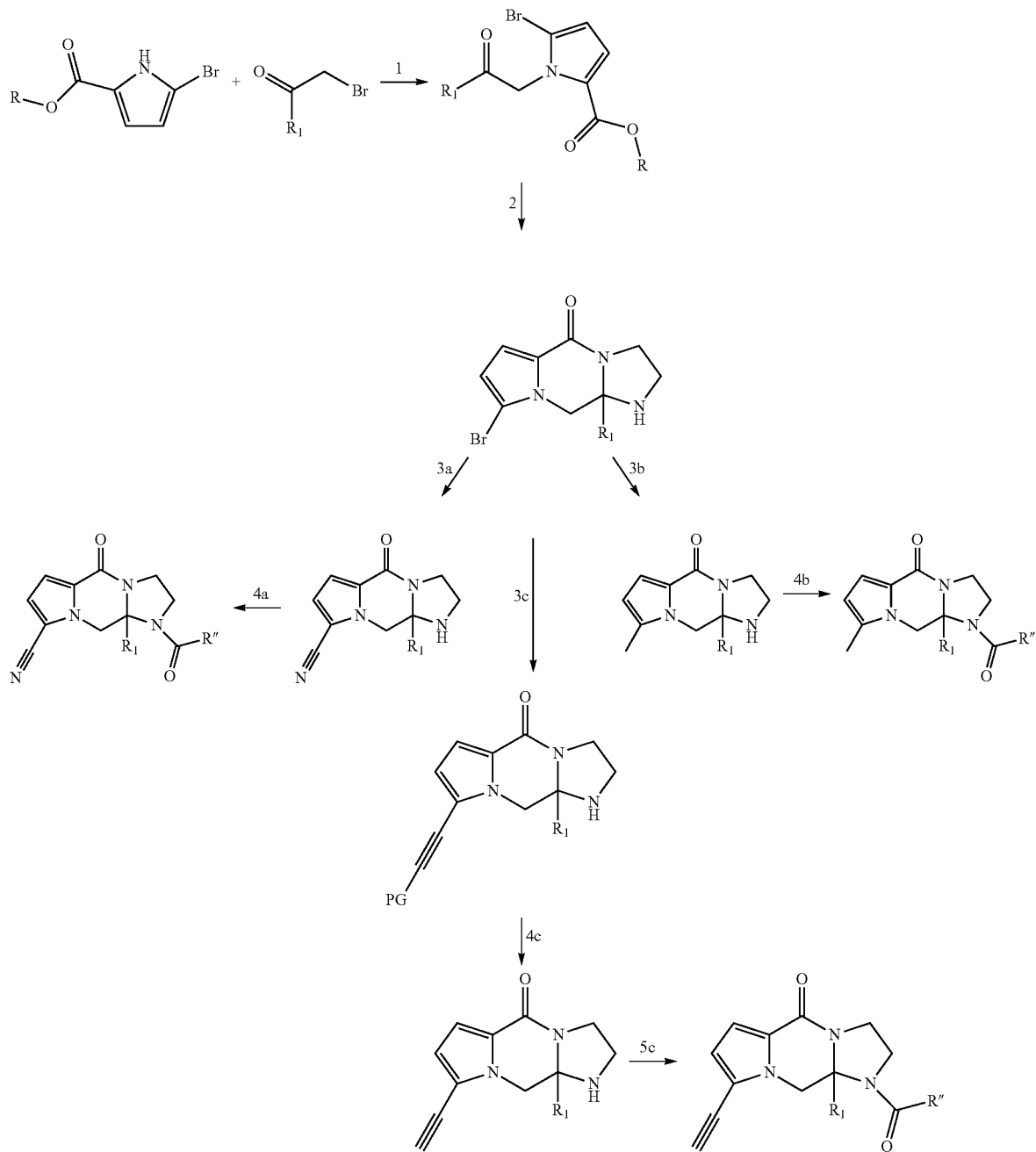

(MgSO$_4$), filtrated and concentrated in vacuo and the resultant residue purified by flash chromatography.

Step 2

Refer to step 3 in general method A.
Route (a)

Step 3a

An appropriate mixture of bromo pyrrole derivative, appropriate palladium catalyst, such as tetrakis(triphenylphosphine)-palladium(0) (0.1 equivalents) and cyanide source, such as Zn(CN)$_2$ (1.4 equivalents) in appropriate solvent such as DMF is sealed under Argon and heated conventionally or in a microwave reactor at the appropriate temperature and time. The outcome of the reaction is monitored by LCMS. Further tetrakis(triphenylphosphine)-palladium(0) and Zn(CN)$_2$ is added if required. Upon completion water is added and the mixture extracted with an organic solvent, such as CH$_2$Cl$_2$. The organic layer is then dried (MgSO$_4$), filtrated and concentrated in vacuo to give a residue that is purified by flash chromatography.

Step 4a

Refer to step 4a general method A.
Route (b)

Step 3b

To a mixture of an appropriate bromo pyrrole tricyclic compound derivative (1 equivalent) and an appropriate palladium catalyst, such as [1,1'-Bis(diphenylphosphino)ferrocene]dichloropalladium(II)CH$_2$Cl$_2$ and trimethylboroxine (3.5 M solution in THF, 5 equivalents) in an appropriate solvent, such as 1,4-dioxane is added potassium fluoride (3 equivalent) in water. The suspension is flushed with argon and heated at 140° C. in the microwave reactor. After complete consumption of the starting material (monitored by LCMS) the mixture is diluted with CH$_2$Cl$_2$, filtered and the organic layer is dried (MgSO$_4$), filtered and concentrated in vacuo and the resulting residue purified by flash chromatography.

Step 4b

Refer to step 4a general method A.
Route (c)

Step 3c

One equivalent of an appropriate bromo pyrrole derivative is mixed with copper iodide (25 mol %) and an appropriate palladium catalyst, such as Pd(PPh$_3$)$_2$Cl$_2$ (10 mol %) in an appropriate solvent, such as DMF. Triethylamine (5 equivalents) and an appropriate protected acetylene, such as trimethylsilylacetylene (5 equivalents) are added and the resulting suspension flushed with argon. The reaction vessel is sealed and heated at 80° C. until complete consumption of the starting material. The reaction mixture is diluted with an organic solvent, such as EtOAc and washed with brine. The organic layer is then dried (Na$_2$SO$_4$), filtered and concentrated in vacuo to give a residue that is purified by flash chromatography (EtOAc/hexanes).

Step 4c

One equivalent of an appropriately protected acetylene in an appropriate solvent, such as methanol is treated with a base, such as potassium carbonate (2 equivalents). The suspension is stirred at room temperature until completion and then concentrated in vacuo to give a residue that is purified by flash chromatography

Step 5c

Refer to step 4a general method A.
General Method N

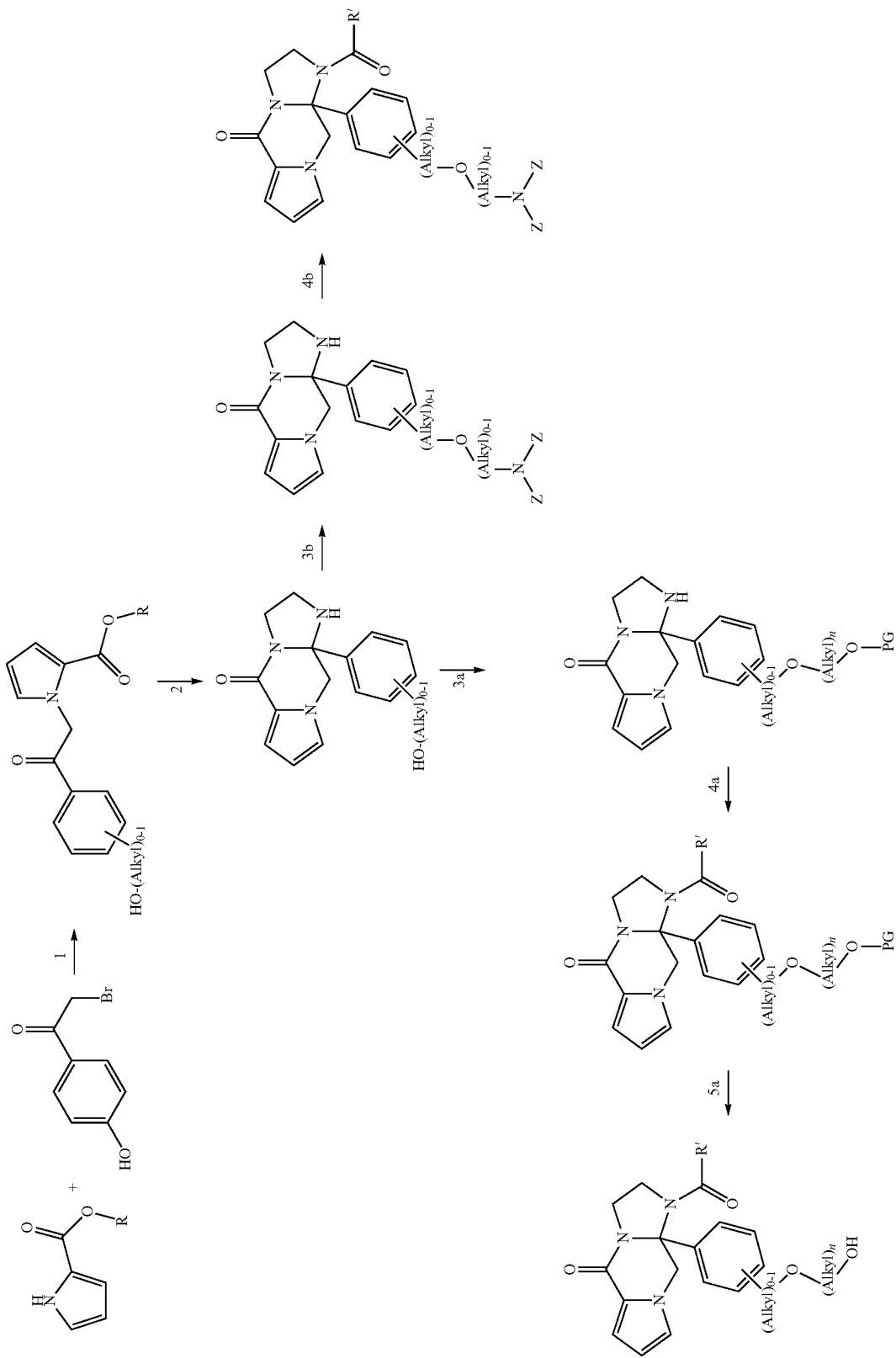

where PG is an optional protecting group and N(Z)$_2$ represents an amino moiety such as N(R$_6$)$_2$ or a heterocyclyl containing nitrogen such as morpholinyl or piperidinyl.

Steps 1 and 2

Refer to step 1 and 3 general method A.
Route (a)

Step 3a

To an appropriate phenyl alcohol derivative (1 equivalent) is added a base, such as potassium carbonate (3 equivalents) and a halo alkoxysilane derivative, such as (2-bromoethoxy)(tert-butyl)dimethylsilane (3 equivalents) in a solvent, such as DMF. The mixture is refluxed at 100° C. until the reaction is complete (monitored by LCMS). The mixture is then diluted with a saturated aqueous solution of NH$_4$Cl and extracted with an organic solvent, such as EtOAc. The organic layers were dried (MgSO$_4$), filtrated and concentrated in vacuo to give a residue that is purified by flash chromatography.

Step 4a

Refer to step 4a general method A.

Step 5a

Refer to step 5 general method D.
Route (b)

Step 3b

A mixture of an appropriate phenyl alcohol derivative (1 equivalent) and an appropriate halo alkylamine (3 equivalents) is treated with a base, such as potassium carbonate (4 equivalents) in a solvent such as DMF. The mixture is heated at reflux until completion. Brine and water are then added and the mixture extracted with an organic solvent, such as EtOAc. The organic are dried (MgSO$_4$), filtrated and concentrated in vacuo to give a residue that is purified by flash chromatography.

Step 4b

Refer to step 4a general method A.

General Method O

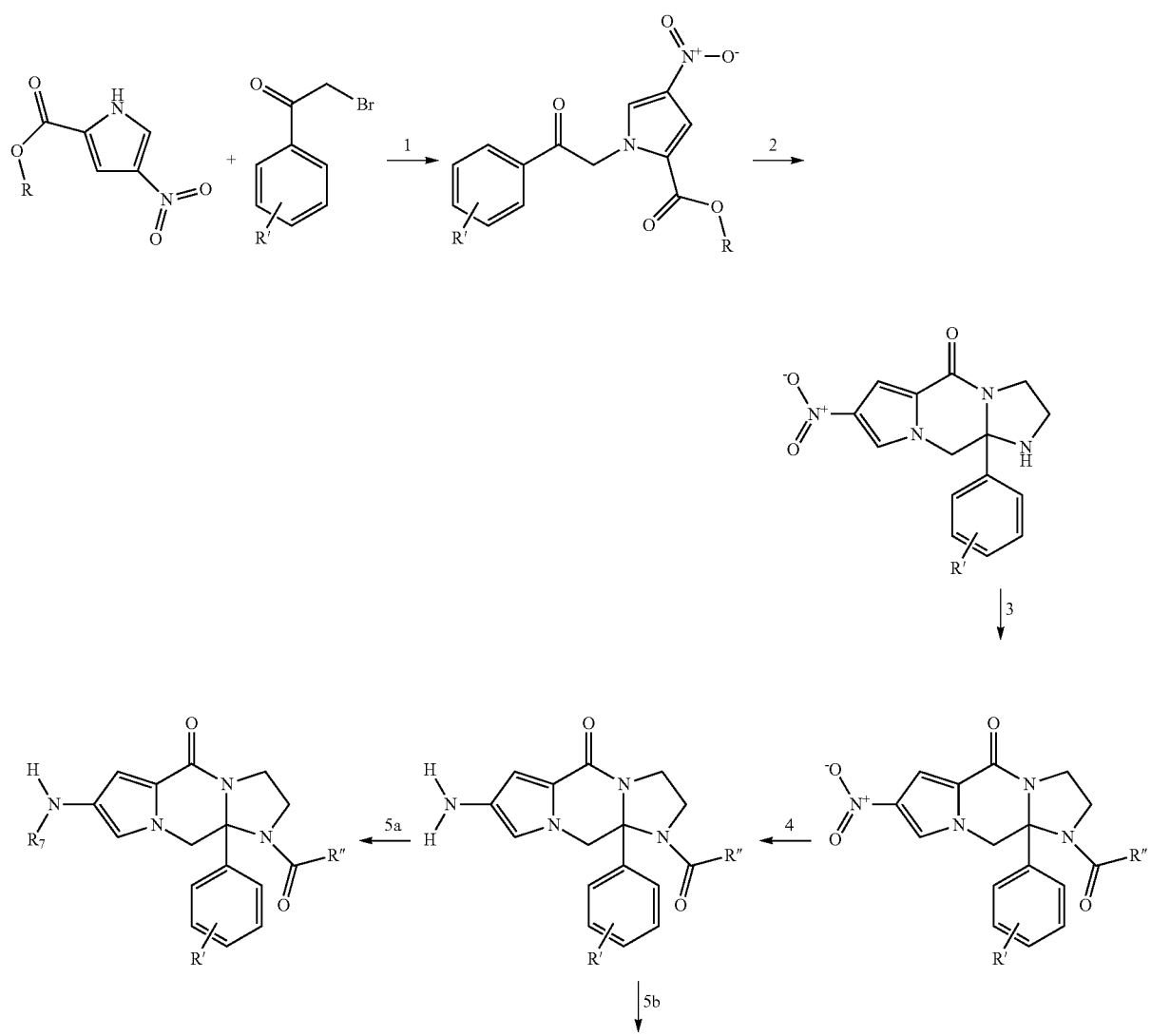

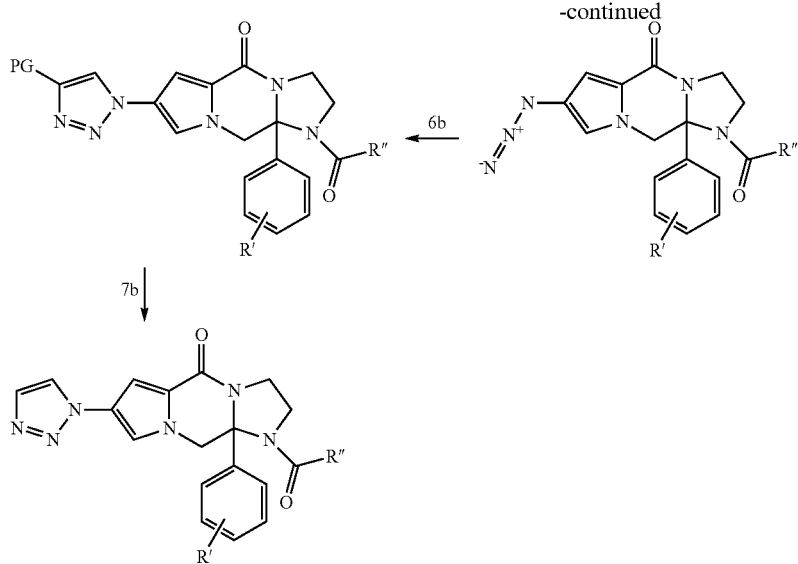

where PG is an optional protecting group.

Steps 1, 2 and 3

Refer to steps 1, 3 and 4a in general method A.

Step 4

To a solution of an appropriate nitro-pyrrole derivative (1 equivalent) in an appropriate solvent, such as methanol is added an appropriate catalyst, such as Iron (II) heptahydrate sulphate (8-10 equivalents) in water. Ammonium hydroxide solution is then added (15 equivalents) and the mixture heated at 50° C. When complete the reaction mixture is partially concentrated in vacuo and then neutralised with a saturated aqueous solution of ammonium chloride. The aqueous mixture is then extracted with an organic solvent, such as EtOAc, dried ($MgSO_4$) filtered, concentrated in vacuo to give a residue that is purified by column flash chromatography.
Route (a)

Step 5a

To one equivalent of an appropriate amine derivative is added an appropriate ketone or aldehyde (1 equivalent) in an appropriate solvent, such as $CH_2Cl_2$. The mixture is treated with acetic acid (1.5 equivalents) followed by the addition of an appropriate reducing agent, such as sodium triacetoxyborohydride (1.5 equivalents). The mixture is stirred at room temperature until completion. If required more ketone and acetic acid are added. The mixture is then quenched with saturated aqueous solution of sodium carbonate and extracted with an organic solvent such as $CH_2Cl_2$. The organic layers are dried ($Na_2SO_4$), filtrated and concentrated in vacuo to give a residue that is purified by column chromatography.
Route (b)

Step 5b

An appropriate amino pyrrole derivative (1 equivalent) is treated with concentrated HCl. An aqueous solution of sodium nitrite (1.5 equivalents) is then added dropwise at such rate that the temperature doesn't exceed 0-5° C. After 30 minutes a solution of sodium azide (1.5 equivalents) and sodium acetate (15 equivalents) in water is added dropwise at 0° C. The mixture is allowed to warm to room temperature and stirred overnight. The mixture is then extracted with an organic solvent, such as EtOAc. The organic layers are washed with brine, dried ($Na_2SO_4$), filtrated and concentrated in vacuo to give a residue that is purified by flash chromatography.

Step 6b

An appropriate azide derivative (1 equivalent) is treated with a protected alykyne derivative, such as trimethylsilylethyne (2 equivalents) and a base, such as diisopropylethylamine (1.2 equivalents) and a catalyst, such as copper iodide (0.5 equivalents) in an appropriate solvent such as DMF at 0° C. The mixture is stirred at that temperature until the reaction is complete (monitored by LCMS) and then quenched with a saturated aqueous solution of ammonium chloride containing a drop of ammonia. The mixture is then extracted with an organic solvent, such as EtOAc and the organic layers washed with brine, dried ($Na_2SO_4$), filtrated and concentrated in vacuo to give a residue that is purified by flash chromatography.

Step 7b

An appropriate azide (1 equivalent) derivative is dissolved in a mixture acetic acid/water/THF (3:1:1) and the mixture heated at 60° C. When complete the reaction is partially concentrated in vacuo, diluted with water and neutralised with a saturated solution of sodium carbonate. The aqueous mixture is then extracted with EtOAc and the organic layer separated and washed with brine, dried ($Na_2SO_4$), filtrated and concentrated in vacuo. The residue obtained is purified by flash chromatography General Method P

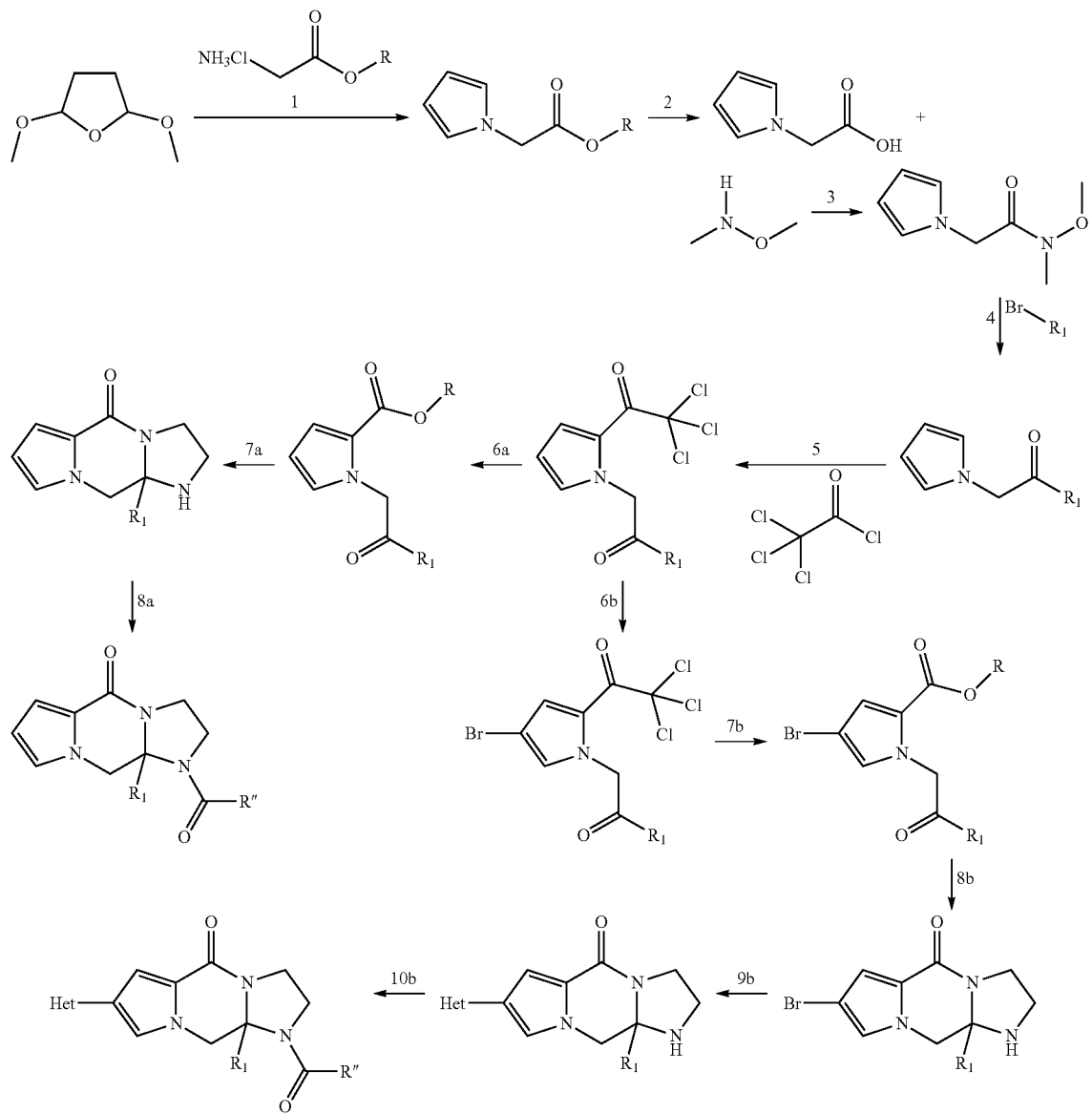

where $R_1$ is an optionally substituted aryl or optionally substituted heterocyclyl and Het is an optionally substituted heterocyclyl including but not limited to 5-membered heteroaryls such as pyrazolyl, imidazolyl, triazolyl and tetrazolyl and 6-membered heteroaryls such as pyridinyl, pyridazinyl, pyrazinyl and pyrimidinyl wherein optional substituents may include but are not limited to $C_{1-6}$alkyl such as methyl, $C_{1-3}$alkylhalo such as $CF_3$ and $C_{1-3}$alkoxyl such as methoxy.

Step 1

Refer to step 1 in general method L.

Step 2

A solution of an appropriate ester derivative (1 equivalent) in a solvent such as methanol is treated with a base, such as aqueous sodium hydroxide (1 equivalent) and the mixture is stirred at room temperature. When complete (monitored by TLC) the reaction mixture is quenched with an aqueous solution of HCl (1 M) and then extracted with an organic solvent such as EtOAc. The organic extracts were combined, dried ($Na_2SO_4$), filtered and concentrated in vacuo to give the crude target product.

Step 3

An appropriate acid derivative (1 equivalent) is mixed with N,N-dimethylhydroxylamine hydrochloride (1.3 equivalents) and a base such as N,N-dimethylpyridin-4-amine (0.1 equivalents) in a solvent, such as $CH_2Cl_2$ at 0° C. A coupling agent such as N-(3-dimethylaminopropyl)-N'-ethylcarbodiimide hydrochloride (1.2 equivalents) is added followed by a base, such as triethylamine (1.7 equivalent). The mixture is allowed to warm to room temperature and stirred for 2 days. The mixture is washed with an aqueous solution of HCl (1 M)

and a saturated aqueous solution of NaHCO$_3$. The organic layer is dried (MgSO$_4$), filtered and concentrated in vacuo to give the target compound.

Step 4

To a solution of an appropriate haloaryl or haloheteroaryl (1 equivalent) such as a 3-bromopyridine in a solvent such as THF is added a base such as n-BuLi (hexanes solution; 1.05 equivalents) at −78° C. followed by the addition of a solution of an appropriate pyrrole amide derivative (1.2 equivalents) in a solvent such as THF. The mixture is stirred between −78° C. and room temperature (1-3 hours). The reaction mixture is quenched with a saturated aqueous solution of NH$_4$Cl at −78° C. or at room temperature, then extracted with an organic solvent such as dichloromethane. The organic layers are dried (MgSO$_4$), filtrated and concentrated in vacuo to give a residue that is purified by flash chromatography.

Step 5

Refer to step 3 general method L.
Route (a)

Step 6a

An appropriate trichloroacetyl derivative (1 equivalent) in methanol is treated with a base, such as aqueous sodium hydroxide at 0° C. The reaction mixture is stirred at room temperature until completion. The solution is then acidified with HCl (1 M), diluted with water and the resulting aqueous mixture extracted with an organic solvent, such as EtOAc (3 times). The organic layer is dried (Na$_2$SO$_4$), filtrated and concentrated in vacuo to give the target ester that is used such as without purification.

Step 7a

Refer to step 3 in general method A.

Step 8a

Refer to step 4a in general method A.
Route (b)

Step 6b

To an appropriate unsubstituted pyrrole derivative in an organic solvent, such as THF is added N-bromosuccinimide (1 equivalent) at −15° C. The reaction is stirred at a temperature ranging from −15° C. to room temperature until complete. Water or a saturated aqueous solution of NH$_4$Cl is added and the mixture is extracted with an organic solvent, such as CH$_2$Cl$_2$. The organic layer is then dried and concentrated in vacuo to give a residue that is purified by flash chromatography.

Step 7b

Refer to step 6a in general method P.

Step 8b

Refer to step 3 in general method A.

Step 9b

Refer to step 4a in general method E.

Step 10b refer step 4a in general method A.
General Method Q

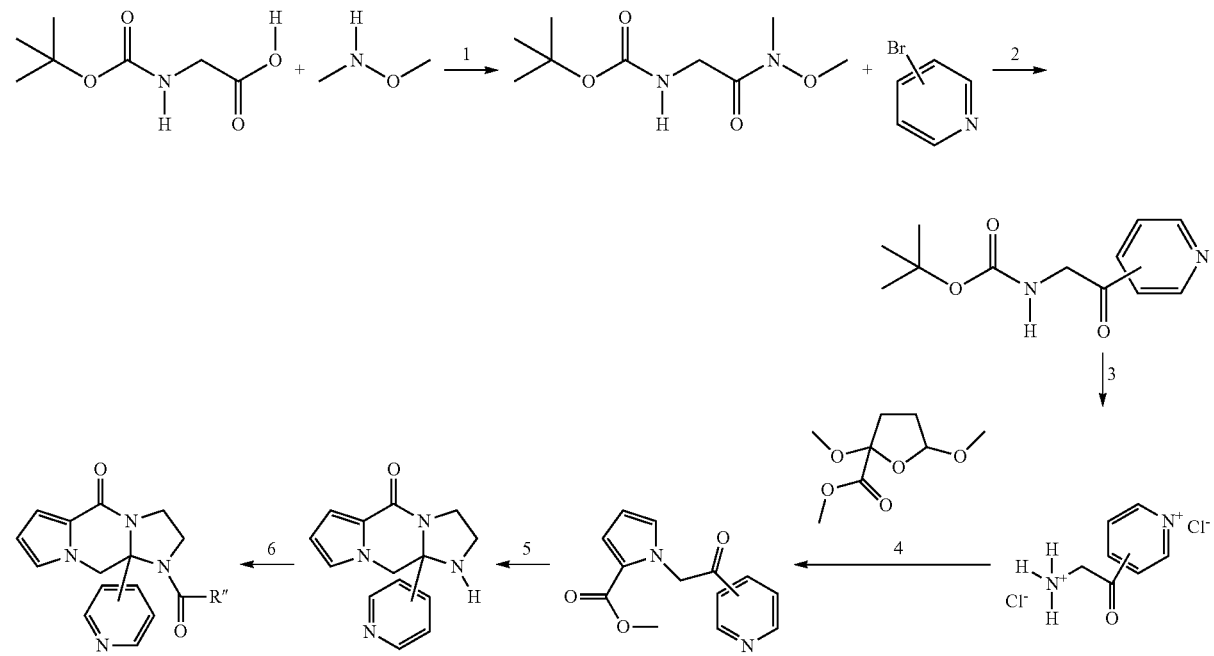

Step 1

Refer to step 3 in general method P

Step 2

An appropriate grignard reagent, such as isopropylmagnesium chloride (1 equivalent) is added to a suspension of tert-butyl {2-[methoxy(methyl)amino]-2-oxoethyl}carbamate (1 equivalent) in a solvent, such as THF at 0° C. The mixture is added to a suspension of aryl Grignard (1.2 equivalents) formed from an appropriate halo-aryl or haloheteroaryl derivative such as bromopyridine and an appropriate grignard reagent such as isopropylmagnesium chloride in a solvent such as THF. The suspension is stirred overnight. Water and brine (1:1) are added and the mixture extracted with an organic solvent, such as EtOAc. The organic layer is dried (MgSO$_4$), filtrated and concentrated in vacuo to give a residue that is purified by flash chromatography.

Step 3

An appropriate carbamate derivative (1.0 equivalent) in a solvent, such as methanol is treated with a solution of acetyl chloride (8 equivalents) in methanol at 0° C. The mixture is allowed to warm at room temperature. When complete (monitored by LCMS) the mixture is concentrated in vacuo to give a residue that is used without purification.

Step 4

An appropriate amino ketone derivative (1.0 equivalent), methyl 2,5-dimethoxytetrahydrofuran-2-carboxylate (1.1 equivalents) and sodium acetate (4 equivalents) are suspended in glacial acetic acid and the mixture heated at 100° C. After 4 hours ice is added. The mixture is then neutralised with solid NaHCO$_3$ and allowed to warm to room temperature. The suspension is diluted with a solvent, such as dichloromethane and filtered. The filtrate is then extracted with a solvent, such as CH$_2$Cl$_2$ (3 times). The organic layers are dried (MgSO$_4$), filtrated and concentrated in vacuo to give a residue that is purified by flash chromatography.

Steps 5 and 6

Refer to step 3 and 4a in general method A.

General Method R

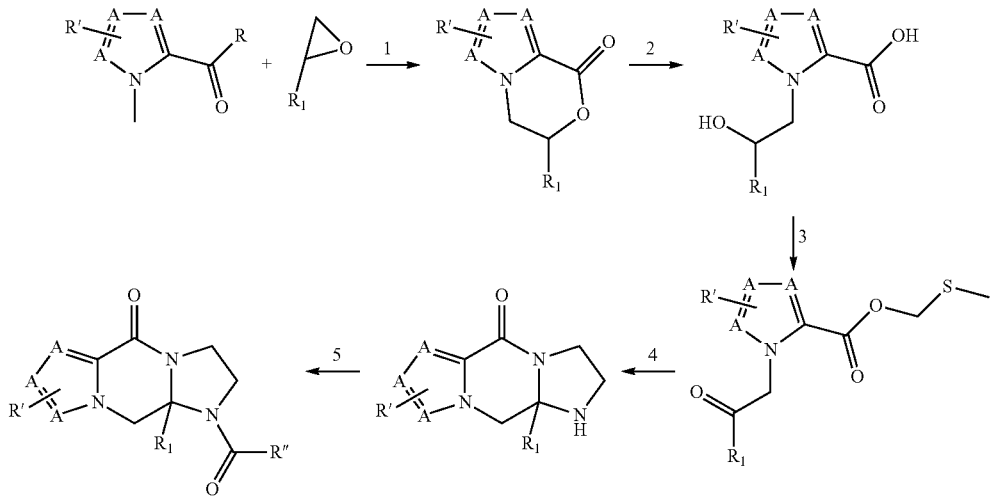

where each A is independently C or N and R can be, but is not limited to, a leaving group such as O-alkyl.

Step 1

An appropriate substituted heterocycle, such as ethyl 5-methyl-1H-pyrrole-2-carboxylate is reacted with an appropriate epoxide in the presence of a base such as potassium carbonate or potassium tert-butoxide in a suitable organic solvent, such as DMF. The reaction is heated until completion. The reaction mixture is then partitioned between brine (10 mL) and an organic solvent such as EtOAc and the organic layer separated. The aqueous layer can be extracted further with EtOAc if required. The organic layer is dried (MgSO$_4$) and concentrated in vacuo to give a residue that is purified by flash chromatography.

Step 2

An appropriate lactone derivative is treated with a base such as lithium hydroxide in a suitable solvent, such as THF: water (9:1). The reaction is stirred at room temperature until completion. The reaction mixture is then diluted with an organic solvent, such as EtOAc, and acidified (approx. pH 1-2) with a mineral acid such as 1 M HCl. The organic layer is separated and the aqueous extracted further with EtOAc if required. The combined organic layers are washed with water, dried (MgSO$_4$) and concentrated in vacuo to give a residue that is used without further purification.

Step 3

An appropriate hydroxy carboxylic acid derivative in a suitable organic solvent such as CH$_2$Cl$_2$ is treated under standard Swern oxidation conditions at −65° C. to room temperature until completion. The reaction mixture is then partitioned between water and an organic solvent such as $CH_2Cl_2$ and the organic layer separated. The aqueous layer can be extracted further with $CH_2Cl_2$ if required. The organic layer is dried ($MgSO_4$) and concentrated in vacuo to give a residue that is purified by flash chromatography.

Step 4

In general, one equivalent of an appropriate keto thioester is reacted with 1-3 equivalents of an appropriate diamine, such as ethane-1,2-diamine in a suitable solvent, such as chloroform with a catalytic amount of acetic acid. The mixture is heated at a temperature ranging from 30° C. to reflux for 4-84 hours. After this time the reaction is partitioned between an aqueous saturated solution of $NaHCO_3$ or water and an organic solvent, such as $CH_2Cl_2$ and the organic layer separated. The aqueous layer can be extracted further with $CH_2Cl_2$ if required. The organic layer is dried ($MgSO_4$) and concentrated in vacuo to give a residue that can either be used without further purification, or purified by flash chromatography.

Step 5

Refer to step 4a in general method A.
General Method S

Step 1 tert-Butyl carbazate is reacted with a base such as potassium carbonate in a suitable solvent such as DMF at 0° C. After 10 minutes, an appropriate bromoketone is added and the reaction is stirred at 0° C. or room temperature until completion. The reaction mixture is worked-up to give a residue that is used without further purification.

Step 2

An appropriate hydrazine is reacted with diethyl but-2-ynedioate in a suitable solvent such as ethanol at 0° C. The reaction is stirred at 0° C. or room temperature until completion. The reaction mixture is concentrated in vacuo to give a residue that is used without further purification.

Step 3

An appropriate hydrazine is treated with polyphosphoric acid in a suitable solvent such as toluene at 85° C. The reaction is stirred at 85° C. until completion. The mixture is then diluted with water and extracted with ethyl acetate. The organic layers are combined, washed with an aqueous saturated solution of $NaHCO_3$, dried ($Na_2SO_4$) and concentrated

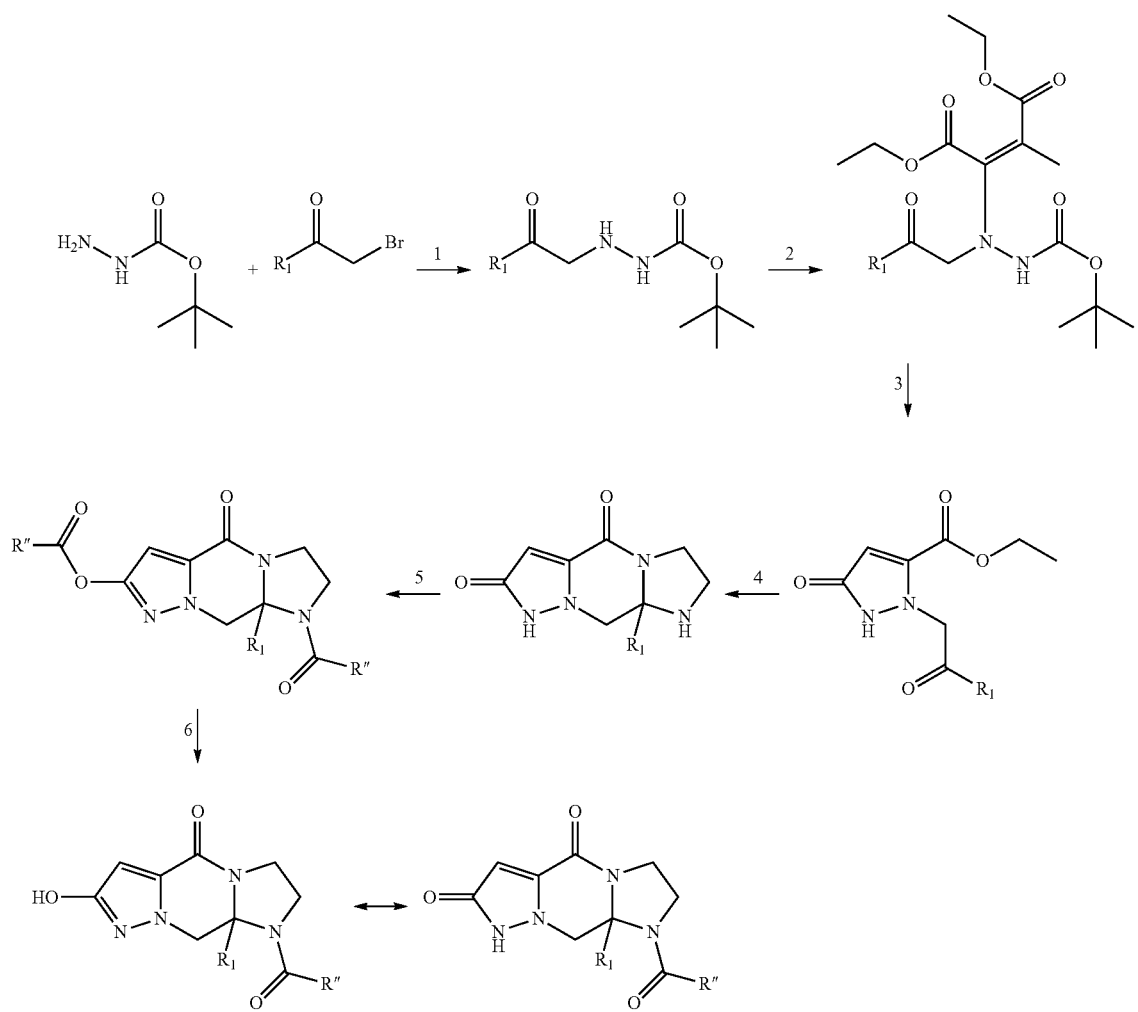

in vacuo to give a residue that can be used without further purification, or purified by chromatography or trituration.

Step 4

Refer to step 3 in general method A.

Steps 5 and 6

Refer to steps 4a and 5b in general method A.
General Method to Separate Stereoisomers by Chiral Chromatography Selected compounds of the invention may be separated into single stereoisomers by HPLC using chromatographic columns with a chiral stationary phase. For example, racemic compounds may be separated into enantiomers under the conditions detailed below.
Column: Chiracel OD-H (250 mm×4.6 mm) 5 uM,
Isocratic Elution: Hexane:Ethanol (90:10 v/v)
Detector wavelength: 220 nm
Flow rate: 1.2 ml/min
Concentration: 1.0 mg/mL
Injection Volume: 10 µL
Column Temperature: 25° C.

In an embodiment of the invention compounds of formula (I) may be prepared by a process involving the step of reacting a compound of formula (II) as defined above with a compound of general formula R—R$_8$, R—C(=O)R$_8$, R—C(=S)R$_8$ or R—S(O)$_2$R$_8$ wherein R is a leaving group or an activated ester group.

The leaving group may be any suitable known type such as those disclosed in J. March, "Advanced Organic Chemistry: Reactions, Mechanisms and Structure" 4$^{th}$ Edition, pp 352-357, John Wiley & Sons, New York, 1992 which was incorporated herein by reference. Preferably, the leaving group is halo, more preferably chloro.

The activated ester group will be known to those in the art, for example as described in Montalbetti, C. A. G. N., and Falque, V., Tetrahedron (2005) 61:10827-10852.

It will be understood that a reaction intermediate may be optionally protected during the course of a reaction with one or more appropriately selected protecting groups. Suitable protecting groups will be known to those skilled in the art and are also described in "Protective Groups in Organic Synthesis" 3$^{rd}$ Edition 1999 Greene T. W. and Wuts P. G. M, John Wiley & Sons, Inc.

Compounds of formula (II) are reaction intermediates, embodiments of which are described in more detail in the examples which follow.

EXAMPLES

In order to exemplify the nature of the present invention such that it may be more clearly understood, the following non-limiting examples are provided. However, those skilled in the art will appreciate that the invention described herein is susceptible to variations and modifications other than those specifically described as follows.
Compound Synthesis $^1$H NMR spectra were recorded on either a Bruker Ultrashield™ 400 or AM 300 spectrometer. Spectra were recorded in CDCl$_3$, d$_6$-acetone, CD$_3$OD or d$_6$-DMSO using the residual solvent peak as a reference. Chemical shifts are reported on the 6 scale in parts per million (ppm) using the following conventions to assign the multiplicity: s (singlet), d (doublet), t (triplet), q (quartet) m (multiplet) and prefixed br (broad). Mass spectra (ESI) were recorded on a Thermo Finnigan LCQ Advantage or LCQ Deca mass spectrometer coupled with a Thermo Finnigan Surveyor HPLC system. Unless stated otherwise, chromatography was performed with Phenomenex C8(2) or C18(2) columns. Water containing 0.1% formic acid (solvent A) and acetonitrile containing 0.1% formic acid (solvent B) were used for separations at acidic pH. Ammonium acetate (5 mM, solvent A) and methanol (solvent B) were used for separations at neutral pH. Flash chromatography was performed on 40-63 µm silica gel 60 (Merck No. 9385) or using a Biotage SP4 (GraceResolv™ Silica Flash cartridges or C18 silica cartridges plugged in). Preparative LCMS was carried out using binary Agilent G1361 pumps and an Agilent G1310A isocratic pump for makeup flow into the MS. An Agilent 6120 mass spectrometer operating in ESI mode and a G1315D diode array detector were used for simultaneous UV and MS directed collection of peaks. All fractions were collected into an Agilent G1364/3 fraction collector. Unless stated otherwise, the prep LCMS system employed a Varian Pursuit C18 column using 0.1% formic acid in water (solvent A) and acetonitrile (solvent B) for low pH separations, or 5 mM ammonium acetate (solvent A) and methanol (solvent B) for neutral pH separations.

Preparative HPLC was carried out using a Gilson 322 pump with a Gilson 215 liquid handler and a HP1100 PDA detector.

The abbreviations used in the Examples are as follows unless indicated otherwise:
ACN: acetonitrile
conc.: concentrated
DCM: dichloromethane
DMF: N,N-dimethylformamide
DMSO: dimethylsulfoxide
ESI: electrospray ionisation
h: hour(s)
HPLC: high performance liquid chromatography
LCMS: liquid chromatography coupled mass spectrometry
min: minute(s)
MS: mass spectrometry
NMR: nuclear magnetic resonance
RT: room temperature
THF: tetrahydrofuran
TLC: thin-layer chromatography
UV: ultraviolet Example of General Method A Route (a)

10a-[4-(difluoromethoxy)phenyl]-1-[(3-methyl-1,2-oxazol-4-yl)carbonyl]-2,3,10,10a-tetrahydro-1H,5H-imidazo[1,2-a]pyrrolo[1,2-d]pyrazin-5-one (1)

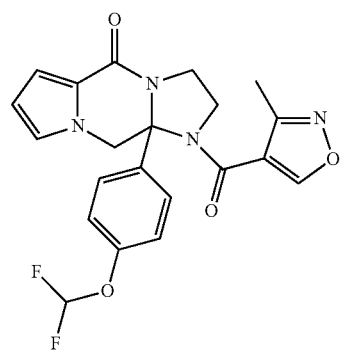 [SMILES: Cc1nocc1C(=O)N1CCN2C(=O)c3cccn3CC12c1ccc(OC(F)F)cc1]

¹H NMR (400 MHz, CDCl₃): δ 2.45 (s, 3H), 3.72-3.90 (m, 2H), 4.01-4.11 (m, 1H), 4.34-4.44 (m, 1H), 4.57 (d, 1H, J 12.9 Hz), 5.64 (d, 1H, J 12.4 Hz), 6.20 (dd, 1H, J 3.6, 2.8 Hz), 6.47 (t, 1H, J 73.4 Hz), 6.71 (s, 1H), 6.94 (d, 1H, J 3.0 Hz), 7.04 (d, 2H, J 8.8 Hz), 7.40 (d, 2H, J 8.8 Hz), 8.56 (s, 1H). ESI-MI m/z [M+H]⁺: 429.1

Step 1

Potassium tert-butoxide (430 mg, 3.82 mmol) was added to a solution of methyl 1H-pyrrole-2-carboxylate (435 mg, 3.48 mmol), and 2-bromo-1-[4-(difluoromethoxy)phenyl]ethanone (1.01 g, 3.82 mmol) in DMF (7.5 mL) at 0° C., the resulting red suspension was stirred from 0° C. to room temperature for 18 h. The reaction mixture was diluted with EtOAc (30 mL) and water (10 mL). The organic layers were then separated and washed with further water (10 mL), dried (MgSO₄) filtered and concentrated in vacuo to give an orange residue. The residue was purified by flash column chromatography (Biotage SP4, 40 g cartridge, 10%-20% EtOAc gradient in n-hexanes) to give methyl 1-{2-[4-(difluoromethoxy)phenyl]-2-oxoethyl}-1H-pyrrole-2-carboxylate as a yellow gum, (417 mg, yield 38%). ¹H NMR (400 MHz, CDCl₃): δ 3.69 (s, 3H), 5.69 (s, 2H), 6.23 (dd, 1H, J 4.0, 2.6 Hz), 6.60 (t, 1H, J 73.0 Hz), 6.82 (dd, 1H, J 2.5, 1.9 Hz), 7.03 (dd, 1H, J 4.0, 1.8 Hz), 7.19 (d, 2H, J 8.8 Hz), 7.97-8.03 (m, 2H).

Step 2

Sodium hydroxide solution (1 M, 2.02 mL) was added to a solution of methyl 1-{2-[4-(difluoromethoxy)phenyl]-2-oxoethyl}-1H-pyrrole-2-carboxylate (417 mg, 1.35 mmol) in 1,4-dioxane (10 mL) and the stirred heated at 70° C. for 2 h. The reaction mixture was cooled to room temperature and concentrated in vacuo to 80% of its starting volume. CH₂Cl₂ (10 mL) was added followed by the addition of aqueous HCl (1 M) (1.78 mL) until the pH was approximately 4. The organic layer was separated and aqueous layer was further extracted with 20% propan-2-ol/CH₂Cl₂ solution (2×20 mL). The organic layers were combined and washed with brine, dried (MgSO₄), filtered and concentrated in vacuo to give of a pale yellow solid corresponding to 1-{2-[4-(difluoromethyl)phenyl]-2-oxoethyl}-1H-pyrrole-2-carboxylic acid (341 mg, 85%). ¹H NMR (400 MHz, MeOD): δ 5.82 (s, 2H), 6.19 (dd, 1H, J 3.9, 2.6 Hz), 6.96-6.98 (m, 1H), 6.98-7.00 (m, 1H), 7.00 (t, 1H, J 73.3 Hz), 7.26-7.30 (m, 2H), 8.08-8.13 (m, 2H). ESI-MI m/z [M+]⁺ 319.9

Step 3

1-{2-[4-(difluoromethyl)phenyl]-2-oxoethyl}-1H-pyrrole-2-carboxylic acid (341 mg, 1.15 mmol) in 1,4-dioxane (10 ml) was added ethane-1,2-diamine (0.61 mL, 9.16 mmol). The mixture was heated at 105° C. After 18 h the LCMS analysis showed the reaction was not complete and further ethane-1,2-diamine (0.61 ml, 9.16 mmol) was added. The reaction was then stirred at 105° C. for a further 18 h. The mixture was concentrated in vacuo and the resultant residue was partitioned between CH₂Cl₂ (10 mL) and water. The aqueous layer was extracted with CH₂Cl₂ (2×20 mL) and washed with brine (10 mL). The combined organic layers were dried (MgSO₄), filtered, concentrated in vacuo to give a residue that was purified by flash chromatography (Biotage SP4, 40 g cartridge, 0-5% MeOH gradient in CH₂Cl₂) to give 10a[4-(difluoromethoxy)phenyl]-2,3,10,10a-tetrahydro-1H, 5H-imidazo[1,2-a]pyrrolo[1,2-d]pyrazin-5-one as a white solid (222 mg, yield 60%). ¹H NMR (400 MHz, CDCl₃): δ 2.37 (br s, 1H), 2.95 (dt, 1H, J 12.3, 7.7 Hz), 3.32 (ddd, 1H, J 12.1, 7.6, 4.0 Hz), 3.52 (ddd, 1H, J 11.6, 7.7, 4.1 Hz), 3.90 (dt, 1H, J 11.2, 7.6 Hz), 4.22 (d, 1H, J 12.0 Hz), 4.43 (d, 1H, J 12.0 Hz), 6.13 (dd, 1H, J 3.8, 2.6 Hz), 6.46 (t, 1H, J 73.7 Hz), 6.49 (dd, 1H, J 2.5, 1.6 Hz), 6.93 (dd, 1H, J 3.9, 1.6 Hz), 6.99-7.05 (m, 2H), 7.34-7.38 (m, 2H).

Step 4a

To generate the acid chloride, 3-methyl-1,2-oxazole-4-carboxylic acid (95.53 mg, 0.75 mmol) was dissolved in CH₂Cl₂ (10 mL). Oxalyl chloride (0.22 mL, 2.63 mmol) and a drop of DMF were added at 0° C. The ice bath was removed and the mixture stirred for 1 h before the solvent and the unreacting oxalyl chloride was removed with a stream of nitrogen. The residue was further dried in vacuo. 10a-[4-(difluoromethoxy)phenyl]-2,3,10,10a-tetrahydro-1H,5H-imidazo[1,2-a]pyrrolo[1,2-d]pyrazin-5-one (60 mg, 0.19 mmol) was dissolved in pyridine (4 ml) and the solution added to the previously generated acid chloride in pyridine (1 mL) at 0° C. The ice bath was removed after 15 min and the mixture stirred at room temperature for 18 h. LCMS analysis showed only a trace amount of product. Further 4 equivalent of acid chloride were prepared as described above and added to the reaction mixture. The resultant mixture was then heated at 50° C. until completion (28 h, monitored by LCMS). The resultant suspension was then concentrated in vacuo and the residue partitioned between CH₂Cl₂ (20 mL) and a saturated aqueous solution of NaHCO₃ (10 mL). The organic layers were washed with further a saturated aqueous solution of NaHCO₃ (10 mL) and brine (5 mL), dried (MgSO₄), filtered and concentrated in vacuo to give a yellow residue. This residue was purified by flash column chromatography (Biotage SP4, 12 g cartridge, 70-100% EtOAc gradient in n-hexanes) to give 10a-[4-(difluoromethoxy)phenyl]-1-[(3-methyl-1,2-oxazol-4-yl)carbonyl]-2,3,10,10a-tetrahydro-1H,5H-imidazo[1,2-a]pyrrolo[1,2-d]pyrazin-5-one compound (I) as a white solid (42 mg, yield 52%).

10a-(4-chlorophenyl)-1-[(3-methyl-1,2-oxazol-4-yl)carbonyl]-7-(pyridin-2-yl)-2,3,10,10a-tetrahydro-1H, 5H-imidazo[1,2-a]pyrazolo[1,5-d]pyrazin-5-one (63)

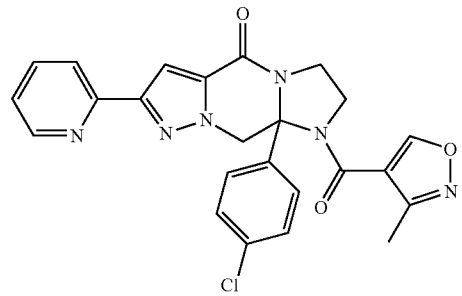 [SMILES: Cc1nocc1C(=O)N1CCN2C(=O)c3cc(-c4ccccn4)nn3CC12c1ccc(Cl)cc1]

¹H-NMR (400 MHz, d6-DMSO): δ 2.3 (s, 3H), 3.80 (dt, 1H J 11.2, 7.9 Hz), 4.11-4.20 (m, 2H), 4.23-4.32 (m, 1H), 5.10 (d, 1H, J 13.4 Hz), 5.79 (d, 1H, J 13.4 Hz), 7.27 (s, 1H), 7.33-7.45 (m, 5H), 7.87 (dt, 1H, J 7.6, 1.6 Hz), 7.96-8.0 (m, 1H), 8.60-8.63 (1H, m), 9.41 (s, 1H). ESI-MI m/z [M+H]⁺ 475.1.

Step 1

Potassium tert-butoxide (290 mg, 2.58 mmol) was added to a solution of commercially available ethyl 3-(pyridin-2-yl)-

1H-pyrazole-5-carboxylate (500 mg, 2.35 mmol), and 2-bromo-1-(4-chlorophenyl)ethanone (0.6 g, 2.58 mmol) in DMF at 0° C. The resultant red suspension was let to come back to room temperature and stirred for 18 hours. Water was added (10 mL) and the mixture extracted with EtOAc (30 mL). The organic layers were washed with further water (10 mL), dried (MgSO$_4$) filtered and concentrated in vacuo to give an orange residue. The residue was purified by flash column chromatography (Biotage SP4, 40 g cartridge, gradient 15 to 80% EtOAc in hexanes) to give a solid (630 mg, yield: 72%) identified to be ethyl 1-[2-(4-chlorophenyl)-2-oxoethyl]-3-(pyridin-2-yl)-1H-pyrazole-5-carboxylate (major) in a mixture with its regioisomer (ethyl 1-[2-(4-chlorophenyl)-2-oxoethyl]-5-(pyridin-2-yl)-1H-pyrazole-3-carboxylate, minor) in a 5 to 1 ratio. ESI-MI m/z [M+H]$^+$ 370.1.

Step 3

Ethyl 1-[2-(4-chlorophenyl)-2-oxoethyl]-3-(pyridin-2-yl)-1H-pyrazole-5-carboxylate (630 mg, 1.77 mmol) and ethane-1,2-diamine (1.77 mL, 26.6 mmol) was combined and stirred at reflux in 1,4-dioxane. After 48 hours (monitored by LCMS) the reaction mixture was concentrated in vacuo and the residue partitioned between CH$_2$Cl$_2$ (20 mL) and brine (10 mL). The organic layer was separated and the aqueous layer extracted with further CH$_2$Cl$_2$ (2×10 mL). The combined organic layers were dried (MgSO$_4$), filtered and evaporated in vacuo to give a yellow residue that was purified by flash column chromatography (Biotage SP4, 40 g cartridge, gradient 2 to 15% methanol in CH$_2$Cl$_2$). To give 10a-(4-chlorophenyl)-7-(pyridin-2-yl)-2,3,10,10a-tetrahydro-1H,5H-imidazo[1,2-a]pyrazolo[1,5-d]pyrazin-5-one as an off white solid (150 mg, yield: 23%). ESI-MI m/z [M+H]$^+$ 366.1.

Step 4a

To generate the acid chloride: to a chilled suspension of 3-methylisoxazole-4-carboxylic acid (231 mg, 1.8 mmol) in dry CH$_2$Cl$_2$ (3.0 mL) was added oxalyl chloride (0.31 mL, 3.7 mmol) followed by DMF (1 drop). The suspension was stirred at 0° C. for 5 minutes and then at room temperature for 1 hour. The resulting solution was concentrated in vacuo at ambient temperature to yield an oil, dried by stirring under nitrogen. 10a-(4-chlorophenyl)-7-(pyridin-2-yl)-2,3,10,10a-tetrahydro-1H,5H-imidazo[1,2-a]pyrazolo[1,5-d]pyrazin-5-one (111 mg, 0.3 mmol) in pyridine (3.5 mL) was added to a mixture of the acid chloride (generated as above, 1.8 mmol) in pyridine (2 mL) at 0° C. and stirred at 0° C. to room temperature for 1 hour. LCMS after this time indicated the reaction was complete. The suspension was then diluted with water (15 mL) and extracted with CH$_2$Cl$_2$ (3×10 mL). The extracts were combined, dried (Na$_2$SO$_4$), filtered and concentrated in vacuo to yield a yellow residue. The material was purified by trituration with EtOAc/hexanes (9:1) to give 10a-(4-chlorophenyl)-1-[(3-methyl-1,2-oxazol-4-yl)carbonyl]-7-(pyridin-2-yl)-2,3,10,10a-tetrahydro-1H,5H-imidazo[1,2-a]pyrazolo[1,5-d]pyrazin-5-one (63) as a beige solid (70 mg, yield 49%).

11a-(4-chlorophenyl)-1,2,3,4,11,11a-hexahydro-6H-pyrrolo[1',2':4,5]pyrazino[1,2-a]pyrimidin-6-one (123)

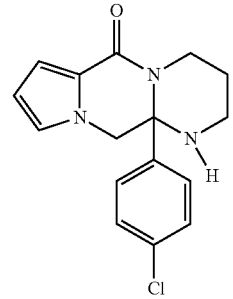 [SMILES: O=C1c2cccn2CC2(c3ccc(Cl)cc3)NCCCN12]

$^1$H-NMR (400 MHz, CDCl$_3$): δ 1.61-1.77 (m, 2H), 2.56-2.66 (m, 1H), 2.77-2.87 (m, 1H), 2.93-3.01 (m, 1H), 4.10 (dd, 2H, J 18.2, 12.4 Hz), 4.69-4.77 (m, 1H), 6.14 (dd, 1H, J 3.8, 2.6 Hz), 6.43-6.46 (m, 1H), 6.69 (dd, 1H, J 3.8, 1.5 Hz), 7.28 (br s, 4H). ESI-MI m/z [M+H]$^+$ 301.9.

Step 3

Methyl 1-[2-(4-chlorophenyl)-2-oxoethyl]-1H-pyrrole-2-carboxylate (100 mg, 0.36 mmol) was mixed with propane-1,3-diamine (0.9 g, 12.14 mmol) in xylenes (2 mL) and the mixture heated in the microwave at 180° C. for 1 hour (monitored by LCMS). The mixture was concentrated in vacuo and purified by flash chromatography using 2 to 10% MeON in CH$_2$Cl$_2$, to give 11a-(4-chlorophenyl)-1,2,3,4,11,11a-hexahydro-6H-pyrrolo[1',2':4,5]pyrazino[1,2-a]pyrimidin-6-one (123) (11.5 mg, yield 10%).

1-[(3-methyl-1,2-oxazol-4-yl)carbonyl]-10a-(pyridin-3-yl)-2,3,10,10a-tetrahydro-1H,5H-imidazo[1,2-a]pyrrolo[1,2-d]pyrazin-5-one (101)

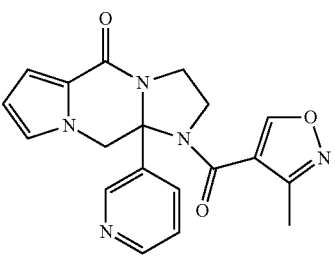 [SMILES: Cc1nocc1C(=O)N1CCN2C(=O)c3cccn3CC12c1cccnc1]

$^1$H-NMR (400 MHz, CDCl$_3$): δ 2.44 (s, 3H), 3.76 (dt, 1H, J 11.7, 7.7 Hz), 3.92 (dt, 1H, J 8.5, 4.12 Hz), 4.09 (dd, 1H, J 16.6, 9.0 Hz), 4.46 (ddd, 1H, J 12.1, 8.7, 4.0 Hz), 4.54 (d, 1H, J 13.0 Hz), 5.68 (d, 1H, J 13.0 Hz), 6.23 (t, 1H, J 2.8 Hz), 6.75 (br s, 1H), 6.96 (d, 1H, J 3.64 Hz), 7.23 (dd, 1H, J 8.2, 4.8 Hz), 7.57-7.62 (m, 1H), 8.56 (d, 1H, J 1.6 Hz), 8.61 (br s, 1H), 8.67 (d, 1H, J 2.4 Hz). ESI-MI m/z [M+H]$^+$ 364.1.

Step 1

To a chilled solution of methyl 2-pyrrole carboxylate (200 mg, 1.6 mmol) in dry DMF (5 mL) was added sodium hydride (60% dispersion in mineral oil, 160 mg, 4.0 mmol) portionwise under nitrogen. Extra DMF (2 mL) was added and the suspension was stirred for 30 minutes. 3-(Bromoacetyl)pyridine hydrobromide (600 mg, 2.1 mmol) was added portionwise and the mixture was allowed at room temperature and stirred overnight. Saturated aqueous solution of aqueous NH$_4$Cl (10 mL) followed by EtOAc (30 mL) were added. The organic layer was washed with brine (10 mL), dried (MgSO$_4$), filtered and concentrated in vacuo to give an orange liquid that was purified by flash chromatography (Biotage SP4, 40 g cartridge, gradient 0-80% EtOAc in hexanes) to yield methyl 1-[2-oxo-2-(pyridin-3-yl)ethyl]-1H-pyrrole-2-carboxylate as a colourless oil (75 mg, yield 19%). $^1$H-NMR (400 MHz, CDCl$_3$): δ 3.72 (s, 3H), 5.72 (s, 2H), 6.26 (dd, 1H, J 4.0, 2.6 Hz), 6.85 (dd, 1H, J 2.6, 1.8 Hz), 7.04 (dd, 1H, J 4.0, 1.8 Hz), 7.46 (ddd, 1H, J 7.9, 4.8, 0.8 Hz), 8.25-8.28 (m, 1H), 8.83 (dd, 1H, J 4.8, 1.7 Hz), 9.21 (dd, 1H, J 0.8, 2.2 Hz).

Step 3

10a-(pyridin-3-yl)-2,3,10,10a-tetrahydro-1H,5H-imidazo[1,2-a]pyrrolo[1,2-d]pyrazin-5-one (102)

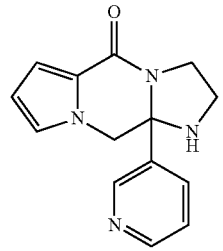 [SMILES: O=C1c2cccn2CC2(c3cccnc3)NCCN12]

$^1$H-NMR (400 MHz, MeOD): δ 2.79 (dt, 1H, J 8.2 Hz), 3.34-3.42 (m, 1H), 3.55 (ddd, 1H, 10.8, 7.8, 2.9 Hz), 3.71-3.80 (m, 1H), 4.37 (d, 1H, J 12.6 Hz), 4.69 (d, 1H, J 6.8 Hz), 6.12 (dd, 1H, J 3.8, 2.6 Hz), 6.69-6.72 (m, 1H), 6.84-6.88 (m, 1H), 7.36 (dd, 1H, J 8.0, 4.9 Hz), 7.75-7.82 (m, 1H), 8.44 (dd, 1H, J 4.9, 1.5 Hz), 8.52-8.55 (m, 1H). ESI-MI m/z calculated [M+H]$^+$ 255.1.

To a solution of methyl 1-[2-oxo-2-(pyridin-3-yl)ethyl]-1H-pyrrole-2-carboxylate (84 mg, 0.34 mmol) in 1,4-dioxane (15 mL) was added ethane-1,2-diamine (0.65 mL, 9.7 mmol). The solution was heated at reflux for 3 days. The mixture was then concentrated in vacuo to give an oily solid. The material was purified by flash chromatography (Silica gel, gradient 5-9% methanol in CH$_2$Cl$_2$) to yield 10a-(pyridin-3-yl)-2,3,10,10a-tetrahydro-1H,5H-imidazo[1,2-a]pyrrolo[1,2-d]pyrazin-5-one (102) as an off-white solid (75 mg, yield 86%).

Step 4a

To generate the acid chloride: to a chilled suspension of 3-methylisoxazole-4-carboxylic acid (100 mg, 0.79 mmol) in dry CH$_2$Cl$_2$ (1 mL) was added oxalyl chloride (0.2 mL, 2.4 mmol) followed by DMF (1 drop). The mixture was stirred at 0° C. to room temperature for 1 hour. The resulting yellow solution was concentrated in vacuo and the resultant residue was azeotroped with dry CH$_2$Cl$_2$ to yield the acid chloride as an oil.

A suspension of 10a-(pyridin-3-yl)-2,3,10,10a-tetrahydro-1H,5H-imidazo[1,2-a]pyrrolo[1,2-d]pyrazin-5-one, (102) (65 mg, 0.26 mmol) in pyridine (0.8 mL) was added to a suspension of the acid chloride (generated as above, 0.79 mmol) in pyridine (0.7 mL) at 0° C. and stirred at 0° C. to room temperature for 1.25 hour (monitored by LCMS). Water was then added (5 mL) and the mixture extracted with CH$_2$Cl$_2$ (3×2 mL). The extracts were combined, dried (MgSO$_4$), filtered and concentrated in vacuo to give a residue that was purified by flash chromatography (Silica gel, 60 to 70% acetone-hexanes). To give 1-[(3-methyl-1,2-oxazol-4-yl)carbonyl]-10a-(pyridin-3-yl)-2,3,10,10a-tetrahydro-1H, 5H-imidazo[1,2-a]pyrrolo[1,2-d]pyrazin-5-one (101) as a white solid (70 mg, yield 75%).

1-[(3-methyl-1,2-oxazol-4-yl)carbonyl]-10a-(1-oxidopyridin-3-yl)-2,3,10,10a-tetrahydro-1H,5H-imidazo[1,2-a]pyrrolo[1,2-d]pyrazin-5-one (78)

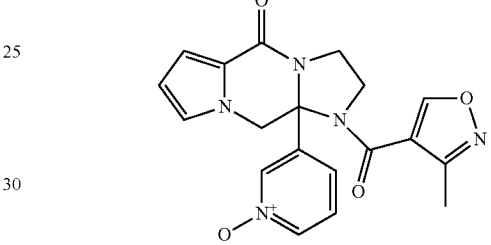

$^1$H-NMR (400 MHz, CDCl$_3$): δ 2.45 (s, 3H), 3.76 (dt, 1H, J 12.0, 7.8 Hz), 3.97 (dt, 1H J 8.3, 4.0 Hz), 4.09 (dd, 1H, J 8.7, 1.7 Hz), 4.44-4.53 (m, 1H), 4.49 (d, 1H, J 13.3 Hz), 5.65 (d, 1H, J 13.2 Hz), 6.25-6.28 (m, 1H), 6.77-6.80 (m, 1H), 6.97-6.99 (m, 1H), 7.09-7.13 (m, 1H), 7.17-7.23 (m, 1H), 8.13 (d, 1H, J 6.3 Hz), 8.39 (br s, 1H), 8.64 (br s, 1H). ESI-MI m/z [M+H]$^+$ 380.1.

Step 5a

To a solution of 1-[(3-methyl-1,2-oxazol-4-yl)carbonyl]-10a-(pyridin-3-yl)-2,3,10,10a-tetrahydro-1H,5H-imidazo[1, 2-a]pyrrolo[1,2-d]pyrazin-5-one (15 mg, 0.041 mmol) in CH$_2$Cl$_2$ (0.5 mL) was added methyltrioxorhenium (VII) (1 mg, 0.004 mmol) followed by hydrogen peroxide (30% aqueous solution, 70 µL, 0.62 mmol). The resulting solution was stirred vigorously at room temperature. After 4.5 hours the reaction was complete (monitored by LCMS). Water (2 mL) was then added and the mixture extracted with CH$_2$Cl$_2$ (3×1 mL). The extracts were combined, dried (MgSO$_4$), filtered and concentrated in vacuo to give an oil that was purified by flash chromatography (Biotage SP4, 4 g cartridge, gradient 0 to 10% methanol in CH$_2$Cl$_2$). The compound 1-[(3-methyl-1,2-oxazol-4-yl)carbonyl]-10a-(1-oxidopyridin-3-yl)-2,3, 10,10a-tetrahydro-1H,5H-imidazo[1,2-a]pyrrolo[1,2-d] pyrazin-5-one (78) was isolated as a colourless oil (2 mg, yield 12%).

The following compounds were similarly prepared using General Method A: Route (a).

| Cpd. No. | Structure | ESI-MI m/z [M + H]+/1H-NMR |
|---|---|---|
| 2 | 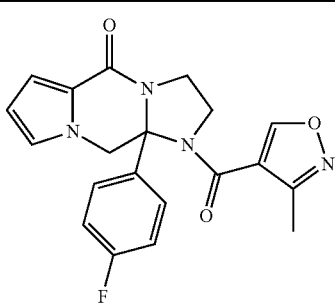 | ESI-MI m/z [M + H]+ 381.1. 1H NMR (400 MHz, d6-acetone): δ 2.35 (d, 3H, J 0.4 Hz), 3.71-3.77 (m, 1H), 4.17-4.34 (m, 3H), 4.60 (d, 1H, J 12.8 Hz), 5.76 (d, 1H, J 13.0 Hz), 6.17 (d, 1H, J 4.1, 2.8 Hz), 6.70 (dd, 1H, J 2.8, 1.7 Hz), 7.03-7.10 (m, 3H), 7.45-7.51 (m, 2H), 9.16 (s, 1H). |
| 3 | 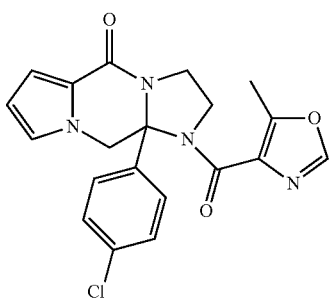 | ESI-MI m/z [M + H]+ 397.0. 1H NMR (400 MHz, CDCl3): δ 2.62 (s, 3H), 3.67-3.76 (m, 1H), 4.26-4.40 (m, 2H), 4.53 (d, 1H, J 13.4 Hz), 4.57-4.66 (m, 1H), 5.69 (d, 1H, J 12.8 Hz), 6.20 (dd, 1H, J 4.0, 2.6 Hz), 6.72 (dd, 1H, J 2.4, 1.6 Hz), 6.92 (dd, 1H, J 3.8, 1.5 Hz), 7.21-7.32 (m, 4H), 7.71 (s, 1H). |
| 4 | 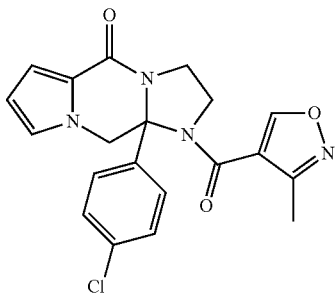 | ESI-MI m/z [M + H]+ 397.0. 1H NMR (400 MHz, CDCl3): δ 2.44 (s, 3H), 3.73-3.86 (m, 2H), 4.00-4.11 (m, 1H), 4.33-4.41 (m, 1H), 4.57 (d, 1H, J 13.4 Hz), 5.64 (d, 1H, J 13.0 Hz), 6.19 (dd, 1H, J 4.0, 2.5 Hz), 6.70 (dd, 1H, J 2.4, 1.6 Hz), 6.93 (dd, 1H, J 3.8, 1.4 Hz), 7.24-7.35 (m, 4H), 8.55 (s, 1H). |
| 5 | 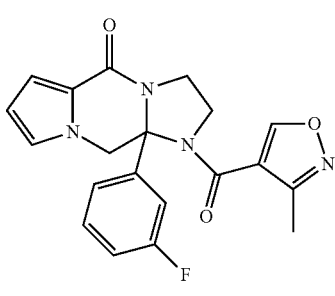 [SMILES: Cc1nocc1C(=O)N1CCN2C(=O)c3cccn3CC12c1cccc(F)c1] | ESI-MI m/z [M + H]+ 381.1. 1H NMR (400 MHz, CDCl3): δ 2.45 (s, 3H), 3.73-3.90 (m, 2H), 4.01-4.11 (m, 1H), 4.40 (ddd, 1H, J 11.0, 8.9, 4.2 Hz), 4.57 (d, 1H, J 13.0 Hz), 5.65 (d, 1H, J 12.9 Hz), 6.21 (dd, 1H, J 3.5, 2.6 Hz), 6.72 (br s, 1H), 6.93-6.97 (m, 1H), 6.98-7.06 (m, 1H), 7.09-7.17 (m, 2H), 7.22-7.31 (m, 1H), 8.56 (s, 1H). |
| 6 | 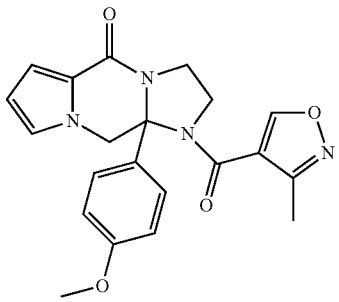 [SMILES: COc1ccc(C23Cn4cccc4C(=O)N2CCN3C(=O)c2conc2C)cc1] | ESI-MI m/z [M + H]+ 393.1. 1H NMR (400 MHz, d6-acetone): δ 2.36 (s, 3H), 3.69-3.76 (m, 1H), 3.74 (s, 3H), 4.07-4.15 (m, 1H), 4.19-4.31 (m, 2H), 4.57 (d, 1H, J 12.8 Hz), 5.73 (d, 1H, J 13.0 Hz), 6.15 (dd, 1H, J 3.8, 2.4 Hz), 6.69 (dd, 1H, J 3.8, 1.6 Hz), 6.80-6.86 (m, 2H), 7.02-7.04 (m, 1H), 7.33-7.37 (m, 2H), 9.12 (s, 1H). |

| Cpd. No. | Structure | ESI-MI m/z [M + H]⁺/¹H-NMR |
|---|---|---|
| 7 | 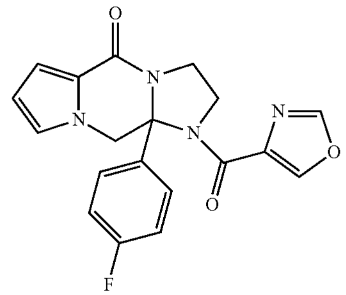 [SMILES: O=C(c1cocn1)N1CCN2C(=O)c3cccn3CC12c1ccc(F)cc1] | ESI-MI m/z [M + H]⁺ 367.0. ¹H NMR (400 MHz, d6-acetone): δ 3.75-3.84 (m, 1H), 4.33 (ddd, 1H, J 11.5, 8.7, 3.9 Hz), 4.49 (ddd, 1H, J 11.0, 8.0, 4.1 Hz), 4.56 (d, 1H, J 13.0 Hz), 4.57-4.66 (m, 1H), 5.83 (d, 1H, J 13.0 Hz), 6.15 (dd, 1H, J 3.8, 2.6 Hz), 6.69 (dd, 1H, J 3.8, 1.6 Hz), 7.01-7.08 (m, 3H), 7.47-7.53 (m, 2H), 8.33 (d, 1H, J 1.2 Hz), 8.52 (d, 1H, J 1.2 Hz). |
| 8 | 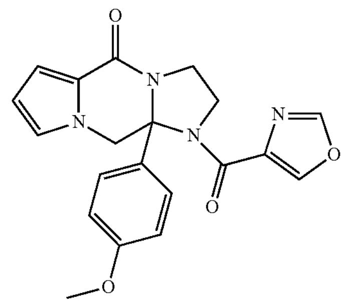 [SMILES: COc1ccc(C23Cn4cccc4C(=O)N2CCN3C(=O)c2cocn2)cc1] | ESI-MI m/z [M + H]⁺ 379.0. ¹H NMR (400 MHz, d6-acetone): δ 3.73 (s, 3H), 3.73-3.82 (m, 1H), 4.30 (ddd, 1H, J 11.6, 7.2, 4.2), 4.37 (ddd, 1H, J 11.2, 8.2, 4.4), 4.53 (d, 1H, J 13.1 Hz), 4.58-4.66 (m, 1H), 5.80 (d, 1H, J 12.9 Hz), 6.14 (dd, 1H, J 3.8, 2.5), 6.67 (dd, 1H, J 3.9, 1.7), 6.79-6.84 (m, 2H), 7.02 (dd, 1H, J 2.6, 1.8 Hz), 7.34-7.39 (m, 2H), 8.31 (d, 1H, J 1.0 Hz), 8.50 (d, 1H, J 1.2 Hz). |
| 9 | 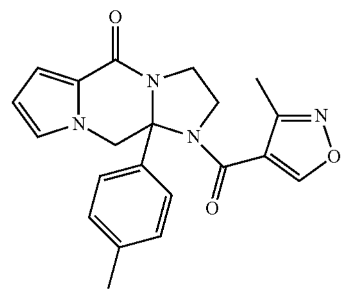 [SMILES: Cc1ccc(C23Cn4cccc4C(=O)N2CCN3C(=O)c2conc2C)cc1] | ESI-MI m/z [M + H]⁺ 377.2. ¹H NMR (400 MHz, d6-acetone): δ 2.26 (s, 3H), 2.35 (s, 3H), 3.69-3.75 (m, 1H), 4.08-4.16 (m, 1H), 4.21-4.31 (m, 2H), 4.60 (d, 1H, J 13.0 Hz), 5.75 (d, 1H, J 12.9 Hz), 6.15 (dd, 1H, J 3.8, 2.4 Hz), 6.69 (dd, 1H, J 3.8, 1.6 Hz), 7.03 (dd, 1H, J 2.4, 1.7 Hz), 7.08-7.13 (m, 2H), 7.28-7.33 (m, 2H), 9.13 (s, 1H). |
| 10 | 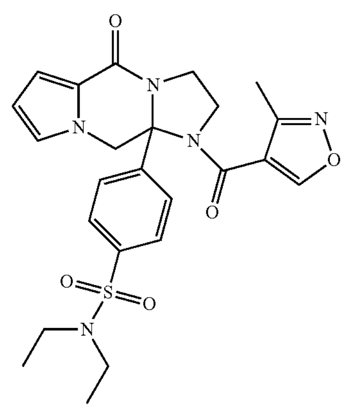 [SMILES: CCN(CC)S(=O)(=O)c1ccc(C23Cn4cccc4C(=O)N2CCN3C(=O)c2conc2C)cc1] | ESI-MI m/z [M + H]⁺ 498.1. ¹H NMR (400 MHz, d6-acetone): δ 1.06 (t, 6H, J 7.2 Hz), 2.33 (s, 3H), 3.19 (q, 4H, J 7.1 Hz), 3.70-3.79 (m, 1H), 4.19-4.34 (m, 3H), 4.64 (d, 1H, J 13.3 Hz), 5.80 (d, 1H, J 13.4 Hz), 6.19 (dd, 1H, J 3.8, 2.6 Hz), 6.72 (dd, 1H, J 4.0, 1.5 Hz), 7.10 (t, 1H, J 1.8 Hz), 7.59-7.63 (m, 2H), 7.73-7.77 (m, 2H), 9.17 (s, 1H). |
| 11 | 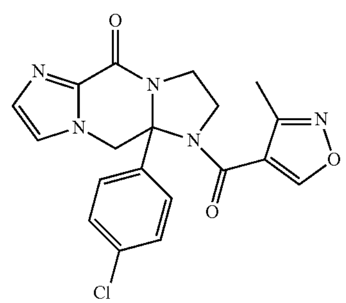 [SMILES: Cc1nocc1C(=O)N1CCN2C(=O)c3nccn3CC12c1ccc(Cl)cc1] | ESI-MI m/z [M + H]⁺ 398.1. ¹H NMR (400 MHz, CDCl₃): δ 2.45 (s, 3H), 3.79-3.94 (m, 2H), 4.10-4.16 (m, 1H), 4.36-4.46 (m, 1H), 4.74 (d, 1H, J 13.1 Hz), 5.76 (d, 1H, J 13.6 Hz), 6.95 (s, 1H), 7.23 (s, 1H), 7.26-7.44 (m, 4H), 8.56 (s, 1H). |

| Cpd. No. | Structure | ESI-MI m/z [M + H]⁺/¹H-NMR |
|---|---|---|
| 12 | 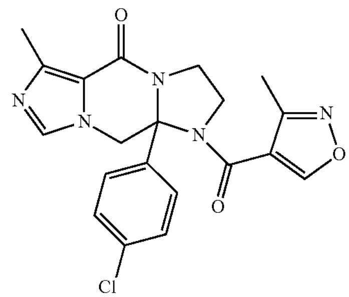 [SMILES: Cc1nocc1C(=O)N1CCN2C(=O)c3c(C)ncn3CC12c1ccc(Cl)cc1] | ESI-MI m/z [M + H]⁺ 412.1. 11-1 NMR (400 MHz, CDCl₃): δ 2.44 (s, 3H), 2.51 (s, 3H), 3.77-3.86 (m, 2H), 4.02-4.10 (m, 1H), 4.31-4.38 (m, 1H), 4.50 (d, 1H, J 12.8 Hz), 5.80 (d, 1H, J 13.2 Hz), 7.21-7.38 (m, 4H), 7.40 (s, 1H), 8.55 (s, 1H). |
| 13 | 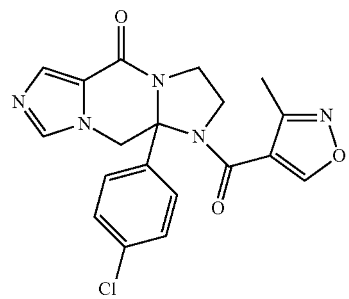 [SMILES: Cc1nocc1C(=O)N1CCN2C(=O)c3cncn3CC12c1ccc(Cl)cc1] | ESI-MI m/z [M + H]⁺ 398.1. ¹H NMR (400 MHz, CDCl₃): δ 2.45 (s, 3H), 3.78-3.88 (m, 2H), 4.06-4.12 (m, 1H), 4.30-4.40 (m, 1H), 4.56 (d, 1H, J 13.1 Hz), 5.90 (d, 1H, J 13.2 Hz), 7.27-7.40 (m, 4H), 7.53 (br s, 1H), 7.74 (br s, 1H), 8.54 (s, 1H). |
| 14 | 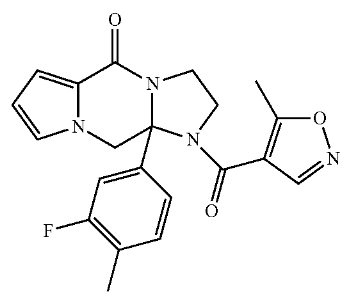 [SMILES: Cc1ccc(C23Cn4cccc4C(=O)N2CCN3C(=O)c2cnoc2C)cc1F] | ESI-MI m/z [M + H]⁺ 395.1. ¹H NMR (400 MHz, d6-acetone): δ 2.18 (d, 3H, J 1.8 Hz), 2.56 (d, 3H, J 0.6 Hz), 3.72-3.79 (m, 1H), 3.97-4.33 (m, 3H), 4.59 (d, 1H, J 13.0 Hz), 5.76 (d, 1H, J 13.0 Hz), 6.17 (dd, 1H, J 3.8, 2.6 Hz), 6.70 (dd, 1H, J 3.8, 1.5 Hz), 7.06-7.21 (m, 4H), 8.74 (s, 1H). |
| 15 | 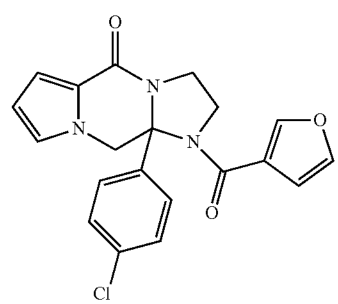 [SMILES: O=C(c1ccoc1)N1CCN2C(=O)c3cccn3CC12c1ccc(Cl)cc1] | ESI-MI m/z [M + H]⁺ 382.1. ¹H NMR (400 MHz, CDCl₃): δ 3.68-3.78 (m, 1H), 3.92 (ddd, 1H, J 9.4, 8.4, 4.4 Hz), 4.17 (dt, 1H, J 9.3, 7.0 Hz), 4.41 (ddd, 1H, J 11.7, 8.8, 4.3 Hz), 4.55 (d, 1H, J 13.0 Hz), 5.65 (d, 1H, J 13.0 Hz), 6.21 (dd, 1H, J 3.8, 2.6 Hz), 6.71 (dd, 1H, J 2.3, 1.8 Hz), 6.73 (dd, 1H, J 1.9, 1.8 Hz), 6.92-6.94 (m, 1H), 7.22-7.26 (m, 2H), 7.29-7.33 (m, 2H), 7.48 (t, 1H, J 1.6 Hz), 7.84-7.85 (m, 1H). |
| 16 | 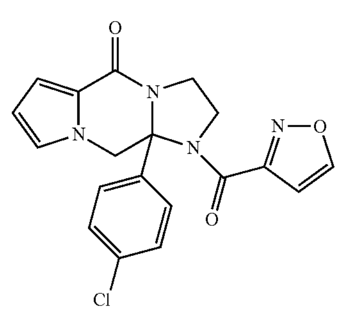 [SMILES: O=C(c1ccon1)N1CCN2C(=O)c3cccn3CC12c1ccc(Cl)cc1] | ESI-MI m/z [M + H]⁺ 383.1. ¹H NMR (400 MHz, CDCl₃): δ 3.72-3.80 (m, 1H), 4.26 (ddd, 1H, J 8.3, 4.0 Hz), 4.37-4.56 (m, 2H), 4.56 (d, 1H, J 12.9 Hz), 5.67 (d, 1H, J 12.9 Hz), 6.21 (dd, 1H, J 4.0, 2.6 Hz), 6.73 (dd, 1H, J 2.4, 1.7 Hz), 6.81 (d, 1H, J 1.7 Hz), 6.94 (dd, 1H, J 3.9, 1.4 Hz), 7.24-7.29 (m, 2H), 7.31-7.37 (m, 2H), 8.51 (d, 1H, J 1.7 Hz). |

| Cpd. No. | Structure | ESI-MI m/z [M + H]+/1H-NMR |
|---|---|---|
| 17 | 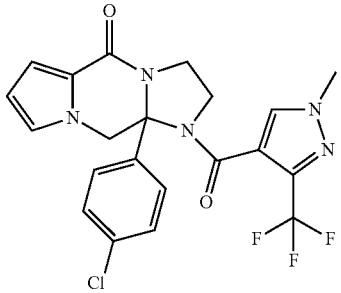 [SMILES: Cn1cc(C(=O)N2CCN3C(=O)c4cccn4CC23c2ccc(Cl)cc2)c(C(F)(F)F)n1] | ESI-MI m/z [M + H]+ 464.1. 1H NMR (400 MHz, CDCl3): δ 3.57 (ddd, 1H, J 10.1, 8.3, 5.6 Hz), 3.70 (ddd, 1H, J 11.4, 8.2, 5.9 Hz), 3.82 (ddd, 1H, J 10.1, 8.7, 5.8 Hz), 3.99 (s, 3H), 4.25 (ddd, 1H, J 11.3, 8.7, 5.4 Hz), 4.55 (d, 1H, J 13.0 Hz), 5.61 (d, 1H, 13.0 Hz), 6.17 (d, 1H, J 3.9, 2.6 Hz), 6.67 (dd, 1H, J 3.8, 1.4 Hz). 6.93 (dd, 1H, J 3.8, 1.4 Hz), 7.25-7.29 (m, 2H), 7.37-7.42 (m, 2H), 7.57 (br s, 1H). |
| 18 | 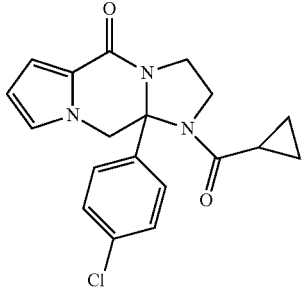 [SMILES: O=C1c2cccn2CC2(c3ccc(Cl)cc3)N1CCN2C(=O)C1CC1] | ESI-MI m/z [M + H]+ 356.1. 1H NMR (400 MHz, CDCl3): δ 0.83-0.95 (m, 2H), 0.99-1.11 (m, 2H), 1.63-1.71 (m, 1H), 3.68 (td, 1H, J 11.7, 8.12 Hz), 3.92 (dt, 1H, J 8.6, 3.9 Hz), 4.16 (q, 1H, J 9.1 Hz), 4.38 (d, 1H, J 11.8, 8.9, 3.8 Hz), 4.41-4.49 (m, 1H), 5.52 (d, 1H, J 12.9 Hz), 6.17 (dd, 1H, J 3.8, 2.6 Hz), 6.63-6.66 (m, 1H), 6.91 (dd, 1H, J 3.8, 1.4 Hz), 7.20-7.29 (m, 4H). |
| 19 | 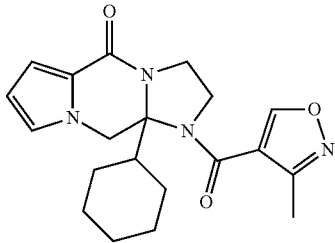 [SMILES: Cc1nocc1C(=O)N1CCN2C(=O)c3cccn3CC12C1CCCCC1] | ESI-MI m/z [M + H]+ 369.2. 1H NMR (400 MHz, d6-Acetone): δ 0.85-0.97 (m, 1H), 1.02-1.21 (m, 4H), 1.34-1.42 (m, 1H), 1.52-1.64 (m, 2H), 1.70-1.77 (m, 1H), 1.78-1.86 (m, 1H), 2.39 (d, 3H, J 0.4 Hz), 2.50-2.59 (m, 1H), 3.61 (dt, 1H, J 11.5, 8.3 Hz), 4.07-4.11 (m, 2H), 4.25-4.32 (m, 1H), 4.31 (d, 1H, J 13.2 Hz), 5.35 (d, 1H, J 13.2 Hz), 6.19 (dd, 1H, J 3.8, 2.5 Hz), 6.67 (dd, 1H, J 3.8, 1.6 Hz), 6.99 (t, 1H, J 4.0 Hz), 9.15 (s, 1H). |
| 20 | 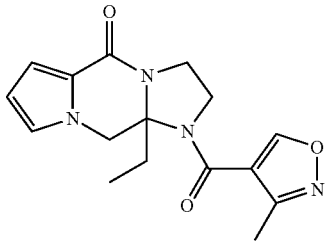 [SMILES: CCC12Cn3cccc3C(=O)N1CCN2C(=O)c1conc1C] | ESI-MI m/z [M + H]+ 315.1. 1H-NMR (400 MHz, CDCl3): δ 0.87 (t, 3H, J 7.5 Hz), 1.92-2.04 (m, 1H), 2.41-2.53 (m, 1H), 2.47 (s, 3H), 3.70 (dt, 1H, J 11.7, 8.5 Hz), 3.88-3.99 (m, 2H), 4.08 (d, 1H, J 12.4 Hz), 4.37 (ddd, 1H, J 11.3, 8.0, 3.2 Hz), 5.12 (d, 1H, J 12.4 Hz), 6.24 (dd, 1H, J 3.8, 2.6 Hz), 6.75-6.77 (m, 1H), 6.91-6.95 (m, 1H), 8.63 (s, 1H). |
| 21 | 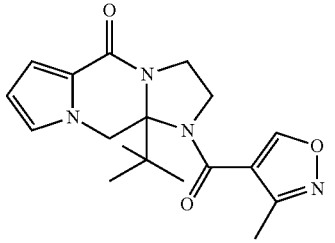 [SMILES: Cc1nocc1C(=O)N1CCN2C(=O)c3cccn3CC12C(C)(C)C] | ESI-MI m/z [M + H]+: 343.2. 1H-NMR (400 MHz, CDCl3): δ 1.00 (s, 9H), 2.44 (s, 3H), 3.73-3.82 (m, 1H, J 11.7, 9.8, 5.0 Hz), 3.89-4.03 (m, 2H), 4.32 (d, 1H, J 13.8 Hz), 4.41 (ddd, 1H, J 11.7, 9.8, 5.0 Hz), 5.53 (d, 1H, J 13.8 Hz), 6.22-6.26 (m, 1H), 6.75-6.78 (m, 1H), 6.85-6.89 (m, 1H), 8.58 (s, 1H). |

| Cpd. No. | Structure | ESI-MI m/z [M + H]+/1H-NMR |
|---|---|---|
| 48 | 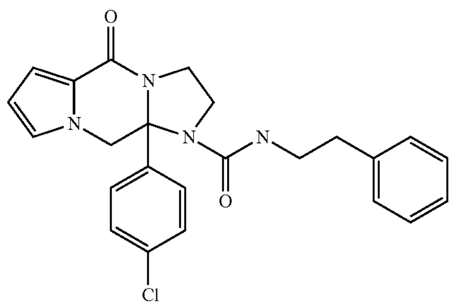 [SMILES: O=C(NCCc1ccccc1)N1CCN2C(=O)c3cccn3CC12c1ccc(Cl)cc1] | ESI-MI m/z [M + H]+ 435. 1H-NMR (400 MHz, CDCl3): δ 2.84 (t, 2H, J 6.8 Hz), 3.36 (td, 1H, J 8.1, 4.1 Hz), 3.48-3.73 (m, 4H), 4.30-4.38 (m, 1H), 4.40 (d, 1H, J 13.0 Hz), 5.50 (d, 1H, J 13.0 Hz), 6.16 (dd, 1H, J 3.9, 2.5 Hz), 6.66 (dd, 1H, J 2.4, 1.6 Hz), 6.90 (dd, 1H, J 3.9, 1.5 Hz), 7.19-7.11 (m, 2H), 7.39-7.19 (m, 7H). |
| 49 | 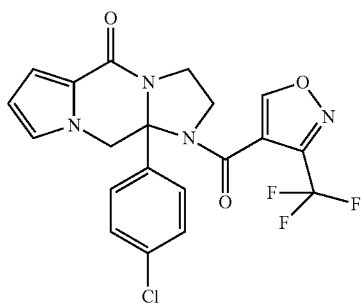 [SMILES: O=C(c1conc1C(F)(F)F)N1CCN2C(=O)c3cccn3CC12c1ccc(Cl)cc1] | ESI-MI m/z [M + H]+ 451.1. 1H-NMR (400 MHz, CDCl3): δ 3.60-3.70 (m, 1H), 3.75 (ddd, 1H, J 11.3, 8.1, 6.1 Hz), 3.82-3.92 (m, 1H), 4.35 (ddd, 1H, J 11.3, 8.6, 5.0 Hz), 4.55 (d, 1H, J 12.9 Hz), 5.60 (d, 1H, J 12.9 Hz), 6.19 (dd, 1H, J 3.9, 2.6 Hz), 6.69 (dd, 1H, J 2.4, 1.6 Hz), 6.94 (dd, 1H, J 3.9, 1.4 Hz), 7.28-7.32 (2H, m), 7.36-7.43 (m, 2H), 8.73 (1H, s). |
| 50 | 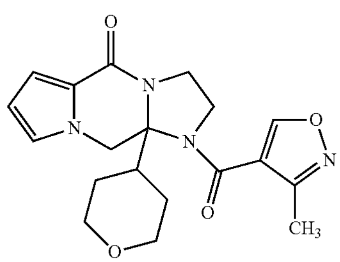 [SMILES: Cc1nocc1C(=O)N1CCN2C(=O)c3cccn3CC12C1CCOCC1] | ESI-MI m/z [M + H]+ 371.1. 1H NMR (400 MHz, CDCl3): δ 1.12 (d, 1H, J 12.7 Hz). 1.36 (qd, 1H, J 12.3, 4.6 Hz), 1.46-1.55 (m, 2H), 2.46 (s, 3H), 2.70-2.82 (m, 1H), 3.19-3.32 (m, 2H), 3.71 (dt, 1H, J 11.8, 8.3 Hz), 3.84 (dd, 1H, J 11.4, 3.9 Hz), 3.88-4.00 (m, 3H), 4.20 (d, 1H, J 13.2 Hz,), 4.45 (ddd, 1H, J 12.0, 8.6, 3.6 Hz), 5.34 (d, 1H, J 13.2 Hz), 6.25 (dd, 1H, J 3.8, 2.6 Hz), 6.73 (d, 1H, J 1.6 Hz), 6.87-6.91 (m, 1H), 8.64 (s, 1H). |
| 51 | 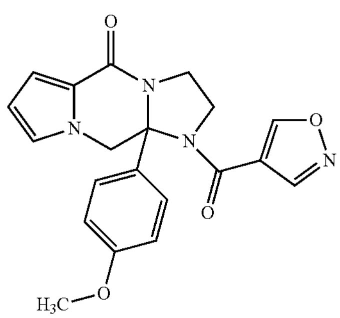 [SMILES: COc1ccc(C23Cn4cccc4C(=O)N2CCN3C(=O)c2cnoc2)cc1] | ESI-MI m/z [M + H]+ 379.1. 1H NMR (400 MHz, d6-acetone): δ 3.74 (d, 3H, J 4.8 Hz), 3.75-3.83 (m, 1H), 4.21-4.29 (m, 1H), 4.31-4.41 (m, 2H), 4.54 (d, 1H, J 12.9 Hz), 5.75 (d, 1H, J 13.0 Hz), 6.15 (dd, 1H, J 3.7, 2.6 Hz), 6.70 (br d, 1H, J 2.5 Hz), 6.81 (br d, 2H, J 8.9 Hz), 7.03 (br s, 1H), 7.35 (br d, 2H, J 8.9 Hz), 8.78 (s, 1H), 9.32 (s, 1H). |
| 52 | 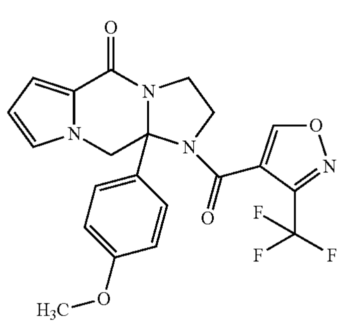 [SMILES: COc1ccc(C23Cn4cccc4C(=O)N2CCN3C(=O)c2conc2C(F)(F)F)cc1] | ESI-MI m/z [M + H]+ 447.1. 1H NMR (400 MHz, CDCl3): δ 3.61-3.70 (m, 1H), 3.76 (s, 4H), 3.79-3.88 (m, 1H), 4.27-4.35 (m, 1H), 4.54 (d, 1H, J 12.8 Hz), 5.59 (d, 1H, J 12.6 Hz), 6.15-6.19 (m, 1H), 6.68 (br s, 1H), 6.81 (br d, 2H, J 8.9 Hz), 6.90-6.96 (m, 1H), 7.35 (d, 2H, J 8.7 Hz), 8.73 (br s, 1H). |

| Cpd. No. | Structure | ESI-MI m/z [M + H]⁺/¹H-NMR |
|---|---|---|
| 53 | 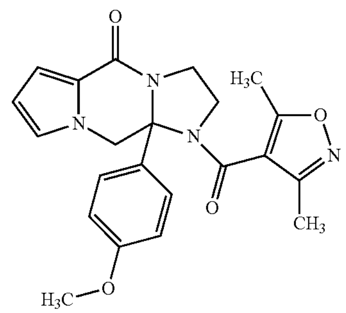 [SMILES: COc1ccc(C23Cn4cccc4C(=O)N2CCN3C(=O)c2c(C)noc2C)cc1] | ESI-MI m/z [M + H]⁺ 407.1. ¹H NMR (400 MHz, d6-acetone): δ 2.21 (s, 3H), 2.41 (s, 3H), 2.81 (s, 3H), 3.68-3.75 (m, 2H), 4.00-3.90 (m, 1H), 4.24-4.13 (m, 1H), 4.64 (d, 1H, J 12.9 Hz) 5.70 (d, 1H, J 12.9 Hz), 6.09-6.17 (m, 1H), 6.66-6.71 (m, 1H), 6.87 (d, 2H, J 8.9 Hz), 7.01 (br s, 1H), 7.41 (br d, 2H, J 8.9 Hz). |
| 54 | 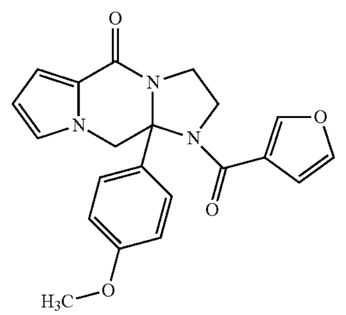 [SMILES: COc1ccc(C23Cn4cccc4C(=O)N2CCN3C(=O)c2ccoc2)cc1] | ESI-MI m/z [M + H]⁺ 378.0. ¹H NMR (400 MHz, d6-acetone): δ 3.72 (d, 3H, J 8.7 Hz), 3.74-3.81 (m, 1H), 4.20-4.10 (m, 1H), 4.36-4.25 (m, 2H), 4.52 (d, 1H, J 13.0 Hz), 5.76 (d, 1H, J 13.0 Hz), 6.14 (dd, 1H, J 3.7, 2.6 Hz), 6.71-6.67 (m, 1H), 6.81 (d, 3H, J 9.2 Hz), 7.00-7.04 (m, 1H), 7.34 (br d, 2H, J 8.9 Hz), 7.63-7.66 (m, 1H), 8.13 (br s, 1H). |
| 55 | 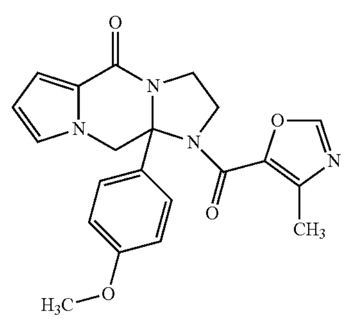 [SMILES: COc1ccc(C23Cn4cccc4C(=O)N2CCN3C(=O)c2ocnc2C)cc1] | ESI-MI m/z [M + H]⁺ 393.1. ¹H NMR (400 MHz, CDCl₃): δ 2.52 (s, 3H), 3.73 (s, 3H), 3.81-3.74 (m, 1H), 4.08-4.20 (m, 1H), 4.45-4.29 (m, 2H), 4.54 (d, 1H, J 12.9 Hz), 5.68 (d, 1H, J 12.9 Hz), 6.19 (dd, 1H, J 3.8, 2.6 Hz), 6.72 (br d, 1H, J 1.6 Hz), 6.78 (br d, 2H, J 8.9 Hz), 6.90-6.94 (m, 1H), 7.28 (br d, 2H, J 2.0 Hz), 7.85 (s, 1H). |
| 56 | 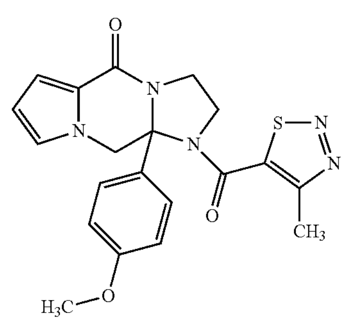 [SMILES: COc1ccc(C23Cn4cccc4C(=O)N2CCN3C(=O)c2snnc2C)cc1] | ESI-MI m/z [M + H]⁺ 410.0. ¹H NMR (400 MHz, CDCl₃): δ 2.71 (s, 3H), 3.61-3.49 (m, 1H), 3.64-3.74 (m, 1H), 3.74-3.78 (m, 1H), 3.77 (s, 3H), 4.30 (ddd, 1H, J 11.2, 8.6, 5.3 Hz), 4.61 (d, 1H, J 12.7 Hz), 5.61 (d, 1H, J 12.5 Hz), 6.18 (dd, 1H, J 3.7, 2.6 Hz), 6.70 (br s, 1H), 6.84 (br d, 2H, J 8.9 Hz), 6.94 (br d, 1H, J,2.6 Hz), 7.38 (d, 2H, J 8.7 Hz). |
| 57 | 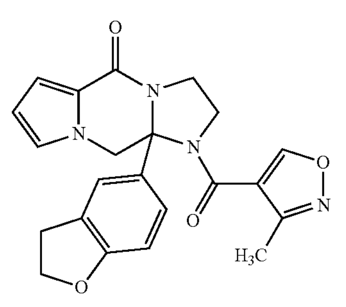 [SMILES: Cc1nocc1C(=O)N1CCN2C(=O)c3cccn3CC12c1ccc2c(c1)CCO2] | ESI-MI m/z [M + H]⁺ 405.1. ¹H NMR (400 MHz, CDCl₃): δ 2.48 (s, 3H), 3.13 (t, 2H, J 8.7 Hz), 3.67-3.86 (m, 2H), 3.93-4.07 (m, 1H), 4.21-4.40 (m, 1H), 4.40-4.72 (m, 3H), 5.62 (d, 1H, J 12.8 Hz), 6.03-6.30 (m, 1H), 6.57-6.77 (m, 2H), 6.93 (d, 1H, J 2.7 Hz), 7.17 (d, 1H, J 8.4 Hz), 7.21 (s, 1H), 8.51 (s, 1H). |

| Cpd. No. | Structure | ESI-MI m/z [M + H]⁺/¹H-NMR |
|---|---|---|
| 58 | 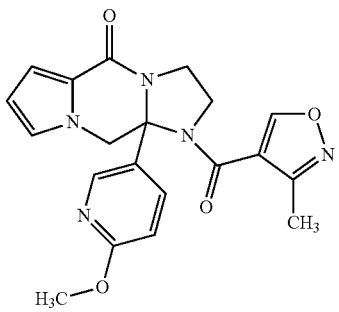 [SMILES: COc1ccc(C23Cn4cccc4C(=O)N2CCN3C(=O)c2conc2C)cn1] | ESI-MI m/z [M + H]⁺ 394.2. ¹H NMR (400 MHz, CDCl₃): δ 2.44 (s, 3H), 3.80-3.68 (m, 1H), 3.88 (s, 3H), 3.89-3.94 (m, 1H), 4.06 (dt, 1H, J 16.1, 8.1 Hz), 4.41 (ddd, 1H, J 12.8, 8.7, 4.3 Hz), 4.51 (d, 1H, J 12.9 Hz), 5.63 (d, 1H, J 12.9 Hz), 6.15-6.31 (m, 1H), 6.66 (d, 1H, J 8.8 Hz), 6.74 (s, 1H), 6.96 (t, 1H, J 10.9 Hz), 7.55 (dd, 1H, J 8.8, 2.7 Hz), 8.15 (d, 1H, J 2.7 Hz), 8.58 (s, 1H). |
| 59 | 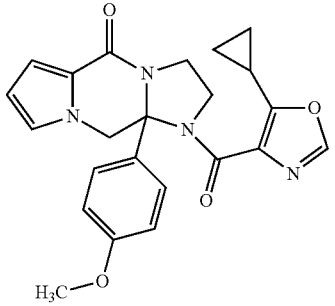 [SMILES: COc1ccc(C23Cn4cccc4C(=O)N2CCN3C(=O)c2ncoc2C2CC2)cc1] | ESI-MI m/z [M + H]⁺ 419.1. ¹H NMR (400 MHz, CDCl₃): δ 1.01-1.19 (m, 4H), 2.73-2.83 (m, 1H), 3.73 (s, 3H), 3.74-3.79 (m, 1H), 4.29 (dddd, 2H, J 19.1, 11.3, 8.5, 4.8 Hz), 4.56 (d, 1H, J 12.9 Hz), 4.62 (dt, 1H, J 11.1, 8.4 Hz), 5.71 (d, 1H, J 12.9 Hz), 6.19 (dd, 1H, J 3.7, 2.6 Hz), 6.71 (br s, 1H), 6.77 (br d, 2H, J 8.9 Hz), 6.93-6.89 (m, 1H), 7.30 (d, 2H, J 8.9 Hz), 7.57 (s, 1H). |
| 60 | 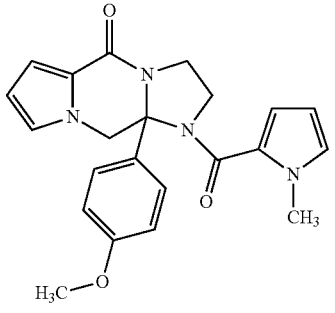 [SMILES: COc1ccc(C23Cn4cccc4C(=O)N2CCN3C(=O)c2cccn2C)cc1] | ESI-MI m/z [M + H]⁺ 391. ¹H NMR (400 MHz, CDCl₃): δ 7.26 (br d, 2H, J 8.8 Hz), 6.92 (br d, 1H, J 3.7 Hz), 6.77 (br d, 2H, J 8.9 Hz, 3H), 6.69 (br s, 1H), 6.46-6.51 (m, 1H), 6.09-6.20 (m, 2H), 5.64 (d, 1H, J 12.9 Hz), 4.64 (d, 1H, J 12.9 Hz), 4.16-4.33 (m, 2H), 3.85-3.95 (m, 1H), 3.83 (s, 3H), 3.75-3.79 (m, 1H), 3.74 (s, 3H). |
| 61 | 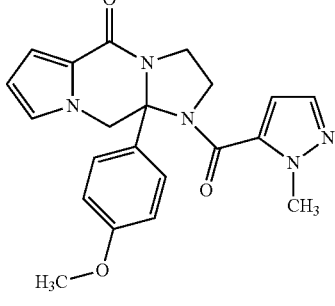 | ESI-MI m/z [M + H]⁺ 392.1. ¹H NMR (400 MHz, CDCl₃): δ 3.76 (s, 3H), 3.81 (dd, 2H, J 12.4, 7.6 Hz), 4.03 (s, 3H), 4.05-4.14 (m, 1H), 4.20-4.32 (m, 1H), 4.61 (d, 1H, J 12.8 Hz), 5.64 (d, 1H, J 12.8 Hz), 6.10-6.25 (m, 1H), 6.43 (br s, 1H), 6.70 (br s, 1H), 6.80 (br d, 2H, J 8.8 Hz), 6.92 (br d, 1H, J 2.9 Hz), 7.31 (br d, 2H, J 8.8 Hz), 7.48 (d, 1H, J 1.8 Hz). |
| 64 | 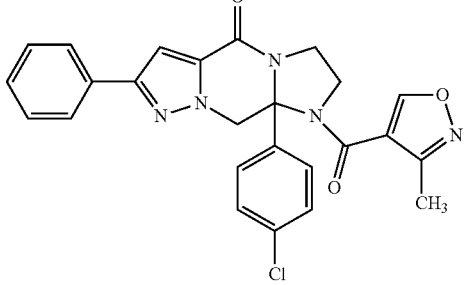 | ESI-MI m/z [M + H]⁺ 474.0. ¹H NMR (400 MHz, CDCl₃): δ 2.43 (s, 3H), 3.83-3.96 (m, 2H), 4.06-4.17 (m, 1H), 4.42 (dt, 1H, J 14.5, 6.1 Hz), 4.78 (d, 1H, J 13.6 Hz), 6.07 (d, 1H, J 13.6 Hz), 7.14 (s, 1H), 7.27-7.47 (m, 7H), 7.78 (br d, 2H), 8.54 (s, 1H). |

| Cpd. No. | Structure | ESI-MI m/z [M + H]⁺/¹H-NMR |
|---|---|---|
| 65 | 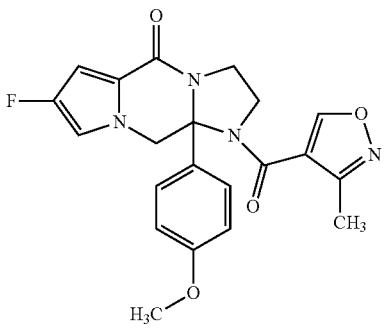 [SMILES: COc1ccc(C23Cn4cc(F)cc4C(=O)N2CCN3C(=O)c2conc2C)cc1] | ESI-MI m/z [M + H]⁺ 411.0. ¹H NMR (400 MHz, CDCl₃): δ 2.44 (s, 3H), 3.77 (s, 3H), 3.78-3.84 (m, 2H), 3.94-4.06 (m, 1H), 4.27-4.36 (m, 1H), 4.53 (d, 1H, J 12.8 Hz), 5.49 (d, 1H, J 12.9 Hz), 6.48 (dd, 1H, J 3.5, 1.8 Hz), 6.62 (d, 1H, J 1.5 Hz), 6.83 (br d, 2H, J 8.8 Hz), 7.33 (br d, 2H, J 8.8 Hz), 8.46 (s, 1H). |
| 66 | 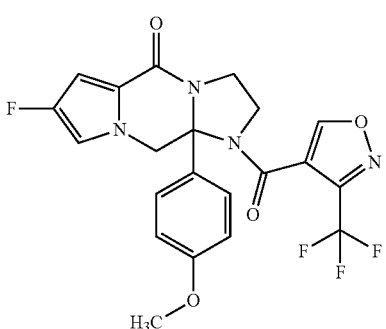 | ESI-MI m/z [M + H]⁺ 465.1. ¹H NMR (400 MHz, CDCl₃): δ 3.59-3.68 (m, 1H), 3.78 (s, 3H), 3.74-3.85 (m, 2H), 4.29 (ddd, 1H, J 11.1, 9.7, 5.5 Hz), 4.50 (d, 1H, J 12.8 Hz), 5.46 (d, 1H, J 12.1 Hz), 6.47 (dd, 1H, J 3.7, 1.9 Hz), 6.62 (d, 1H, J 1.8 Hz), 6.81-6.88 (m, 2H), 7.37 (d, 2H, J 8.9 Hz), 8.70 (s, 1H). |
| 67 | 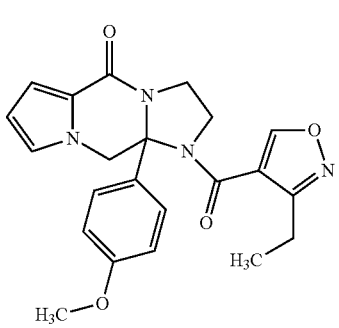 [SMILES: CCc1nocc1C(=O)N1CCN2C(=O)c3cccn3CC12c1ccc(OC)cc1] | ESI-MI m/z [M + H]⁺ 407.2. ¹H NMR (400 MHz, CDCl₃): δ 1.27 (t, 3H, J 7.5 Hz), 2.86 (dd, 2H, J 14.8, 7.4 Hz), 3.71-3.86 (m, 2H), 3.75 (s, 3H), 3.92-4.05 (m, 1H), 4.22-4.42 (m, 1H), 4.55 (d, 1H, J 12.8 Hz), 5.63 (d, 1H, J 12.8 Hz), 6.15-6.21 (m, 1H), 6.69 (s, 1H), 6.79 (d, 2H, J 8.8 Hz), 6.91 (d, 1H, J 2.8 Hz), 7.31 (d, 2H, J 8.7 Hz), 8.50 (s, 1H). |
| 68 | 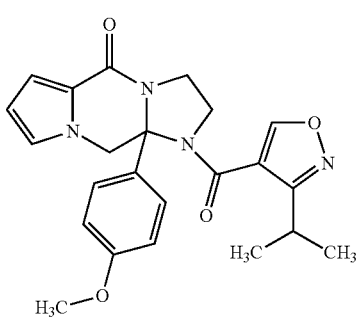 [SMILES: COc1ccc(C23Cn4cccc4C(=O)N2CCN3C(=O)c2conc2C(C)C)cc1] | ESI-MI m/z [M + H]⁺ 421.0. ¹H NMR (400 MHz, CDCl₃): δ 1.32 (d, 6H, J 7.1 Hz), 3.29 (hept, 1H J 6.9 Hz), 3.76 (s, 3H), 3.73-3.83 (m, 2H), 3.95 (ddd, 1H, J 11.2, 10.5, 7.4 Hz), 4.24-4.36 (m, 1H), 4.56 (d, 1H, J 12.8 Hz), 5.64 (d, 1H, J 12.8 Hz), 6.18 (dd, 1H, J 3.9, 2.6 Hz), 6.69 (dd, 1H J 2.4, 1.6 Hz), 6.78-6.83 (m, 2H), 6.92 (dd, 1H, J 3.9, 1.5 Hz), 7.30-7.42 (m, 2H), 8.45 (s, 1H). |
| 70 | 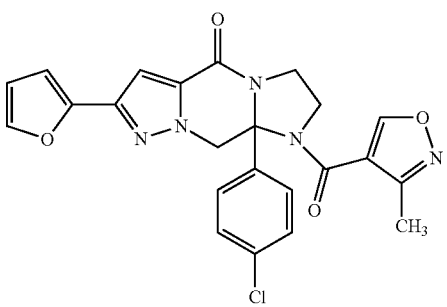 [SMILES: Cc1nocc1C(=O)N1CCN2C(=O)c3cc(-c4ccco4)nn3CC12c1ccc(Cl)cc1] | ESI-MI m/z [M + H]⁺ 464.1. ¹H NMR (400 MHz, CDCl₃): δ 2.42 (s, 3H), 3.84-3.94 (m, 2H), 4.06-4.16 (m, 1H), 4.34-4.45 (m, 1H), 4.76 (d, 1H, J 13.7 Hz), 6.07 (d, 1H, J 13.6 Hz), 6.46 (dd, 1H, J 3.4, 1.8 Hz), 6.68 (dd, 1H, J 3.4, 0.7 Hz), 7.03 (s, 1H), 7.27-7.32 (m, 2H), 7.34-7.40 (m, 2H), 7.45 (dd, 1H, J 1.8, 0.7 Hz), 8.53 (s, 1H). |

| Cpd. No. | Structure | ESI-MI m/z [M + H]⁺/¹H-NMR |
|---|---|---|
| 71 | 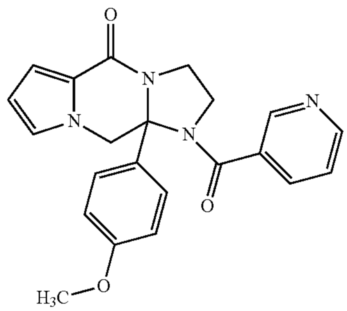 [SMILES: COc1ccc(C23Cn4cccc4C(=O)N2CCN3C(=O)c2cccnc2)cc1] | ESI-MI m/z [M + H]⁺ 389.1. ¹H NMR (400 MHz, Acetone): δ 3.65-3.74 (m, 1H), 3.76 (s, 3H), 3.83 (ddd, 1H, J 17.1, 9.8, 5.9 Hz), 4.01 (dt, 1H, J 16.9, 7.7 Hz), 4.21 (ddd, 1H, J 11.3, 8.5, 4.5 Hz), 4.67 (d, 1H, J 12.9 Hz), 5.74 (d, 1H, J 12.9 Hz), 6.15 (dd, 1H, J 3.6, 2.7 Hz), 6.68-6.72 (m, 1H), 6.86 (br d, 2H, J 8.9 Hz), 7.03 (br s, 1H), 7.41 (br d, 2H, J 8.9 Hz), 7.48 (dd, 1H, J 7.7, 4.9 Hz), 7.94 (br d, 1H, J 7.8 Hz), 8.68 (dd, 1H, J 4.8, 1.5 Hz), 8.74 (br s, 1H). |
| 72 | 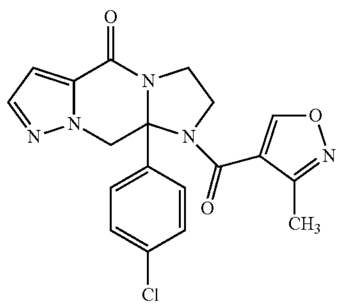 [SMILES: Cc1nocc1C(=O)N1CCN2C(=O)c3ccnn3CC12c1ccc(Cl)cc1] | ESI-MI m/z [M + H]⁺ 398.0. ¹H NMR (400 MHz, CDCl₃): δ 2.43 (s, 3H), 3.82-3.95 (m, 2H), 4.11 (ddd, 1H, J 13.6, 10.1, 7.4 Hz), 4.35-4.45 (m, 1H), 4.74 (d, 1H, J 13.6 Hz), 6.05 (d, 1H, J 13.6 Hz), 6.85 (d, 1H, J 2.0 Hz), 7.27-7.35 (m, 4H), 7.54 (d, 1H, J 2.0 Hz), 8.54 (s, 1H). |
| 73 | 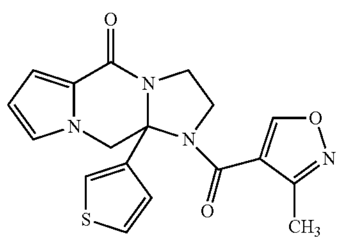 [SMILES: Cc1nocc1C(=O)N1CCN2C(=O)c3cccn3CC12c1ccsc1] | ESI-MI m/z [M + H]⁺ 369.1. ¹H NMR (400 MHz, CDCl₃): δ 2.44 (s, 3H), 3.73 (dt, 1H, J 11.5, 7.9 Hz), 3.92 (td, 1H, J 8.7, 3.8 Hz), 3.99-4.08 (m, 1H), 4.39 (ddd, 1H, J 12.1, 8.5, 3.8 Hz), 4.44 (d, 1H, J 12.7 Hz), 5.59 (d, 1H, J 12.4 Hz), 6.22 (dd, 1H, J 3.9, 2.6 Hz), 6.72-6.75 (m, 1H), 6.95 (ddd, 2H, J 5.0, 4.4, 1.1 Hz), 7.11 (dd, 1H, J 2.8, 1.2 Hz), 7.23 (dd, 1H, J 5.1, 3.0 Hz), 8.59 (br s, 1H). |
| 74 | 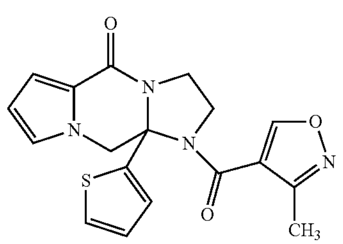 [SMILES: Cc1nocc1C(=O)N1CCN2C(=O)c3cccn3CC12c1cccs1] | ESI-MI m/z [M + H]⁺ 369.1. ¹H NMR (400 MHz, CDCl₃): δ 2.45 (s, 3H), 3.78 (dt, 1H, J 11.5, 8.0 Hz), 3.95-4.09 (m, 2H), 4.32-4.42 (m, 1H), 4.43 (dd, 1H, J 10.5, 8.2 Hz), 5.64 (d, 1H, J 12.6 Hz), 6.24 (dd, 1H, J 3.9, 2.6 Hz), 6.78 (dd, 1H, J 2.4, 1.6 Hz), 6.81 (dd, 1H, J 3.7, 1.3 Hz), 6.85 (dd, 1H, J 5.1, 3.7 Hz), 6.94 (dd, 1H, J 3.9, 1.5 Hz), 7.19 (dd, 1H, J 5.1, 1.3 Hz), 8.61 (br s, 1H). |
| 76 | 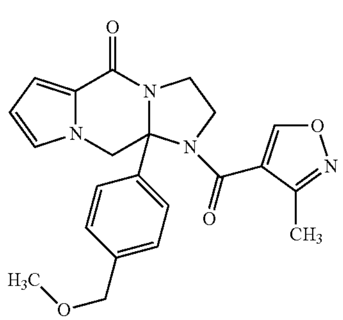 [SMILES: COCc1ccc(C23Cn4cccc4C(=O)N2CCN3C(=O)c2conc2C)cc1] | ESI-MI m/z [M + H]⁺ 407.1. ¹H NMR (400 MHz, CDCl₃): δ 2.44 (s, 3H), 3.37 (s, 3H), 3.72-3.84 (m, 2H), 3.99-4.07 (m, 1H), 4.30-4.36 (m, 1H), 4.38 (s, 2H), 4.59 (d, 1H, J 12.9 Hz), 5.65 (d, 1H, J 12.9 Hz), 6.17 (dd, 1H, J 3.9, 2.6 Hz), 6.68 (dd, 1H, J 2.4, 1.6 Hz), 6.92 (dd, 1H, J 3.9, 1.5 Hz), 7.25-7.29 (m, 2H), 7.34-7.38 (m, 2H), 8.52 (s, 1H). |

-continued

| Cpd. No. | Structure | ESI-MI m/z [M + H]+/1H-NMR |
|---|---|---|
| 77 | 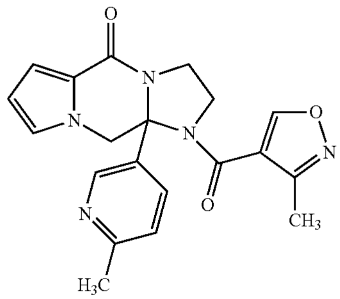 | ESI-MI m/z [M + H]+ 378.0. 1H NMR (400 MHz, CDCl3): δ 2.26 (s, 3H), 2.35 (s, 3H), 3.96-4.09 (m, 2H), 4.12-4.20 (m, 1H), 4.33-4.40 (m, 1H), 4.47 (d, 1H, J 13.0 Hz), 5.74 (d, 1H, J 13.0 Hz), 6.28 (dd, 1H, J 3.9, 2.6 Hz), 6.86-6.91 (m, 2H), 6.93 (d, 1H, J 8.1 Hz), 7.36 (ddd, 1H, J 8.1, 2.2, 0.6 Hz), 8.29 (dd, 1H, J 1.5, 0.7 Hz), 8.62 (s, 1H). |
| 125 | 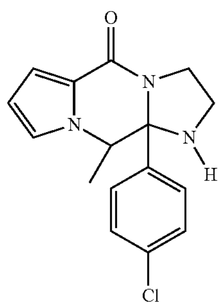 [SMILES: CC1n2cccc2C(=O)N2CCNC12c1ccc(Cl)cc1] | ESI-MI m/z [M + H]+ 302.1. |
| 126 | 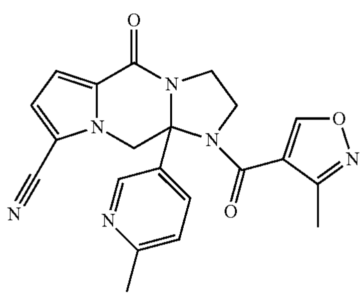 [SMILES: Cc1ccc(C23Cn4c(C#N)ccc4C(=O)N2CCN3C(=O)c2conc2C)cn1] | ESI-MI m/z [M + H]+ 403.13. 1H NMR (400 MHz, CDCl3): δ 2.44 (s, 3H), 2.52 (s, 3H), 3.80-3.99 (m, 2H), 4.03-4.18 (m, 1H), 4.37-4.46 (m, 1H), 4.51 (d, 1H, J 13.4 Hz), 5.99 (d, 1H, J 13.4 Hz), 6.78 (d, 1H, J 4.2 Hz), 6.90 (d, 1H, J 4.2 Hz), 7.15 (d, 1H, J 8.1 Hz), 7.69 (dd, 1H, J 8.3, 2.5 Hz), 8.46 (brs, 1H), 8.57 (s, 1H). |
| 127 | 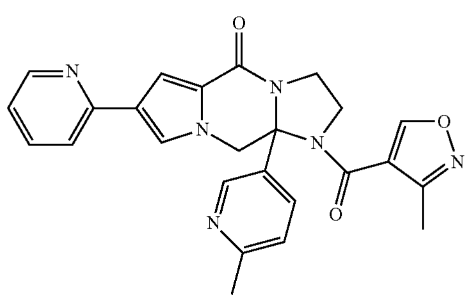 [SMILES: Cc1ccc(C23Cn4cc(-c5ccccn5)cc4C(=O)N2CCN3C(=O)c2conc2C)cn1] | ESI-MI m/z [M + H]+ 455.16. 1H NMR (400 MHz, CDCl3): δ 2.44 (s, 3H), 2.49 (s, 3H), 3.79 (ddd, 1H, J 11.6, 8.1, 7.1 Hz), 3.84-3.96 (m, 1H), 3.98-4.20 (m, 1H), 4.43 (ddd, 1H, J 11.7, 8.7, 4.2 Hz), 4.59 (d, 1H, J 13.0 Hz), 5.71 (d, 1H, J 13.1 Hz), 7.03-7.12 (m, 2H), 7.36 (d, 1H, J 1.6 Hz), 7.42 (d, 1H, J 1.6 Hz), 7.45 (d, 1H, J 8.0 Hz), 7.57 (dd, 1H, J 8.3, 2.7 Hz), 7.60-7.69 (m, 1H), 8.50 (ddd, 1H, J 4.9, 1.7, 0.9 Hz), 8.55 (d, 1H, J 2.4 Hz), 8.60 (s, 1H). |
| 128 | 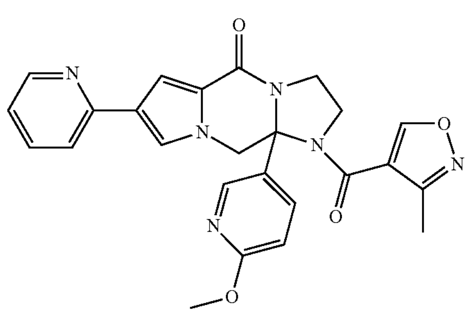 [SMILES: COc1ccc(C23Cn4cc(-c5ccccn5)cc4C(=O)N2CCN3C(=O)c2conc2C)cn1] | ESI-MI m/z [M + H]+ 471.15. 1H NMR (400 MHz, CDCl3): δ 2.45 (s, 3H), 3.73-3.85 (m, 1H), 3.87 (s, 3H), 3.86-3.93 (m, 1H), 3.98-4.15 (m, 1H), 4.43 (ddd, 1H, J 11.6, 8.7, 4.3 Hz), 4.57 (d, 1H, J 13.0 Hz), 5.69 (d, 1H, J 13.1 Hz), 6.66 (dd, 1H, J 8.8, 0.4 Hz), 7.09 (ddd, 1H, J 7.4, 4.9, 1.0 Hz), 7.37 (d, 1H, J 1.6 Hz), 7.42 (d, 1H, J 1.6 Hz), 7.46 (d, 1H, J 8.0 Hz), 7.59-7.69 (m, 2H), 8.18 (d, 1H, J 2.4 Hz), 8.51 (ddd, 1H, J 4.8, 1.6, 0.8 Hz), 8.59 (s, 1H). |

| Cpd. No. | Structure | ESI-MI m/z [M + H]+/1H-NMR |
|---|---|---|
| 129 | 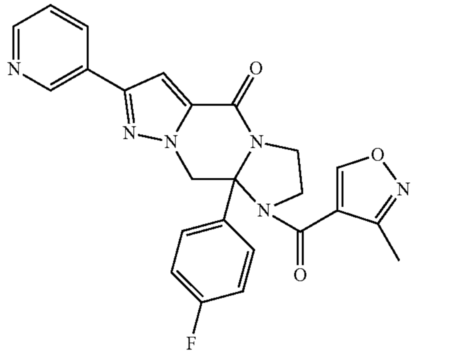 [SMILES: Cc1nocc1C(=O)N1CCN2C(=O)c3cc(-c4cccnc4)nn3CC12c1ccc(F)cc1] | ESI-MI m/z [M + H]+ 459.00. 1H NMR (400 MHz, CDCl3): δ 2.43 (s, 3H), 3.74-3.97 (m, 2H), 4.04-4.18 (m, 1H), 4.30-4.47 (m, 1H), 4.82 (d, 1H, J 13.6 Hz), 6.11 (d, 1H, J 13.6 Hz), 7.00 (t, 2H, J 8.5 Hz), 7.20-7.26 (m, 1H), 7.37-7.51 (m, 3H), 7.73 (t, 1H, J 7.7 Hz), 7.88 (d, 1H, J 7.9 Hz), 8.54 (s, 1H), 8.64 (d, 1H, J 4.3 Hz). |
| 130 | 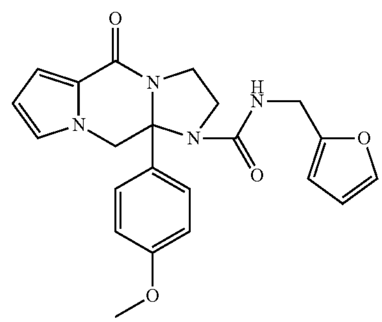 [SMILES: COc1ccc(C23Cn4cccc4C(=O)N2CCN3C(=O)NCc2ccco2)cc1] | ESI-MI m/z [M + H]+ 407.06. 1H NMR (400 MHz, CDCl3): δ 3.45-3.59 (m, 1H), 3.63-3.76 (m, 5H), 4.30-4.51 (m, 4H), 4.79 (t, 1H, J 5.2 Hz), 5.51 (d, 1H, J 12.9 Hz), 6.15 (dd, 1H, J 3.9, 2.6 Hz), 6.23 (dd, 1H, J 3.2, 0.6 Hz), 6.33 (dd, 1H, J 3.2, 1.9 Hz), 6.66 (dd, 1H, J 2.4, 1.7 Hz), 6.76 (d, 2H, J 9.0 Hz), 6.88 (dd, 1H, J 3.8, 1.4 Hz), 7.27 (d, 2H, J 9.1 Hz), 7.35 (dd, 1H, J 1.8, 0.8 Hz). |
| 131 | 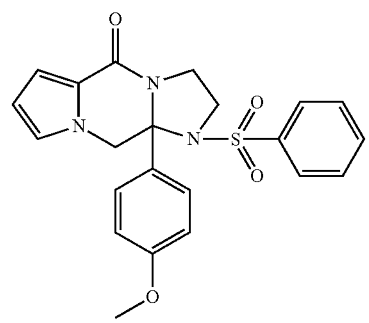 [SMILES: COc1ccc(C23Cn4cccc4C(=O)N2CCN3S(=O)(=O)c2ccccc2)cc1] | ESI-MI m/z [M + H]+ 424.05. 1H NMR (400 MHz, CDCl3): δ 3.45-3.59 (m, 1H), 3.74 (s, 3H), 3.80-3.96 (m, 2H), 4.05-4.20 (m, 1H), 4.52 (d, 1H, J 12.8 Hz), 5.45 (d, 1H, J 12.8 Hz), 6.07-6.22 (m, 1H), 6.69 (d, 2H, J 8.8 Hz), 6.74 (brs, 1H), 6.80 (d, 1H, J 2.8 Hz), 7.23 (d, 2H, J 8.8 Hz), 7.36 (t, 2H, J 7.8 Hz), 7.42-7.60 (m, 3H). |
| 132 | 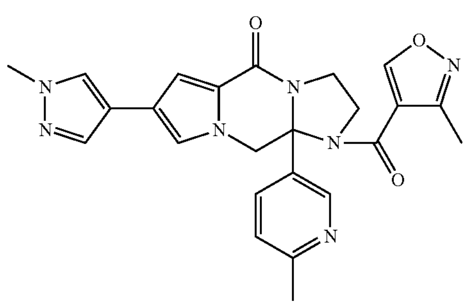 | ESI-MI m/z [M + H]+ 458.18. 1H NMR (400 MHz, CD3OD): δ 2.34 (s, 3H), 2.45 (s, 3H), 3.77-3.85 (m, 1H), 3.85 (s, 3H), 4.09-4.25 (m, 2H), 4.35 (ddd, 1H, J 11.7, 8.1, 3.7 Hz), 4.55 (d, 1H, J 13.2 Hz), 5.77 (d, 1H, J 13.2 Hz), 6.94 (d, 1H, J 1.7 Hz), 7.17-7.33 (m, 2H), 7.58 (d, 1H, J 0.7 Hz), 7.69 (s, 1H), 7.75 (dd, 1H, J 8.3, 2.6 Hz), 8.44 (d, 1H, J 2.1 Hz), 9.10 (s, 1H). |
| 133 | 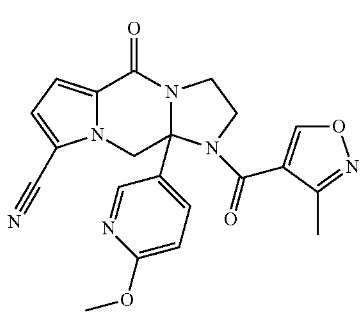 [SMILES: COc1ccc(C23Cn4c(C#N)ccc4C(=O)N2CCN3C(=O)c2conc2C)cn1] | ESI-MI m/z [M + H]+ 419.10. 1H NMR (400 MHz, CDCl3): δ 2.44 (s, 3H), 3.83-3.96 (m, 5H), 4.03-4.15 (m, 1H), 4.32-4.46 (m, 1H), 4.50 (d, 1H, J 13.3 Hz), 5.95 (d, 1H, J 13.3 Hz), 6.72 (d, 1H, J 8.9 Hz), 6.78 (d, 1H, J 4.2 Hz), 6.90 (d, 1H, J 4.2 Hz), 7.73 (dd, 1H, J 8.9, 2.8 Hz), 8.12 (d, 1H, J 2.8 Hz), 8.56 (s, 1H). |

| Cpd. No. | Structure | ESI-MI m/z [M + H]⁺/¹H-NMR |
|---|---|---|
| 134 | 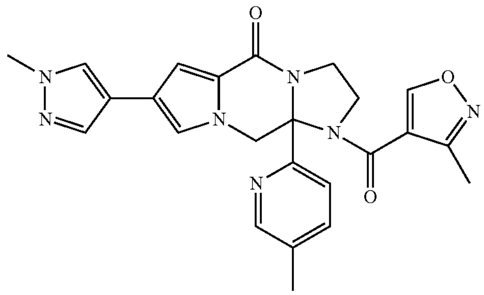 [SMILES: Cc1ccc(C23Cn4cc(-c5cnn(C)c5)cc4C(=O)N2CCN3C(=O)c2conc2C)nc1] | ESI-MI m/z [M + H]⁺ 458.11. ¹H NMR (400 MHz, CDCl₃): δ 2.27 (s, 3H), 2.36 (s, 3H), 3.91 (s, 3H), 3.96-4.10 (m, 2H), 4.11-4.22 (m, 1H), 4.29-4.43 (m, 1H), 4.48 (d, 1H, J 13.0 Hz), 5.72 (d, 1H, J 13.0 Hz), 6.95 (s, 2H), 7.02 (d, 1H, J 8.1 Hz), 7.37 (ddd, 1H, J 8.1, 2.2, 0.7 Hz), 7.45 (s, 1H), 7.60 (d, 1H, J 0.6 Hz), 8.26-8.34 (m, 1H), 8.62 (s, 1H). |
| 135 | 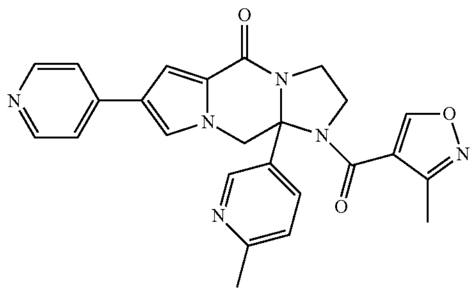 [SMILES: Cc1ccc(C23Cn4cc(-c5ccncc5)cc4C(=O)N2CCN3C(=O)c2conc2C)cn1] | ESI-MI m/z [M + H]⁺ 455.17. ¹H NMR (400 MHz, CDCl₃): δ 2.44 (s, 3H), 2.50 (s, 3H), 3.73-3.85 (m, 1H), 3.85-3.96 (m, 1H), 4.04-4.18 (m, 1H), 4.44 (ddd, 1H, J 11.7, 8.7, 4.3 Hz), 4.58 (d, 1H, J 13.0 Hz), 5.74 (d, 1H, J 13.1 Hz), 7.10 (d, 1H, J 8.3 Hz), 7.15 (d, 1H, J 1.6 Hz), 7.29 (d, 1H, J 1.5 Hz), 7.32 (d, 2H, J 6.1 Hz), 7.56 (dd, 1H, J 8.3, 2.6 Hz), 8.53 (d, 2H, J 6.1 Hz), 8.57 (d, 1H, J 2.5 Hz), 8.60 (s, 1H). |
| 136 | 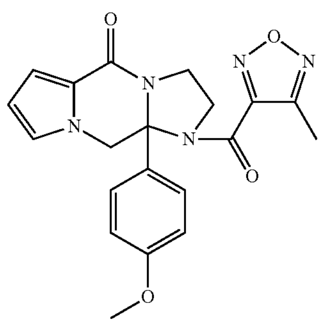 [SMILES: COc1ccc(C23Cn4cccc4C(=O)N2CCN3C(=O)c2nonc2C)cc1] | ESI-MI m/z [M + H]⁺ 394.11. ¹H NMR (400 MHz, CDCl₃): δ 2.57 (s, 3H), 3.75 (s, 3H), 3.77-3.83 (m, 1H), 4.14-4.23 (m, 1H), 4.32-4.44 (m, 2H), 4.56 (d, 1H, J 12.7 Hz), 5.66 (d, 1H, J 12.7 Hz), 6.20 (dd, 1H, J 3.9, 2.6 Hz), 6.72 (dd, 1H, J 2.4, 1.6 Hz), 6.80 (d, 2H, J 9.0 Hz), 6.93 (dd, 1H, J 3.9, 1.5 Hz), 7.31 (d, 2H, J 9.0 Hz). |
| 137 | 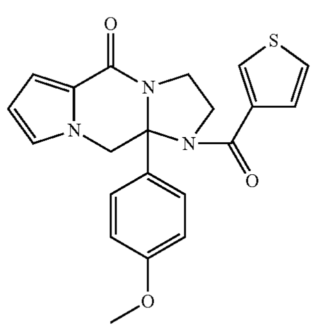 [SMILES: COc1ccc(C23Cn4cccc4C(=O)N2CCN3C(=O)c2ccsc2)cc1] | ESI-MI m/z [M + H]⁺ 394.08. ¹H NMR (400 MHz, CDCl₃): δ 3.69-3.86 (m, 5H), 4.02-4.12 (m, 1H), 4.26 (ddd, 1H, J 11.0, 8.8, 4.8 Hz), 4.62 (d, 1H, J 12.9 Hz), 5.64 (d, 1H, J 12.9 Hz), 6.18 (dd, 1H, J 3.9, 2.5 Hz), 6.70 (dd, 1H, J 2.4, 1.6 Hz), 6.80 (d, 2H, J 9.0 Hz), 6.92 (dd, 1H, J 3.9, 1.5 Hz), 7.30 (dd, 1H, J 5.1, 1.3 Hz), 7.33 (d, 2H, J 9.0 Hz), 7.37 (dd, 1H, J 5.1, 2.9 Hz), 7.64 (dd, 1H, J 2.9, 1.2 Hz). |
| 138 | 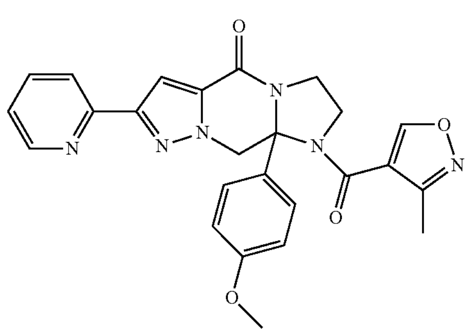 [SMILES: COc1ccc(C23Cn4nc(-c5ccccn5)cc4C(=O)N2CCN3C(=O)c2conc2C)cc1] | ESI-MI m/z [M + H]⁺ 471.20. ¹H NMR (400 MHz, CDCl₃): δ 2.43 (s, 3H), 3.74 (s, 3H), 3.82-3.96 (m, 2H), 4.00-4.18 (m, 1H), 4.31-4.46 (m, 1H), 4.81 (d, 1H, J 13.5 Hz), 6.08 (d, 1H, J 13.3 Hz), 6.81 (d, 2H, J 9.0 Hz), 7.21-7.24 (m, 1H), 7.35 (d, 2H, J 8.9 Hz), 7.44 (s, 1H), 7.72 (td, 1H, J 7.8, 1.6 Hz), 7.88 (d, 1H, J 7.9 Hz), 8.49 (brs, 1H), 8.63 (d, 1H, J 4.2 Hz). |

| Cpd. No. | Structure | ESI-MI m/z [M + H]+/1H-NMR |
|---|---|---|
| 139 | 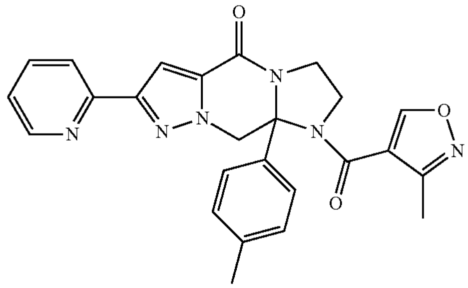 [SMILES: Cc1ccc(C23Cn4nc(-c5ccccn5)cc4C(=O)N2CCN3C(=O)c2conc2C)cc1] | ESI-MI m/z [M + H]+ 455.20. 1H NMR (400 MHz, d6-DMSO): δ 2.22 (s, 3H), 2.30 (s, 3H), 3.73-3.84 (m, 1H), 4.07-4.20 (m, 2H), 4.21-4.32 (m, 1H), 5.08 (d, 1H, J 13.3 Hz), 5.80 (d, 1H, J 13.3 Hz), 7.15 (d, 2H, J 8.0 Hz), 7.24 (s, 1H), 7.26 (d, 2H, J 8.4 Hz), 7.36 (ddd, 1H, J 7.5, 4.9, 1.2 Hz), 7.86 (td, 1H, J 7.7, 1.8 Hz), 7.97 (dt, 1H, J 8.0, 1.1 Hz), 8.60 (ddd, 1H, J 4.8, 1.7, 0.9 Hz), 9.39 (s, 1H). |
| 140 | 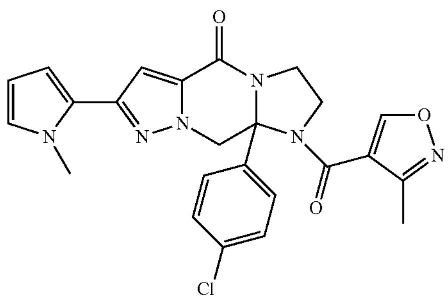 [SMILES: Cc1nocc1C(=O)N1CCN2C(=O)c3cc(-c4cccn4C)nn3CC12c1ccc(Cl)cc1] | ESI-MI m/z [M + H]+ 477.11. 1H NMR (400 MHz, CDCl3): δ 2.43 (s, 3H), 3.83-3.97 (m, 5H), 4.06-4.17 (m, 1H), 4.41 (ddd, 1H, J 11.5, 8.7, 3.9 Hz), 4.74 (d, 1H, J 13.6 Hz), 6.00 (d, 1H, J 13.5 Hz), 6.13 (dd, 1H, J 3.7, 2.6 Hz), 6.44 (dd, 1H, J 3.7, 1.8 Hz), 6.61-6.68 (m, 1H), 6.94 (s, 1H), 7.29 (d, 2H, J 9.0 Hz), 7.35 (d, 2H, J 9.0 Hz), 8.55 (s, 1H). |
| 141 | 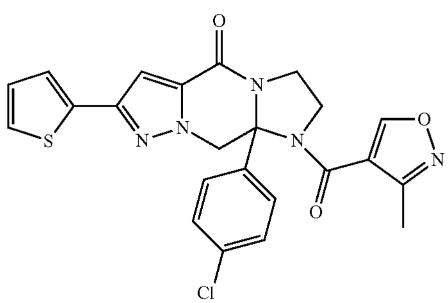 [SMILES: Cc1nocc1C(=O)N1CCN2C(=O)c3cc(-c4cccs4)nn3CC12c1ccc(Cl)cc1] | ESI-MI m/z [M + H]+ 480.04. 1H NMR (400 MHz, CDCl3): δ 2.38 (s, 3H), 3.75-3.90 (m, 2H), 3.98-4.13 (m, 1H), 4.17-4.45 (m, 1H), 4.70 (d, 1H, J 13.6 Hz), 6.00 (d, 1H, J 13.6 Hz), 6.97 (s, 1H), 7.00 (dd, 1H, J 5.0, 3.6 Hz), 7.20-7.27 (m, 3H), 7.28 (dd, 1H, J 3.5, 0.9 Hz), 7.33 (d, 2H, J 8.8 Hz), 8.50 (s, 1H). |
| 157 | 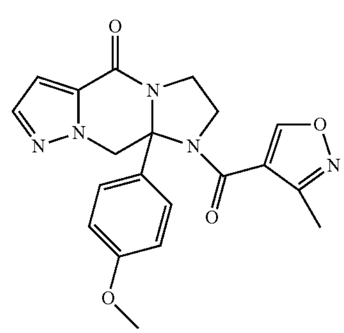 [SMILES: COc1ccc(C23Cn4nccc4C(=O)N2CCN3C(=O)c2conc2C)cc1] | ESI-MI m/z [M + H]+ 394.0. 1H NMR (400 MHz, CDCl3): δ 2.42 (s, 3H), 3.76 (s, 3H), 3.80-3.96 (m, 2H), 4.01-4.14 (m, 1H), 4.28-4.44 (m, 1H), 4.74 (d, 1H, J 13.5 Hz), 6.02 (d, 1H, J 13.6 Hz), 6.81 (d, 2H, J 9.0 Hz), 6.84 (d, 1H, J 2.0 Hz), 7.30 (d, 2H, J 9.0 Hz), 7.52 (d, 1H, J 2.0 Hz), 8.49 (s, 1H). |

Example of General Method A

Route (b)

4-{1-[(3-methyl-1,2-oxazol-4-yl)carbonyl]-5-oxo-2,3-dihydro-1H,5H-imidazo[1,2-a]pyrrolo[1,2-d]pyrazin-10a(10H)-yl}benzyl 3-methyl-1,2-oxazole-4-carboxylate (79)

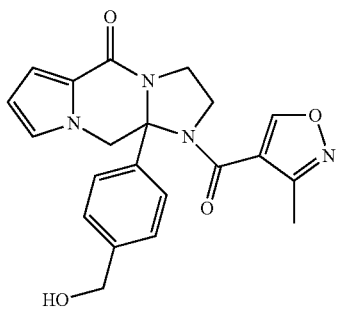 [SMILES: Cc1nocc1C(=O)N1CCN2C(=O)c3cccn3CC12c1ccc(CO)cc1]

$^1$H-NMR (400 MHz, CDCl$_3$ with MeOH (a drop)): δ 2.42 (s, 3H), 3.73-3.85 (m, 2H), 3.97-4.08 (m, 1H), 4.28-4.39 (m, 1H), 4.58 (d, 1H, J 12.9 Hz), 4.61 (s, 2H), 5.65 (d, 1H, J 12.9 Hz), 6.15-6.20 (m, 1H), 6.68-6.71 (m, 1H), 6.89-6.92 (m, 1H), 7.25-7.37 (m, 4H). ESI-MI m/z [M+H]$^+$ 393.1.

Step 1

To a chilled solution of methyl 2-pyrrolecarboxylate (500 mg, 4.0 mmol) in dry DMF (15 mL) was added sodium hydride (60% dispersion in mineral oil, 300 mg, 7.5 mmol) portion wise. The mixture was stirred at 0° C. for 1 hour and a solution of 2-bromo-1-[4-(hydroxymethyl)phenyl]ethanone (750 mg, 3.3 mmol) in DMF (5 mL) was added and the mixture was allowed to warm to room temperature and stirred for 1.5 hour. A saturated aqueous solution of NH$_4$Cl (35 mL) was added followed by EtOAc (100 mL). The organic layer was then washed with brine (35 mL), dried (MgSO$_4$), filtered and concentrated in vacuo to yield a oil. The material was purified by flash chromatography (Biotage SP4, 40 g cartridge, gradient 0-80% EtOAc in hexanes) to give methyl 1-{2-[4-(hydroxymethyl)phenyl]-2-oxoethyl}-1H-pyrrole-2-carboxylate as a white solid (150 mg, yield: 17%). ESI-MI m/z [M+H]$^+$: 273.8.

Step 3

To a solution of methyl 1-{2-[4-(hydroxymethyl)phenyl]-2-oxoethyl}-1H-pyrrole-2-carboxylate (150 mg, 0.55 mmol) in 1,4-dioxane (25 mL) was added ethane-1,2-diamine (0.75 mL, 11 mmol). The solution was heated at reflux for 54 hours. The mixture was concentrated in vacuo to give a yellow oil, which was then portioned between water (30 mL) and CH$_2$Cl$_2$ (30 mL). Brine was added, and the organic layer was separated. The aqueous was further extracted with CH$_2$Cl$_2$ (2×30 mL) and the combined organic layers were dried (MgSO$_4$), filtered and concentrated in vacuo to yield a yellow solid, which was purified by flash chromatography (Biotage SP4, 12 g cartridge, gradient 0 to 10% methanol in EtOAc) to give 10a[4-(hydroxymethyl)phenyl]-2,3,10,10a-tetrahydro-1H,5H-imidazo[1,2-a]pyrrolo[1,2-d]pyrazin-5-one as an off-white solid (90 mg, yield: 57%). ESI-MI m/z [M+H]$^+$ 283.9.

Step 4

4-{1-[(3-methyl-1,2-oxazol-4-yl)carbonyl]-5-oxo-2,3-dihydro-1H,5H-imidazo[1,2-a]pyrrolo[1,2-d]pyrazin-10a(10H)-yl}benzyl 3-methyl-1,2-oxazole-4-carboxylate (62)

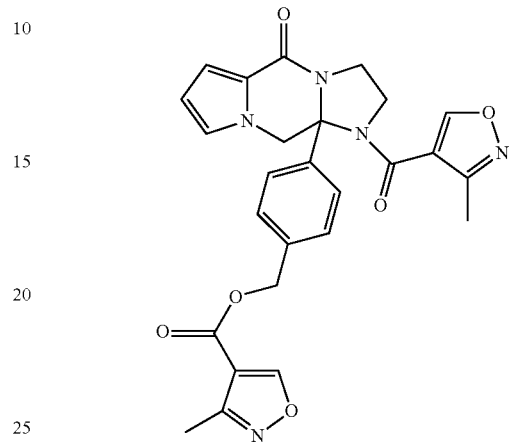

$^1$H-NMR (400 MHz, CDCl$_3$): δ 2.44 (s, 3H), 2.48 (s, 3H), 3.71-3.79 (m, 1H), 3.81-3.88 (m, 1H), 4.06 (dt, 1H, J 9.2, 6.8 Hz), 4.38 (ddd, J 11.4, 8.6, 4.2 Hz), 4.58 (d, 1H, J 12.9 Hz), 5.23 (s, 2H), 5.66 (d, 1H, J 12.9 Hz), 6.20 (dd, 1H, J 3.8, 2.6 Hz), 6.70-6.73 (m, 1H), 6.92-6.95 (m, 1H), 7.29-7.40 (m, 4H), 8.55 (s, 1H), 8.83 (s, 1H).
ESI-MI m/z [M+H]$^+$ 502.0.

To generate the acid chloride: to a chilled suspension of 3-methylisoxazole-4-carboxylic acid (220 mg, 1.7 mmol) in dry CH$_2$Cl$_2$ (3.5 mL) was added oxalyl chloride (0.5 mL, 5.9 mmol) followed by DMF (1 drop, catalytic). The mixture was stirred at 0° C. to room temperature for 1 hour. The resulting yellow solution was concentrated in vacuo and the resultant residue was azeotroped with dry CH$_2$Cl$_2$ to yield the acid chloride as an oil.

A suspension of 10a-[4-(hydroxymethyl)phenyl]-2,3,10,10a-tetrahydro-1H,5H-imidazo[1,2-a]pyrrolo[1,2-d]pyrazin-5-one (90 mg, 0.32 mmol) in pyridine (2.5 mL) was added to a suspension of the acid chloride (generated as above, 1.7 mmol) in pyridine (2.5 mL) at 0° C. The resultant suspension was then stirred at 0° C. to room temperature for 1.5 hour. When complete (reaction monitored by LCMS) the suspension was diluted with water (20 mL) and extracted with CH$_2$Cl$_2$ (3×8 mL). The extracts were combined, dried (MgSO$_4$), filtered and concentrated in vacuo to give a residue that was purified by flash chromatography (Silica gel, gradient 40% acetone in hexanes). The desired product was obtained as a solid that was dissolved in CH$_2$Cl$_2$ and washed with a saturated aqueous solution of NaHCO$_3$ and water. The organic layer was dried (MgSO$_4$), filtered and the filtrate diluted with hexanes and concentrated in vacuo to give 4-{1-[(3-methyl-1,2-oxazol-4-yl)carbonyl]-5-oxo-2,3-dihydro-1H,5H-imidazo[1,2-a]pyrrolo[1,2-d]pyrazin-10a(10H)-yl}benzyl 3-methyl-1,2-oxazole-4-carboxylate (62) as an off-white solid (60 mg, yield 37%). ESI-MI m/z [M+H]$^+$ 502.0.

Step 5b

To a solution of 4-{1-[(3-methyl-1,2-oxazol-4-yl)carbonyl]-5-oxo-2,3-dihydro-1H,5H-imidazo[1,2-a]pyrrolo[1,2- d]pyrazin-10a(10H)-yl}benzyl 3-methyl-1,2-oxazole-4-carboxylate (85 mg, 0.17 mmol) in THF (3.5 mL) was added a aqueous solution of lithium hydroxide (0.1 M) (3.5 mL, 0.35 mmol). The mixture was stirred at room temperature. The outcome of the reaction was monitored by LCMS. After 1 hour the reaction was complete and diluted with water (10 mL) and then extracted with $CH_2Cl_2$ (3×7 mL). The extracts were combined, dried ($MgSO_4$), filtered and concentrated in vacuo to yield a solid that was purified by flash chromatography (Biotage SP4, 12 g cartridge; gradient 0-10% methanol in $CH_2Cl_2$) to give 4-{1-[(3-methyl-1,2-oxazol-4-yl)carbonyl]-5-oxo-2,3-dihydro-1H,5H-imidazo[1,2-a]pyrrolo[1,2-d]pyrazin-10a(10H)-yl}benzyl 3-methyl-1,2-oxazole-4-carboxylate (79) as a white solid (42 mg, yield 64%).

The following compounds were similarly prepared using General Method A: Route (b).

| Cpd. No. | Structure | ESI-MI m/z [M + H]⁺/¹H-NMR |
|---|---|---|
| 69 | 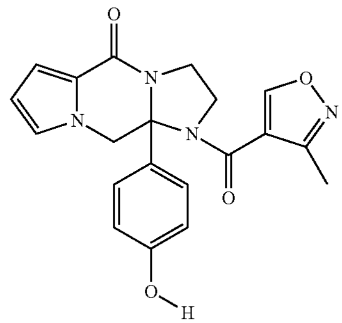 [SMILES: Cc1nocc1C(=O)N1CCN2C(=O)c3cccn3CC12c1ccc(O)cc1] | ESI-MI m/z [M + H]⁺ 379.2. ¹H NMR (400 MHz, d6-acetone): δ 2.36 (s, 3H), 3.65-3.76 (m, 1H), 4.01-4.13 (m, 1H), 4.17-4.29 (m, 2H), 4.56 (d, 1H, J 12.9 Hz), 5.70 (d, 1H, J 12.9 Hz), 6.14 (dd, 1H, J 3.5, 2.7 Hz), 6.67-6.77 (m, 3H), 7.25 (br d, 2H, J 8.8 Hz), 8.52 (br s, 1H), 9.10 (s, 1H). |
| 142 | 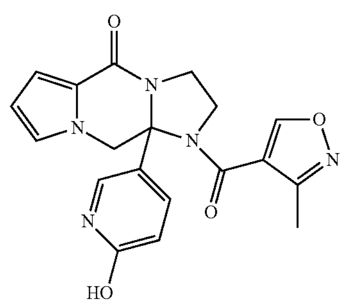 [SMILES: Cc1nocc1C(=O)N1CCN2C(=O)c3cccn3CC12c1ccc(O)nc1] | ESI-MI m/z [M + H]⁺ 380.11. ¹H NMR (400 MHz, d6-acetone): δ 2.37 (s, 3H), 3.70-3.84 (m, 1H), 4.16-4.34 (m, 3H), 4.50 (d, 1H, J 13.1 Hz), 5.68 (d, 1H, J 13.1 Hz), 6.18 (dd, 1H, J 3.8, 2.6 Hz), 6.28 (d, 1H, J 9.8 Hz), 6.72 (dd, 1H, J 3.7, 1.3 Hz), 7.01-7.20 (m, 1H), 7.38 (d, 1H, J 2.9 Hz), 7.57 (dd, 1H, J 9.8, 3.0 Hz), 9.16 (s, 1H). |
| 143⁽¹⁾ | | ESI-MI m/z [M + H]⁺ 394.16. ¹H NMR (400 MHz, CDCl₃): δ 2.44 (s, 3H), 3.42 (s, 3H), 3.77 (ddd, 1H, J 11.6, 8.2, 6.6 Hz), 3.90 (ddd, 1H, J 9.6, 8.3, 4.8 Hz), 3.98-4.13 (m, 1H), 4.37 (ddd, 1H, J 11.6, 8.8, 4.8 Hz), 4.44 (d, 1H, J 13.0 Hz), 5.53 (d, 1H, J 13.0 Hz), 6.24 (dd, 1H, J 3.9, 2.6 Hz), 6.49 (d, 1H, J 9.7 Hz), 6.75 (dd, 1H, J 2.5, 1.6 Hz), 6.95 (dd, 1H, J 3.9, 1.5 Hz), 7.18 (d, 1H, J 2.8 Hz), 7.53 (dd, 1H, J 9.7, 2.9 Hz), 8.61 (s, 1H). |

| Cpd. No. | Structure | ESI-MI m/z [M + H]⁺/¹H-NMR |
|---|---|---|
| 144 | 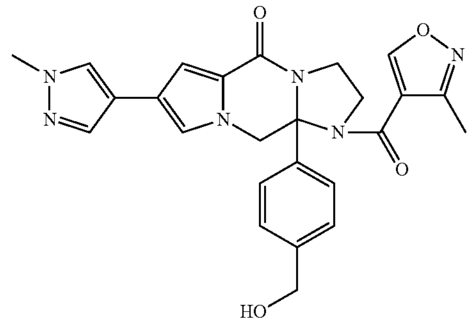 | ESI-MI m/z [M + H]⁺ 473.13. ¹H NMR (400 MHz, CD₃OD): δ 2.36 (s, 3H), 3.75-3.91 (m, 4H), 3.96-4.08 (m, 1H), 4.12-4.24 (m, 1H), 4.30 (ddd, 1H, J 11.3, 8.6, 4.4 Hz), 4.54 (s, 2H), 4.64 (d, 1H, J 13.1 Hz), 5.77 (d, 1H, J 13.1 Hz), 6.92 (d, 1H, J 1.7 Hz), 7.18 (d, 1H, J 1.7 Hz), 7.32 (d, 2H, J 8.6 Hz), 7.42 (d, 2H, J 8.5 Hz), 7.59 (s, 1H), 7.70 (s, 1H), 9.06 (s, 1H). |

⁽¹⁾Methylation Step: To a solution of 10a-(6-hydroxypyridin-3-yl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (142) (20 mg, 0.053 mmol) and cesium carbonate (10 mg, 0.031 mmol) in DMF (2 mL) was added methyl iodide (20 μL, 0.32 mmol). LCMS after 2.5 hours showed approx. 50% conversion so extra methyl iodide (30 μL, 0.48 mmol) was added. LCMS after a further 1.75 hours showed no additional progress, so extra cesium carbonate (15 mg, 0.046 mmol) was added. LCMS after 1.5 hours showed the reaction was almost complete, and after 2 hours the mixture was diluted with water (approx. 10 mL) and freeze-dried to yield a white solid. The solid was partitioned between water (5 mL) and dichloromethane (5 mL). The organic layer was separated and the aqueous layer extracted with dichloromethane (2 × 5 mL). The organic layers were combined, dried (MgSO₄), and concentrated in vacuo to yield a white solid. The material was purified by flash chromatography using the Biotage SP4 (4 g cartridge, dichloromethane 3 CV, 0 to 10% methanol-dichloromethane 20 CV, hold 5 CV) and freeze-dried from acetonitrile-water to give 1-[(3-methyl-1,2-oxazol-4-yl)carbonyl]-10a-(1-methyl-6-oxo-1,6-dihydropyridin-3-yl)-2,3,10,10a-tetrahydro-1H,5H-imidazo[1,2-a]pyrrolo[1,2-d]pyrazin-5-one (143) as a white solid (20 mg, 96%).

Example of General Method A

Route (c)

10a-(4-methoxyphenyl)-1-[(3-methyl-1,2-oxazol-4-yl)carbonyl]-7-(1H-tetrazol-5-yl)-2,3,10,10a-tetrahydro-1H,5H-imidazo[1,2-a]pyrrolo[1,2-d]pyrazin-5-one (75)

10a-(4-methoxyphenyl)-1-[(3-methyl-1,2-oxazol-4-yl)carbonyl]-7-(1-methyl-1H-tetrazol-5-yl)-2,3,10,10a-tetrahydro-1H,5H-imidazo[1,2-a]pyrrolo[1,2-d]pyrazin-5-one (145) and 10a-(4-methoxyphenyl)-1-[(3-methyl-1,2-oxazol-4-yl)carbonyl]-7-(2-methyl-2H-tetrazol-5-yl)-2,3,10,10a-tetrahydro-1H,5H-imidazo[1,2-a]pyrrolo[1,2-d]pyrazin-5-one (146)

¹H-NMR (400 MHz, CDCl₃): δ 2.30 (s, 3H), 3.69 (s, 3H), 3.73-3.84 (m, 1H), 4.00-4.15 (m, 2H), 4.15-4.24 (m, 1H), 4.65 (d, 1H, J 13.2 Hz), 5.96 (d, 1H, J 13.2 Hz), 6.86 (br d, 2H, J 8.9 Hz), 7.13 (s, 1H), 7.36 (br d, 2H), 7.36 (d, 1H, J 8.8 Hz), 7.93 (br s, 1H), 9.36 (s, 1H). ESI-MI m/z [M+H]⁺ 461.0.

Step 5c

Sodium azide (33 mg, 0.51 mmol) and ammonium chloride (27 mg, 0.51 mmol) was added to a solution of 10a-(4-methoxyphenyl)-7-(1H-tetrazol-5-yl)-2,3,10,10a-tetrahydro-1H,5H-imidazo[1,2-a]pyrrolo[1,2-d]pyrazin-5-one (150 mg, 0.43 mmol) in DMF and heated in a sealed tube at 120° C. for 16 hours. The reaction mixture was concentrated and purified by flash chromatography to give 10a-(4-methoxyphenyl)-1-[(3-methyl-1,2-oxazol-4-yl)carbonyl]-7-(1H-tetrazol-5-yl)-2,3,10,10a-tetrahydro-1H,5H-imidazo[1,2-a]pyrrolo[1,2-d]pyrazin-5-one (75) as a white solid (28 mg, yield 13%). Compounds 145 and 146 were similarly prepared using General Method A: Route (c) as follows.

¹H NMR (400 MHz, CDCl₃): δ 2.50 (s, 3H), 3.80 (s, 3H), 3.82-4.00 (m, 2H), 4.04-4.17 (m, 1H), 4.20 (s, 3H), 4.38 (ddd, 1H, J 10.6, 9.0, 5.0 Hz), 4.73 (d, 1H, J 13.0 Hz), 5.85 (d, 1H, J 13.1 Hz), 6.86 (d, 2H, J 9.0 Hz), 7.30-7.31 (m, 1H), 7.40 (d, 2H, J 9.0 Hz), 7.48 (d, 1H, J 1.7 Hz), 8.58 (s, 1H). ESI-MI m/z [M+H]⁺ 475.15.

$^1$H NMR (400 MHz, CDCl$_3$): δ 2.45 (s, 3H), 3.74 (s, 3H), 3.75-3.89 (m, 2H), 4.00-4.11 (m, 1H), 4.28-4.39 (m, 4H), 4.64 (d, 1H, J 12.9 Hz), 5.72 (d, 1H, J 12.9 Hz), 6.80 (d, 2H, J 8.9 Hz), 7.29-7.38 (m, 3H), 7.42 (d, 1H, J 1.5 Hz), 8.53 (s, 1H). ESI-MI m/z [M+H]$^+$ 474.80.

Methylation Step

Potassium carbonate (2 equivalents) was added to a solution of 10a-(4-methoxyphenyl)-1-[(3-methyl-1,2-oxazol-4-yl)carbonyl]-7-(1H-tetrazol-5-yl)-2,3,10,10a-tetrahydro-1H,5H-imidazo[1,2-a]pyrrolo[1,2-d]pyrazin-5-one (75) (150 mg, 0.33 mmol) in DMF. The mixture was stirred for 10 minutes and methyl iodide was added. The reaction was stirred at room temperature for 1 hour. The crude material was purified by preparative HPLC to give 10a-(4-methoxyphenyl)-1-[(3-methyl-1,2-oxazol-4-yl)carbonyl]-7-(1-methyl-1H-tetrazol-5-yl)-2,3,10,10a-tetrahydro-1H,5H-imidazo[1,2-a]pyrrolo[1,2-d]pyrazin-5-one (145) as a white solid (45 mg, 29%) and 10a-(4-methoxyphenyl)-1-[(3-methyl-1,2-oxazol-4-yl)carbonyl]-7-(2-methyl-2H-tetrazol-5-yl)-2,3,10,10a-tetrahydro-1H,5H-imidazo[1,2-a]pyrrolo[1,2-d]pyrazin-5-one (146) as a white solid (43 mg, 28%).

Example of General Method B 8-chloro-10a-(4-chlorophenyl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (22)

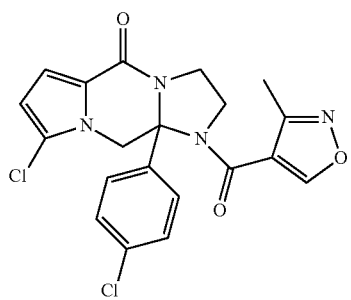 [SMILES: Cc1nocc1C(=O)N1CCN2C(=O)c3ccc(Cl)n3CC12c1ccc(Cl)cc1]

$^1$H NMR (400 MHz, d6-acetone): δ 2.35 (s, 3H), 3.78-3.88 (m, 1H), 4.18-4.24 (m, 1H), 4.26-4.35 (m, 2H), 4.50 (d, 1H, J 13.2 Hz), 5.89 (d, 1H, J 13.2 Hz), 6.20 (d, 1H, J 4.0 Hz), 6.73 (d, 1H, J 4.1 Hz), 7.36-7.49 (m, 4H), 9.16 (s, 1H).
ESI-MI m/z [M+H]$^+$ 432.7.

Step 1

Potassium carbonate (1.34 g, 9.72 mmol) was added to a solution of methyl 1H-pyrrole-2-carboxylate (850 mg, 6.8 mmol) in DMF (7.5 mL) and stirred at room temperature for 5 min. 2-bromo-1-(4-chlorophenyl)ethanone (1.58 g, 6.8 mmol) was added to the resulting suspension. After 18 h at room temperature the mixture was poured into water and extracted with EtOAc (3×10 mL). The organic layers were combined and dried (MgSO$_4$), concentrated in vacuo and the resulting residue was purified by flash chromatography (Biotage SP4, 40 g cartridge, 5%-20% EtOAc gradient in n-hexanes) giving a pale yellow oil, which was a mixture of starting material, a co-eluting product and a less polar product by T.L.C. Crystals were formed upon treatment with EtOH (5 mL) and n-hexanes (10 mL). Filtration gave methyl 1-[2-(4-chlorophenyl)-2-oxoethyl]-1H-pyrrole-2-carboxylate as white crystals (550 mg, 25%). $^1$H NMR (400 MHz, CDCl$_3$): δ 3.73 (s, 3H), 5.71 (s, 2H), 6.26 (dd, 1H, J 4.0, 2.6 Hz), 6.84 (dd, 1H, J 2.5, 1.9 Hz), 7.04 (dd, 1H, J 4.0, 1.7 Hz), 7.47-7.51 (m, 2H), 7.93-7.97 (m, 2H).

Step 2

Lithium hydroxide (116.73 mg, 2.15 mmol) was added to a solution of methyl 1-[2-(4-chlorophenyl)-2-oxoethyl]-1H-pyrrole-2-carboxylate (515 mg, 1.85 mmol) in THF (9 mL) water (1 mL) and stirred at room temperature overnight. The mixture was acidified to pH 2 with aqueous HCl (1 M) and extracted with EtOAc (3×10 mL). The organic layers were combined and dried (MgSO$_4$), filtered, concentrated in vacuo to give a cream white solid. The solid was triturated with cold CH$_2$Cl$_2$ to give 1-[2-(4-chlorophenyl)-2-oxoethyl]-1H-pyrrole-2-carboxylic acid as a white solid (310 mg, 64%). $^1$H NMR (400 MHz, d6-DMSO): δ 5.86 (s, 2H), 6.16 (dd, 1H, J 3.9, 2.6 hz), 6.86 (dd, 1H, J 3.9, 1.8 Hz), 7.08 (t, 1H, J 2.1 Hz), 7.65-7.70 (m, 2H), 8.02-8.08 (m, 2H), 12.07 (br s, 1H).

Step 3

1-[2-(4-chlorophenyl)-2-oxoethyl]-1H-pyrrole-2-carboxylic acid (300 mg, 1.14 mmol) and ethane-1,2-diamine (3.04 mL, 46 mmol) were mixed in 1,2-dichloroethane (30 mL) and stirred at reflux overnight. The analyse of the crude by LCMS indicated that the desired product was the major product [M+H]$^+$ 288.1. The reaction mixture was concentrated in vacuo to give an orange residue that was partitioned between CH$_2$Cl$_2$ (20 mL) and water (10 mL). The aqueous layer was extracted with EtOAc (4×20 mL). The combined organic layers were dried (MgSO$_4$), filtered and concentrated in vacuo to give a solid residue (300 mg) which was further purified by triturating with cold EtOH to give 10a-(4-chlorophenyl)-2,3,10,10a-tetrahydro-1H,5H-imidazo[1,2-a]pyrrolo[1,2-d]pyrazin-5-one as a white solid (163 mg, 49% yield). $^1$H NMR (400 MHz, d6-acetone): δ 3.30-3.45 (m, 3H), 3.71 (dt, 1H, J 10.8, 7.8 Hz), 4.40 (d, 1H, J 12.4 Hz), 4.66 (d, 1H, J 12.4 Hz), 6.04 (dd, 1H, J 3.8, 2.6 Hz), 6.65-6.69 (m, 2H), 7.29-7.33 (m, 2H), 7.35-7.39 (m, 2H).

Step 4a

To a solution of 10a-(4-chlorophenyl)-2,3,10,10a-tetrahydro-1H,5H-imidazo[1,2-a]pyrrolo[1,2-d]pyrazin-5-one (50 mg, 0.17 mmol) in THF (2 mL) was added N-chlorosuccinimide (23.2 mg, 0.17 mmol) and the reaction mixture was stirred at room temperature for 1 h. LCMS analysis showed that the reaction mixture contained predominantly starting material (288 m/z), along with a trace amount of desired product (322 m/z). The reaction mixture was heated at 50° C.

for 2.5 h and then heated at 60° C. for 2 h (monitored by LCMS). The reaction mixture was then concentrated in vacuo to give a residue that was purified by flash chromatography (Biotage SP4, 12 g cartridge, 0-5% MeOH gradient in CH₂Cl₂) to give 8-chloro-10a-(4-chlorophenyl)-2,3,10,10a-tetrahydro-1H,5H-imidazo[1,2-a]pyrrolo[1,2-d]pyrazin-5-one as a white solid (14.3 mg, yield 25%). ¹H NMR (400 MHz, d6-acetone): δ 3.31 (m, 1H), 3.42-3.49 (m, 2H), 3.73 (dt, 1H, J 10.9, 7.8 Hz), 4.20 (d, 1H, J 12.5 Hz), 4.74 (d, 1H, J 12.5 Hz), 6.06 (d, 1H, J 4.0 Hz), 6.70 (d, 1H, J 4.0 Hz), 7.33-7.43 (m, 4H).

Step 5a

To generate the acid chloride, oxalyl chloride (40 μL, 0.47 mmol) and DMF (1 drop) were added to a suspension of 3-methyl-1,2-oxazole-4-carboxylic acid (49 mg, 0.39 mmol) in CH₂Cl₂ (0.5 mL) at 0° C. The resultant suspension was stirred at 0° C. to room temperature for 2 h. The resulting solution was concentrated in vacuo to give an oil, which was azeotroped with n-hexane (2×1 mL) in vacuo to give the acid chloride as an oil.

A cloudy suspension of 8-chloro-10a-(4-chlorophenyl)-2,3,10,10a-tetrahydro-1H,5H-imidazo[1,2-a]pyrrolo[1,2-d]pyrazin-5-one (14.3 mg, 44 mmol) in pyridine (0.5 mL) was added to a suspension of the acid chloride (generated as described above; 0.39 mmol) in pyridine (0.5 mL) and CH₂Cl₂ (0.5 mL) at 0° C. The resulting brown reaction mixture was warmed to room temperature and stirred until completion (24 h, monitored by LCMS). The suspension was then diluted with water and extracted with CH₂Cl₂. The extracts were combined, dried (MgSO₄), filtered and concentrated in vacuo to give a residue. The material was partially purified using flash chromatography (Biotage SP4, 12 g cartridge, 0-10% MeOH gradient in CH₂Cl₂) to give a mixture that was further purified using reverse-phase chromatography (Biotage SP4, 12 g cartridge, C18 phase, 20-40% acetonitrile gradient in water) to give 8-chloro-10a-(4-chlorophenyl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (22) as a white solid (10.9 mg, 57% yield).

8-chloro-1-[(3-methyl-1,2-oxazol-4-yl)carbonyl]-10a-(tetrahydro-2H-pyran-4-yl)-2,3,10,10a-tetrahydro-1H,5H-imidazo[1,2-a]pyrrolo[1,2-d]pyrazin-5-one (81)

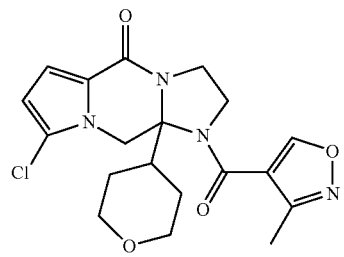 [SMILES: Cc1nocc1C(=O)N1CCN2C(=O)c3ccc(Cl)n3CC12C1CCOCC1]

¹H-NMR (400 MHz, CDCl₃): δ 1.07-1.17 (m, 1H), 1.24-1.40 (m, 1H), 1.45-1.56 (m, 3H), 2.48 (s, 3H), 2.70-2.88 (m, 1H), 3.23-3.33 (m, 2H), 3.66-3.77 (m, 1H), 3.83-3.92 (m, 1H), 3.92-4.05 (m, 3H), 4.44 (ddd, 1H, J 11.9, 8.0, 3.8 Hz), 5.52 (d, 1H, J 13.4 Hz), 6.19 (d, 1H, J 4.4 Hz), 6.89 (d, 1H, J 4.1 Hz), 8.63 (s, 1H). ESI-MI m/z [M+H]⁺ 405.0.

Step 5b

1-[(3-methyl-1,2-oxazol-4-yl)carbonyl]-10a-(tetrahydro-2H-pyran-4-yl)-2,3,10,10a-tetrahydro-1H,5H-imidazo[1,2-a]pyrrolo[1,2-a]pyrazin-5-one1 (50), (30 mg, 0.081 mmol) and N-chlorosuccinimide (13 mg, 0.097 mmol) were heated at 60° C. in dry THF (1 mL). After 1.5 hour the reaction was complete (monitored by LCMS). The mixture was then concentrated in vacuo. The material obtained was purified by flash chromatography (Silica gel, gradient 30 to 40% acetone in hexanes). 8-chloro-1-[(3-methyl-1,2-oxazol-4-yl)carbonyl]-10a-(tetrahydro-2H-pyran-4-yl)-2,3,10,10a-tetrahydro-1H,5H-imidazo[1,2-a]pyrrolo[1,2-d]pyrazin-5-one (81) was then isolated for characterisation and testing (contaminated with 17% of the 7-chloro-isomer: 7-chloro-1-[(3-methyl-1,2-oxazol-4-yl)carbonyl]-10a-(tetrahydro-2H-pyran-4-yl)-2,3,10,10a-tetrahydro-1H,5H-imidazo[1,2-a]pyrrolo[1,2-d]pyrazin-5-one).

The following compounds were similarly prepared using general method B.

| Cpd. No. | Structure | ESI-MI m/z [M + H]⁺/¹H-NMR |
|---|---|---|
| 23 | (structure shown) | ESI-MI m/z [M + H]⁺ 427.1. ¹H-NMR (400 MHz, CDCl₃): δ 2.43 (s, 3H), 3.76 (s, 3H), 3.81-3.89 (m, 2H), 3.99-4.08 (m, 1H), 4.27 (d, 1H, J 13.1 Hz), 4.26-4.37 (m, 1H), 5.89 (d, 1H, J 13.1 Hz), 6.10 (d, 1H, J 4.1 Hz), 6.80-6.84 (m, 2H), 6.87 (d, 1H, J 4.1 Hz), 7.31-7.36 (m, 2H), 8.51 (s, 1H). |

| Cpd. No. | Structure | ESI-MI m/z [M + H]⁺/¹H-NMR |
|---|---|---|
| 80 | 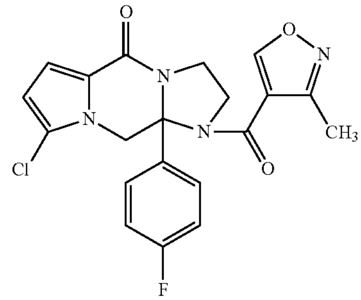 [SMILES: Cc1nocc1C(=O)N1CCN2C(=O)c3ccc(Cl)n3CC12c1ccc(F)cc1] | ESI-MI m/z [M + H]⁺ 415.0. ¹H NMR (400 MHz, CDCl₃): δ 2.43 (s, 3H), 3.78-3.89 (m, 2H), 4.01-4.09 (m, 1H), 4.27 (d, 1H, J 13.2 Hz), 4.31-4.40 1H), 5.90 (d, 1H, J 13.2 Hz), 6.11 (d, 1H, J 4.1 Hz), 6.87 (d, 1H, J 4.1 Hz), 6.96-7.03 (m, 2H), 7.36-7.45 (m, 2H), 8.55 (s, 1H). |

Example of General Method C 7-acetyl-10a-(4-chlorophenyl)-1-[(5-methyl-1,2-oxazol]-4-yl)carbonyl]-2,3,10,10a-tetrahydro-1H,5H-imidazo[1,2-a]pyrrolo[1,2-d]pyrazin-5-one (24)

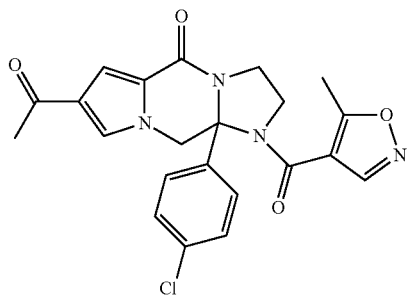 [SMILES: CC(=O)c1cc2n(c1)CC1(c3ccc(Cl)cc3)N(C(=O)c3cnoc3C)CCN1C2=O]

¹H NMR (400 MHz, d6-acetone): δ 2.33 (s, 3H), 2.56 (s, 3H), 3.80-3.88 (m, 1H), 4.12-4.18 (m, 1H), 4.22-4.36 (m, 2H), 4.73 (d, 1H, J 13.1 Hz), 5.91 (d, 1H, J 13.3 Hz), 7.07 (d, 1H, J 1.6 Hz), 7.33-7.38 (m, 2H), 7.49-7.54 (m, 2H), 7.76 (d, 1H, J 1.6 Hz), 8.72 (s, 1H). ESI-MI m/z [M+H]⁺ 439.1.

Preparation of 10a-(4-chlorophenyl)-2,3,10,10a-tetrahydro-1H,5H-imidazo[1,2-a]pyrrolo[1,2-d]pyrazin-5-one was described in general method B steps 1, 2 and 3.

Step 4

10a-(4-chlorophenyl)-2,3,10,10a-tetrahydro-1H,5H-imidazo[1,2-a]pyrrolo[1,2-d]pyrazin-5-one (50 mg, 0.17 mmol) and aluminium chloride (53 mg, 0.40 mmol) were suspended in 1,2-dichloroethane (1 mL). Acetyl chloride (15 µL, 0.21 mmol) in 1,2-dichloroethane was added dropwise to the reaction mixture. After 16 h at room temperature the reaction was not completed and another portion of acetyl chloride (15 µL, 0.21 mmol) was added. The reaction was still incomplete after a further 6 h at room temperature, therefore further acetyl chloride (15 µL, 0.21 mmol) and aluminium chloride (53 mg) were added and the reaction mixture was heated at 60° C. for 2 h. LCMS analysis showed a large amount of doubly acetylated product (372 m/z), along with target product (330 m/z) and a smaller amount of starting material (288 m/z). The reaction mixture was diluted with saturated aqueous solution of NaHCO₃ (25 mL) and extracted with CH₂Cl₂ containing 20% of propan-2-ol (2×25 mL). The organic layers were combined, dried and concentrated in vacuo to give a brown oil. The crude mixture was purified using flash chromatography (Biotage SP4, 12 g cartridge, 0-20% MeOH gradient in CH₂Cl₂) to give 7-acetyl-10a-(4-chlorophenyl)-2,3,10,10a-tetrahydro-1H,5H-imidazo[1,2-a]pyrrolo[1,2-d]pyrazin-5-one (23 mg, 40% yield). ESI-MI m/z [M+H]⁺ 329.9.

Step 5

To generate the acid chloride a suspension of 5-methyl-1,2-oxazole-4-carboxylic acid (39 mg, 0.30 mmol) in CH₂Cl₂ (0.5 mL) at 0° C. was added oxalyl chloride (50 µL, 1.2 mmol) and DMF (1 drop). The suspension was allowed to stir for a further 15 min at 0° C. followed by 2 h at room temperature. The resulting mixture was concentrated in vacuo to give a dark oil. The oil was twice suspended in n-hexanes (2×1 mL) and concentrated in vacuo. A solution of 7-acetyl-10a-(4-chlorophenyl)-2,3,10,10a-tetrahydro-1H,5H-imidazo[1,2-a]pyrrolo[1,2-d]pyrazin-5-one (20 mg, 61 µmol) in pyridine (0.5 mL) was added to a suspension of the acid chloride (generated as above; 0.30 mmol) in pyridine (0.5 mL) and CH₂Cl₂ (0.5 mL) at 0° C. The resultant mixture was warmed to room temperature and stirred for 16 h. The reaction mixture was diluted with a saturated aqueous solution of NaHCO₃ (25 mL) and extracted with CH₂Cl₂ containing 20% of propan-2-ol (3×25 mL). The organic layers were combined, dried and concentrated in vacuo to yield a crude brown residue that was partially purified using flash chromatography (Biotage SP4, 12 g cartridge, 0-10% MeOH gradient in CH₂Cl₂) to give a mixture (10 mg) containing the desired product which was further purified by flash chromatography (2× Biotage SP4, 12 g cartridge, C18 phase, 20-40% acetonitrile gradient in water) to give 7-acetyl-10a-(4-chlorophenyl)-1-[(5-methyl-1,2-oxazol-4-yl)carbonyl]-2,3,10,10a-tetrahydro-1H,5H-imidazo[1,2-a]pyrrolo[1,2-d]pyrazin-5-one (24) as a solid (3.5 mg, yield 14%).

Example of General Method D 10a-(4-chlorophenyl)-1-[(3-methyl-1,2-oxazol-4-yl)carbonyl]-8-(morpholin-4-ylmethyl)-2,3,10,10a-tetrahydro-1H,5H-imidazo[1,2-a]pyrrolo[1,2-d]pyrazin-5-one (25)

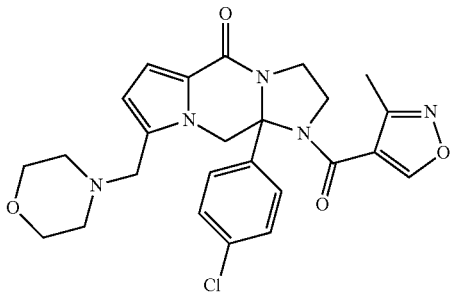 [SMILES: Cc1nocc1C(=O)N1CCN2C(=O)c3ccc(CN4CCOCC4)n3CC12c1ccc(Cl)cc1]

$^1$H NMR (400 MHz, CDCl$_3$): δ 2.20-2.39 (m, 4H), 2.44 (s, 3H), 3.29 (d, 1H, J 13.7 Hz), 3.44-3.65 (m, 5H), 3.70-3.85 (m, 2H), 3.98-4.08 (m, 1H), 4.31-4.39 (m, 2H), 6.02 (d, 1H, J 13.0 Hz), 6.05 (d, 1H, J 3.8 Hz), 6.86 (d, 1H, J 3.8 Hz), 7.24-7.30 (m, 2H), 7.38 (d, 2H, J 8.7 Hz), 8.52 (s, 1H). ESI-MI m/z [M+H]$^+$ 496.0.

Step 1

Potassium tert-butoxide (460 mg, 4.08 mmol) was added to a solution of methyl 5-({[tert-butyl(dimethyl)silyl]oxy}methyl)-1H-pyrrole-2-carboxylate (1.0 g, 3.71 mmol), and 2-bromo-1-(4-chlorophenyl)ethanone (890 mg, 4.08 mmol) in DMF at 0° C. The mixture was stirred from 0° C. to room temperature for 18 h. Water (10 mL) was added and the mixture extracted with EtOAc (30 mL). The organic layers were separated and washed with water (10 mL), dried (MgSO$_4$), filtered and concentrated in vacuo to give an orange residue. The residue was purified by flash column chromatography (Biotage SP4, 40 g cartridge, 5%-15% EtOAc gradient n-hexanes) to give a colourless gum (1 g) identified as a mixture of methyl 5-({[tert-butyl(dimethyl)silyl]oxy}methyl)-1-[2-(4-chlorophenyl)-2-oxoethyl]-1H-pyrrole-2-carboxylate and starting material (=3:1 ratio). The mixture was used without further purification. $^1$H NMR (400 MHz, CDCl$_3$): δ 0.09 (s, 6H), 0.92 (s, 9H), 3.71 (s, 3H), 4.62 (s, 2H), 5.66 (s, 2H), 6.79 (d, 1H, J 1.9 Hz), 6.95 (d, 1H, J 1.9 Hz), 7.46-7.51 (m, 2H), 7.91-7.97 (m, 2H).

Step 2

Aqueous sodium hydroxide solution (1 M, 1.78 mL) was added to a solution of methyl 5-({[tert-butyl(dimethyl)silyl]oxy}methyl)-1-[2-(4-chlorophenyl)-2-oxoethyl]-1H-pyrrole-2-carboxylate (375 mg, 0.89 mmol) in 1,4-dioxane (10 mL) and stirred at 70° C. for 2 h. The resultant brown solution was cooled to room temperature and concentrated in vacuo to −50% of its starting volume. The reaction mixture was acidified to ~pH 4 by the addition of aqueous HCl (1 M, 1.78 mL) and extracted with EtOAc. The aqueous layer was further extracted with EtOAc (2×10 mL) The combined organic layers were washed with brine, dried (MgSO$_4$), filtered and concentrated in vacuo to give 5-({[tert-butyl (dimethyl)silyl]oxy}methyl)-1-[2-(4-chlorophenyl)-2-oxoethyl]-1H-pyrrole-2-carboxylic acid as a brown gum (70% purity, 270 mg, yield ~95%) The mixture was used without further purification. ESI-MI m/z [M+Na]$^+$ 432.0.

Step 3

5-({[tert-butyl(dimethyl)silyl]oxy}methyl)-1-[2-(4-chlorophenyl)-2-oxoethyl]-1H-pyrrole-2-carboxylic acid (~70% pure, 268 mg, 0.46 mmol) was stirred at reflux in 1,2-dichloroethane with ethane-1,2-diamine (938 mL) for 18 h. The resultant suspension was concentrated in vacuo to give a residue. The mixture was treated with CH$_2$Cl$_2$ (30 mL) and water (30 mL) to form an emulsion that was filtered through a filter system. The organic layer was then separated. The aqueous layer was extracted with further CH$_2$Cl$_2$ (2×30 mL). The combined organic layers were dried (MgSO$_4$), filtered and concentrated in vacuo to give a waxy solid. Purification by flash column chromatography (Biotage SP4, 4 g cartridge, 0-5% MeOH gradient in CH$_2$Cl$_2$) gave 8-({[tert-butyl(dimethyl)silyl]oxy}methyl)-10a-(4-chlorophenyl)-2,3,10,10a-tetrahydro-1H,5H-imidazo[1,2-a]pyrrolo[1,2-d]-pyrazin-5-one as a off-white solid (85%, yield 42%). $^1$H NMR (400 MHz, MeOD): δ−0.11 (s, 3H), −0.04 (s, 3H), 0.79 (s, 9H), 2.79 (dt, 1H, J 12.2, 8.2 Hz), 3.32-3.37 (m, 1H), 3.51 (ddd, 1H, J 11.0, 7.9, 3.1 Hz), 3.71-3.79 (m, 1H), 4.20 (d, 1H, J 12.5 Hz), 4.44 (d, 1H, J 13.2 Hz), 4.56 (d, 1H, J 13.2 Hz), 4.76 (d, 1H, J 12.5 Hz), 6.05 (d, 1H, J 3.8 Hz), 6.77 (d, 1H, J 3.8 Hz), 7.25-7.35 (m, 4H).

Step 4

To generate the acid chloride 3-methyl-1,2-oxazole-4-carboxylic acid (100 mg, 0.79 mmol) was dissolved in CH$_2$Cl$_2$ (10 mL). Oxalyl chloride (0.6 mL, 2.75 mmol) and a drop of DMF were added at 0° C. The ice bath was removed and the mixture stirred for 1 h before the solvent and excess of oxalyl chloride were removed with a strong stream of nitrogen. The residue was further dried in vacuo. 8-({[tert-butyl(dimethyl)silyl]oxy}methyl)-10a-(4-chlorophenyl)-2,3,10,10a-tetrahydro-1H,5H-imidazo[1,2-a]pyrrolo[1,2-d]pyrazin-5-one (85 mg, 0.20 mmol) was dissolved in pyridine (4 mL) and the solution added to the previously generated acyl chloride in pyrine (1 mL) at 0° C. The ice bath was removed after 15 min and the mixture stirred at room temperature until completion (18 h). The resulting suspension was concentrated in vacuo and the residue partitioned between CH$_2$Cl$_2$ (20 mL) and a saturated aqueous solution of NaHCO$_3$ (10 mL). The organic layers were separated and washed further with a saturated aqueous solution of NaHCO$_3$ (10 mL) and brine (5 mL), dried (MgSO$_4$), filtered and concentrated in vacuo to give a yellow gum. This gum was purified by flash column chromatography (Biotage SP4, 12 g cartridge, 70-100% EtOAc gradient in n-hexanes) to give 8-({[tert butyl(dimethyl)silyl]oxy}methyl)-10a-(4-chlorophenyl)-1-[(3-methyl-1,2-oxazol-4-yl)carbonyl]-2,3,10,10a-tetrahydro-1H,5H-imidazo[1,2-a]pyrrolo[1,2-d]pyrazin-5-one as a pale yellow solid (76 mg, yield 71%). $^1$H NMR (400 MHz, MeOD): δ 0.11 (d, 6H, J 6.9 Hz), 0.90 (s, 9H), 2.35 (s, 3H), 3.78 (dt, 1H, J 11.5, 8.0 Hz), 4.05-4.21 (m, 2H), 4.31 (ddd, 1H, J 11.6, 8.5, 3.9 Hz), 4.46 (d, 1H, J 13.2 Hz), 4.65-4.77 (m, 2H), 5.96 (d, 1H, J 13.2 Hz), 6.16 (d, 1H, J 3.9 Hz), 6.77 (d, 1H, J 3.9 Hz), 7.26-7.32 (m, 2H), 7.38-7.43 (m, 2H), 9.10 (s, 1H).

Step 5

8-({[tert-butyl(dimethyl)silyl]oxy}methyl)-10a-(4-chlorophenyl)-1-[(3-methyl-1,2-oxazol-4-yl)carbonyl]-2,3,10,10a-tetrahydro-1H,5H-imidazo[1,2-a]pyrrolo[1,2-d]

pyrazin-5-one (75 mg, 0.14 mmol) was dissolved in a mixture acetic acid/THF/water (3:1:1, 2.5 mL). The solution was stirred at room temperature overnight. After this time there was not anymore starting material (monitored by LCMS). $CH_2Cl_2$ was added (20 mL) and washed with saturated aqueous solution of $NaHCO_3$ (3×7 mL). The organic layers were dried ($MgSO_4$), filtered and the filtrate concentrated in vacuo to yield a colourless gum. Purification by flash column chromatography (Biotage SP4, 4 g cartridge, 0-10% MeOH gradient in $CH_2Cl_2$) gave 10a-(4-chlorophenyl)-8-(hydroxymethyl)-1-[(3-methyl-1,2-oxazol-4-yl)carbonyl]-2,3,10,10a-tetrahydro-1H,5H-imidazo[1,2-a]pyrrolo[1,2-d]pyrazin-5-one as a white solid (33 mg, 55% yield). $^1$H NMR (400 MHz, d6-acetone): δ 2.32 (d, 3H, J 0.5 Hz), 3.75-3.85 (m, 1H), 4.19-4.36 (m, 3H), 4.43-4.47 (d, 1H, J 13.1 Hz), 4.58-4.69 (m, 2H), 6.03 (d, 1H, J 13.2 Hz), 6.09 (d, 1H, J 3.8 Hz), 6.61 (d, 1H, J 3.8 Hz), 7.28-7.32 (m, 2H), 7.50-7.54 (m, 2H), 9.16 (s, 1H).

ESI-MI m/z [M+H]$^+$ 427.2.

Step 6

10a-(4-chlorophenyl)-8-(hydroxymethyl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (26 mg, 0.061 mmol) in $CH_2Cl_2$ (50 mL) was added $MnO_2$ (26.5 mg, 0.30 mmol) and the reaction mixture was heated at 50° C. for 18 h. LCMS analysis after this time showed complete conversion of the starting material alcohol to the target aldehyde. The reaction mixture was filtered twice with a syringe filter and the filtrate was concentrated in vacuo to give 10a-(4-chlorophenyl)-1-[(3-methyl-1,2-oxazol-4-yl)carbonyl]-5-oxo-2,3,10,10a-tetrahydro-1H,5H-imidazo[1,2-a]pyrrolo[1,2-d]pyrazine-8-carbaldehyde as a white solid (24 mg, yield 92%) The crude product was used in the next step without further purification. ESI-MI m/z [m+H]$^+$ 425.1.

Step 7

10a-(4-chlorophenyl)-1-[(3-methyl-1,2-oxazol-4-yl)carbonyl]-5-oxo-2,3,10,10a-tetrahydro-1H,5H-imidazo[1,2-a]pyrrolo[1,2-d]pyrazine-8-carbaldehyde (25 mg, 0.059 mmol) and morpholine (10.2 µL) were combined and stirred at room temperature in 1,2-dichloroethane for 10 min. To the mixture was added sodium triacetoxyborohydride (24.7 mg). After 18 h at room temperature the reaction was quenched by the addition of a saturated aqueous solution of $NaHCO_3$ (1 mL) and $CH_2Cl_2$ (5 mL). The organic layers were washed with brine, dried ($MgSO_4$), filtered and evaporated in vacuo to give a yellow solid. The solid was purified by flash column chromatography (Biotage SP4, 4 g cartridge, 0-5% MeOH gradient in $CH_2Cl_2$) to give 10a-(4-chlorophenyl)-1-[(3-methyl-1,2-oxazol-4-yl)carbonyl]-8-(morpholin-4-ylmethyl)-2,3,10,10a-tetrahydro-1H,5H-imidazo[1,2-a]pyrrolo[1,2-d]pyrazin-5-one (25) as a white solid (26 mg, yield 89%).

The following compounds were similarly prepared using general method D.

| Cpd. No. | Structure | ESI-MI m/z [M + H]$^+$/$^1$H-NMR |
|---|---|---|
| 26 | 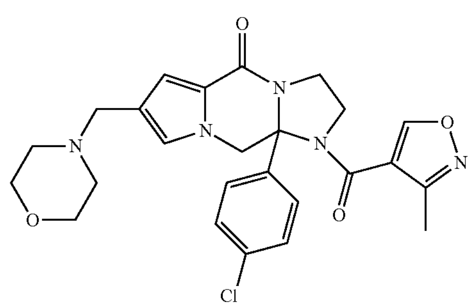 [SMILES: Cc1nocc1C(=O)N1CCN2C(=O)c3cc(CN4CCOCC4)cn3CC12c1ccc(Cl)cc1] | ESI-MI m/z [M + H]$^+$ 496.0. $^1$H NMR (400 MHz, CDCl$_3$): 2.40 (br s, 4H), 2.44 (s, 3H), 3.34 (s, 2H), 3.69 (br s, 4H), 3.73-3.86 (m, 2H), 4.00-4.10 (m, 1H), 4.32-4.41 (m, 1H), 4.54 (d, 1H, J 13.0 Hz), 5.58 (d, 1H, J 13.0 Hz), 6.65 (s, 1H), 6.86 (s, 1H), 7.22-7.38 (m, 4H), 8.54 (s, 1H). |
| 27 | 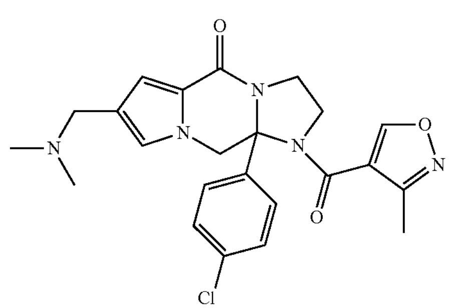 [SMILES: Cc1nocc1C(=O)N1CCN2C(=O)c3cc(CN(C)C)cn3CC12c1ccc(Cl)cc1] | ESI-MI m/z [M + H]$^+$ 454.0. $^1$H NMR (400 MHz, CDCl$_3$): δ 2.40 (br s, 6H), 2.44 (s, 3H), 3.41-3.54 (m, 1H), 3.60 (br s, 1H), 3.74-3.87 (m, 2H), 4.00-4.10 (m, 1H), 4.30-4.40 (m, 1H), 4.56 (d, 1H, J 13.0 Hz), 5.65 (d, 1H, J 13.4 Hz), 6.86 (s, 1H), 6.97 (br s, 1H), 7.23-7.39 (m, 4H), 8.53 (s, 1H). |

| Cpd. No. | Structure | ESI-MI m/z [M + H]+/1H-NMR |
|---|---|---|
| 28 | (structure: pyrrolo-imidazo-pyrazinone with HOCH2-pyrrole, 4-chlorophenyl, and 3-methylisoxazole-4-carbonyl substituents) | ESI-MI m/z [M + H]+ 427.2. 1H NMR (400 MHz, d6-acetone): δ 2.32 (d, 3H, J 0.5 Hz), 3.75-3.85 (m, 1H), 4.19-4.36 (m, 3H), 4.43-4.47 (d, 1H, J 13.1 Hz), 4.58-4.69 (m, 2H), 6.03 (d, 1H, J 13.2 Hz), 6.09 (d, 1H, J 3.8 Hz), 6.61 (d, 1H, J 3.8 Hz), 7.28-7.32 (m, 2H), 7.50-7.54 (m, 2H), 9.16 (s, 1H). |
| 29 | (structure: regioisomeric pyrrolo-imidazo-pyrazinone with HOCH2-pyrrole, 4-chlorophenyl, and 3-methylisoxazole-4-carbonyl substituents) | ESI-MI m/z [M + H]+ 427.2. 1H NMR (400 MHz, CDCl3): δ 2.44 (s, 3H), 3.74-3.84 (m, 2H), 4.00-4.09 (m, 1H), 4.33-4.41 (m, 1H), 4.51 (d, 2H, J 5.6 Hz), 5.55 (d, 1H, J 12.8 Hz), 5.61 (d, 1H, J 13.2 Hz), 6.72 (d, 1H, J 1.8 Hz), 6.91 (d, 1H, J 1.6 Hz), 7.26-7.39 (m, 4H), 8.54 (s, 1H). |

Example of General Method E

Route (a)

10a-(4-chlorophenyl)-1-[(3-methyl-1,2-oxazol-4-yl)carbonyl]-7-(pyridin-3-yl)-2,3,10,10a-tetrahydro-1H,5H-imidazo[1,2-a]pyrrolo[1,2-d]pyrazin-5-one (30)

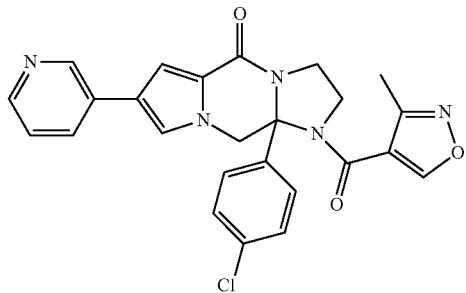 [SMILES: Cc1nocc1C(=O)N1CCN2C(=O)c3cc(-c4cccnc4)cn3CC12c1ccc(Cl)cc1]

1H NMR (400 MHz, d6-acetone): δ 2.36 (s, 3H), 3.76-3.88 (m, 1H), 4.17-4.25 (m, 1H), 4.27-4.38 (m, 2H), 4.72 (d, 1H, J 13.2 Hz), 5.85 (d, 1H, J 13.4 Hz), 7.17 (d, 1H, J 1.7 Hz), 7.29-7.38 (m, 3H), 7.50-7.55 (m, 2H), 7.64 (d, 1H, J 1.7 Hz), 7.92 (ddd, 1H, J 7.9, 2.3, 1.9 Hz), 8.38 (dd, 1H, J 4.8, 1.6 Hz), 8.82 (d, 1H, J 2.0 Hz), 9.2 (s, 1H). ESI-MI m/z [M+H]+ 474.2.

Step 1

Methyl 4-bromo-1H-pyrrole-2-carboxylate (250 mg, 1.23 mmol) and 2-bromo-1-(4-chloro-phenyl)-ethanone (315 mg, 1.35 mmol) were dissolved in DMF (50 mL). The reaction mixture was cooled to 0° C. before potassium tert-butoxide (125 mg, 1.11 mmol) was added to the reaction mixture in small portions. The resulting suspension was allowed to warm to room temperature then stirred for 10 min. The reaction mixture was diluted with water (100 mL) and extracted with CH2Cl2 (3×100 mL). The organic layers were combined, dried and concentrated in vacuo to give a residue that was purified using flash chromatography (Biotage SP4, 40 g cartridge, 0-15% EtOAc gradient in n-hexanes) to give the target compound methyl 4-bromo-1-[2-(4-chlorophenyl)-2-oxoethyl]-1H-pyrrole-2-carboxylate (244 mg) contaminated with an impurity. The mixture was used in the next step without further purification.

Step 2

LiOH H2O (0.2 M, 6.8 mL, 1.36 mmol) was added portionwise to a solution of crude methyl 4-bromo-1-[2-(4-chlorophenyl)-2-oxoethyl]-1H-pyrrole-2-carboxylate (210 mg, 0.39 mmol) in THF (0.5 mL), and the mixture stirred at 40° C. for 3 h, after which time the TLC analysis showed consumption of starting material ester. The reaction mixture was diluted with aqueous NaOH solution (1 M) (50 mL) and the mixture washed with CH2Cl2 (100 mL). The aqueous layer was acidified to pH 2 with aqueous HCl solution (1 M) and was extracted with CH2Cl2 containing 30% of propan-2-ol (2×150 mL). The organic layers were combined, dried (MgSO4) and concentrated in vacuo to give 4-bromo-1-[2-(4-chlorophenyl)-2-oxoethyl]-1H-pyrrole-2-carboxylic acid (100 mg, yield 75%). This crude material was used in the next step without further purification.

Step 3

To a solution of crude 4-bromo-1-[2-(4-chlorophenyl)-2-oxoethyl]-1H-pyrrole-2-carboxylic acid (100 mg, 0.29 mmol) dissolved in a mixture of xylenes (10 mL) and ethanol (3 mL) was added ethane-1,2-diamine (100 μL, 1.5 mmol). The reaction mixture was heated at reflux. After 90 minutes (monitored by LCMS) the mixture was concentrated in vacuo and the resultant residue purified flash chromatography (Biotage SP4, 40 g cartridge, 0-5% MeOH gradient in CH$_2$Cl$_2$) to give 7-bromo-10a-(4-chlorophenyl)-2,3,10,10a-tetrahydro-1H,5H-imidazo[1,2-a]pyrrolo[1,2-d]pyrazin-5-one as a light yellow solid (73 mg, yield: 68%).

$^1$H NMR (400 MHz, d6-acetone): δ 2.74-2.82 (m, 1H), 3.30-3.38 (m, 1H), 3.44 (ddd, 1H, J 7.7, 3.4, 1.3 Hz), 3.67-3.75 (m, 1H), 4.39 (d, 1H, J 12.5 Hz), 4.69 (d, 1H, J 12.5 Hz), 6.68 (d, 1H, 1.8 Hz), 6.79 (d, 1H, J 1.7 Hz), 7.32-7.40 (m, 4H).

Step 4a 7-bromo-10a-(4-chlorophenyl)-2,3,10,10a-tetrahydro-1H,5H-imidazo[1,2-a]pyrrolo[1,2-d]pyrazin-5-one (50 mg, 0.14 mmol), pyridine-3-boronic acid (18.5 mg, 0.15 mmol), dichlorobis(triphenylphosphine)palladium(II) (1.9 mg, 2.7 μmol) and sodium carbonate (22 mg, 0.21 mmol) were suspended in a mixture of 1,2-dimethoxyethane (1.4 mL), ethanol (200 μL) and water (300 μL). The reaction vessel was flushed with argon, sealed and heated in a microwave reactor at 150° C. for 10 min. After this time water (50 mL) was added and the mixture extracted with CH$_2$Cl$_2$. The organic layer was separated, dried (MgSO$_4$) and concentrated in vacuo to give a crude mixture. This mixture was purified by flash chromatography (Biotage SP4, 12 g cartridge, 0-10% MeOH gradient in CH$_2$Cl$_2$) to give 10a-(4-chlorophenyl)-7-(pyridin-3-yl)-2,3,10,10a-tetrahydro-1H,5H-imidazo[1,2-a]pyrrolo[1,2-d]pyrazin-5-one as a white solid (20 mg, 40% yield). $^1$H NMR (400 MHz, d6-acetone): δ 3.30-3.31 (m, 1H), 3.33-3.40 (m, 1H), 3.43-3.50 (m, 1H). 3.75 (dt, 1H, J 10.8, 8.0 Hz), 4.46 (d, 1H, J 12.4 Hz), 4.74 (d, 1H, J 12.4 Hz), 7.14 (d, 1H, J 1.8 Hz), 7.23 (d, 1H, J 1.8 Hz), 7.27 (ddd, 1H, J 8.0, 4.8, 0.9 Hz), 7.32-7.36 (m, 2H), 7.40-7.44 (m, 2H), 7.85 (ddd, 1H, J 7.9, 2.4, 1.7 Hz), 8.34 (dd, 1H, J 4.7, 1.6 Hz), 8.75 (dd, 1H, J 2.4, 0.8 Hz).

Step 5a

To generate the acid chloride, oxalyl chloride (45 μL, 0.55 mmol) and DMF (1 drop) were added to a suspension of 3-methyl-1,2-oxazole-4-carboxylic acid (35 mg, 0.27 mmol) in CH$_2$Cl$_2$ (0.5 mL) at 0° C. The suspension was allowed to stir for a further 15 min at 0° C. followed by 2 h at room temperature. The resulting solution was concentrated in vacuo (without heating) to give a brown oil that was azeotroped with n-hexanes (2×1 mL) in vacuo to give the acid chloride as an oil. A cloudy suspension of 10a-(4-chlorophenyl)-7-(pyridin-3-yl)-2,3,10,10a-tetrahydro-1H,5H-imidazo[1,2-a]pyrrolo[1,2-d]pyrazin-5-one (20 mg, 55 umol) in pyridine (0.5 mL) was added to a suspension of the acid chloride (generated as above, 0.27 mmol) in pyridine (0.5 mL) and CH$_2$Cl$_2$ (0.5 mL) at 0° C. The resultant mixture was stirred at 0° C. to room temperature for 18 h. The reaction (monitored by LCMS) required the addition of a second batch of acid chloride (prepared as above) and was stirred for a further 3 h at room temperature. The resultant reaction mixture was then quenched with a saturated aqueous solution of NaHCO$_3$ (25 mL) and extracted with CH$_2$Cl$_2$ (2×25 mL). The organic fractions were combined, dried (MgSO$_4$) and concentrated in vacuo to yield an oil that was purified using flash chromatography (Biotage SP4, 12 g cartridge, 0-10% MeOH gradient in EtOAc) and reverse-phase chromatography (Biotage SP4, 12 g cartridge, C18 phase, 35-50% acetonitrile gradient in water) to give 10a-(4-chlorophenyl)-1-[(3-methyl-1,2-oxazol-4-yl)carbonyl]-7-(pyridin-3-yl)-2,3,10,10a-tetrahydro-1H,5H-imidazo[1,2-a]pyrrolo[1,2-d]pyrazin-5-one (30) as a white solid (13 mg, yield 50%).

10a-[4-(hydroxymethyl)phenyl]-1-[(3-methyl-1,2-oxazol-4-yl)carbonyl]-7-(pyridin-3-yl)-2,3,10,10a-tetrahydro-1H,5H-imidazo[1,2-a]pyrrolo[1,2-d]pyrazin-5-one (95)

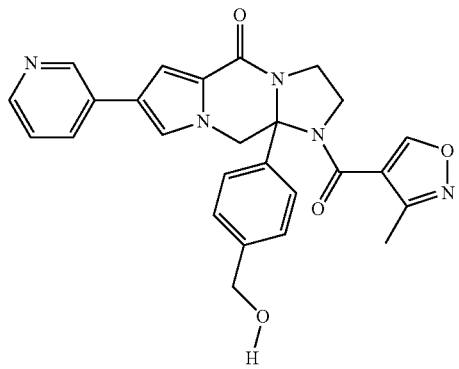 [SMILES: Cc1nocc1C(=O)N1CCN2C(=O)c3cc(-c4cccnc4)cn3CC12c1ccc(CO)cc1]

$^1$H-NMR (400 MHz, CDCl$_3$): δ 2.45 (br s, 3H), 3.78-3.88 (m, 2H), 4.03-4.11 (m, 1H), 4.32-4.44 (m, 1H), 4.66 (s, 2H), 4.67 (d, 1H, J 12.9 Hz), 5.74 (d, 1H, J 13.0 Hz), 7.03 (d, 1H, J 1.8 Hz), 7.22 (d, 1H, J 1.8 Hz), 7.25 (ddd, 1H, J 7.9, 4.8, 0.8 Hz), 7.31-7.35 (m, 2H), 7.42-7.46 (m, 2H), 7.71 (ddd, 1H, J 7.9, 2.3, 1.6 Hz), 8.43 (dd, 1H, J 4.8, 1.6 Hz), 8.53 (br s, 1H), 8.72 (dd, 1H, J 2.3, 0.8 Hz). ESI-MI m/z [M+H]$^+$ 470.2.

Step 4a 7-bromo-10a-[4-(hydroxymethyl)phenyl]-2,3,10,10a-tetrahydro-1H,5H-imidazo[1,2-a]pyrrolo[1,2-d]-pyrazin-5-one (84 mg, 0.23 mmol), dichlorobis(triphenylphosphine)palladium(II) (6.5 mg, 9.3 μmol), 3-pyridine boronic acid (34 mg, 0.28 mmol) and an aqueous solution of sodium carbonate (2M) (58 mg, 28.8 μl, 0.41 mmol) were suspended in a mixture of 1,2-dimethoxyethane (2.5 mL), ethanol (200 μL) and water (300 μL). The reaction vessel was flushed with argon and heated at 120° C. After 45 minutes the reaction was complete. The mixture was diluted with CH$_2$Cl$_2$ (5 mL) then washed with H$_2$O. The aqueous was extracted with CH$_2$Cl$_2$ (2×5 mL). The combined organic was evaporated to dryness to give crude 10a-[4-(hydroxymethyl)phenyl]-7-(pyridin-3-yl)-2,3,10,10a-tetrahydro-1H,5H-imidazo[1,2-a]pyrrolo[1,2-d]pyrazin-5-one (80 mg) that was used in the next step without further purification. ESI-MI m/z [M+H]$^+$ 361.9.

Step 5a

To generate the acid chloride, oxalyl chloride (56 μl, 0.67 mmol) and DMF (1 drop) were added to 3-methyl-1,2-oxazole-4-carboxylic acid (85 mg, 0.67 mmol) in CH$_2$Cl$_2$ (2 mL) at 0° C. The suspension was allowed to stir 15 min at 0° C. followed by 1 hour at room temperature. The resulting solution was concentrated in vacuo (without heating) to give an oil that was dissolved in CH$_2$Cl$_2$ and concentrated in vacuo. To a chilled (0° C.) suspension of the acid chloride (generated as above, 0.67 mmol) in pyridine (0.5 mL) was added a cloudy mixture of 10a-[4-(hydroxymethyl)phenyl]-7-(pyridin-3-yl)-2,3,10,10a-tetrahydro-1H,5H-imidazo[1,2-a]pyrrolo[1,2-d]pyrazin-5-one (80 mg, 0.22 mmol max) in pyridine (1 mL). The reaction mixture was warmed to room temperature and stirred overnight. To the reaction mixture was then added another batch of freshly prepared acid chloride (0.67 mmol, generated as above) in pyridine and the mixture stirred over the weekend. Water (5 mL) was added and the mixture extracted with CH$_2$Cl$_2$ (3×5 mL). The organic fractions were combined, dried (MgSO$_4$) and concentrated in vacuo. The crude residue obtained was purified by flash chromatography (Biotage SP4, 12 g cartridge, 0 to 10% MeOH in EtOAc 10 CV and hold 10% MeOH 5 CV) to give 4-{1-[(3-methyl-1,2-oxazol-4-yl)carbonyl]-5-oxo-7-(pyridin-3-yl)-2,3-dihydro-1H,5H-imidazo[1,2-a]pyrrolo[1,2-d]pyrazin-10a(10H)-yl}benzyl 3-methyl-1,2-oxazole-4-carboxylate (9.3 mg, yield 7% over two steps). ESI-MI m/z [M+H]$^+$ 579.2.

Step 6a

Aqueous LiOH solution (1M)(0.75 mg, 0.018 mmol) was added to a solution of 4-{1-[(3-methyl-1,2-oxazol-4-yl)carbonyl]-5-oxo-7-(pyridin-3-yl)-2,3-dihydro-1H,5H-imidazo[1,2-a]pyrrolo[1,2-d]-pyrazin-10a(10H)-yl}benzyl 3-methyl-1,2-oxazole-4-carboxylate (9.6 mg, 0.016 mmol) in a mixture MeOH/CH$_3$CN (2 mL) and stirred at room temperature for 3 h. Brine (1 mL) was added and the resultant mixture was extracted with EtOAc (3×1 mL). The organic layers were combined, dried (MgSO$_4$) and concentrated in vacuo to give a residue that was purified by flash chromatography (Biotage SP4 gradient 0-10% MeOH in EtOAc, 10CV and hold 10CV). The compound 10a-[4-(hydroxymethyl)phenyl]-1-[(3-methyl-1,2-oxazol-4-yl)carbonyl]-7-(pyridin-3-yl)-2,3,10,10a-tetrahydro-1H,5H-imidazo[1,2-a]pyrrolo[1,2-d]pyrazin-5-one (95) was isolated as a white solid (2.8 mg, yield 37%).

The following compounds were similarly prepared using general method E: Route (a).

| Cpd. No. | Structure | ESI-MI m/z [M + H]$^+$/$^1$H-NMR |
|---|---|---|
| 31 | 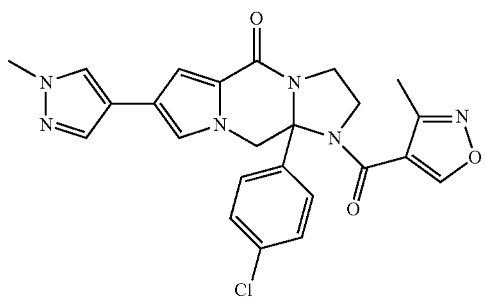 [SMILES: Cc1nocc1C(=O)N1CCN2C(=O)c3cc(-c4cnn(C)c4)cn3CC12c1ccc(Cl)cc1] | ESI-MI m/z [M + H]$^+$ 477.2. $^1$H NMR (400 MHz, d6-acetone): δ 2.35 (s, 3H), 3.71-3.79 (m, 1H), 3.84 (s, 3H), 4.14-4.23 (m, 1H), 4.24-4.35 (m, 2H), 4.63 (d, 1H, J 13.1 Hz), 5.73 (d, 1H, J 13.0 Hz), 6.86 (d, 1H, J 1.8 Hz), 7.23 (d, 1H, J 1.7 Hz), 7.32-7.37 (m, 2H), 7.47-7.52 (m, 2H), 7.55 (s, 1H), 9.16 (s, 1H). |
| 82 | 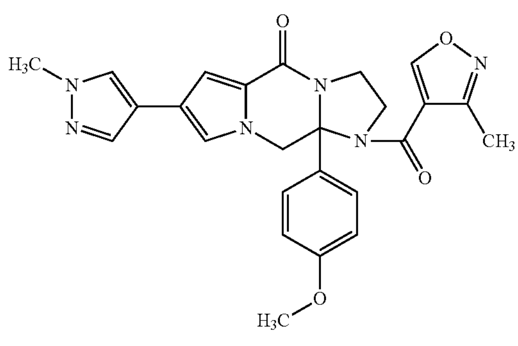 | ESI-MI m/z [M + H]$^+$ 473.0. $^1$H NMR (400 MHz, CDCl$_3$): δ 2.44 (s, 3H), 3.74 (s, 3H), 3.80 (dt, 2H, J 11.5, 5.1 Hz), 3.88 (s, 3H), 3.95-4.07(m, 1H), 4.27-4.39 (m, 1H), 4.57 (d, 1H, J 12.9 Hz), 5.60 (d, 1H, J 12.9 Hz), 6.76-6.83 (m, 3H), 6.97 (s, 1H), 7.33 (d, 2H, J 8.8 Hz), 7.39 (s, 1H), 7.53 (s, 1H), 8.52 (br s, 1H). |
| 83 | 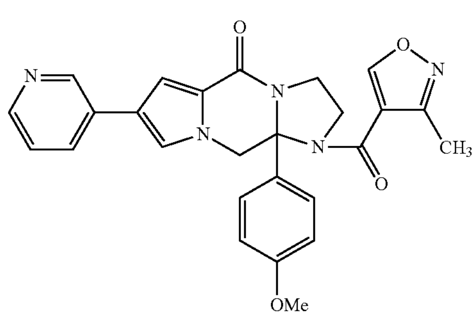 [SMILES: COc1ccc(C23Cn4cc(-c5cccnc5)cc4C(=O)N2CCN3C(=O)c2conc2C)cc1] | ESI-MI m/z [M + H]$^+$ 470.1. $^1$H NMR (400 MHz, CDCl$_3$): δ 2.44 (s, 3H), 3.74 (s, 3H), 3.76-3.88 (m, 2H), 3.98-4.08 (m, 1H), 4.27-4.39 (m, 1H), 4.63 (d, 1H, J 12.9 Hz), 5.69 (d, 1H, J 12.9 Hz), 6.81 (br d, 2H, J 8.9 Hz), 7.04 (d, 1H, J 1.4 Hz), 7.21 (d, 1H, J 1.3 Hz), 7.27-7.32 (m, 1H), 7.33 (dd, 2H, J 20.7, 5.8 Hz), 7.74 (br d, 1H, J 15.3 Hz), 8.42 (br s, 1H), 8.54 (s, 1H), 8.73 (br s, 1H). |

-continued

| Cpd. No. | Structure | ESI-MI m/z [M + H]⁺/¹H-NMR |
|---|---|---|
| 84 | 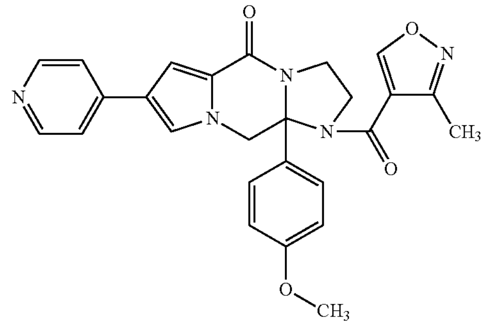 [SMILES: COc1ccc(C23Cn4cc(-c5ccncc5)cc4C(=O)N2CCN3C(=O)c2conc2C)cc1] | ESI-MI m/z [M + H]⁺ 470.1. ¹H NMR (400 MHz, CDCl₃): δ 2.45 (s, 3H), 3.74 (s, 3H), 3.78-3.89 (m, 2H), 4.01-4.08 (m, 1H), 4.29-4.39 (m, 1H), 4.65 (d, 1H, J 13.1 Hz), 5.71 (d, 1H, J 13.0 Hz), 6.82 (br d, 2H, J 8.8 Hz), 7.14 (br s, 1H), 7.29 (d, 1H, J 1.4 Hz), 7.33-7.39 (m, 4H), 8.52 (d, J 6.0 Hz, 3H). |
| 85 | 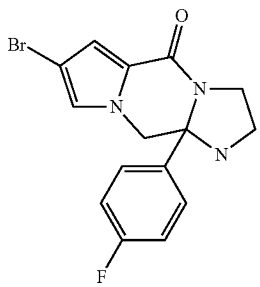 [SMILES: O=C1c2cc(Br)cn2CC2(c3ccc(F)cc3)NCCN12] | ESI-MI m/z [M + H]⁺ 351.8. ¹H NMR (400 MHz, CDCl₃): δ 2.35 (br s, 1H), 2.89-2.99 (m, 1H), 3.31 (ddd, 1H, J 12.0, 7.5, 4.3 Hz), 3.45-3.55 (m, 1H), 3.88 (dt, 1H, J 11.3, 7.5 Hz), 4.18 (d, 1H, J 12.1 Hz), 4.38 (d, 1H, J 12.1 Hz), 6.49 (d, 1H, J 1.7 Hz), 6.90 (d, 1H, J 1.6 Hz), 6.95-7.02 (m, 2H), 7.29-7.35 (m, 2H). |
| 86 | 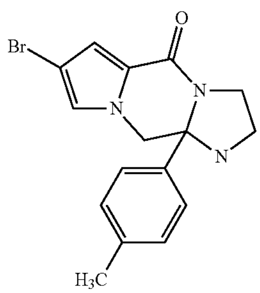 [SMILES: Cc1ccc(C23Cn4cc(Br)cc4C(=O)N2CCN3)cc1] | ESI-MI m/z [M + H]⁺ 346.1. ¹H NMR (400 MHz, CDCl₃): δ 7.21 (d, 2H, J 8.3 Hz), 7.10 (br d, 2H, J 7.9 Hz), 6.88 (d, 1H, J 1.7 Hz), 6.48 (d, 1H, J 1.7 Hz), 4.42 (d, 1H, J 12.0 Hz), 4.17 (d, 1H, J 12.0 Hz), 3.93 (dt, 1H, J 11.2, 7.2 Hz), 3.50 (ddd, 1H, J 11.3, 7.5, 4.9 Hz), 3.27 (ddd, 1H, J 12.2, 7.4, 4.9 Hz), 2.98 (dt, 1H, J 12.2, 7.2 Hz,), 2.34 (br s, 1H), 2.30 (s, 3H). |
| 87 | 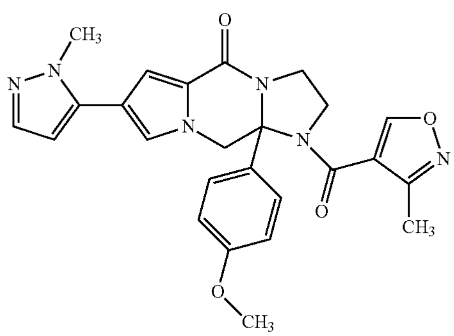 [SMILES: COc1ccc(C23Cn4cc(-c5ccnn5C)cc4C(=O)N2CCN3C(=O)c2conc2C)cc1] | ESI-MI m/z [M + H]⁺ 473.1. ¹H NMR (400 MHz, CDCl₃): δ 2.45 (t, 3H, J 1.8 Hz), 3.77 (s, 3H), 3.80-3.87 (m, 2H), 3.91 (s, 3H), 4.00-4.08 (m, 1H), 4.30-4.41 (m, 1H), 4.64 (d, 1H, J 12.9 Hz), 5.69 (d, 1H, J 13.0 Hz), 6.22 (d, 1H, J 1.9 Hz,), 6.80-6.85 (m, 2H), 6.86 (d, 1H, J 1.7 Hz), 7.06 (d, 1H, J 1.7 Hz), 7.34-7.39 (m, 2H), 7.42 (d, 1H, J 1.9 Hz), 8.52 (s, 1H). |
| 88 | 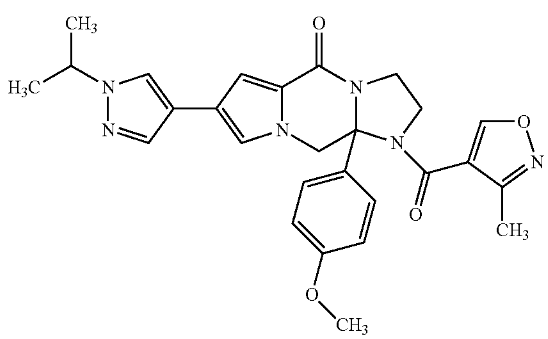 [SMILES: COc1ccc(C23Cn4cc(-c5cnn(C(C)C)c5)cc4C(=O)N2CCN3C(=O)c2conc2C)cc1] | ESI-MI m/z [M + H]⁺ 501.1. ¹H NMR (400 MHz, CDCl₃): δ 1.50 (d, 6H, J 6.7 Hz), 2.45 (s, 3H), 3.75 (s, 3H), 3.76-3.85 (m, 2H), 3.97-4.08 (m, 1H), 4.29-4.39 (m, 1H), 4.47 (hept, 1H, J 6.7 Hz), 4.58 (d, 1H, J 12.8 Hz), 5.60 (d, 1H, J 12.9 Hz), 6.77-6.83 (m, 3H), 7.00 (d, 1H, J 1.7 Hz), 7.31-7.37 (m, 2H), 7.46 (d, 1H, J 0.6 Hz), 7.56 (br d, 1H, J 0.7 Hz), 8.52 (br s, 1H). |

-continued

| Cpd. No. | Structure | ESI-MI m/z [M + H]+/1H-NMR |
|---|---|---|
| 90 | 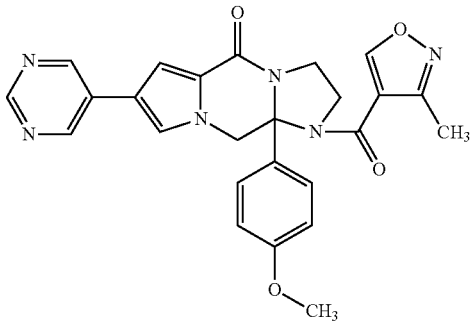 [SMILES: COc1ccc(C23Cn4cc(-c5cncnc5)cc4C(=O)N2CCN3C(=O)c2conc2C)cc1] | ESI-MI m/z [M + H]+ 471.1. 1H NMR (400 MHz, CDCl3) δ 2.45 (s, 3H), 3.74 (s, 3H), 3.75-3.93 (m, 2H), 4.06 (dt, 1H, J 9.1, 7.9 Hz,), 4.29-4.39 (m, 1H), 4.65 (br d, 1H, J 12.9 Hz), 5.73 (d, 1H, J 13.0 Hz), 6.79-6.85 (m, 2H), 7.07 (d, 1H, J 1.3 Hz), 7.23 (d, 1H, J 1.4 Hz), 7.32-7.40 (m, 2H), 8.53 (br s, 1H), 8.80 (d, 2H, J 1.6 Hz), 8.98-9.05 (m, 1H). |
| 91 | 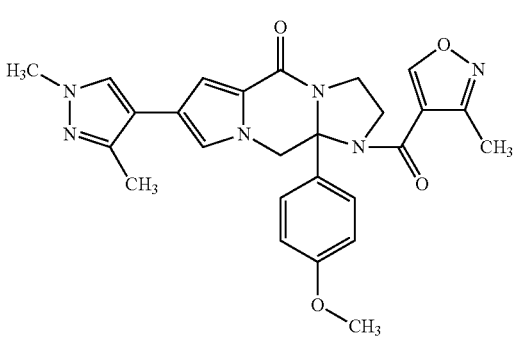 | ESI-MI m/z [M + H]+ 487.2. 1H NMR (400 MHz, CDCl3) δ 2.32 (s, 3H), 2.45 (s, 3H), 3.76 (s, 3H), 3.77-3.81 (m, 2H), 3.82 (s, 3H), 3.98-4.07 (m, 1H), 4.30-4.40 (m, 1H), 4.59 (d, 1H, J 12.8 Hz), 5.62 (d, 1H, J 12.9 Hz), 6.75 (d, 1H, J 1.6 Hz), 6.81 (br d, 2H, J 8.9 Hz), 6.98 (d, 1H, J 1.5 Hz), 7.29-7.38 (m, 3H), 8.52 (br s, 1H). |
| 92 | 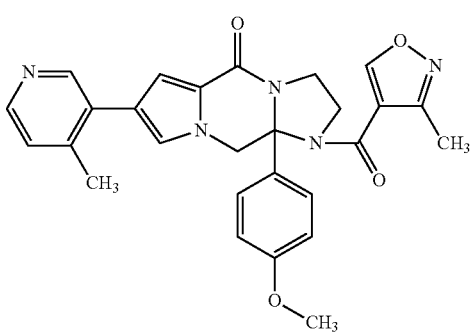 [SMILES: COc1ccc(C23Cn4cc(-c5cnccc5C)cc4C(=O)N2CCN3C(=O)c2conc2C)cc1] | ESI-MI m/z [M + H]+ 484.2. 1H NMR (400 MHz, CDCl3) δ 2.38 (d, 3H, J 11.2 Hz), 2.45 (s, 3H), 3.77 (s, 3H), 3.80-3.89 (m, 2H),- 3.98-4.17 (m, 1H), 4.30-4.42 (m, 1H), 4.66 (d, 1H, J 12.9 Hz), 5.70 (d, 1H, J 12.9 Hz), 6.80-6.87 (m, 3H), 7.09 (br s, 1H), 7.12 (br d, 1H, J 4.8 Hz), 7.37 (br d, 2H, J 8.8 Hz), 8.34 (d, 1H, J 5.0 Hz), 8.48 (s, 1H), 8.53 (br s, 1H). |
| 94 | 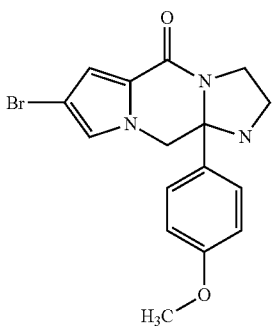 [SMILES: COc1ccc(C23Cn4cc(Br)cc4C(=O)N2CCN3)cc1] | ESI-MI m/z [M + H]+ 363.9. 1H NMR (400 MHz, CDCl3): δ 7.22-7.25 (m, 2H), 6.88 (d, 1H, J 1.7 Hz), 6.78-6.83 (m, 2H), 6.49 (d, 1H, J 1.7 Hz), 4.39 (d, 1H, J 12.0 Hz), 4.16 (d, 1H, J 12.0 Hz), 3.86-3.95 (m, 1H), 3.77 (s, 3H), 3.50 (ddd, 1H, J 11.3, 7.5, 4.7 Hz), 3.22-3.33 (m, 1H), 2.92-3.04 (m, 1H), 2.33 (br s, 1H). |

Example of General Method E

Route (b)

10a-(4-methoxyphenyl)-1-[(3-methyl-1,2-oxazol-4-yl)carbonyl]-5-oxo-2,3,10,10a-tetrahydro-1H,5H-imidazo[1,2-a]pyrrolo[1,2-d]pyrazine-7-carbonitrile (89)

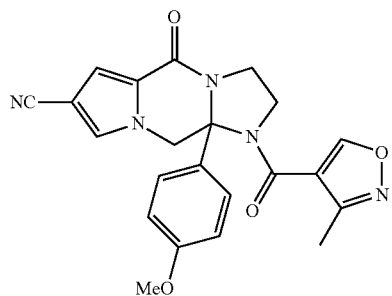 [SMILES: COc1ccc(C23Cn4cc(C#N)cc4C(=O)N2CCN3C(=O)c2conc2C)cc1]

$^1$H-NMR (400 MHz, CDCl$_3$): δ 2.44 (s, 3H), 3.77 (s, 3H), 3.77-3.90 (m, 2H), 4.00-4.09 (m, 1H), 4.31 (ddd, 1H, J 11.4, 9.6, 5.6 Hz), 4.62 (d, 1H, J 13.0 Hz), 5.74 (d, 1H, J 13.0 Hz), 6.80-6.85 (m, 2H), 7.11-7.14 (m, 2H), 7.29-7.33 (m, 2H), 8.51 (s, 1H).
ESI-MI m/z [m+H]$^+$ 418.1.

Step 1

To a mixture of methyl 4-bromo-1H-pyrrole-2-carboxylate (1 g, 4.9 mmol) and 2-bromo-1-(4-methoxyphenyl)ethanone (1.23 g, 5.3 mmol) in DMF (30 mL) was added potassium tert-butoxide (0.60 g, 5.4 mmol) portionwise at −15° C. The mixture was stirred at that temperate for 15 minutes and then at room temperature for 1 hour. The mixture was quenched with aqueous HCl (1M) and then extracted with EtOAc (3×100 mL). The organic layers were washed with brine, water and then concentrated in vacuo to give a liquid. This was azeotroped with toluene to give a residue corresponding to methyl 1-[2-(4-methoxyphenyl)-2-oxoethyl]-1H-pyrrole-2-carboxylate. ESI-MI m/z [M+H]$^+$ 353.8. The crude was used in the next step without purification

Step 3

A mixture of methyl 1-[2-(4-methoxyphenyl)-2-oxoethyl]-1H-pyrrole-2-carboxylate (80% pure) and ethylene diamine (5 mL, 74.9 mmol) in 1,4-dioxane (40 mL) was heated at 110° C. overnight. The reaction mixture was then concentrated in vacuo to give a residue that was purified by flash chromatography (2% to 10% MeOH gradient in CH$_2$Cl$_2$). To give 7-bromo-10a-(4-methoxyphenyl)-2,3,10,10a-tetrahydro-1H,5H-imidazo[1,2-a]pyrrolo[1,2-d]-pyrazin-5-one (1.2 g, 3.3 mmol, yield 67% over two steps). ESI-MI m/z [M+H]$^+$ 363.9.

Step 4b 7-bromo-10a-(4-methoxyphenyl)-2,3,10,10a-tetrahydro-1H,5H-imidazo[1,2-a]pyrrolo[1,2-d]pyrazin-5-one (100 mg, 0.28 mmol), zinc cyanide (50 mg, 0.42 mmol) and palladium (0) tetrakistriphenylphosphine (32 mg, 0.03 mmol) were suspended in dry DMF (3 mL) in a microwave vial flushed with argon. The mixture was heated in the microwave reactor at 160° C. for 20 minutes. A saturated aqueous solution of NaHCO$_3$ (50 mL) was added and the mixture extracted with CH$_2$Cl$_2$ containing 20% of isopropyl alcohol. The organic layers were dried (MgSO$_4$), filtrated and concentrated in vacuo. The resulting residue was purified by flash chromatography (Biotage SP4, 12 g cartridge, gradient 0-5% methanol in CH$_2$Cl$_2$) to give 10a-(4-methoxyphenyl)-5-oxo-2,3,10,10a-tetrahydro-1H,5H-imidazo[1,2-a]pyrrolo[1,2-d]pyrazine-7-carbonitrile (50 mg, yield 58%) ESI-MI m/z [M+H]$^+$ 308.9. Used in the next step without further purification.

Step 5b

To generate the acid chloride, oxalyl chloride (100 μL, 1.18 mmol) and DMF (1 drop) were added to 3-methyl-1,2-oxazole-4-carboxylic acid (100 mg, 0.84 mmol) in CH$_2$Cl$_2$ (2 mL) at 0° C. The suspension was allowed to stir 15 min at 0° C. followed by 1 hour at room temperature. The resulting solution was concentrated in vacuo (without heating) to give an oil that was dissolved in CH$_2$Cl$_2$ and concentrated in vacuo. To a chilled (0° C.) suspension of the acid chloride (generated as above, 0.84 mmol) in pyridine (0.5 mL) was added a cloudy mixture of 10a-(4-methoxyphenyl)-5-oxo-2,3,10,10a-tetrahydro-1H,5H-imidazo[1,2-a]pyrrolo[1,2-d]pyrazine-7-carbonitrile (50 mg, 0.16 mmol) in pyridine (0.5 mL). The reaction mixture was warmed to room temperature and stirred overnight. The reaction mixture was then diluted with water (5 mL) and extracted with CH$_2$Cl$_2$ (3×5 mL). The organic fractions were combined, dried (MgSO$_4$) and concentrated in vacuo to give a crude residue that was purified by flash chromatography (Biotage SP4 12 g cartridge, 0 to 5% MeOH in EtOAc) and reverse phase chromatography (5-50s-55-100% acetonitrile-water, water contained 0.1% formic acid). The compound 10a-(4-methoxyphenyl)-1-[(3-methyl-1,2-oxazol-4-yl)carbonyl]-5-oxo-2,3,10,10a-tetrahydro-1H,5H-imidazo[1,2-a]pyrrolo[1,2-d]pyrazine-7-carbonitrile (89) was isolated as a white solid (2.2 mg, yield 3%).

Compound 147 was similarly prepared using General Method E: Route (b) followed by a reduction step.

7-(aminomethyl)-10a-(4-methoxyphenyl)-1-[(3-methyl-1,2-oxazol-4-yl)carbonyl]-2,3,10,10a-tetrahydro-1H,5H-imidazo[1,2-a]pyrrolo[1,2-d]pyrazin-5-one; trifluoroacetate salt (147)

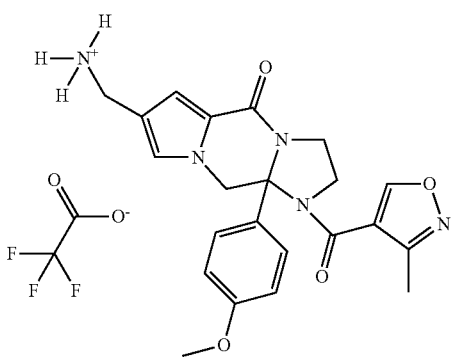 [SMILES: O=C([O-])C(F)(F)F ; COc1ccc(C23Cn4cc(C[NH3+])cc4C(=O)N2CCN3C(=O)c2conc2C)cc1]

$^1$H NMR (400 MHz, d6-DMSO): δ 2.30 (s, 3H), 3.65-3.77 (m, 4H), 3.82 (s, 2H), 3.95-4.12 (m, 2H), 4.12-4.22 (m, 1H), 4.54 (d, 1H, J 13.1 Hz), 5.79 (d, 1H, J 13.1 Hz), 6.76 (s, 1H), 6.85 (d, 2H, J 8.7 Hz), 7.24 (s, 1H), 7.33 (d, 2H, J 8.7 Hz), 9.35 (s, 1H). ESI-MI m/z [M+H]⁺ 422.29.

Reduction Step

To a stirred suspension of 10a-(4-methoxyphenyl)-1-[(3-methyl-1,2-oxazol-4-yl)carbonyl]-5-oxo-2,3,10,10a-tetrahydro-1H,5H-imidazo[1,2-a]pyrrolo[1,2-d]pyrazine-7-carbonitrile (89) (220 mg, 0.53 mmol) in methanol (22 mL) was added Pd/C and conc. HCl (1.1 mL). The reaction was placed under an atmosphere of hydrogen and stirred at room temperature. Analysis by tlc and LCMS indicated a new product was forming. The crude material was purified by preparative HPLC to give 7-(aminomethyl)-10a-(4-methoxyphenyl)-1-[(3-methyl-1,2-oxazol-4-yl)carbonyl]-2,3,10,10a-tetrahydro-1H,5H-imidazo[1,2-a]pyrrolo[1,2-d]-pyrazin-5-one; trifluoroacetate salt (147) as an oil (44 mg, 16%).

Example of General Method E

Route (c)

1-[(3-methyl-1,2-oxazol-4-yl)carbonyl]-10a-(4-methylphenyl)-7-(pyridin-2-yl)-2,3,10,10a-tetrahydro-1H,5H-imidazo[1,2-a]pyrrolo[1,2-d]pyrazin-5-one (93)

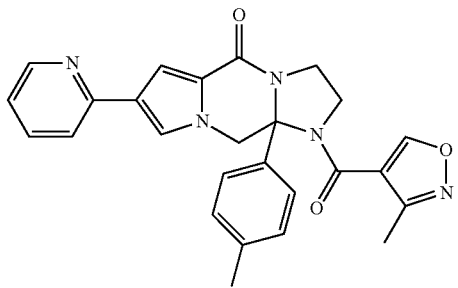 [SMILES: Cc1ccc(C23Cn4cc(-c5ccccn5)cc4C(=O)N2CCN3C(=O)c2conc2C)cc1]

¹H-NMR (400 MHz, CDCl₃): δ 2.27 (s, 3H), 2.45 (br s, 3H), 3.77-3.87 (m, 2H), 4.01-4.09 (m, 1H), 4.31-4.39 (m, 1H), 4.65 (d, 1H, J 12.9 Hz), 5.71 (d, 1H, J 12.9 Hz), 7.05-7.11 (m, 3H), 7.28-7.32 (m, 2H), 7.35 (br d, 1H, J 1.7 Hz), 7.38 (br d, 1H, J 1.6 Hz), 7.44 (dt, 1H, J 8.0, 1.0 Hz), 7.63 (ddd, 1H, J 7.9, 7.6, 1.8 Hz), 8.50 (ddd, 1H, J 4.8, 1.8, 1.0 Hz), 8.52 (br s, 1H).
ESI-MI m/z [M+H]⁺ 454.2.

Step 4c

A suspension of 7-bromo-10a-(4-methylphenyl)-2,3,10,10a-tetrahydro-1H,5H-imidazo[1,2-a]pyrrolo[1,2-d]pyrazin-5-one (100 mg, 0.27 mmol) in DMF (5 mL) was flushed with argon for 20 minutes. Potassium acetate (85 mg, 0.86 mmol) was added followed by 4,4,4',4',5,5,5',5'-octamethyl-2,2'-bi-1,3,2-dioxaborolane (161 mg, 0.63 mmol) and bis(diphenylphosphino)ferrocene]dichloropalladium(II) (20.5 mg, 0.029 mmol). The mixture then heated at 80° C. The outcome of the reaction was monitored by LCMS and after 3 hours the mixture was quenched with water (5 ml). The aqueous layer was washed with CH₂Cl₂, filtrated, concentrated in vacuo to give crude, 10a-(4-methylphenyl)-7-(4,4,5,5-tetramethyl-1,3,2-dioxaborolan-2-yl)-2,3,10,10a-tetrahydro-1H,5H-imidazo[1,2-a]pyrrolo[1,2-d]pyrazin-5-one (100 mg). ESI-MI m/z [M+H]⁺ 394.1.
The material was used in the next step without purification.

Step 5c

A suspension 10a-(4-methylphenyl)-7-(4,4,5,5-tetramethyl-1,3,2-dioxaborolan-2-yl)-2,3,10,10a-tetrahydro-1H,5H-imidazo[1,2-a]pyrrolo[1,2-d]pyrazin-5-one (100 mg, 0.25 mmol) in 1,4-dioxane (3 mL) was degassed by flushing the reaction vessel with argon for 20 minutes. Cesium carbonate (165 mg, 0.51 mmol) in water (100 μL) was added followed by 2-bromopyridine (29 μL, 0.30 mmol). The mixture was flashed with argon prior adding bis(diphenylphosphino)ferrocene]dichloropalladium(II) (18 mg, 0.025 mmol). The mixture was heated at 100° C. for 2 hours. Water was added (5 mL) and the mixture extracted with CH₂Cl₂ (5 mL). The organic layer was dried (MgSO₄), filtrated and concentrated in vacuo to give a residue that was purified by flash chromatography (Biotage SP4 gradient 0-5% MeOH in CH₂Cl₂) to give 10a-(4-methylphenyl)-7-(pyridin-2-yl)-2,3,10,10a-tetrahydro-1H,5H-imidazo[1,2-a]pyrrolo[1,2-d]-pyrazin-5-one (50 mg). The crude was used in the next step without purification. ESI-MI m/z [M+H]⁺ 345.1.

Step 6c

To generate the acid chloride: to a chilled suspension of 3-methylisoxazole-4-carboxylic acid (79 mg, 0.62 mmol) in dry CH₂Cl₂ (2 mL) was added oxalyl chloride (78 μl, 0.93 mmol) followed by DMF (1 drop). The mixture was stirred at 0° C. for 10 minutes and then at room temperature for 1 hour. The resulting solution was concentrated in vacuo at ambient temperature, dissolved in CH₂Cl₂ and re-concentrated in vacuo to give the acid chloride as a oil. To a chilled suspension of the acid chloride (generated as above, 0.62 mmol) in pyridine (0.5 mL) was added a suspension of 10a-(4-methylphenyl)-7-(pyridin-2-yl)-2,3,10,10a-tetrahydro-1H,5H-imidazo[1,2-a]pyrrolo[1,2-d]pyrazin-5-one (50 mg, 0.14 mmol) in pyridine (1 mL). The suspension was allowed at room temperature and stirred over the weekend. The suspension was then diluted with water (5 mL) and extracted with CH₂Cl₂ (3×5 mL). The extracts were combined, dried (MgSO₄), filtered and concentrated in vacuo to give a residue that was purified by flash chromatography (Biotage SP4, 0-5% gradient MeOH in CH₂Cl₂) to give 1-[(3-methyl-1,2-oxazol-4-yl)carbonyl]-10a-(4-methylphenyl)-7-(pyridin-2-yl)-2,3,10,10a-tetrahydro-1H,5H-imidazo[1,2-a]pyrrolo[1,2-d]pyrazin-5-one (93) as a off white solid (4.5 mg, yield 6% over two steps).

Example of General Method F 10a-(4-chlorophenyl)-1-[(5-methyl-1,2-oxazol-4-yl)carbonyl]-8-(pyridin-4-yl)-2,3,10,10a-tetrahydro-1H,5H-imidazo[1,2-a]pyrrolo[1,2-d]pyrazin-5-one (32)

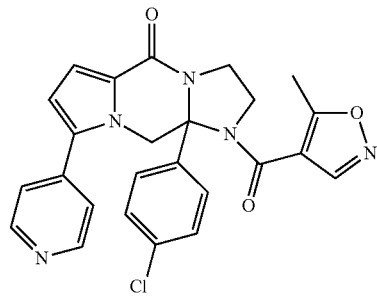 [SMILES: Cc1oncc1C(=O)N1CCN2C(=O)c3ccc(-c4ccncc4)n3CC12c1ccc(Cl)cc1]

¹H NMR (400 MHz, d6-acetone): δ 2.52 (s, 3H), 3.79-3.86 (m, 1H), 4.15-4.24 (m, 1H), 4.28-4.39 (m, 2H), 4.79 (d, 1H, J 13.3 Hz), 5.84 (d, 1H, J 13.3 Hz), 6.53 (d, 1H, J 4.0 Hz), 6.83 (d, 1H, J 4.0 Hz), 7.32 (s, 4H), 7.39-7.42 (m, 2H), 8.66-8.70 (m, 2H), 8.74 (s, 1H). ESI-MI m/z [M+H]⁺ 474.1.

Preparation of 10a-(4-chlorophenyl)-2,3,10,10a-tetrahydro-1H,5H-imidazo[1,2-a]pyrrolo[1,2-d]pyrazin-5-one is described in general method B (steps 1, 2 and 3).

Step 4

7-bromo-10a-(4-chlorophenyl)-2,3,10,10a-tetrahydro-1H,5H-imidazo[1,2-a]pyrrolo[1,2-d]pyrazin-5-one (A) and 8-bromo-10a-(4-chlorophenyl)-2,3,10,10a-tetrahydro-1H,5H-imidazo[1,2-a]pyrrolo[1,2-d]pyrazin-5-one (B)

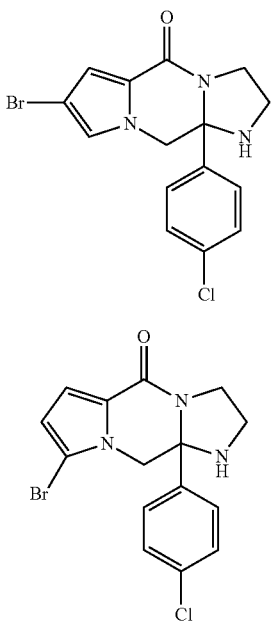

A

B

¹H NMR (400 MHz, d6-acetone): δ 3.29-3.50 (m, 6H$_{A+B}$), 3.67-3.77 (m, 2H$_{A+B}$), 4.22 (d, 1HB, J 12.5 Hz), 4.39 (d, 1H$_A$, J 12.5 Hz), 4.66-4.75 (m, 2H$_{A+B}$), 6.16 (d, 1H$_B$, J 3.96 Hz), 6.68 (d, 1H$_A$, J 1.72 Hz), 6.71 (d, 1H$_B$, J 3.96 Hz), 6.79 (d, 1H$_A$, J 1.72 Hz), 7.32-7.42 (m, 8H$_{A+B}$).

ESI-MI m/z [M+H]⁺ 367.9.

To a solution of 10a-(4-chlorophenyl)-2,3,10,10a-tetrahydro-1H,5H-imidazo[1,2-a]pyrrolo[1,2-d]pyrazin-5-one (100 mg, 0.35 mmol) dissolved in THF (20 mL) was added N-bromosuccinimide (62 mg, 0.35 mmol) and the reaction mixture was stirred at room temperature for 1 h. LCMS analysis showed a mixture of mono brominated product (366/368 m/z), a small amount of dibrominated pyrrole (446 m/z) and debrominated starting material (288 m/z). The reaction mixture was partitioned with water (25 ml) and CH₂CL₂ (25 mL) and the organic layer was separated and concentrated in vacuo to give crude product (light yellow oil). The crude mixture was then purified using flash chromatography (Biotage SP4, 12 g cartridge, 0-10% MeOH gradient in CH₂Cl₂) to give 7-bromo-10a-(4-chlorophenyl)-2,3,10,10a-tetrahydro-1H,5H-imidazo[1,2-a]pyrrolo[1,2-d]pyrazin-5-one (A) and 8-bromo-10a-(4-chlorophenyl)-2,3,10,10a-tetrahydro-1H,5H-imidazo[1,2-a]pyrrolo[1,2-d]pyrazin-5-one (B) in a 0.6:1 ratio (98.4 mg, yield 77%). The mixture was used without further purification in the next step.

Step 5

A (0.6:1) mixture of 7-bromo-10a-(4-chlorophenyl)-2,3,10,10a-tetrahydro-1H,5H-imidazo[1,2-a]pyrrolo[1,2-d]pyrazin-5-one and 8-bromo-10a-(4-chlorophenyl)-2,3,10,10a-tetrahydro-1H,5H-imidazo[1,2-a]pyrrolo[1,2-d]pyrazin-5-one (50 mg, 0.14 mmol), pyridine-4-boronic acid (18 mg, 0.15 mmol), sodium carbonate (20 mg, 0.19), dichlorobis(triphenylphosphine)palladium(II) (2 mg, 3 μmol), 1,2-dimethoxyethane (700 μL), ethanol (200 μL) and water (300 μL) were combined in a sealed tube. The reaction mixture was heated at 150° C. for 10 min in a microwave reactor. The reaction mixture was diluted with brine (50 mL) and extracted with CH₂Cl₂ containing 20% of propan-2-ol (2×50 mL). The organic layers were dried (MgSO₄) and concentrated in vacuo to give crude product that was purified using flash chromatography (Biotage SP4, 12 g cartridge; 0-10% MeOH gradient in CH₂Cl₂) to give 10a-(4-chlorophenyl)-8-(pyridin-4-yl)-2,3,10,10a-tetrahydro-1H,5H-imidazo[1,2-a]pyrrolo[1,2-d]-pyrazin-5-one as a yellow solid (70 mg) contaminated with its regioisomer (7:1 ratio). ¹H NMR (400 MHz, MeOD): δ 2.80-2.91 (m, 1H), 3.28-3.39 (m, 1H), 3.58 (ddd, 1H, J 11.1, 7.6, 3.5 Hz), 3.83 (dt, J 11.1, 7.8 Hz), 4.39 (d, 1H, J 12.5 Hz), 4.72 (d, 1H, J 12.4 Hz), 6.46 (d, 1H, J 4.0 Hz), 6.95 (d, 1H, J 4.0 Hz), 7.20-7.23 (m, 2H), 7.30 (s, 4H), 8.52-8.55 (m, 2H).

The mixture was used in the next step without further purification.

Step 6

To generate the acid chloride oxalyl chloride (100 μL, 1.2 mmol) and a drop of DMF were added to a suspension of 5-methyl-1,2-oxazole-4-carboxylic acid (76 mg, 0.60 mmol) in dichloromethane (0.5 mL) at 0° C. The suspension was allowed to stir for a further 15 min at 0° C., followed by 2 h at room temperature. The resulting solution was concentrated in vacuo to give a dark oil that was twice suspended in n-hexanes (2×1 mL) and concentrated in vacuo. To a chilled (ice bath) suspension of the acid chloride (generated as above; 0.60 mmol) in pyridine (0.5 mL) and CH₂Cl₂ (0.5 mL) was added crude 10a-(4-chlorophenyl)-8-(pyridin-4-yl)-2,3,10,10a-tetrahydro-1H,5H-imidazo[1,2-a]pyrrolo[1,2-d]pyrazin-5-one (50 mg, 0.14 mmol) in pyridine (0.5 mL). The dark reaction mixture was warmed to room temperature and stirred for a further 16 h. LCMS analysis confirmed completion of the reaction. The reaction mixture was diluted with a saturated solution of NaHCO₃ (25 mL) and extracted with CH₂Cl₂ containing 20% of propan-2-ol (3×25 mL). The organic fractions were combined, dried (MgSO₄) and concentrated in vacuo to yield a crude brown solid, which was purified using flash chromatography (Biotage SP4, 12 g cartridge, 0-10% MeOH gradient in CH₂Cl₂) and reverse phase chromatography (Biotage SP4.12 g cartridge, C18 phase, 20-40% acetonitrile gradient in water) to give 10a-(4-chlorophenyl)-1-[(5-methyl-1,2-oxazol-4-yl)carbonyl]-8-(pyridin-4-yl)-2,3,10,10a-tetrahydro-1H,5H-imidazo[1,2-a]pyrrolo[1,2-d]pyrazin-5-one (32) as a white solid (7 mg, yield 12%).

The following compounds were similarly prepared using General Method F.

| Cpd. No. | Structure | ESI-MI m/z [M + H]⁺/¹H-NMR |
|---|---|---|
| 33 | 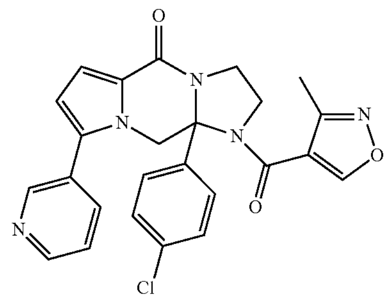 [SMILES: Cc1nocc1C(=O)N1CCN2C(=O)c3ccc(-c4cccnc4)n3CC12c1ccc(Cl)cc1] | ESI-MI m/z [M + H]⁺ 474.1. ¹H NMR (400 MHz, d6-acetone): δ 2.28 (s, 3H), 3.75-3.85 (m, 1H), 4.19-4.27 (m, 1H), 4.30-4.39 (m, 2H), 4.74 (d, 1H, J 13.1 Hz), 5.72 (d, 1H, J 12.8 Hz), 6.44 (d, 1H, J 3.9 Hz), 6.85 (d, 1H, J 3.8 Hz), 7.33 (s, 4H), 7.51 (ddd, 1H, J 7.8, 4.8, 0.9 Hz), 7.81 (ddd, 1H, J 7.9, 2.2, 1.6 Hz), 8.62-8.64 (m, 2H), 9.16 (s, 1H). |
| 34 | 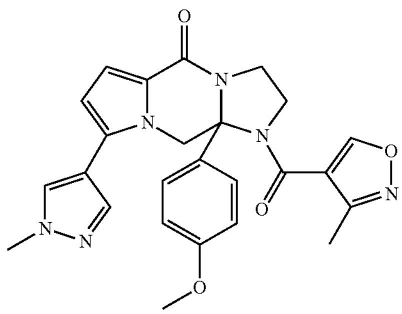 [SMILES: COc1ccc(C23Cn4c(ccc4-c4cnn(C)c4)C(=O)N2CCN3C(=O)c2conc2C)cc1] | ESI-MI m/z [M + H]⁺ 473.0. ¹H-NMR (400 MHz, CDCl₃): δ 2.30 (s, 3H), 3.69 (s, 3H), 3.66-3.86 (m, 2H), 3.89 (3H, s), 4.05 (dt, 1H, J 8.9, 6.5 Hz), 4.28 (d, 1H, J 13.0 Hz), 4.26-4.34 (m, 1H), 5.71 (d, 1H, 12.8 Hz), 6.16 (d, 1H, J 4.0 Hz), 6.74 (d, 2H, J 8.9 Hz), 6.89 (d, 1H, J 3.9 Hz), 7.19 (d, 2H, J 8.8 Hz), 7.33 (s, 1H), 7.46 (s, 1H), 8.60 (br s, 1H). |
| 96 | 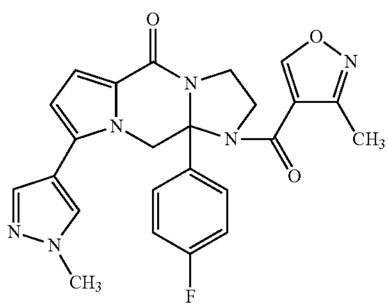 [SMILES: Cc1nocc1C(=O)N1CCN2C(=O)c3ccc(-c4cnn(C)c4)n3CC12c1ccc(F)cc1] | ESI-MI m/z [M + H]⁺ 461.0. ¹H NMR (400 MHz, CDCl₃): δ 2.38 (s, 3H), 3.69-3.89 (m, 2H), 3.92 (s, 3H), 4.08 (dd, 1H, J 16.0, 8.8 Hz,), 4.32 (d, 1H), 4.32-4.43 (m, 1H), 5.74 (d, 1H, J 12.9 Hz), 6.18 (d, 1H, J 3.9 Hz), 6.88-6.98 (m, 3H), 7.24-7.30 (m, 2H), 7.35 (s, 1H), 7.46 (s, 1H), 8.62 (s, 1H). |
| 97 | 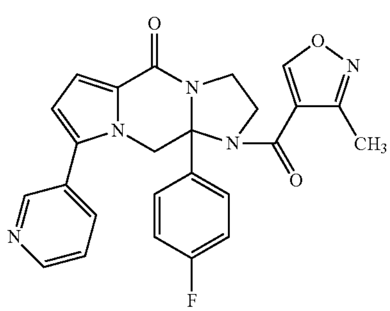 [SMILES: Cc1nocc1C(=O)N1CCN2C(=O)c3ccc(-c4cccnc4)n3CC12c1ccc(F)cc1] | ESI-MI m/z [M + H]⁺ 458.1. ¹H NMR (400 MHz, CDCl₃): δ 2.37 (s, 3H), 3.76-3.88 (m, 2H), 4.03-4.13 (m, 1H), 4.33-4.42 (m, 1H), 4.45 (d, 1H, J 13.0 Hz), 5.72 (d, 1H, J 13.0 Hz), 6.29-6.33 (m, 1H), 6.95-7.05 (m, 3H), 7.30-7.40 (m, 3H), 7.49-7.54 (m, 1H), 8.49 (br s, 1H), 8.56 (br s, 1H), 8.59-8.65 (m, 1H). |
| 98 | 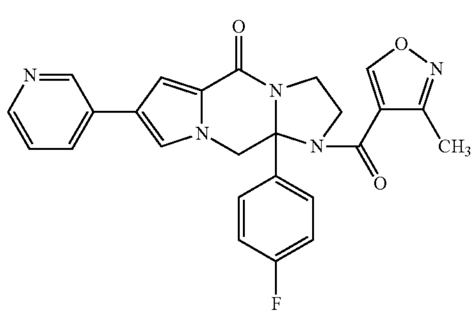 [SMILES: Cc1nocc1C(=O)N1CCN2C(=O)c3cc(-c4cccnc4)cn3CC12c1ccc(F)cc1] | ESI-MI m/z [M + H]⁺ 458.1. ¹H NMR (400 MHz, CDCl₃): δ 2.46 (s, 3H), 3.78-3.88 (m, 2H), 4.04-4.12 (m, 1H), 4.39 (t, J = 8.3 Hz, 1H), 4.65 (d, 1H, J 12.8 Hz), 5.71 (d, 1H, J 12.9 Hz), 6.96-7.07 (m, 3H), 7.19-7.25 (m, 2H), 7.45 (dd, 2H, J 8.6, 5.0 Hz), 7.72 (br d, 1H, J 8.0 Hz), 8.44 (d, 1H, J 4.6 Hz), 8.55 (s, 1H), 8.74 (br s, 1H). |

| Cpd. No. | Structure | ESI-MI m/z [M + H]⁺/¹H-NMR |
|---|---|---|
| 99 | 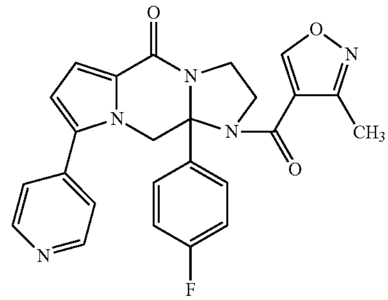 [SMILES: Cc1nocc1C(=O)N1CCN2C(=O)c3ccc(-c4ccncc4)n3CC12c1ccc(F)cc1] | ESI-MI m/z [M + H]⁺ 458.1. ¹H NMR (400 MHz, CDCl₃): δ 2.40 (d, 3H, J 0.6 Hz), 3.77-3.89 (m, 2H), 4.04-4.13 (m, 1H), 4.41 (dt, 1H, J 9.8, 5.8 Hz), 4.50 (d, 1H, J 13.1 Hz), 5.85 (d, 1H, J 13.0 Hz), 6.41 (br d, 1H, J 4.0 Hz), 6.95-7.05 (m, 3H), 7.15 (dd, 2H, J 4.4, 1.7 Hz), 7.31-7.38 (m, 2H), 8.55 (br s, 1H), 8.65-8.69 (m, 2H). |
| 100 | 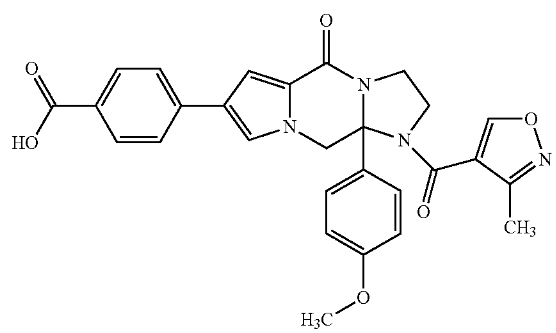 [SMILES: COc1ccc(C23Cn4cc(-c5ccc(C(=O)O)cc5)cc4C(=O)N2CCN3C(=O)c2conc2C)cc1] | ESI-MI m/z [M + H]⁺ 513.2. ¹H NMR (400 MHz, DMSO) δ 2.31 (s, 3H), 3.70 (s, 3H), 3.70-3.78 (m, 1H), 3.99-4.28 (m, 3H), 4.64 (d, 1H, J 13.1 Hz), 5.75 (d, 1H, J 13.2 Hz), 6.87 (d, 2H, J 8.9 Hz), 7.17 (s, 1H), 7.33 (d, 2H, J 8.9 Hz), 7.64 (d, 2H, J 8.2 Hz), 7.79 (s, 1H), 7.88 (d, 2H, J 8.3 Hz), 9.36 (s, 1H). |

Example of General Method G

Compounds 35 and 36 were synthesised using general method G as follows.

1-[(3-methyl-1,2-oxazol-4-yl)carbonyl]-10a-phenyl-2,3,10,10a-tetrahydro-1H,5H-imidazo[1,2-a]pyrrolo[1,2-d]-pyrazin-5-one (35)

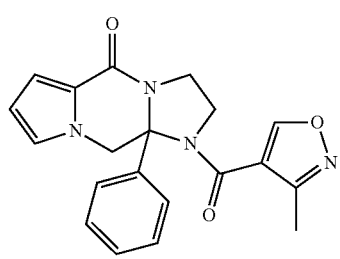 [SMILES: Cc1nocc1C(=O)N1CCN2C(=O)c3cccn3CC12c1ccccc1]

¹H NMR (400 MHz, d6-acetone): δ 2.35 (s, 3H), 3.67-3.76 (m, 1H), 4.11-4.19 (m, 1H), 4.23-4.33 (m, 1H), 4.62 (d, 1H, J 13.1 Hz), 5.62 (s, 1H), 5.77 (d, 1H, J 13.0 Hz), 6.16 (dd, 1H, J 3.8, 2.5 Hz), 6.70 (dd, 1H, J 3.8, 1.6 Hz), 7.04-7.06 (m, 1H), 7.28-7.33 (m, 3H), 7.39-7.45 (m, 2H), 9.14 (s, 1H). ESI-MI m/z [M+H]⁺ 363.2.

1-[(3-methyl-1,2-oxazol-4-yl)carbonyl]-10a-[4-(pyrrolidin-1-yl)phenyl]-2,3,10,10a-tetrahydro-1H,5H-imidazo[1,2-a]pyrrolo[1,2-d]-pyrazin-5-one (36)

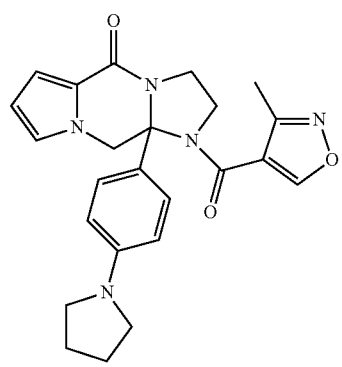 [SMILES: Cc1nocc1C(=O)N1CCN2C(=O)c3cccn3CC12c1ccc(N2CCCC2)cc1]

¹H NMR (400 MHz, d6-acetone): δ 1.94-1.98 (m, 4H), 2.36 (s, 3H), 3.18-3.23 (m, 4H), 3.67-3.76 (m, 1H), 4.02-4.10 (m, 1H), 4.16-4.26 (m, 2H), 4.35 (d, 1H, J 13.1 Hz), 5.70 (d, 1H, J 12.7 Hz), 6.13 (dd, 1H, J 3.8, 2.6 Hz), 6.40-6.45 (m, 2H), 6.67 (dd, 1H, J 3.8, 1.7 Hz), 7.00 (t, 1H, J 1.9 Hz), 7.20-7.26 (m, 2H), 9.10 (br s, 1H).
ESI-MI m/z [M+H]⁺ 432.2.

Step 1

Potassium tert-butoxide (1.04 g, 8.79 mmol) was added portionwise to a solution of methyl 1H-pyrrole-2-carboxylate (1.00 g, 7.99 mmol) in DMF (75 mL) at room temperature. The resultant mixture was stirred for 20 min at room temperature before cooling to 0° C. 2-bromo-1-(4-bromophenyl) ethanone (2.44 g, 8.79 mmol) was then added and the reaction mixture was stirred at 0° C. for 1 h then allowed to warm to room temperature. After 15 min at room temperature the desired product (320/322 m/z) was present along with a large amount of methyl 1H-pyrrole-2-carboxylate. A further portion of potassium tert-butoxide (189 mg, 1.60 mmol) was added, and the reaction mixture was stirred a further 1 h at room temperature. Water (100 ml) was then added and the mixture extracted with $CH_2Cl_2$ (2×100 ml). The organic layers were combined, concentrated in vacuo to give a brown oil, which was purified using flash chromatography (Biotage SP4, 40 g cartridge, 0-20% EtOAc gradient in n-hexanes) to give a mixture of starting material (methyl 1H-pyrrole-2-carboxylate) and methyl 1-[2-(4-bromophenyl)-2-oxoethyl]-1H-pyrrole-2-carboxylate (2:1) as a yellow oil (2.39 g, yield 31%). The mixture was used in the next step without further purification.

Step 2

To a solution of crude methyl 1-[2-(4-bromophenyl)-2-oxoethyl]-1H-pyrrole-2-carboxylate (2.39 g, 2.47 mmol) in THF (30 mL) and water (20 mL) was added lithium hydroxide monohydrate (0.63 g, 15.1 mmol). The dark solution was stirred at room temperature. The outcome of the reaction was monitored by LCMS and after 1 h another portion of lithium hydroxide monohydrate (300 mg) was added to the reaction mixture. After 16 h the reaction mixture was diluted with a aqueous solution of NaOH (1M) (50 mL) then extracted with $CH_2Cl_2$ (100 mL). The pH of the aqueous fraction was adjusted to 1 with aqueous HCl (1M) and then extracted with $CH_2Cl_2$ containing 10% of propan-2-ol (3×75 mL). The organic extracts (from acidic aqueous) were combined, dried ($MgSO_4$) and concentrated in vacuo to give crude (~50% pure) 1-[2-(4-bromophenyl)-2-oxoethyl]-1H-pyrrole-2-carboxylic acid as a yellow solid (1.10 g, yield 72%) The crude material was used without purification.

Step 3

To a suspension of crude 1-[2-(4-bromophenyl)-2-oxoethyl]-1H-pyrrole-2-carboxylic acid (1.1 g, 0.714 mmol) suspended in xylenes (50 mL) was added ethane-1,2-diamine (0.5 mL, 7.5 mmol). The orange reaction mixture was heated at reflux for 1 h. The reaction mixture was concentrated in vacuo to give a dark orange oil that was purified using flash chromatography (Biotage SP4, 40 g cartridge, 0-10% MeOH gradient in EtOAc) to give 10a-(4-bromophenyl)-2,3,10,10a-tetrahydro-1H,5H-imidazo[1,2-a]pyrrolo[1,2-d]pyrazin-5-one as a pale yellow solid (216 mg, 90% yield). $^1$H NMR (400 MHz, d6-acetone): δ 2.71-2.84 (m, 1H), 3.30-3.38 (m, 1H), 3.42 (ddd, 1H, J 11.0, 7.7, 3.2 Hz), 3.70 (dt, 1H, J 10.8, 7.8 Hz), 4.36 (d, 1H, J 12.3 Hz), 4.65 (d, 1H, J 12.3 Hz), 6.03 (dd, 1H, J 3.7, 2.6 Hz), 6.66 (m, 2H), 7.29-7.33 (m, 2H), 7.45-7.49 (m, 2H).

Step 4

10a-(4-bromophenyl)-2,3,10,10a-tetrahydro-1H,5H-imidazo[1,2-a]pyrrolo[1,2-d]pyrazin-5-one (50 mg, 0.15 mmol), pyrrolidine (50 μL, 0.60 mmol), Pd(OAc)$_2$ (3.4 mg, 25 racemic-BINAP (18.7 mg, 0.030 mmol) and $Cs_2CO_3$ (196 mg, 0.60 mmol) were suspended in toluene (1.4 mL) and heated at 150° C. for 15 min in a microwave reactor. LCMS analysis of the resulting dark brown solution showed the presence of target product (323 m/z) and starting bromide (332/334 m/z) in approximately equal amounts. The reaction mixture was heated for a further 20 min at 160° C. Another LCMS analysis showed the presence of target product and absence of starting bromide. The reaction mixture was filtered (syringe filter) and the filtrate concentrated in vacuo to give a residue that was purified by flash chromatography (Biotage SP4, 12 g cartridge; 0-10% MeOH gradient in EtOAc) to give a mixture of 10a-[4-(pyrrolidin-1-yl)phenyl]-2,3,10,10a-tetrahydro-1H, 5H-imidazo[1,2-a]pyrrolo[1,2-d]pyrazin-5-one (36a) ESI-MI m/z [M+H]$^+$ 323.2.

and 10a-phenyl-2,3,10,10a-tetrahydro-1H,5H-imidazo[1, 2-a]pyrrolo[1,2-d]pyrazin-5-one (35a) ESI-MI m/z [M+H]$^+$ 254.1 in a 1:0.6 ratio (15 mg). The mixture was not purified further and was used such as in the next step.

Step 5

1-[(3-methyl-1,2-oxazol-4-yl)carbonyl]-10a-phenyl-2,3, 10,10a-tetrahydro-1H,5H-imidazo[1,2-a]pyrrolo[1,2-d]-pyrazin-5-one (35) was obtained as follows. To generate the acid chloride, oxalyl chloride (140 uL, 1.61 mmol) and DMF (1 drop) were added to a suspension of 3-methyl-1,2-oxazole-4-carboxylic acid (110 mg, 0.86 mmol) in $CH_2Cl_2$ (0.5 mL) at 0° C. The suspension was allowed to stir for a further 15 min at 0° C. followed by 2 h at room temperature. The resulting solution was concentrated in vacuo (without heating) to give an oil that was twice suspended in n-hexanes (2×1 mL) and concentrated in vacuo. To a chilled (ice bath) suspension of the acid chloride (generated as above, 0.86 mmol) in pyridine (0.5 mL) and $CH_2Cl_2$ (0.5 mL) was added a cloudy mixture of 10a-[4-(pyrrolidin-1-yl)phenyl]-2,3,10,10a-tetrahydro-1H, 5H-imidazo[1,2-a]pyrrolo[1,2-d]-pyrazin-5-one and 10a-phenyl-2,3,10,10a-tetrahydro-1H,5H-imidazo[1,2-a]pyrrolo[1,2-d]pyrazin-5-one (50 mg, 0.17 mmol) in pyridine (0.5 mL). The brown reaction mixture was warmed to room temperature and stirred for a further 18 h. The reaction mixture was then diluted with a saturated aqueous solution of $NaHCO_3$ (25 mL) and extracted with $CH_2Cl_2$ (3×25 mL). The organic fractions were combined, dried ($MgSO_4$) and concentrated in vacuo to yield a crude residue. The residue was purified by flash chromatography (Biotage SP4, 12 g cartridge, C18 phase, 20-60% acetonitrile gradient in water) to give 1-[(3-methyl-1,2-oxazol-4-yl)carbonyl]-10a-phenyl-2, 3,10,10a-tetrahydro-1H,5H-imidazo[1,2-a]pyrrolo[1,2-d] pyrazin-5-one (35) as a white solid (3 mg, yield: 5%). 1-[(3-methyl-1,2-oxazol-4-yl)carbonyl]-10a-[4-(pyrrolidin-1-yl) phenyl]-2,3,10,10a-tetrahydro-1H,5H-imidazo[1,2-a] pyrrolo[1,2-a]pyrazin-5-one (36) was similarly obtained by reacting a cloudy mixture of 10a[4-(pyrrolidin-1-yl)phenyl]-2,3,10,10a-tetrahydro-1H,5H-imidazo[1,2-a]pyrrolo[1,2-d]-pyrazin-5-one and 10a-phenyl-2,3,10,10a-tetrahydro-1H, 5H-imidazo[1,2-a]pyrrolo[1,2-d]pyrazin-5-one (35 mg, 74 μmol) with acid chloride (1.10 mmol, generated from oxalyl chloride (190 μL, 2.22 mmol) and 3-methyl-1,2-oxazole-4-carboxylic acid (140 mg, 1.10 mmol)). The reaction mixture was stirred at room temperature to completion (2 h, monitored by LCMS). 1-[(3-methyl-1,2-oxazol-4-yl)carbonyl]-10a-[4-(pyrrolidin-1-yl)phenyl]-2,3,10,10a-tetrahydro-1H, 5H-imidazo[1,2-a]pyrrolo[1,2-d]pyrazin-5-one (36) as a white solid (6.5 mg, yield 24%) was obtained as for com-

Example of General Method H

4-{1-[(3-methyl-1,2-oxazol-4-yl)carbonyl]-5-oxo-2,
3-dihydro-1H,5H-imidazo[1,2-a]pyrrolo[1,2-d]
pyrazin-10a(10H)-yl}benzonitrile (37)

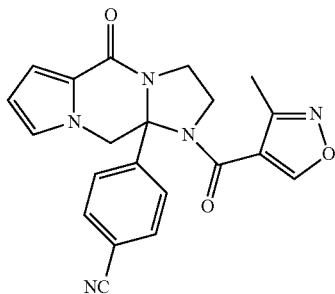 [SMILES: Cc1nocc1C(=O)N1CCN2C(=O)c3cccn3CC12c1ccc(C#N)cc1]

¹H NMR (400 MHz, MeOD): δ 2.36 (s, 3H), 3.79-3.87 (m, 1H), 4.13 (ddd, 1H, J 9.7, 8.0, 3.8 Hz), 4.18-4.26 (m, 1H), 4.37 (ddd, 1H, J 11.8, 8.4, 3.6 Hz), 4.65 (d, 1H, J 13.2 Hz), 5.83 (dd, 1H, J 3.8, 1.3 Hz), 6.26 (dd, 1H, J 3.8, 2.6 Hz), 6.85 (dd, 1H, J 3.8, 1.3), 7.06-7.07 (m, 1H), 7.57-7.73 (m, 4H), 9.11 (s, 1H).
ESI-MI m/z [M+H]⁺ 388.2.

Preparation of 10a-(4-bromophenyl)-2,3,10,10a-tetrahydro-1H,5H-imidazo[1,2-a]pyrrolo[1,2-d]pyrazin-5-one was described in general method G.

Step 4

10a-(4-bromophenyl)-2,3,10,10a-tetrahydro-1H,5H-imidazo[1,2-a]pyrrolo[1,2-d]pyrazin-5-one (50 mg, 0.15 mmol), tetrakis(triphenylphosphine)palladium(0) (8.7 mg, 7.5 µmol), Zn(CN)₂ (27 mg, 0.23 mmol), and DMF (2 mL) were added to a microwave reaction vial that was sealed under argon. The reaction mixture was heated in a microwave reactor at 140° C. for 20 min, resulting in a dark yellow mixture. The reaction mixture was heated for a further 20 min at 150° C. LCMS analysis showed a mixture of target product (279 m/z) and starting bromo core (332/334 m/z). Another portion of tetrakis(triphenylphosphine)palladium (0) (8.7 mg, 7.5 µmol) was added and the mixture heated at 160° C. The reaction went to completion after 20 min. A saturated aqueous solution of NaHCO₃ (50 mL) was added and CH₂Cl₂ containing 20% of propan-2-ol (50 mL). The organic layer was separated, dried (MgSO₄) and concentrated in vacuo to give crude product that was purified using flash chromatography (Biotage SP4, 12 g cartridge; 0-10% MeOH gradient in CH₂Cl₂ to give 4-(5-oxo-2,3-dihydro-1H,5H-imidazo[1,2-a]pyrrolo[1,2-d]pyrazin-10a(10H)-yl)benzonitrile as a brown crystalline solid (48.5 mg, quantitative yield). ¹H NMR (400 MHz, d6-acetone): δ 3.07-3.41 (m, 1H), 3.44 (ddd, 1H, J 10.9, 7.8, 3.2 Hz), 3.48-3.61 (m, 1H), 3.72 (dt, 1H, J 10.8, 7.9 Hz), 4.41 (d, 1H, J 12.5 Hz), 4.72 (d, 1H, J 12.5 Hz), 6.04 (dd, 1H, J 3.8, 2.6 Hz), 6.65-6.67 (m, 1H), 6.70 (dd, 1H, J 3.7, 1.5 Hz), 7.55-7.73 (m, 4H). The product was used in the next step without further purification.

Step 5

To generate the acid chloride, oxalyl chloride (70 µL, 0.83 mmol) and DMF (1 drop) were added to a suspension of 3-methyl-1,2-oxazole-4-carboxylic acid (50 mg, 0.40 mmol) in CH₂Cl₂ (0.5 mL) at 0° C. The suspension was allowed to stir for 15 min at 0° C., followed by 2 h at room temperature. The resulting solution was concentrated in vacuo to give a brown oil that was suspended in n-hexanes (2×1 mL) and concentrated in vacuo. To a chilled (ice bath) suspension of the acid chloride (generated as above; 0.40 mmol) in pyridine (0.5 mL) and CH₂Cl₂ (0.5 mL) was added 4-(5-oxo-2,3-dihydro-1H,5H-imidazo[1,2-a]pyrrolo[1,2-d]pyrazin-10a(10H)-yl)benzonitrile (22 mg, <79 µmol) in pyridine (0.5 mL). The brown reaction mixture was warmed to room temperature and stirred for a further 64 h. Saturated aqueous NaHCO₃ (25 mL) was then added and the mixture extracted with CH₂Cl₂ (3×25 mL). The organic fractions were combined, dried (MgSO₄) and concentrated in vacuo to yield a residue that was purified using flash chromatography (Biotage SP4 12 g cartridge; 0-10% MeOH gradient in CH₂Cl₂) to give a mixture of products containing the desired product. The mixture was further purified using flash chromatography (Biotage SP4, 12 g cartridge, C18 phase, 20-40% acetonitrile gradient in water) to give 4-{1-[(3-methyl-1,2-oxazol-4-yl)carbonyl]-5-oxo-2,3-dihydro-1H,5H-imidazo[1,2-a]pyrrolo[1,2-d]pyrazin-10a(10H)-yl}benzonitrile (37) as a white solid (13 mg, yield 42%).

Example of General Method I 10a-(4-chlorophenyl)-N,N-dimethyl-1-[(3-methyl-1,
2-oxazol-4-yl)carbonyl]-5-oxo-2,3,10,10a-tetrahydro-1H,5H-imidazo[1,2-a]pyrrolo[1,2-d]pyrazine-7-
carboxamide (38)

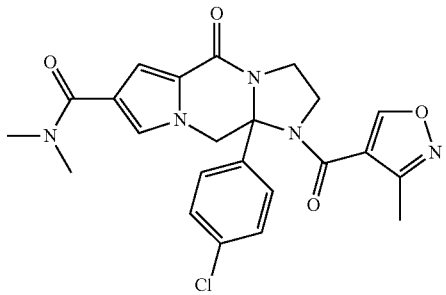 [SMILES: Cc1nocc1C(=O)N1CCN2C(=O)c3cc(C(=O)N(C)C)cn3CC12c1ccc(Cl)cc1]

¹H NMR (400 MHz, d6-acetone): δ 2.34 (s, 3H), 3.07 (br s, 6H), 3.76-3.84 (m, 1H), 4.16-4.56 (m, 3H), 4.67 (d, 1H, J 13.2 Hz), 5.86 (d, 1H, J 13.2 Hz), 6.96 (d, 1H, J 1.7 Hz), 7.33-7.37 (m, 2H), 7.47-7.52 (m, 3H), 9.15 (s, 1H). ESI-MI m/z [M+H]⁺ 468.1.

Preparation of methyl 1-[2-(4-chlorophenyl)-2-oxoethyl]-1H-pyrrole-2-carboxylate is described in general method B (step 1).

Step 2

To a solution of ethyl 1-[2-(4-Chlorophenyl)-2-oxoethyl]-1H-pyrrole-2-carboxylate (150 mg, 0.54 mmol) in CH₂Cl₂ (10 ml) was added trichloroacetyl chloride (120 µL, 1.1 mmol) and aluminium chloride (290 mg, 2.2 mmol). After 16 h the reaction was quenched by the addition of a saturated aqueous solution of NaHCO₃ (50 mL) and extracted with CH₂Cl₂ (3×50 mL). The organic extracts were combined, dried (MgSO₄) and concentrated in vacuo to give a residue that was purified using flash chromatography (2× Biotage SP4, 12 g cartridge, 20-100% EtOAc gradient in n-hexanes) to give methyl 1-[2-(4-chlorophenyl)-2-oxoethyl]-4-(trichloroacetyl)-1H-pyrrole-2-carboxylate (97 mg, yield 42%) as a brown solid.

$^1$H NMR (400 MHz, d6-acetone): δ 3.75 (s, 3H), 6.12 (s, 2H), 7.56 (d, 1H, J 2.0 Hz), 7.64-7.68 (m, 2H), 8.10-8.14 (m, 2H), 8.15 (d, 1H, J 2.0 Hz).

Step 3

To a solution of methyl 1-[2-(4-chlorophenyl)-2-oxoethyl]-4-(trichloroacetyl)-1H-pyrrole-2-carboxylate (97 mg, 0.23 mmol) in THF (2 mL) was added dimethylamine (50 µL, 0.75 mmol). The reaction mixture was stirred at room temperature. After completion (2.5 days, monitored by LCMS) a saturated aqueous solution of ammonium chloride (25 mL) was added and the mixture extracted with CH$_2$Cl$_2$ containing 20% of propan-2-ol (5×25 mL). The organic fractions were combined, dried (MgSO$_4$) and concentrated in vacuo to give crude product mixture that was purified using flash chromatography (Biotage SP4, 12 g cartridge; 0-10% MeOH gradient in CH$_2$Cl$_2$) to give methyl 1-[2-(4-chlorophenyl)-2-oxoethyl]-4-(dimethylcarbamoyl)-1H-pyrrole-2-carboxylate (45 mg, yield 56%). $^1$H NMR (400 MHz, d6-acetone): δ 3.12 (br s, 6H), 3.70 (s, 3H), 5.97 (s, 2H), 7.19 (d, 1H, J 2.0 Hz), 7.48 (d, 1H, J 1.9 Hz), 7.62-7.66 (m, 2H), 8.08-8.13 (m, 2H).

Step 4

To a solution of methyl 1-[2-(4-chlorophenyl)-2-oxoethyl]-4-(dimethylcarbamoyl)-1H-pyrrole-2-carboxylate (90 mg, 0.26 mmol) in THF (1 mL) was added lithium hydroxide monohydrate (22 mg, 0.52 mmol) in water (1 mL). The reaction mixture was stirred at room temperature for 18 h (monitored by LCMS). A aqueous solution of NaOH (1 M) (25 mL) was added and the mixture washed with EtOAc (25 mL) to remove the remaining starting material. The aqueous layer was then acidified to pH 2-3 with an aqueous solution of HCl (1 M) and extracted with a mixture of 20% of propan-2-ol/DCM (2×25 mL). The organic fractions were combined, dried (MgSO$_4$) and concentrated in vacuo to give 1-[2-(4-chlorophenyl)-2-oxoethyl]-4-(dimethylcarbamoyl)-1H-pyrrole-2-carboxylic acid as a yellow solid (90 mg, quantitative yield). ESI-MI m/z [m+H]$^+$ 335.1.

Step 5

To a suspension of 1-[2-(4-chlorophenyl)-2-oxoethyl]-4-(dimethylcarbamoyl)-1H-pyrrole-2-carboxylic acid (90 mg, 0.27 mmol) in 1,4-dioxane (10 mL) was added ethane-1,2-diamine (0.1 mL, 1.5 mmol). The reaction mixture was heated at reflux 4 h (monitored by LCMS). The reaction mixture was then concentrated in vacuo to give an oil that was purified using flash chromatography (Biotage SP4, 12 g cartridge, 0-20% MeOH gradient in CH$_2$Cl$_2$) to give 10a-(4-chlorophenyl)-N,N-dimethyl-5-oxo-2,3,10,10a-tetrahydro-1H,5H-imidazo[1,2-a]pyrrolo[1,2-d]pyrazine-7-carboxamide as a light brown solid (26 mg, yield 27%) $^1$H NMR (400 MHz, d6-acetone): δ 2.75-2.84 (m, 1H), 2.95-3.21 (m, 6H), 3.33 (ddd, 1H, J 11.2, 7.7, 3.3 Hz), 3.49 (ddd, 1H, J 11.0, 7.7, 3.2 Hz), 3.72 (dt, 1H, J 11.0, 8.0 Hz), 4.41 (d, 1H, J 12.6 Hz), 4.75 (d, 1H, J 12.6 Hz), 7.01 (d, 1H, J 1.6 Hz), 7.13 (d, 1H, J 1.6 Hz), 7.26-7.35 (m, 4H).

Used in the next step without further purification.

Step 6

To generate the acid chloride, oxalyl chloride (45 µL, 0.54 mmol) and DMF (1 drop) were added to a suspension of 3-methyl-1,2-oxazole-4-carboxylic acid (35 mg, 0.28 mmol) in CH$_2$Cl$_2$ (0.5 mL) at 0° C. The suspension was allowed to stir for a further 15 min at 0° C., followed by 2 h at room temperature. The resulting solution was concentrated in vacuo to give a oil that was twice suspended in n-hexanes (2×1 mL) and concentrated in vacuo. To a chilled (ice bath) suspension of the acid chloride (generated as above; 0.28 mmol) in pyridine (0.5 mL) and CH$_2$Cl$_2$ (0.5 mL) was added 10a-(4-chlorophenyl)-N,N-dimethyl-5-oxo-2,3,10,10a-tetrahydro-1H,5H-imidazo[1,2-a]pyrrolo[1,2-d]pyrazine-7-carboxamide (12 mg, 33 µmol) in pyridine (0.5 mL). The brown reaction mixture was warmed to room temperature and stirred for 16 h (monitored by LCMS). The reaction mixture was diluted with saturated aqueous solution of NaHCO$_3$ (25 mL) and extracted with CH$_2$Cl$_2$ containing 20% of propan-2-ol (3×25 mL). The organic fractions were combined, dried (MgSO$_4$) and concentrated in vacuo to yield a residue that was purified by flash chromatography (Biotage SP4.12 g cartridge; 0-10% MeOH gradient in CH$_2$Cl$_2$) and reverse phase chromatography (Biotage SP4, 12 g cartridge, C18 phase; 20-40% acetonitrile gradient in water) to give 10a-(4-chlorophenyl)-N,N-dimethyl-1-[(3-methyl-1,2-oxazol-4-yl)carbonyl]-5-oxo-2,3,10,10a-tetrahydro-1H,5H-imidazo[1,2-a]pyrrolo[1,2-d]pyrazine-7-carboxamide (38) as a white solid (3.2 mg, yield 20%).

Example of General Method J 11a-(4-chlorophenyl)-1-[(3-methyl-1,2-oxazol-4-yl)carbonyl]-2,3,11,11a-tetrahydro-1H-imidazo[1,2-a]pyrido[1,2-d]-pyrazine-5,9-dione (39)

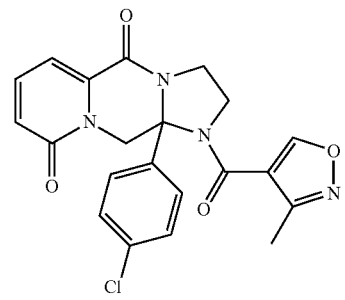 [SMILES: Cc1nocc1C(=O)N1CCN2C(=O)c3cccc(=O)n3CC12c1ccc(Cl)cc1]

$^1$H NMR (400 MHz, d6-DMSO): δ 2.28 (s, 3H), 3.93-4.14 (m, 3H), 4.04 (d, 1H, J 13.6 Hz), 4.28 (ddd, 1H, J 11.2, 7.8, 4.8 Hz), 6.39 (d, 1H, J 13.8 Hz), 6.66 (dd, 1H, J 9.2, 1.3 Hz), 6.87 (dd, 1H, J 6.8, 1.3 Hz), 7.42 (d, 4H, J 2.8 Hz), 7.49 (dd, 1H, J 9.3, 1.3 Hz), 9.36 (s, 1H). ESI-MI m/z [M+H]$^+$ 425.0.

Step 1

To a stirred suspension of methyl 6-hydroxypyridine-2-carboxylate (950 mg, 6.2 mmol) in toluene (31 mL) and water (0.3 mL) was added potassium carbonate (1.7 g, 12 mmol), lithium bromide (1.3 g, 15 mmol), tetrabutylammonium bromide (200 mg, 0.62 mmol) and 2-bromo-4'-chloroacetophenone (2.2 g, 9.4 mmol). The suspension was heated at 80° C. After 40 minutes the TLC analysis showed the absence of starting material. The mixture was diluted with CH$_2$Cl$_2$ and filtered through Filter Aid. The Filter Aid was rinsed thoroughly with CH$_2$Cl$_2$ and the combined filtrates concentrated in vacuo to yield brown oily solid. $^1$H NMR analysis showed the presence of both O-alkylated (undesired) and the N-alkylated (desired) products in a ratio 10:1 together with some unreacted starting material. The mixture was purified by flash chromatography (20-100% EtOAc gradient in n-hexanes) to yield the O-alkylated product (1.3 g) and the desired N-alkylated product methyl 1-[2-(4-chlorophenyl)-2-oxoethyl]-6-oxo-1,6-dihydropyridine-2-carboxylate (130 mg, yield 7%). $^1$H NMR (400 MHz, CDCl$_3$): δ 3.77 (s, 3H), 5.99 (s, 2H), 6.82 (dd, 1H, J 9.5, 1.4 Hz), 7.06 (dd, 1H, J 7.0, 1.3 Hz), 7.39 (dd, 1H, J 9.2, 7.0 Hz), 7.44-7.48 (m, 2H), 7.92-7.96 (m, 2H).

Step 2

To a suspension of methyl 1-[2-(4-chlorophenyl)-2-oxoethyl]-6-oxo-1,6-dihydropyridine-2-carboxylate (130 mg, 0.43 mmol) in MeOH (5 mL) and water (2.5 mL) was added a aqueous solution of NaOH (1 M) (0.8 mL, 0.8 mmol). The resulting dark orange solution was stirred at room temperature until completion (45 minutes, monitored by LCMS). The mixture was then acidified with an aqueous solution of HCl (1 M) and the resulting suspension was concentrated in vacuo to remove the MeOH. The precipitate formed was collected by filtration and washed with water to yield the acid derivative 1-[2-(4-chlorophenyl)-2-oxoethyl]-6-oxo-1,6-dihydropyridine-2-carboxylic acid as a yellow solid (100 mg, 80%). $^1$H NMR (400 MHz, d6-DMSO): 5.84 (s, 2H), 6.73 (dd, 1H, J 9.2, 1.2 Hz), 7.01 (dd, 1H, J 6.8, 1.0 Hz), 7.57 (dd, 1H, J 9.2, 6.9 Hz), 7.66 (d, 2H, J 8.6 Hz), 8.07 (d, 2H, J 8.5 Hz).

Step 3

To a suspension of 1-[2-(4-chlorophenyl)-2-oxoethyl]-6-oxo-1,6-dihydropyridine-2-carboxylic acid (50 mg, 0.17 mmol) in 1,2-dichloroethane (15 mL) was added ethane-1,2-diamine (0.1 mL, 1.5 mmol). The mixture was heated at reflux until completion (2 h, monitored by LMCS) and then diluted with water and extracted with CH$_2$Cl$_2$ (1×10 mL, 2×5 mL). The organic extracts were combined, dried (MgSO$_4$), filtered and the filtrate concentrated in vacuo to yield a yellow oil that was purified by flash chromatography (Biotage SP4, 4 g cartridge, 0-10% MeOH gradient in CH$_2$Cl$_2$) to give 11a-(4-chlorophenyl)-2,3,11,11a-tetrahydro-1H-imidazo[1,2-a]pyrido[1,2-d]pyrazine-5,9-dione as a yellow oil (50 mg, yield 92%). $^1$H NMR (400 MHz, CDCl$_3$): δ 1.73 (br s, 1H), 2.50 (br s, 1H), 2.89-3.02 (m, 1H), 3.33 (ddd, 1H, J 11.8, 7.5, 3.9 Hz), 3.50 (d, 1H, J 13.4 Hz), 3.59 (ddd, 1H, J 11.6, 7.5, 3.9 Hz), 3.97 (dt, 1H, J 11.4, 7.4 Hz), 5.55 (d, 1H, J 13.4 Hz), 6.60 (dd, 1H, J 9.2, 1.3 Hz), 7.07 (dd, 1H, J 6.8, 1.3 Hz), 7.22-7.28 (m, 4H), 7.34 (dd, 1H, J 9.2, 6.8 Hz).

Step 4

To generate the acid chloride, oxalyl chloride (0.15 mL, 1.8 mmol) and DMF (1 drop) were added to a suspension of 3-methyl-1,2-oxazole-4-carboxylic acid (60 mg, 0.47 mmol) in dry CH$_2$Cl$_2$ (1.0 mL) at 0° C. The suspension was stirred at 0° C. for 10 min and then at room temperature for 1.5 h. The resulting solution was then concentrated in vacuo to yield an oily solid. The material was taken up in CH$_2$Cl$_2$ and re-concentrated in vacuo to yield the acid chloride as an oily, off-white solid.

To a chilled (ice bath) suspension of the acid chloride (generated as above, 0.47 mmol) in pyridine (0.7 mL) was added a solution of 11a-(4-chlorophenyl)-2,3,11,11a-tetrahydro-1H-imidazo[1,2-a]pyrido[1,2-d]pyrazine-5,9-dione (50 mg, 0.16 mmol) in pyridine (0.8 mL). The suspension was stirred at 0° C. for 10 min and at room temperature until completion (1.5 h, monitored by LCMS). Water was added (5 mL) and the mixture extracted with CH$_2$Cl$_2$ (3×2 mL). The organic layers were combined, dried (MgSO$_4$), filtered and concentrated in vacuo to yield a yellow residue. The material was purified by flash chromatography (Silica gel, gradient 30-50% acetone in n-hexanes) to give 11a-(4-chlorophenyl)-1-[(3-methyl-1,2-oxazol-4-yl)carbonyl]-2,3,11,11a-tetrahydro-1H-imidazo[1,2-a]pyrido[1,2-d]pyrazine-5,9-dione (39) as a white solid (40 mg, yield 59%).

The following compounds were similarly prepared using General Method J.

| Cpd. No. | Structure | ESI-MI m/z [M + H]$^+$/$^1$H-NMR |
|---|---|---|
| 40 | 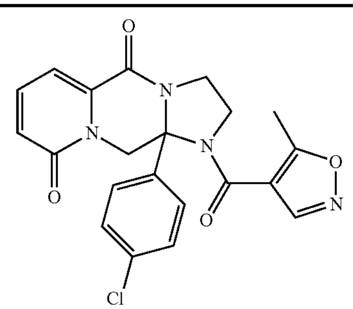 | ESI-MI m/z [M + H]$^+$ 425.0. $^1$H NMR (400 MHz, CDCl$_3$): δ 2.59 (s, 3H), 3.75 (d, 1H, J 14.0 Hz), 3.85-3.93 (m, 1H), 3.98-4.09 (m, 2H), 4.38-4.47 (m, 1H), 6.70 (dd, 1H, J 9.3, 1.4 Hz), 6.78 (d, 1H, J 14.0 Hz), 7.00 (dd, 1H, J 6.8, 1.3 Hz), 7.25-7.35 (m, 3H), 7.41-7.46 (m, 2H), 8.25 (s, 1H). |
| 148 | 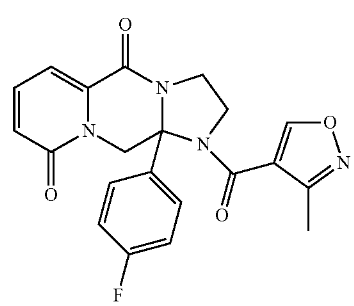 [SMILES: Cc1nocc1C(=O)N1CCN2C(=O)c3cccc(=O)n3CC12c1ccc(F)cc1] | ESI-MI m/z [M + H]$^+$ 409.09. $^1$H NMR (400 MHz, CDCl$_3$): δ 2.40 (s, 3H), 3.76 (d, 1H, J 14.1 Hz), 3.81-3.95 (m, 1H), 3.95-4.15 (m, 2H), 4.30-4.51 (m, 1H), 6.71 (d, 1H, J 9.2 Hz), 6.80 (d, 1H, J 14.0 Hz), 6.93-7.09 (m, 3H), 7.33 (dd, 1H, J 9.0, 7.0 Hz), 7.50 (dd, 2H, J 8.5, 5.0 Hz), 8.48 (s, 1H). |

| Cpd. No. | Structure | ESI-MI m/z [M + H]+/1H-NMR |
|---|---|---|
| 149 | 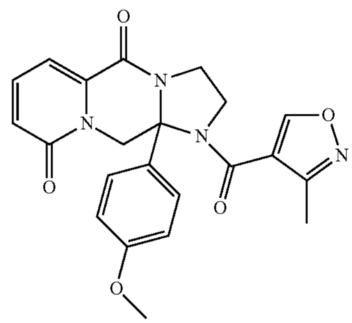 [SMILES: COc1ccc(C23Cn4c(cccc4=O)C(=O)N2CCN3C(=O)c2conc2C)cc1] | ESI-MI m/z [M + H]+ 421.09. 1H NMR (400 MHz, CDCl3): δ 2.40 (s, 3H), 3.72-3.79 (m, 4H), 3.80-3.92 (m, 1H), 3.95-4.10 (m, 2H), 4.38 (ddd, 1H, J 11.2, 9.2, 6.1 Hz), 6.70 (dd, 1H, J 9.2, 1.3 Hz), 6.77 (d, 1H, J 14.0 Hz), 6.82 (d, 2H, J 9.0 Hz), 7.01 (dd, 1H, J 6.8, 1.3 Hz), 7.32 (dd, 1H, J 9.2, 6.8 Hz), 7.40 (d, 2H, J 9.0 Hz), 8.44 (s, 1H). |
| 150 | 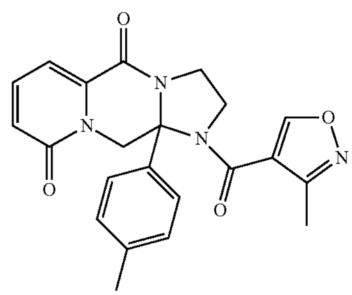 [SMILES: Cc1ccc(C23Cn4c(cccc4=O)C(=O)N2CCN3C(=O)c2conc2C)cc1] | ESI-MI m/z [M + H]+ 405.11. 1H NMR (400 MHz, CDCl3): δ 2.28 (s, 3H), 2.40 (s, 3H), 3.78 (d, 1H, J 14.1 Hz), 3.83-3.90 (m, 1H), 3.96-4.09 (m, 2H), 4.38 (ddd, 1H, J 11.6, 9.5, 6.1 Hz), 6.69 (dd, 1H, J 9.2, 1.4 Hz), 6.77 (d, 1H, J 14.1 Hz), 7.01 (dd, 1H, J 6.8, 1.3 Hz), 7.11 (d, 2H, J 8.0 Hz), 7.29-7.37 (m, 3H), 8.44 (s, 1H). |

Example of General Method K 10a-(4-chlorophenyl)-7-methyl-5-oxo-N-(2-phenylethyl)-2,3,10,10a-tetrahydro-1H,5H-imidazo[1,2-a]pyrazolo[1,5-d]pyrazine-1-carboxamide (41)

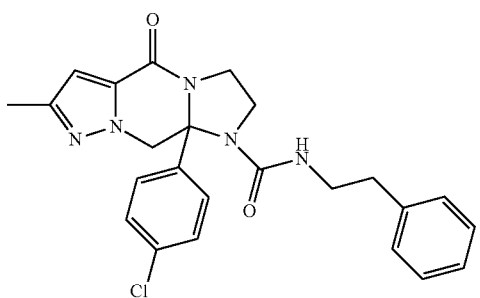 [SMILES: Cc1cc2n(n1)CC1(c3ccc(Cl)cc3)N(C(=O)NCCc3ccccc3)CCN1C2=O]

1H NMR (300 MHz, d6-acetone): δ 2.17 (s, 3H), 2.75-2.77 (t, 2H, J 1.4 Hz), 3.33-3.46 (m, 2H), 3.68 (dt, 1H, J 8.1, 4.6 Hz), 3.75-3.95 (m, 2H), 4.24 (ddd, 1H, J 10.9, 8.3, 3.9 Hz), 4.58 (d, 1H, J 13.4 Hz), 5.77 (d, 1H, J 13.4 Hz), 6.08 (br s, 1H), 6.45 (s, 1H), 7.14-7.30 (m, 5H), 7.30-7.48 (m, 4H). ESI-MI m/z [M+H]+ 450.1.

Step 1

Commercially available ethyl 1-(4'chlorophenylmethyl)-3-methyl-5-pyrazolecarboxylate (52 mg, 0.17 mmol) in xylenes was treated with ethane-1,2-diamine (1 mL, 8.48 mmol) and the solution heated at reflux with a dean stark trap. After one hour there was no trace of cyclised product. A catalytic amount of toluenesulfonic acid monohydrate was then added. After 24 h at reflux the reaction was completed and concentrated in vacuo to dryness. Water was added and the mixture extracted with EtOAc (3×30 ml). The organic layers were dried (MgSO4), filtrated and concentrated in vacuo to give a residue that was purified by flash chromatography (2% MeOH in CH2Cl2) to give 10a-(4-chlorophenyl)-7-methyl-2,3,10,10a-tetrahydro-1H,5H-imidazo[1,2-a]pyrazolo[1,5-d]pyrazin-5-one as a white solid (38 mg, 77% yield). 1H NMR (300 MHz, d6-acetone): δ 2.12 (s, 3H), 3.34-3.57 (m, 3H), 3.67-3.77 (m, 1H), 4.51 (d, 1H, J 12.9 Hz), 4.75 (d, 1H, J 12.5 Hz), 6.49 (s, 1H), 7.33-7.44 (m, 4H). ESI-MI m/z [M+H]+ 302.9

Step 2

To a solution of 10a-(4-chlorophenyl)-7-methyl-2,3,10,10a-tetrahydro-1H,5H-imidazo[1,2-a]pyrazolo[1,5-d]pyrazin-5-one (40 mg, 0.13 mmol) in a mixture of pyridine (400 µl) and CH2Cl2 (400 µl) was added (2-isocyanatoethyl)benzene (150 µl) at 0° C. The mixture was let to come back to room temperature. After 1 h the reaction was complete (monitored by LCMS). Water was then added and the mixture extracted with CH2Cl2. The organic fractions were then stirred overnight with PS-trisamine resin to remove the excess of isocyanate. Filtration through a cotton wool plug and concentration in vacuo gave a residue that was purified by flash chromatography (Silica gel, gradient 2:3 acetone/hexane) to give 10a-(4-chlorophenyl)-7-methyl-5-oxo-N-(2-phenylethyl)-2,3,10,10a-tetrahydro-1H,5H-imidazo[1,2-a]pyrazolo[1,5-d]pyrazine-1-carboxamide (41) as a white solid (58 mg, yield 99%).

The following compounds were similarly prepared using General Method K.

| Cpd. No. | Structure | ESI-MI m/z [M + H]+/1H-NMR |
|---|---|---|
| 42 | 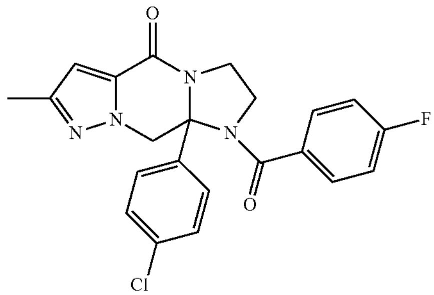 [SMILES: Cc1cc2n(n1)CC1(c3ccc(Cl)cc3)N(C(=O)c3ccc(F)cc3)CCN1C2=O] | ESI-MI m/z [M + H]+ 425.0. 1H NMR (300 MHz, d6-acetone): δ 2.21 (s, 3H), 3.80 (ddd, 1H, J 11.0, 8.0, 6.8 Hz), 3.92 (ddd, 1H, J 10.2, 7.9, 4.3 Hz), 4.03-4.15 (m, 1H), 4.25 (ddd, 1H, J 11.1, 8.2, 4.2 Hz), 4.90 (d, 1H, J 13.6 Hz), 5.82 (d, 1H, J 13.6 Hz), 6.52 (s, 1H), 7.20-7.30 (m, 2H), 7.36-7.42 (m, 2H), 7.48-7.54 (m, 2H), 7.60-7.68 (m, 2H). |
| 43 | 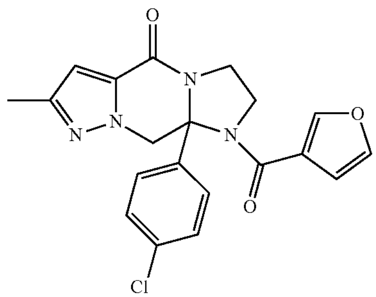 [SMILES: Cc1cc2n(n1)CC1(c3ccc(Cl)cc3)N(C(=O)c3ccoc3)CCN1C2=O] | ESI-MI m/z [M + H]+ 397.0. 1H NMR (300 MHz, d6-acetone): δ 2.21 (s, 3H), 3.80-3.94 (m, 1H), 4.24-4.44 (m, 3H), 4.77 (d, 1H, J 13.3 Hz), 5.85 (d, 1H, J 13.5 Hz), 6.51 (s, 1H), 6.83 (dd, 1H, J 2.0, 0.9 Hz), 7.32-7.47 (m, 4H), 7.66 (dd, 1H, J 1.9, 1.4 Hz), 8.15 (dd, 1H, J 1.4, 0.9 Hz). |
| 44 | 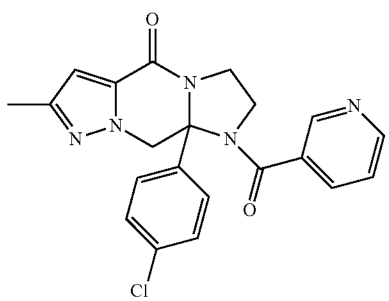 [SMILES: Cc1cc2n(n1)CC1(c3ccc(Cl)cc3)N(C(=O)c3cccnc3)CCN1C2=O] | ESI-MI m/z [M + H]+ 408.1. 1H NMR (300 MHz, d6-acetone): δ 2.21 (s, 3H), 3.76-3.86 (m, 1H), 3.98 (ddd, 1H, J 10.0, 8.0, 4.2 Hz), 4.08-4.18 (m, 1H), 4.28 (ddd, 1H, J 11.2, 8.2, 4.3 Hz), 4.93 (d, 1H, J 13.4 Hz), 5.82 (d, 1H, J 13.3 Hz), 6.53 (s, 1H), 7.37-7.43 (m, 2H), 7.46-7.55 (m, 3H), 7.97 (dd, 1H, J 8.0, 2.3, 1.8 Hz), 8.69 (dd, 1H, J 4.9, 1.7 Hz), 8.77 (d, 1H, J 1.7 Hz). |
| 45 | 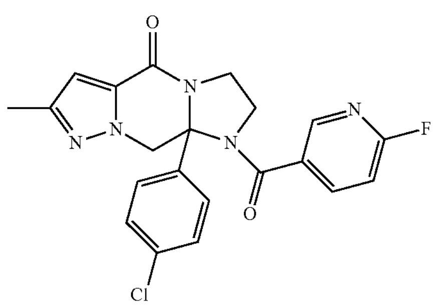 [SMILES: Cc1cc2n(n1)CC1(c3ccc(Cl)cc3)N(C(=O)c3ccc(F)nc3)CCN1C2=O] | ESI-MI m/z [M + H]+ 426.0. 1H NMR (300 MHz, d6-acetone): δ 2.20 (s, 3H), 3.76-3.88 (m, 1H), 4.02 (ddd, 1H, J 9.9, 7.9. 4.2 Hz), 4.11-4.22 (1H, m), 4.29 (ddd, 1H, J 11.1, 8.0, 4.2 Hz), 4.92 (d, 1H, J 13.4 Hz), 5.81 (d, 1H, J 13.3 Hz), 6.53 (s, 1H), 7.21 (ddd, 1H, J 8.5, 2.8, 0.6 Hz), 7.36-7.42 (m, 2H), 7.49-7.55 (m, 2H), 8.20 (ddd, 1H, J 8.5, 7.7, 2.4 Hz), 8.47-8.50 (m, 1H). |
| 46 | 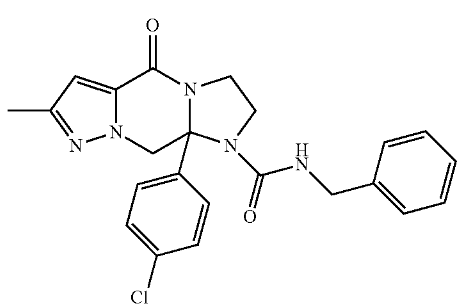 [SMILES: Cc1cc2n(n1)CC1(c3ccc(Cl)cc3)N(C(=O)NCc3ccccc3)CCN1C2=O] | ESI-MI m/z [M + H]+ 436.1. 1H NMR (300 MHz, d6-acetone): δ 2.17 (s, 3H), 3.78-3.88 (m, 2H), 4.03 (ddd, 1H, J 10.8, 4.1, 2.0 Hz), 4.22-4.32 (m, 1H), 4.39 (d, 2H, J 5.9 Hz), 4.64 (d, 1H, J 13.7 Hz), 5.78 (d, 1H, J 13.4 Hz), 6.47 (s, 1H), 6.52-6.60 (m, 1H), 7.18-7.29 (m, 5H), 7.31-7.36 (m, 2H), 7.45-7.51 (m, 2H). |

| Cpd. No. | Structure | ESI-MI m/z [M + H]+/1H-NMR |
|---|---|---|
| 47 | 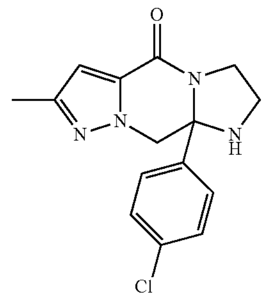 [SMILES: Cc1cc2n(n1)CC1(c3ccc(Cl)cc3)NCCN1C2=O] | ESI-MI m/z [M + H]+ 302.9. 1H NMR (300 MHz, d6-acetone): δ 2.12 (s, 3H), 3.34-3.57 (m, 3H), 3.67-3.77 (m, 1H), 4.51 (d, 1H, J 12.9 Hz), 4.75 (d, 1H, J 12.5 Hz), 6.49 (s, 1H), 7.33-7.44 (m, 4H). |

Example of General Method L

1-[(3-methyl-1,2-oxazol-4-yl)carbonyl]-10a-(pyridin-2-yl)-2,3,10,10a-tetrahydro-1H,5H-imidazo[1,2-a]pyrrolo[1,2-d]pyrazin-5-one (103)

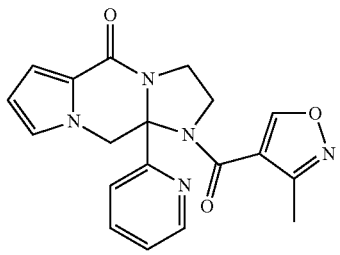 [SMILES: Cc1nocc1C(=O)N1CCN2C(=O)c3cccn3CC12c1ccccn1]

1H-NMR (400 MHz, CDCl3): δ 2.34 (s, 3H), 3.97-4.12 (m, 2H), 4.14-4.23 (m, 1H), 4.34-4.43 (m, 1H), 4.49 (d, 1H, J 13.0 Hz), 5.76 (d, 1H, J 13.0 Hz), 6.29 (dd, 1H, J 3.7, 2.6 Hz), 6.86-6.92 (m, 2H), 7.02 (d, 1H, J 8.0 Hz), 7.17 (dd, 1H, J 7.3, 4.9 Hz), 7.57 (dt, 1H, J 7.8, 1.7 Hz), 8.46-8.50 (m, 1H), 8.64 (br s, 1H). ESI-MI m/z [M+H]+ 364.1.

Step 1

Glycine ethyl ester hydrochloride (1.0 g, 7.2 mmol) and sodium acetate (960 mg, 12 mmol) were dissolved in water (5 mL). Acetic acid (10 mL) was then added. The solution was heated to reflux and 2,5-dimethoxytetrahydrofuran (0.95 mL, 7.3 mmol) was added. The mixture was heated at reflux for 4 hours before being allowed to cool to room temperature. The dark brown solution was diluted with water (40 mL), neutralised with solid NaHCO3 (16 g) and extracted with CH2Cl2 (3×40 mL). The organic layers were dried (MgSO4), filtered, concentrated in vacuo to give a dark brown liquid. The material was purified by flash chromatography (Biotage SP4, 40 g cartridge, gradient 0-60% gradient EtOAc in hexanes) to give ethyl 1H-pyrrol-1-ylacetate as a colourless liquid (720 mg, yield 65%). 1H-NMR (400 MHz, CDCl3): δ 1.28 (t, 3H, J 7.1 Hz), 4.22 (q, 2H, J 7.2 Hz), 4.62 (s, 2H), 6.20-6.22 (m, 2H), 6.65-6.67 (m, 2H).

Step 2

To a solution of 2-bromopyridine (380 μL, 4.0 mmol) in dry THF (15 mL) was added n-BuLi (1.6 M in hexanes, 2.5 mL, 4.0 mmol) at −78° C. The dark brown mixture was stirred for 30 minutes before a solution of ethyl 1H-pyrrol-1-ylacetate (720 mg, 4.7 mmol) in THF (5 mL) was added. The brown solution was stirred at −78° C. for 40 minutes and then at room temperature for 2 hours. The solution was poured into a saturated aqueous solution of NH4Cl (30 mL) and extracted with EtOAc (3×20 mL). The organic layers were dried (MgSO4), filtered and concentrated in vacuo to give a dark yellow oil that was purified by flash chromatography (Biotage SP4, 40 g cartridge, gradient 0-60% EtOAc in hexanes). To give 1-(Pyridine-2-yl)-2-(1H-pyrrol-1-yl)ethanone as a oil (470 mg, yield 63%). 1H-NMR (400 MHz, CDCl3): δ 5.60 (s, 2H), 6.23-6.27 (m, 2H), 6.69-6.72 (m, 2H), 7.54 (ddd, 1H, J 7.5, 4.8, 1.1 Hz), 7.88 (dt, 1H, J 7.7, 1.7 Hz), 8.06-8.10 (m, 1H), 8.69-8.73 (m, 1H).

Step 3

To a solution of 1-(pyridin-2-yl)-2-(1H-pyrrol-1-yl)ethanone (470 mg, 2.5 mmol) in dry CH2Cl2 (30 mL) was added trichloroacethyl chloride (0.57 mL, 5.1 mmol) at 0° C. The mixture was allowed to warm to room temperature and stirred overnight. The LCMS analysis showed the presence of the desired product and some remaining starting material. The mixture was cooled to 0° C. and trichloroacetyl chloride (0.2 mL, 1.8 mmol) was added. After 6 hours the LCMS analysis showed completion of the reaction. The mixture was quenched at 0° C. with chilled a saturated aqueous solution of NaHCO3 (25 mL). The organic layers were extracted with CH2Cl2 (2×15 mL), dried (MgSO4), filtrated and concentrated in vacuo to give a pale brown solid. The material was purified by flash chromatography (Biotage SP4, 40 g cartridge, EtOAc gradient in hexanes) to give 2,2,2-trichloro-1-{1-[2-oxo-2-(pyridin-2-yl)ethyl]-1H-pyrrol-2-yl}ethanone as a yellow solid (690 mg, yield 84%).
1H-NMR (400 MHz, CDCl3): 6.01 (s, 2H), 6.37 (dd, 1H, J 2.5 Hz), 7.01-7.05 (m, 1H), 7.54 (ddd, 1H, J 7.6, 4.8, 1.2 Hz), 7.64 (dd, 1H, J 4.4, 1.5 Hz), 7.88 (dt, 1H, J 7.7, 1.6 Hz), 8.06-8.10 (m, 1H), 8.70-8.74 (m, 1H).

Step 4

To a solution of 2,2,2-trichloro-1-{1-[2-oxo-2-(pyridin-2-yl)ethyl]-1H-pyrrol-2-yl}ethanone (600 mg, 1.8 mmol) in 1,4-dioxane (20 ml) was added a solution of a aqueous solution of sodium hydroxide (1 M) (3.6 mL, 3.6 mmol) at 0° C. The mixture was allowed to warm to room temperature. After completion (30 minutes; reaction monitored by LCMS) water was added (40 mL). The mixture was then acidified with aqueous HCl (1 M) and extracted with EtOAc (3×40 mL). The organic layers were dried (Na2SO4), filtrated and concentrated in vacuo to give 1-[2-oxo-2-(pyridin-2-yl)ethyl]-1H-pyrrole-2-carboxylic acid as a pale brown solid that was used such as in the next step without purification (500 mg). ESI-MI m/z [M+H]$^+$ 245.0.

Step 5

To a solution of 1-[2-oxo-2-(pyridin-2-yl)ethyl]-1H-pyrrole-2-carboxylic acid (500 mg, 2.2 mmol) in 1,4-dioxane (50 mL) was added ethane-1,2-diamine (2.9 mL, 43 mmol). The solution was heated at reflux. The outcome of the reaction was monitored by LCMS. After two days the starting material and target compound were both present in the mixture. Ethane-1,2-diamine (1.0 mL, 15 mmol) was added and the solution heated at reflux for a further two days. LCMS showed mainly the desired product in presence of a small amount of starting material. The yellow solution was concentrated in vacuo to give a oil, which was purified by flash chromatography (Biotage SP4, 40 g cartridge, 0 to 10% MeOH gradient in CH$_2$Cl$_2$) to give 10a-(pyridin-2-yl)-2,3,10,10a-tetrahydro-1H,5H-imidazo[1,2-a]pyrrolo[1,2-d]pyrazin-5-one as a pale yellow solid (350 mg, yield 63%). $^1$H-NMR (400 MHz, MeOD): δ 2.84-2.94 (m, 1H), 3.27-3.36 (m, 1H), 3.86 (dt, 1H, J 11.0, 7.8 Hz), 4.25 (d, 1H, J 12.1 Hz), 5.05 (d, 1H, J 12.1 Hz), 6.06 (dd, 1H, J 2.6, 3.9 Hz), 6.68-6.72 (m, 1H), 6.76-6.72 (m, 1H), 6.76-6.79 (m, 1H), 7.25-7.30 (m, 2H), 7.70 (dt, 1H, J 7.8, 1.7 Hz), 8.54-8.58 (m, 1H).

Step 6

To generate the acid chloride, 3-methyl-1,2-oxazole-4-carboxylic acid (75 mg, 0.59 mmol) was dissolved in CH$_2$Cl$_2$ (1 mL). Oxalyl chloride (0.15 mL, 1.8 mmol) and then a drop of DMF were added at 0° C. The ice bath was removed after 10 minutes and the mixture stirred for 1 hour at room temperature before the solvent and the excess of oxalyl chloride were removed in vacuo to give an oil. CH$_2$Cl$_2$ was added and the mixture concentrated in vacuo to give the acid chloride as a orange oil. 10a-(pyridin-2-yl)-2,3,10,10a-tetrahydro-1H,5H-imidazo[1,2-a]pyrrolo[1,2-d]-pyrazin-5-one (50 mg, 0.20 mmol) was dissolved in pyridine (1 mL) and the solution added to the previously generated acid chloride (0.59 mmol) in pyridine (0.5 mL) at 0° C. The ice bath was removed after 5 minutes and the mixture stirred at room temperature for 2 h 15 min. The suspension was then diluted with water (5 mL) and extracted with CH$_2$Cl$_2$ (3×2 mL). The extracts were combined, dried (MgSO$_4$), filtered and concentrated in vacuo to give a dark residue that was purified by flash chromatography (40-60% acetone in hexanes) to give 1-[(3-methyl-1,2-oxazol-4-yl)carbonyl]-10a-(pyridin-2-yl)-2,3,10,10a-tetrahydro-1H,5H-imidazo[1,2-a]pyrrolo[1,2-d]pyrazin-5-one (103) as a white solid (54 mg, yield 34%).

The following compounds were similarly prepared using General Method L.

| Cpd. No. | Structure | ESI-MI m/z [M + H]$^+$/$^1$H-NMR |
|---|---|---|
| 101 | 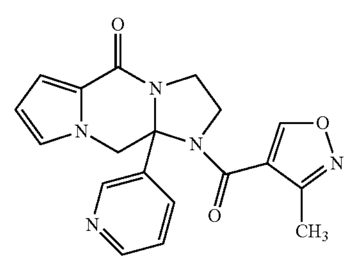 [SMILES: Cc1nocc1C(=O)N1CCN2C(=O)c3cccn3CC12c1cccnc1] | ESI-MI m/z [M + H]$^+$ 364.1. $^1$H NMR (400 MHz, CDCl$_3$): δ 2.44 (s, 3H), 3.76 (dt, 1H, J 11.6, 7.7 Hz), 3.92 (td, 1H, J 8.8, 4.1 Hz), 4.05-4.14 (m, 1H), 4.41-4.50 (m, 1H), 4.54 (d, 1H, J 13.0 Hz), 5.68 (d, 1H, J 13.0 Hz), 6.20-6.25 (m, 1H), 6.75 (br s, 1H), 6.95 (br d, 1H, J 3.7 Hz), 7.24 (dd, 1H, J 8.2, 4.8 Hz), 7.56-7.63 (m, 1H), 8.56 (d, 1H, J 4.7 Hz), 8.61 (s, 1H), 8.67 (d, 1H, J 2.4 Hz). |
| 102 | 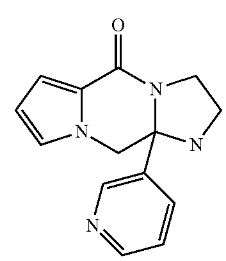 [SMILES: O=C1c2cccn2CC2(c3cccnc3)NCCN12] | ESI-MI m/z [M + H]$^+$ 255. $^1$H NMR (400 MHz, MeOD): δ 2.80 (dt, 1H J 12.2, 8.3 Hz), 3.34-3.44 (m, 1H), 3.55 (ddd, 1H, J 10.9, 7.8, 2.8 Hz), 3.70-3.81 (m, 1H), 4.37 (d, 1H, J 12.6 Hz), 4.69 (d, 1H, J 12.6 Hz), 6.13 (dd, 1H, J 3.8, 2.6 Hz), 6.68-6.73 (m, 1H), 6.83-6.88 (m, 1H), 7.33-7.40 (m, 1H), 7.78 (ddd, 1H, J 8.1, 2.4, 1.6 Hz), 8.44 (dd, 1H, J 4.9, 1.5 Hz), 8.52-8.56 (m, 1H). |
| 104 | 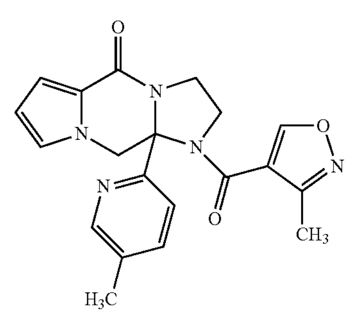 [SMILES: Cc1ccc(C23Cn4cccc4C(=O)N2CCN3C(=O)c2conc2C)nc1] | ESI-MI m/z [M + H]$^+$ 378.1. $^1$H NMR (400 MHz, CDCl$_3$): δ 2.26 (s, 3H), 2.35 (s, 3H), 3.96-4.09 (m, 2H), 4.12-4.20 (m, 1H), 4.33-4.40 (m, 1H), 4.47 (d, 1H, J 13.0 Hz), 5.74 (d, 1H, J 13.0 Hz), 6.28 (dd, 1H, J 3.9, 2.6 Hz), 6.86-6.91 (m, 2H), 6.93 (d, 1H, J 8.1 Hz), 7.36 (ddd, 1H, J 8.1, 2.2, 0.6 Hz), 8.29 (dd, 1H, J 1.5, 0.7 Hz), 8.62 (s, 1H). |

-continued

| Cpd. No. | Structure | ESI-MI m/z [M + H]+/1H-NMR |
|---|---|---|
| 105 | 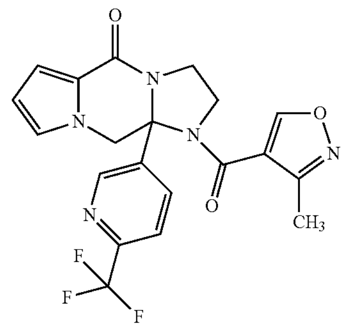 [SMILES: Cc1nocc1C(=O)N1CCN2C(=O)c3cccn3CC12c1ccc(C(F)(F)F)nc1] | ESI-MI m/z [M + H]+ 432.1. 1H NMR (400 MHz, CDCl3): δ 2.34 (s, 3H), 4.02 (dt, 1H, J 10.8, 8.3 Hz), 4.11 (dd, 1H, J 16.4, 8.1 Hz), 4.23 (td, 1H, J 8.4, 2.6 Hz), 4.43 (ddd, 1H, J 10.8, 8.0, 2.6 Hz), 4.50 (d, 1H, J 13.2 Hz), 5.78 (d, 1H, J 13.2 Hz), 6.32 (dd, 1H, J 3.8, 2.7 Hz), 6.87-6.94 (m, 2H), 7.17 (d, 1H, J 8.4 Hz), 7.83 (dd, 1H, J 8.4, 2.1 Hz), 8.67 (s, 1H), 8.75 (br s, 1H). |

Example of General Method M

Route (a)

10a-(4-methoxyphenyl)-1-[(3-methyl-1,2-oxazol-4-yl)carbonyl]-5-oxo-2,3,10,10a-tetrahydro-1H,5H-imidazo[1,2-a]pyrrolo[1,2-d]pyrazine-8-carbonitrile (106)

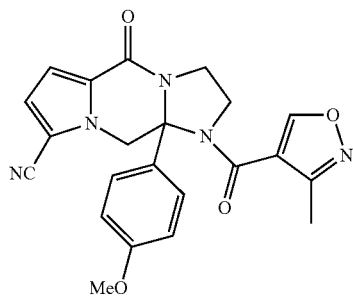 [SMILES: COc1ccc(C23Cn4c(C#N)ccc4C(=O)N2CCN3C(=O)c2conc2C)cc1]

1H-NMR (CDCl3, 400 MHz): δ 2.43 (s, 4H), 3.76 (s, 3H), 3.78-3.86 (m, 1H), 3.86-3.95 (m, 1H), 4.68 (dt, 1H, J 8.8, 5.1 Hz), 4.27-4.36 (m, 1H), 4.56 (d, 1H, J 13.2 Hz), 5.98 (d, 1H, J 13.2 Hz), 6.76 (d, 1H, J 4.1 Hz), 6.81-6.85 (m, 2H), 6.87 (d, 1H, J 4.2 Hz), 7.33-7.38 (m, 2H), 8.51 (s, 1H). ESI-MI m/z [M+H]+ 418.1.

Step 1

To a solution of methyl 5-bromopyrrole-2-carboxylate (340 mg, 1.7 mmol) in dry DMF (8 mL) was added sodium hydride (60% dispersion in mineral oil, 75 mg, 1.9 mmol) portionwise under nitrogen. After 1 hour at 0° C. a solution of 2-bromo-1-(4-methoxyphenyl)ethanone (500 mg, 2.2 mmol) in DMF (4 mL) was added. The resulting yellow solution was then stirred at room temperature for 2.5 hours. Saturated aqueous solution of NH4Cl (30 mL) was added and the mixture extracted with EtOAc (100 mL). The organic layer was washed with brine (35 mL), dried (MgSO4), filtered and concentrated in vacuo to give a liquid that was purified by flash chromatography (Biotage SP4, 40 g silica cartridge, 0 to 50% EtOAc gradient in hexanes) to give methyl 5-bromo-1-[2-(4-methoxyphenyl)-2-oxoethyl]-1H-pyrrole-2-carboxylate as a white solid (525 mg, yield 88%).

1H-NMR (400 MHz, CDCl3): δ 3.73 (s, 3H), 3.90 (s, 3H), 5.89 (s, 2H), 6.33 (d, 1H, J 4.1 Hz), 6.99-7.02 (m, 2H), 7.05 (d, 1H), 7.99-8.02 (m, 2H).

Step 2

To a solution of methyl 5-bromo-1-[2-(4-methoxyphenyl)-2-oxoethyl]-1H-pyrrole-2-carboxylate (250 mg, 0.71 mmol) in 1,4-dioxane (50 mL) was added ethane-1,2-diamine (1.0 mL, 15 mmol). The solution was heated at reflux one week. During that time a batch of ethane-1,2-diamine (1.5 mL, 22 mmol) was added. The mixture was concentrated in vacuo to give a oil that was partitioned between water (30 mL) and CH2Cl2 (30 mL). The aqueous layer was further extracted with CH2Cl2 (2×30 mL). The organic layers were dried (MgSO4), filtered and concentrated in vacuo to give a oil that was purified by flash chromatography (Biotage SP4, 12 g cartridge, gradient 0-10% methanol in CH2Cl2) to give 8-bromo-10a-(4-methoxyphenyl)-2,3,10,10a-tetrahydro-1H,5H-imidazo[1,2-a]pyrrolo[1,2-d]pyrazin-5-one as a pale yellow solid (135 mg, yield 52%). ESI-MI m/z calculated [M+H]+ 364.0.

Step 3a 8-bromo-10a-(4-methoxyphenyl)-2,3,10,10a-tetrahydro-1H,5H-imidazo[1,2-a]pyrrolo[1,2-d]pyrazin-5-one (50 mg, 0.14 mmol), zinc cyanide (24 mg, 0.20 mmol) and palladium (0) tetrakistriphenylphosphine (32 mg, 0.03 mmol) were suspended in dry DMF (2.5 mL) in a microwave vial flushed with argon. The mixture was heated in the microwave at 160° C. for 20 minutes. Water was added and the mixture extracted with CH2Cl2. The organic layers were dried (MgSO4), filtrated and concentrated in vacuo. The resulting residue was purified by flash chromatography (Biotage SP4 12 g cartridge, gradient 0-10% MeOH in CH2Cl2) to give 10a-(4-methoxyphenyl)-5-oxo-2,3,10,10a-tetrahydro-1H,5H-imidazo[1,2-a]pyrrolo[1,2-d]pyrazine-8-carbonitrile as a brown solid (45 mg, yield 71%) ESI-MI m/z [M+H]+ 309.1.

Step 4a

To generate the acid chloride, oxalyl chloride (150 μL, 1.61 mmol) and DMF (1 drop) were added to a suspension of 3-methyl-1,2-oxazole-4-carboxylic acid (65 mg, 0.51 mmol) in CH2Cl2 (1 mL) at 0° C. The suspension was allowed to stir for a further 15 minutes at 0° C. followed by 1 hour at room temperature. The resulting solution was concentrated in vacuo (without heating) to give an oil that was dissolved in CH2Cl2 and concentrated in vacuo. To a chilled (ice bath) suspension of the acid chloride (generated as above, 0.51 mmol) in pyridine (1 mL) was added a cloudy mixture of 10a-(4-methoxyphenyl)-5-oxo-2,3,10,10a-tetrahydro-1H, 5H-imidazo[1,2-a]pyrrolo[1,2-d]-pyrazine-8-carbonitrile (45 mg, 0.1 mmol) in pyridine (1 mL). The reaction mixture was warmed to room temperature and stirred for 1.5 hour. The reaction mixture was then diluted with water (5 mL) and extracted with CH$_2$Cl$_2$ (3×2 mL). The organic fractions were combined, dried (MgSO$_4$) and concentrated in vacuo to yield a crude residue that was purified by flash chromatography (Biotage SP4, 4 g cartridge, gradient 0-100% EtOAc in hexanes) and reverse phase chromatography (Biotage SP4.12 g cartridge, C18, 5-50s-55-100% acetonitrile in water; water contained 0.1% formic acid) to give 10a-(4-methoxyphenyl)-1-[(3-methyl-1,2-oxazol-4-yl)carbonyl]-5-oxo-2,3,10,10a-tetrahydro-1H,5H-imidazo[1,2-a]pyrrolo[1,2-d]pyrazine-8-carbonitrile (106) as a white solid (17 mg, yield 40%).

Example of General Method M

Route (b)

10a-(4-methoxyphenyl)-8-methyl-1-[(3-methyl-1,2-oxazol-4-yl)carbonyl]-2,3,10,10a-tetrahydro-1H,5H-imidazo[1,2-a]pyrrolo[1,2-d]pyrazin-5-one (107)

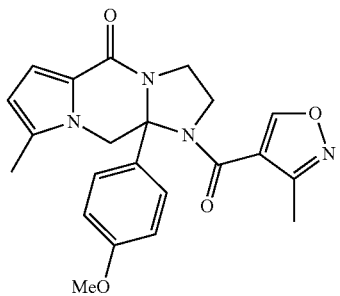 [SMILES: COc1ccc(C23Cn4c(C)ccc4C(=O)N2CCN3C(=O)c2conc2C)cc1]

$^1$H-NMR (400 MHz, CDCl$_3$): δ 2.20 (s, 3H), 2.44 (s, 3H), 3.74 (s, 3H), 3.75-3.84 (m, 2H), 3.98-4.07 (m, 1H), 4.26-4.40 (m, 2H), 5.63 (d, 1H, J 5.6 Hz), 5.93 (d, 1H, J 5.6 Hz), 6.79 (br d, 2H, J 8.9 Hz), 6.84 (d, 1H, J 3.76 Hz), 7.30 (br d, 2H, J 8.8 Hz), 8.54 (br s, 1H). ESI-MI m/z [m+H]$^+$ 407.2.

Step 3b

To a suspension of 8-bromo-10a-(4-methoxyphenyl)-2,3,10,10a-tetrahydro-1H,5H-imidazo[1,2-a]pyrrolo[1,2-d]pyrazin-5-one (60 mg, 0.17 mmol), [1,1'-bis(diphenylphosphino)ferrocene]dichloropalladium(II), complex with CH$_2$Cl$_2$ (13 mg, 0.016 mmol) and trimethylboroxine solution in THF (3.5, M, 0.84 mmol, 0.24 mL) in 1,4-dioxane (1.5 mL) was added a solution of potassium fluoride (30 mg, 0.52 mmol) in water (0.5 mL). The reaction vessel was flushed with argon and then heated at 140° C. for 20 minutes in the microwave. The suspension was then diluted with CH$_2$Cl$_2$ and filtered. The organic layer was separated, dried (MgSO$_4$), filtered and concentrated in vacuo to give a residue that was purified by flash chromatography (Biotage SP4, 12 g cartridge, CH$_2$Cl$_2$ 3 CV, gradient 0-10% MeOH in CH$_2$Cl$_2$ 15 CV) to give 10a-(4-methoxyphenyl)-8-methyl-2,3,10,10a-tetrahydro-1H,5H-imidazo[1,2-a]pyrrolo[1,2-d]pyrazin-5-one as off-white solid (25 mg, yield 40%). ESI-MI m/z [M+H]$^+$ 298.0.

Step 4b

To generate the acid chloride to a suspension of 3-methyl-isoxazole-4-carboxylic acid (45 mg, 0.35 mmol) in dry CH$_2$Cl$_2$ (1.0 mL) was added oxalyl chloride (0.12 mL, 1.4 mmol) followed by DMF (1 drop, catalytic) under nitrogen at 0° C. The mixture was stirred at 0° C. for 10 minutes and then at room temperature for 1.5 h. The resulting solution was concentrated in vacuo at room temperature to give a oil that was dissolved in CH$_2$Cl$_2$ and re-concentrated to give the acid chloride. To a chilled suspension of the acid chloride (generated as above, 0.35 mmol) in pyridine (0.5 mL) was added a solution of 10a-(4-methoxyphenyl)-8-methyl-2,3,10,10a-tetrahydro-1H,5H-imidazo[1,2-a]pyrrolo[1,2-d]pyrazin-5-one (25 mg, 0.08 mmol) in pyridine (1.0 mL). The suspension was stirred at 0° C. for 5 minutes and then at room temperature until completion (monitored by LCMS). After one hour the suspension was diluted with water (5 mL) and extracted with CH$_2$Cl$_2$ (3×2 mL). The organic extracts were combined, dried (MgSO$_4$), filtered and concentrated in vacuo to give a residue that was purified by flash chromatography (Silica gel, gradient 30-50% acetone in hexanes) to give 10a-(4-methoxyphenyl)-8-methyl-1-[(3-methyl-1,2-oxazol-4-yl)carbonyl]-2,3,10,10a-tetrahydro-1H,5H-imidazo[1,2-a]pyrrolo[1,2-d]pyrazin-5-one (107) as a white solid (14 mg, yield 43%).

The following compounds were similarly prepared using General Method M: Route (b).

| Cpd. No. | Structure | ESI-MI m/z [M + H]$^+$/$^1$H-NMR |
|---|---|---|
| 151 | 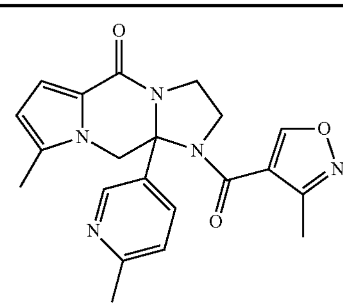 | ESI-MI m/z [M + H]$^+$ 392.11. $^1$H NMR (400 MHz, CDCl$_3$): δ 2.24 (s, 3H), 2.43 (s, 3H), 2.49 (s, 3H), 3.63-3.80 (m, 1H), 3.91 (ddd, 1H, J 9.4, 8.2, 3.9 Hz), 4.00-4.14 (m, 1H), 4.23 (d, 1H, J 13.0 Hz), 4.41 (ddd, 1H, J 12.1, 8.5, 3.9 Hz), 5.64 (d, 1H, J 13.0 Hz), 5.96 (d, 1H, J 3.8 Hz), 6.85 (d, 1H, J 3.8 Hz), 7.07 (d, 1H, J 8.3 Hz), 7.43 (dd, 1H, J 8.3, 2.6 Hz), 8.50 (d, 1H, J 1.9 Hz), 8.62 (s, 1H). |

-continued

| Cpd. No. | Structure | ESI-MI m/z [M + H]⁺/¹H-NMR |
|---|---|---|
| 152 | 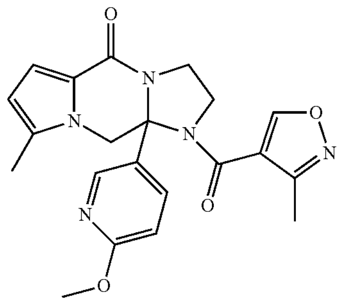 [SMILES: COc1ccc(C23Cn4c(C)ccc4C(=O)N2CCN3C(=O)c2conc2C)cn1] | ESI-MI m/z [M + H]⁺ 408.14. ¹H NMR (400 MHz, CDCl₃): δ 2.24 (s, 3H), 2.44 (s, 3H), 3.64-3.80 (m, 1H), 3.82-3.96 (m, 4H), 3.97-4.10 (m, 1H), 4.23 (d, 1H, J 13.0 Hz), 4.40 (ddd, 1H, J 11 .7 , 8.6, 4.1 Hz), 5.62 (d, 1H, J 13.0 Hz), 5.97 (dd, 1H, J 3.8, 0.6 Hz), 6.66 (dd, 1H, J 8.8, 0.5 Hz), 6.87 (d, 1H, J 3.8 Hz), 7.52 (dd, 1H, J 8.8, 2.8 Hz), 8.14 (d, 1H, J 2.7 Hz), 8.60 (s, 1H). |
| 153⁽¹⁾ | | ESI-MI m/z [M + H]⁺ 407.15. ¹H NMR (400 MHz, CDCl₃): δ 1.69 (t, 1H, J 5.8 Hz), 2.22 (s, 3H), 2.44 (d, 3H, J 0.5 Hz), 3.73-3.87 (m, 2H), 3.97-4.10 (m, 1H), 4.28-4.42 (m, 2H), 4.65 (d, 2H, J 5.8 Hz), 5.68 (d, 1H, J 12.9 Hz), 5.93 (dd, 1H, J 3.8, 0.7 Hz), 6.86 (d, 1H, J 3.8 Hz), 7.30 (d, 2H, J 8.6 Hz), 7.38 (d, 2H, J 8.5 Hz), 8.53 (s, 1H). |

⁽¹⁾Di-acylation and hydrolysis of the intermediate performed according to steps 4b and 5b of general method A.

Example of General Method M

Route (c)

8-ethynyl-10a-(4-methoxyphenyl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (108)

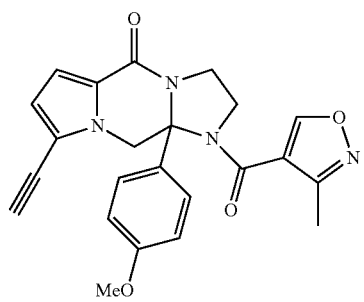 [SMILES: C#Cc1ccc2n1CC1(c3ccc(OC)cc3)N(C(=O)c3conc3C)CCN1C2=O]

¹H-NMR (400 MHz, CDCl₃): δ 2.42 (s, 3H), 3.42 (s, 1H), 3.75 (s, 3H), 3.80-3.90 (m, 2H), 3.99-4.07 (m, 1H), 4.28-4.37 (m, 1H), 4.36 (d, 1H, J 13.2 Hz), 5.95 (d, 1H, J 13.2 Hz), 6.44 (d, 1H, J 4.0 Hz), 6.81 (br d, 2H, J 9.1 Hz), 6.83 (s, 1H), 7.30 (br d, 2H, J 8.9 Hz), 8.51 (br s, 1H). ESI-MI m/z [M+H]⁺: 417.1.

Step 3c 8-bromo-10a-(4-methoxyphenyl)-2,3,10,10a-tetrahydro-1H,5H-imidazo[1,2-a]pyrrolo[1,2-d]pyrazin-5-one (120 mg, 0.33 mmol), Pd(PPh₃)₂Cl₂ (23 mg, 0.033 mmol) and copper (I) iodide (15 mg, 0.079 mmol) were added to a 10 mL round bottom flask that was then evacuated and then filled back with argon twice. Dry DMF (5 mL) was added and the solution degassed with argon for 10 minutes. Triethylamine (0.24 mL, 1.7 mmol) and trimethylsilylacetylene (0.24 mL, 1.7 mmol) were added and the resulting brown solution was degassed with argon for a further minute. The reaction flask was sealed and heated at 80° C. until full consumption of the starting material (4 hours; monitored by LCMS). The solution was diluted with ethyl acetate (50 mL) and washed with brine (3×15 mL). The organic layer was dried (Na₂SO₄), filtered and concentrated in vacuo to give a material that was purified by flash chromatography (2× Biotage SP4, 12 g cartridge, CH₂Cl₂ 3 CV, gradient 0-10% MeOH in CH₂Cl₂ 15 CV, hold for 5 CV) and (Biotage SP4, 12 g cartridge, gradient 50-100% EtOAc in hexanes 10 CV, hold for 15 CV) to give 10a-(4-methoxyphenyl)-8-[(trimethylsilyl)ethynyl]-2,3,10,10a-tetrahydro-1H,5H-imidazo[1,2-a]pyrrolo[1,2-d]pyrazin-5-one as a yellow solid (84 mg, yield 62%). ESI-MI m/z [M+H]⁺ 380.0.

Step 4c

To a solution of 10a-(4-methoxyphenyl)-8-[(trimethylsilyl)ethynyl]-2,3,10,10a-tetrahydro-1H,5H-imidazo[1,2-a]pyrrolo[1,2-d]pyrazin-5-one (84 mg, 0.22 mmol) in methanol (5 mL) was added potassium carbonate (60 mg, 0.43 mmol). The suspension was stirred at room temperature until the reaction was complete (monitored by LCMS). The solid was suspended in CH₂Cl₂, filtered and concentrated in vacuo to give a residue that was purified by flash chromatography (Biotage SP4, 12 g cartridge, CH₂Cl₂ 3CV, gradient 0-10% MeOH in CH₂Cl₂ 10CV). To give 8-Ethynyl-10a-(4-methoxyphenyl)-2,3,10,10a-tetrahydro-1H,5H-imidazo[1,2-a]pyrrolo[1,2-d]pyrazin-5-one as a yellow solid (60 mg, yield 89%). ESI-MI m/z [M+H]⁺ 308.0.

Step 5c

To generate the acid chloride, to a chilled (0° C.) suspension of 3-methylisoxazole-4-carboxylic acid (75 mg, 0.59 mmol) in dry $CH_2Cl_2$ (1 mL) was added oxalyl chloride (0.15 mL, 1.8 mmol) followed by DMF (1 drop) under nitrogen. The mixture was stirred at 0° C. for 5 minutes and at room temperature for 1 h. The resulting solution was concentrated in vacuo to yield a oil corresponding to the acyl chloride. To a chilled (0° C.) suspension of the acid chloride generated as above (0.59 mmol) in pyridine (0.5 mL) was added a suspension of 8-ethynyl-10a-(4-methoxyphenyl)-2,3,10,10a-tetrahydro-1H,5H-imidazo[1,2-a]pyrrolo[1,2-d]pyrazin-5-one (60 mg, 0.20 mmol) in pyridine (1 mL). The suspension was stirred at 0° C. for 5 minutes and then at room temperature until the reaction was complete (1.5 hour; monitored by LCMS). The suspension was then diluted with water (5 mL) and extracted with $CH_2Cl_2$ (3×2.5 mL). The organic layers were combined, dried ($MgSO_4$), filtered and concentrated in vacuo to give a residue that was purified by flash chromatography (Silica gel, 30 to 40% acetone-hexanes). The compound 8-ethynyl-10a-(4-methoxyphenyl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (108) was isolated as a yellow solid (49 mg, yield 59%).

Example of General Method N

Route (a)

10a-[4-(2-hydroxyethoxy)phenyl]-1-[(3-methyl-1,2-oxazol-4-yl)carbonyl]-2,3,10,10a-tetrahydro-1H,5H-imidazo[1,2-a]pyrrolo[1,2-d]pyrazin-5-one (109)

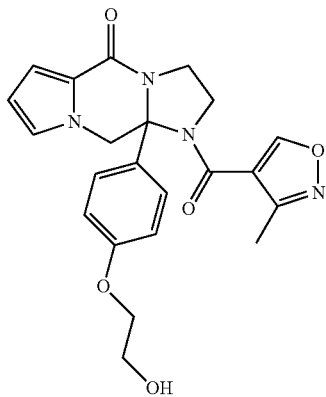 [SMILES: Cc1nocc1C(=O)N1CCN2C(=O)c3cccn3CC12c1ccc(OCCO)cc1]

$^1$H NMR (400 MHz, $CDCl_3$): δ 2.43 (s, 3H), 3.72-3.83 (m, 2H), 3.89-3.93 (m, 2H), 3.99-4.05 (m, 3H), 4.28-4.37 (m, 1H), 4.54 (d, 1H, J 12.8 Hz), 5.61 (d, 1H, J 12.8 Hz), 6.17 (dd, 1H, J 3.9, 2.6 Hz), 6.69 (dd, 1H, J 2.4, 1.6 Hz), 6.78-6.83 (m, 2H), 6.90 (dd, 1H, J 3.8, 1.5 Hz), 7.27-7.32 (m, 2H), 8.53 (s, 1H). ESI-MI m/z [M+H]$^+$ 423.2.

Step 1

To a chilled solution of methyl 1H-pyrrole-2-carboxylate (1.0 g, 8.0 mmol) in dry DMF (20 mL) was added sodium hydride (60% in mineral oil, 320 mg, 8.0 mmol) portionwise. The mixture was stirred at 0° C. for 1 hour before a solution of 2-bromo-1-(4-hydroxyphenyl)ethanone (780 mg, 3.6 mmol) in DMF (5 mL) was added. The resulting yellow solution was allowed to warm to room temperature. After 2.5 hours the reaction was complete (monitored by LCMS). A saturated aqueous solution of $NH_4Cl$ (40 mL) was added and the mixture was extracted with EtOAc (1×20 mL). The organic layer was concentrated in vacuo to yield a residue that was purified by flash chromatography using the (Biotage SP4, 40 g cartridge, 0 to 100% EtOAc gradient in hexane) to give methyl 1-[2-(4-hydroxyphenyl)-2-oxoethyl]-1H-pyrrole-2-carboxylate as a white solid (810 mg, yield 87%).

$^1$H-NMR (400 MHz, d6-acetone): δ 3.66 (s, 3H), 5.86 (s, 2H), 6.16 (dd, 1H, J 3.9, 2.6 Hz), 6.92 (dd, 1H, J 4.0, 1.8 Hz), 6.96-7.00 (m, 2H), 7.04-7.06 (m, 1H), 7.95-8.00 (m, 2H, 9.23 (br s, 1H).

Step 2

To a solution of methyl 1-[2-(4-hydroxyphenyl)-2-oxoethyl]-1H-pyrrole-2-carboxylate (200 mg, 0.77 mmol) in 1,4-dioxane (40 mL) was added ethane-1,2-diamine (1 mL, 15 mmol), after 48 h extra ethane-1,2-diamine (1 mL, 15 mmol) was added and the mixture heated for 48 additional hours. After that time 90% of the starting material was converted into the above product. The resulting mixture was then concentrated in vacuo to give a residue that was purified by flash chromatography (Biotage SP4, 12 g cartridge, gradient 0-10% MeOH in $CH_2Cl_2$) to give 10a-(4-hydroxyphenyl)-2,3,10,10a-tetrahydro-1H,5H-imidazo[1,2-a]pyrrolo[1,2-d]pyrazin-5-one (180 mg, yield: 86%). ESI-MI m/z [M+H]$^+$ 270.1.

Step 3a

To a suspension of 10a-(4-hydroxyphenyl)-2,3,10,10a-tetrahydro-1H,5H-imidazo[1,2-a]pyrrolo[1,2-d]pyrazin-5-one (50 mg, 0.19 mmol) and potassium carbonate (77 mg, 0.56 mmol) in DMF (1 mL) was added (2-bromoethoxy)-tert-butyldimethylsilane (120 μL, 0.56 mmol). The mixture was heated at 100° C. The outcome of the reaction was monitored by LCMS. After completion (45 minutes) the mixture was diluted with a saturated aqueous solution of $NH_4Cl$ (6 mL) and extracted with ethyl acetate (3×2.5 mL). The combined organic layers were dried ($MgSO_4$), filtered and concentrated in vacuo to yield a pale yellow solid that was purified by flash chromatography (Biotage SP4, 12 g silica cartridge, gradient 0-10% MeOH in $CH_2Cl_2$) to give 10a-[4-(2-{[tert-butyl(dimethyl)silyl]oxy}ethoxy)phenyl]-2,3,10,10a-tetrahydro-1H,5H-imidazo[1,2-a]pyrrolo[1,2-d]pyrazin-5-one (86 mg, quantitative yield). ESI-MI m/z [M+H]$^+$ 428.2.

Step 4a

To generate the acid chloride: to a chilled suspension of 3-methyl-1,2-oxazole-4-carboxylic acid (70 mg, 0.55 mmol) in dry $CH_2Cl_2$ (1.0 mL) was added oxalyl chloride (0.15 mL, 1.8 mmol) followed by DMF (1 drop). The mixture was stirred at 0° C. for 10 minutes and then at room temperature for 1 hour. The resulting solution was concentrated in vacuo at ambient temperature to give a oil. The material was dissolved in $CH_2Cl_2$ and re-concentrated to give the acid chloride.

To a chilled suspension of the acid chloride (generated as above, 0.55 mmol) in pyridine (0.5 mL) was added a suspension of 10a-[4-(2-{[tert-butyl(dimethyl)silyl]oxy}ethoxy)phenyl]-2,3,10,10a-tetrahydro-1H,5H-imidazo[1,2-a]pyrrolo[1,2-d]pyrazin-5-one (85 mg, 0.18 mmol) in pyridine (1.0 mL). The suspension was stirred at 0° C. for 5 minutes and then at room temperature for 45 minutes (reaction monitored by LCMS). Water (5 mL) was then added and the mixture extracted with CH$_2$Cl$_2$ (3×2 mL). The extracts were combined, dried (MgSO$_4$), filtered and concentrated in vacuo to give a residue that was purified by flash chromatography (Silica gel, gradient 20 to 30% acetone in hexanes) to give 10a-[4-(2-{[tert-butyl(dimethyl)silyl]oxy}ethoxy)phenyl]-1-[(3-methyl-1,2-oxazol-4-yl)carbonyl]-2,3,10,10a-tetrahydro-1H,5H-imidazo[1,2-a]pyrrolo[1,2-d]pyrazin-5-one (80 mg, yield 83%). ESI-MI m/z [m+H]$^+$ 537.2.

Step 5a

10a-[4-(2-{[tert-butyl(dimethyl)silyl]oxy}ethoxy)phenyl]-1-[(3-methyl-1,2-oxazol-4-yl)carbonyl]-2,3,10,10a-tetrahydro-1H,5H-imidazo[1,2-a]pyrrolo[1,2-d]pyrazin-5-one (80 mg, 0.14 mmol) was treated with a 3:1:1 mixture of acetic acid/THF/water (2 mL). The solution was stirred at room temperature overnight. The mixture was then diluted with CH$_2$Cl$_2$ (20 mL) and washed with a saturated aqueous solution of NaHCO$_3$ (3×6 mL). The organic layer was dried (MgSO$_4$), filtered and concentrated in vacuo to give a gummy solid that was purified by flash chromatography (Biotage SP4, 12 g silica column gradient 0-10% MeOH in CH$_2$Cl$_2$) to give 10a-[4-(2-hydroxyethoxy)phenyl]-1-[(3-methyl-1,2-oxazol-4-yl)carbonyl]-2,3,10,10a-tetrahydro-1H,5H-imidazo[1,2-a]pyrrolo[1,2-d]pyrazin-5-one (109) (38 mg, yield 64%).

Example of General Method N

Route (b)

1-[(3-methyl-1,2-oxazol-4-yl)carbonyl]-10a-{4-[2-(morpholin-4-yl)ethoxy]phenyl}-2,3,10,10a-tetrahydro-1H,5H-imidazo[1,2-a]pyrrolo[1,2-d]pyrazin-5-one (110)

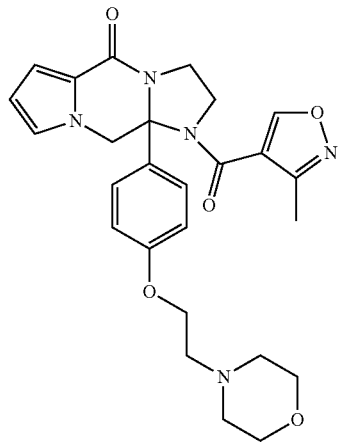 [SMILES: Cc1nocc1C(=O)N1CCN2C(=O)c3cccn3CC12c1ccc(OCCN2CCOCC2)cc1]

$^1$H NMR (400 MHz, CDCl$_3$): δ 2.44 (s, 3H), 2.52-2.57 (m, 4H), 2.76 (t, 2H, J 5.7 Hz), 3.68-3.73 (m, 4H), 3.75-3.85 (m, 2H), 4.03 (ddd, 3H, J 19.1, 9.5, 6.4 Hz), 4.30-4.39 (m, 1H), 4.57 (d, 1H, J 12.8 Hz), 5.62 (d, 1H, J 12.8 Hz), 6.18 (dd, 1H, J 3.9, 2.6 Hz), 6.70 (dd, 1H, J 2.4, 1.6 Hz), 6.77-6.83 (m, 2H), 6.92 (dd, 1H, J 3.9, 1.5 Hz), 7.27-7.32 (m, 2H), 8.51 (br s, 1H). ESI-MI m/z [M+H]$^+$ 492.2.

Step 3b 10a-(4-hydroxyphenyl)-2,3,10,10a-tetrahydro-1H,5H-imidazo[1,2-a]pyrrolo[1,2-d]pyrazin-5-one (50 mg, 0.19 mmol), 4-(2-chloroethyl)morpholine hydrochloride (106 mg, 0.57 mmol) and potassium carbonate (105 mg, 0.76 mmol) were suspended in DMF (1 mL) and the mixture heated at 100° C. The reaction was complete after 3 hours. Brine (5 mL) and water (1 mL) were then added. The mixture was then extracted with ethyl acetate (3×3 mL) and the extracts were combined, dried (MgSO$_4$), filtered and concentrated in vacuo to yield a residue that was purified by flash chromatography (Biotage SP4, gradient 0 to 10% methanol-dichloromethane). The material isolated required a second purification by reverse phase chromatography (Biotage SP4, C18 column, 5 to 100% 10 mM NH$_4$OAC (aq)-MeOH) to give 10a-{4-[2-(morpholin-4-yl)ethoxy]phenyl}-2,3,10,10a-tetrahydro-1H,5H-imidazo[1,2-a]pyrrolo[1,2-d]pyrazin-5-one (75% pure, 22 mg, yield: 22%). The product was used in the next step without further purification. ESI-MI m/z [M+H]$^+$ 383.2.

Step 4b

To generate the acid chloride, oxalyl chloride (0.1 mL, 1.2 mmol) and DMF (1 drop) were added to 3-methyl-1,2-oxazole-4-carboxylic acid (30 mg, 0.24 mmol) in CH$_2$Cl$_2$ (0.5 mL) at 0° C. The suspension was allowed to stir 15 minutes at 0° C. followed by 1 hour at room temperature. The resulting solution was concentrated to give an oil that was further dried under nitrogen. To a chilled suspension of the acid chloride (generated as above, 0.24 mmol) in pyridine (0.5 mL) was added 10a-{4-[2-(morpholin-4-yl)ethoxy]phenyl}-2,3,10,10a-tetrahydro-1H,5H-imidazo[1,2-a]pyrrolo[1,2-d]pyrazin-5-one (20 mg, 75% pure, 0.039 mmol) in pyridine (0.3 mL). The reaction mixture was stirred at 0° C. and then at room temperature. After 2.5 hours an additional batch of acid chloride (0.24 mmol) was prepared as above, diluted in pyridine (0.3 mL) and added to the reaction mixture. The mixture was stirred overnight at room temperature. Water (2 mL) was then added and the mixture extracted with dichloromethane (3×1.5 mL). The organic layers were dried (MgSO$_4$), filtrated and concentrated in vacuo to give a residue that was purified by preparative LCMS (reverse phase, acetonitrile-water containing 0.1% formic acid) to give 1-[(3-methyl-1,2-oxazol-4-yl)carbonyl]-10a-{4-[2-(morpholin-4-yl)ethoxy]phenyl}-2,3,10,10a-tetrahydro-1H,5H-imidazo[1,2-a]pyrrolo[1,2-d]pyrazin-5-one (110) (7 mg, yield 36%).

Example of General Method O

Route (a)

7-(cyclohexylamino)-10a-(4-methoxyphenyl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (112)

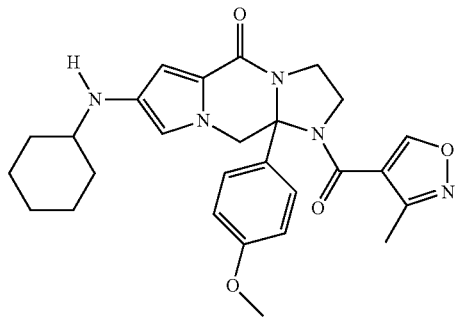 [SMILES: COc1ccc(C23Cn4cc(NC5CCCCC5)cc4C(=O)N2CCN3C(=O)c2conc2C)cc1]

$^1$H-NMR (400 MHz, CDCl$_3$): δ 1.00-1.37 (m, 6H), 1.62-1.80 (m, 2H), 1.96-2.06 (m, 2H), 2.43 (s, 3H), 2.83-2.90 (m, 1H), 3.70-3.82 (m, 2H), 3.76 (s, 3H), 3.93-4.00 (m, 1H), 4.27-4.35 (m, 1H), 4.46 (d, 1H, J 12.7 Hz), 5.40 (d, 1H, J 12.4 Hz), 6.17 (d, 1H, J 1.9 Hz), 6.45 (d, 1H, J 1.8 Hz), 6.77-6.82 (m, 2H), 7.28-7.33 (m, 2H), 8.49 (br s, 1H). ESI-MI m/z [M+H]$^+$ 490.1.

Step 1

To a solution of ethyl 4-nitro-1H-pyrrole-2-carboxylate (884 mg, 4.8 mmol) in DMF (11 ml) was added NaH (60% dispersion in mineral oil, 190 mg, 4.8 mmol) at 0° C. After 5 min the reaction mixture was added to a solution of 2-bromo-1-(4-methoxy-phenyl)-ethanone (1 g, 4.4 mmol) at 0° C. and the resultant mixture was allowed to warm to room temperature. After one hour the LCMS analysis showed the presence of the desired product and the complete consumption of the bromo-ketone stating material was confirmed by TLC (EtOAc/Hexanes 1:1). An aqueous solution of HCl (1 M) was then added until a white precipitate appeared. Water was added and the white solid filtrated, rinsed with water and dried in vacuo to give ethyl 1-[2-(4-methoxyphenyl)-2-oxoethyl]-4-nitro-1H-pyrrole-2-carboxylate as a white solid (1.32 g, yield 83%). $^1$H-NMR (400 MHz, CDCl$_3$): δ 1.29 (t, 3H, J 7.1 Hz), 3.90 (s, 3H), 4.22 (q, 2H, J 7.2 Hz), 5.77 (s, 2H), 6.98-7.20 (m, 2H), 7.50 (d, 1H, J 1.8 Hz), 7.63 (d, 1H, J 1.8 Hz), 7.95-8.00 (m, 2H).

Step 2

Ethyl 1-[2-(4-methoxyphenyl)-2-oxoethyl]-4-nitro-1H-pyrrole-2-carboxylate (610 mg, 1.8 mmol) was mixed with 1,4-dioxane (7 mL) and ethylene-1,2-diamine (1.7 mL) and the mixture heat at 105° C. After 24 hours the reaction was complete (monitored by LCMS). The reaction was concentrated in vacuo and the resultant residue purified by flash chromatography (Biotage SP4, gradient 0-10% MeOH in EtOAc) to give 10a-(4-methoxyphenyl)-7-nitro-2,3,10,10a-tetrahydro-1H,5H-imidazo[1,2-a]pyrrolo[1,2-d]pyrazin-5-one (200 mg, yield 34%). ESI-MI m/z [M+H]$^+$ 328.9.

Step 3

10a-(4-methoxyphenyl)-1-[(3-methyl-1,2-oxazol-4-yl)carbonyl]-7-nitro-2,3,10,10a-tetrahydro-1H,5H-imidazo[1,2-a]pyrrolo[1,2-d]pyrazin-5-one (124)

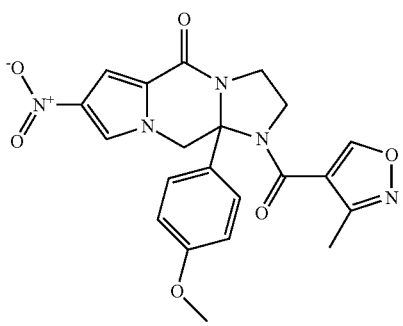

$^1$H-NMR (400 MHz, d6-DMSO): δ 2.30 (s, 3H), 3.71 (s, 3H), 3.85 (dt, 1H, J 11.1, 7.7 Hz), 4.00-4.24 (m, 3H), 4.70 (d, 1H, J 13.2 Hz), 6.00 (d, 1H, J 13.4 Hz), 6.90 (d, 2H, J 8.9 Hz), 7.17 (d, 1H, J 1.6 Hz), 7.37 (d, 2H, J 8.9 Hz), 8.36 (d, 1H, J 1.5 Hz), 9.36 (s, 1H).

To generate the acid chloride, oxalyl chloride (600 μL, 7.0 mmol) and DMF (1 drop) were added to 3-methyl-1,2-oxazole-4-carboxylic acid (441 mg, 3.47 mmol) in CH$_2$Cl$_2$ (6 mL) at 0° C. The suspension was allowed to stir 15 minutes at 0° C. followed by 1 hour at room temperature. The resulting solution was concentrated in vacuo (without heating) to give a oil that was further dried under nitrogen. To a chilled suspension of the acid chloride (generated as above, 3.47 mmol) in pyridine (3 mL) was added 10a-(4-methoxyphenyl)-7-nitro-2,3,10,10a-tetrahydro-1H,5H-imidazo[1,2-a]pyrrolo[1,2-d]pyrazin-5-one (190 mg, 0.58 mmol) in pyridine (4 mL). The reaction mixture was stirred at 0° C. to room temperature for 45 minutes and was then quenched with water (15 mL) and extracted with CH$_2$Cl$_2$ (4×15 mL).

The organic fractions were washed with brine, dried (MgSO$_4$), filtered and concentrated to yield a residue that was purified by triturating with acetone to give 10a-(4-methoxyphenyl)-1-[(3-methyl-1,2-oxazol-4-yl)carbonyl]-7-nitro-2,3,10,10a-tetrahydro-1H,5H-imidazo[1,2-a]pyrrolo[1,2-d]pyrazin-5-one (124) (170 mg, yield 68%).

Step 4

7-amino-10a-(4-methoxyphenyl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (111)

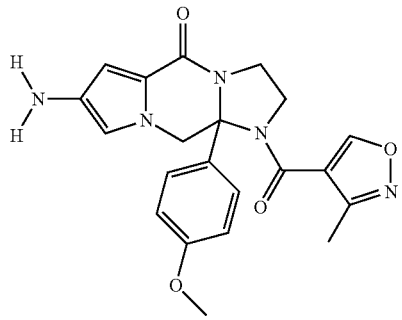 [SMILES: COc1ccc(C23Cn4cc(N)cc4C(=O)N2CCN3C(=O)c2conc2C)cc1]

$^1$H-NMR (400 MHz, CDCl$_3$): δ 2.43 (br s, 3H), 3.69-3.82 (s, 2H), 3.76 (s, 3H), 3.94-4.03 (m, 1H), 4.28-4.35 (m, 1H), 4.46 (d, 1H, J 12.8 Hz), 5.41 (d, 1H, J 12.7 Hz), 6.26 (d, 1H, J 1.9 Hz), 6.47 (d, 1H, J 1.9 Hz), 6.79-6.83 (m, 2H), 7.29-7.33 (m, 2H), 8.50 (br s, 1H). ESI-MI m/z [M+H]$^+$ 408.1.

To a solution of 10a-(4-methoxyphenyl)-1-[(3-methyl-1,2-oxazol-4-yl)carbonyl]-7-nitro-2,3,10,10a-tetrahydro-1H,5H-imidazo[1,2-a]pyrrolo[1,2-d]pyrazin-5-one (107 mg, 0.24 mmol) in MeOH (2.4 mL) was added Iron(II) heptahydrate sulfate (544 mg, 2 mmol) in water (2.4 mL). A solution of ammonium hydroxide (28%, 0.7 mL) was added and the mixture was heated at 50° C. for 45 min. The reaction mixture was then partially concentrated in vacuo (half volume), neutralized with a saturated aqueous solution of NH$_4$Cl and then extracted with EtOAc. The combined organic layers were dried (Na$_2$SO$_4$), filtered and concentrated in vacuo to give a residue that was purified by flash chromatography (Biotage SP4 gradient 0-7% MeOH in EtOAc) to give 7-amino-10a-(4-methoxyphenyl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (111) (38 mg, yield 39%).

Step 5a

To a solution of 7-amino-10a-(4-methoxyphenyl)-1-[(3-methyl-1,2-oxazol-4-yl)carbonyl]-2,3,10,10a-tetrahydro-1H,5H-imidazo[1,2-a]pyrrolo[1,2-d]-pyrazin-5-one (33 mg, 0.081 mmol) in CH$_2$Cl$_2$ (0.5 mL) was added cyclohexanone (9 µL, 0.081 mmol), acetic acid (7 µL, 0.12 mmol) followed by sodium triacetoxyborohydride (26 mg, 0.12 mmol). After stirring the mixture for three further hours, cyclohexanone (20 µL, 0.18 mmol) was added followed by the addition of additional acetic acid (20 µL, 0.34 mmol). The mixture was quenched with a saturated aqueous solution of NaHCO$_3$. Additional CH$_2$Cl$_2$ (3 mL) was added and the organic layer separated, the aqueous layer was further extracted with CH$_2$Cl$_2$ (3 mL). The organic layers were combined dried (Na$_2$SO$_4$), filtrated, concentrated in vacuo to give a residue that was purified by flash chromatography (Biotage SP4, gradient 0-10% MeOH in EtOAc) and reverse phase chromatography (Biotage SP4, 12 g C18 cartridge; gradient ACN in water). The compound 7-(cyclohexylamino)-10a-(4-methoxyphenyl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (112) was isolated as a solid (1.6 mg, yield 1%).

Example of General Method O

Route (b)

10a-(4-methoxyphenyl)-1-[(3-methyl-1,2-oxazol-4-yl)carbonyl]-7-(1H-1,2,3-triazol-1-yl)-2,3,10,10a-tetrahydro-1H,5H-imidazo[1,2-a]pyrrolo[1,2-d]pyrazin-5-one (113)

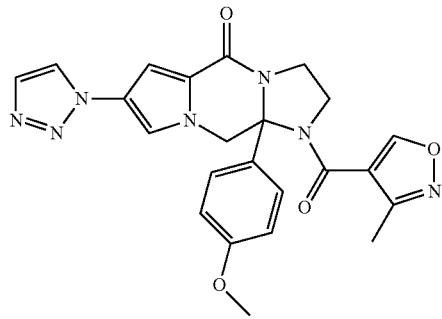 [SMILES: COc1ccc(C23Cn4cc(-n5ccnn5)cc4C(=O)N2CCN3C(=O)c2conc2C)cc1]

$^1$H-NMR (400 MHz, CDCl$_3$): δ 2.45 (s, 3H), 3.76 (s, 3H), 3.78-3.91 (m, 2H), 4.07 (dt, 1H, J 8.3, 7.2 Hz), 4.31-4.38 (m, 1H), 4.67 (d, 1H, J 13.0 Hz), 5.72 (d, 1H, J 13.0 Hz), 6.81-6.86 (m, 2H), 7.08 (d, 1H, J 1.8 Hz), 7.20 (d, 1H, J 1.8 Hz), 7.36-7.40 (m, 2H), 7.76 (s, 2H), 8.53 (s, 1H). ESI-MI m/z [M+H]$^+$ 460.1.

Step 5b 7-amino-10a-(4-methoxyphenyl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (190 mg, 0.47 mmol) was mixed with concentrated HCl (0.4 mL) and water (0.4 mL) and the mixture cooled down at 0° C. Aqueous NaNO$_2$ solution (49 mg, 0.70 mmol) in water (0.4 mL) was added dropwise at such rate that the temperature didn't exceed 0-5° C. The mixture was stirred at that temperature for 30 minutes. A solution of sodium azide (44 mg, 0.68 mmol) and sodium acetate (565 mg, 6.9 mmol) in water (2 mL) was then added dropwise at 0-5° C. and the mixture allowed at room temperature and stirred overnight. The mixture was then extracted with EtOAc (4×10 mL). The combined organic layers were washed with brine, dried (Na$_2$SO$_4$), filtrated and concentrated in vacuo to give a residue that was purified by flash chromatography (Biotage SP4, gradient EtOAc 5 CV, 0%-10% MeOH in EtOAc 9 CV, hold 10% 3 CV and 10-30% 3 CV) to give 7-azido-10a-(4-methoxyphenyl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (57 mg, yield: 28%).

$^1$H-NMR (400 MHz, CDCl$_3$): δ 2.42 (s, 3H), 3.76 (s, 3H), 3.77-3.83 (m, 2H), 3.98-4.04 (m, 1H), 4.26-4.34 (m, 1H), 4.53 (d, 1H, J 12.9 Hz), 5.54 (d, 1H, J 12.9 Hz), 6.47 (d, 1H, J 1.8 Hz), 6.71 (d, 1H, J 1.8 Hz), 6.79-6.84 (m, 2H), 7.29-7.34 (m, 2H), 8.51 (br s, 1H).

Step 6b

To a solution of 7-azido-10a-(4-methoxyphenyl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (50 mg, 0.116 mmol) in DMF (2.5 mL) at 0° C. was added ethynyl-trimethyl-silane (33 µL, 0.23 mmol) followed by ethyl-diiso-propyl-amine (24 µL, 0.14 mmol) and copper iodide (11 mg) and the mixture was stirred at 0° C. After one hour the reaction was complete (monitored by LCMS). A saturated aqueous solution of NH$_4$Cl containing a drop of ammonia was added and the mixture extracted with EtOAc (3 times). The organics were washed with brine, dried (Na$_2$SO$_4$), filtrated and concentrated in vacuo. The resulting material was purified by flash chromatography (Biotage SP4, gradient 50-100% EtOAc in hexanes 10 CV; hold 100% EtOAc 7CV) to give 10a-(4-methoxyphenyl)-1-[(3-methyl-1,2-oxazol-4-yl)carbonyl]-7-[4-(trimethylsilyl)-1H-1,2,3-triazol-1-yl]-2,3,10,10a-tetrahydro-1H,5H-imidazo[1,2-a]pyrrolo[1,2-d]-pyrazin-5-one (14 mg, yield: 23%). ESI-MI m/z [M+H]$^+$ 532.2.

Step 7b 10a-(4-methoxyphenyl)-1-[(3-methyl-1,2-oxazol-4-yl)carbonyl]-7-[4-(trimethylsilyl)-1H-1,2,3-triazol-1-yl]-2,3,10,10a-tetrahydro-1H,5H-imidazo[1,2-a]pyrrolo[1,2-d]pyrazin-5-one (10.6 mg, 0.012 mmol) was dissolved in a mixture of acetic acid/water/THF (3:1:1; 1 mL). The mixture was stirred at 60° C. When the reaction was complete (48 hours; monitored by LCMS) water was added followed by a saturated aqueous solution of NaHCO$_3$. The mixture was then extracted with EtOAc (3 times) and the organics washed with brine, dried (Na$_2$SO$_4$), filtrated and concentrated in vacuo. The resulting material was purified by flash chromatography (Silica gel, EtOAc/Hex 3:1 followed by 100% EtOAc) to give compound 10a-(4-methoxyphenyl)-1-[(3-methyl-1,2-oxazol-4-yl)carbonyl]-7-(1H-1,2,3-triazol-1-yl)-2,3,10,10a-tetrahydro-1H,5H-imidazo[1,2-a]pyrrolo[1,2-d]pyrazin-5-one (113) as a white solid (2.28 mg, yield 25%)

Example of General Method P

Route (a)

1-[(3-methyl-1,2-oxazol-4-yl)carbonyl]-10a-[5-(trifluoromethyl)pyridin-2-yl]-2,3,10,10a-tetrahydro-1H,5H-imidazo[1,2-a]pyrrolo[1,2-d]pyrazin-5-one (116)

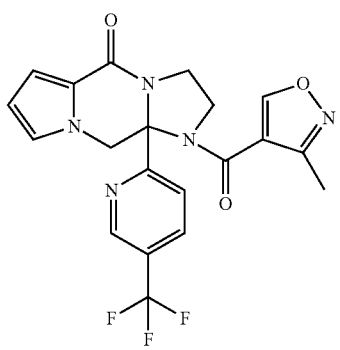 [SMILES: Cc1nocc1C(=O)N1CCN2C(=O)c3cccn3CC12c1ccc(C(F)(F)F)cn1]

¹H-NMR (400 MHz, CDCl₃): δ 2.34 (s, 3H), 4.03 (dt, 1H, J 8.2, 10.5 Hz), 4.11 (dd, 1H, J 16.5, 8.2 Hz), 4.22 (dt, 1H, J 8.5, 2.9 Hz), 4.43 (dt, 1H, J 10.4, 7.8, 2.2 Hz), 4.50 (d, 1H, J 13.2 Hz), 5.78 (d, 1H, J 13.2 Hz), 6.32 (dd, 1H, J 3.7, 2.7 Hz), 6.89-6.93 (m, 2H), 7.15-7.19 (d, 1H, J 8.4 Hz), 7.84 (dd, 1H, J 8.4, 2.1 Hz), 8.67 (s, 1H), 8.75 (br s, 1H). ESI-MI m/z [M+H]⁺ 432.0.

Step 4

To a solution of 2-bromo-5-(trifluoromethyl)pyridine (100 mg, 0.44 mmol) in dry diethyl ether (2 mL) was added n-BuLi (1.5 M solution in hexanes, 0.3 mL, 0.45 mmol) dropwise, at −78° C. and under nitrogen. The dark red-brown solution was stirred at −78° C. for 20 minutes before a solution of the Weinreb amide N-methoxy-N-methyl-2-(1H-pyrrol-1-yl)acetamide (80 mg, 0.48 mmol) in diethyl ether (1 mL) was added. The solution was stirred at −78° C. for 1.5 hour before the cold bath was removed and the reaction allowed at room temperature. After 50 minutes the dark brown solution was poured into a saturated aqueous solution of NH₄Cl (15 mL) and extracted with CH₂Cl₂ (3×10 mL). The extracts were combined, dried (MgSO₄), filtered and concentrated in vacuo to give dark brown solid. The material obtained was purified by flash chromatography (Biotage SP4, 12 g cartridge, gradient 1 CV hexanes, 0-60% 10 CV EtOAc in hexanes, hold 60% 5 CV) to give 2-(1H-pyrrol-1-yl)-1-[5-(trifluoromethyl)pyridin-2-yl]ethanone (66 mg, 80% pure, yield 46%).

¹H-NMR (400 MHz, CDCl₃): δ 5.60 (s, 2H), 6.26 (t, 2H, J 2.1 Hz), 6.70 (t, 2H, J 2.1 Hz), 8.11-8.15 (m, 1H), 8.18-8.22 (m, 1H), 8.98-8.99 (m, 1H).

Step 5

To a chilled (0° C.) solution of the 2-(1H-pyrrol-1-yl)-1-[5-(trifluoromethyl)pyridin-2-yl]ethanone (100 mg, approx. 90% pure, 0.35 mmol) in dry CH₂Cl₂ (5 mL) was added trichloroacetyl chloride (90 µL, 0.80 mmol) under nitrogen. The mixture was allowed to warm to room temperature. After completion (44 hours, monitored by LCMS) the mixture was cooled to 0° C. and quenched with a saturated aqueous solution of NaHCO₃ (5 mL). The aqueous layer was then extracted with CH₂Cl₂ (2×2 mL). The organic layers were combined, dried (MgSO₄), filtered and concentrated in vacuo to yield a residue that was purified by flash chromatography (Biotage, 12 g cartridge, gradient hexanes 1 CV, 0-60% EtOAc in hexanes 10 CV) to give 2,2,2-trichloro-1-(1-{2-oxo-2-[5-(trifluoromethyl)pyridin-2-yl]ethyl}-1H-pyrrol-2-yl)ethanone as an orange oil (105 mg, yield: 75%). ESI-MI m/z [M+H]⁺ 398.9.

Step 6a

To a chilled (0° C.) solution of 2,2,2-trichloro-1-(1-{2-oxo-2-[5-(trifluoromethyl)pyridin-2-yl]ethyl}-1H-pyrrol-2-yl)ethanone (105 mg, 0.26 mmol) in MeOH (7 mL) was added an aqueous solution of sodium hydroxide (1 M), (0.26 mL, 0.26 mmol). The solution was allowed at room temperature. After one hour the reaction was complete (monitored by LCMS). The mixture was acidified with 1 M HCl (aq), diluted with water (10 mL) and partially concentrated in vacuo to remove the MeOH. The aqueous mixture was then extracted with CH₂Cl₂ (3×4 mL). The organic layers were combined, dried (MgSO₄), filtered and the filtrate concentrated in vacuo to yield methyl 1-{2-oxo-2-[5-(trifluoromethyl)pyridin-2-yl]ethyl}-1H-pyrrole-2-carboxylate as a brown oil (85 mg, quantitative yield) ESI-MI m/z [M+H]⁺ 312.9.

Step 7a

To a solution of methyl 1-{2-oxo-2-[5-(trifluoromethyl)pyridin-2-yl]ethyl}-1H-pyrrole-2-carboxylate (85 mg, 0.26 mmol) in 1,4-dioxane (20 mL) was added ethane-1,2-diamine (0.65 mL, 9.7 mmol). The solution was heated at reflux. After 4 days the reaction was complete (monitored by LCMS). The mixture was then concentrated in vacuo to give an oily solid. The material was purified by flash chromatography (Biotage SP4, 12 g cartridge, gradient CH₂Cl₂ 1CV, 0-10% MeOH in CH₂Cl₂ 10 CV) to give 10a-[5-(trifluoromethyl)pyridin-2-yl]-2,3,10,10a-tetrahydro-1H,5H-imidazo[1,2-a]pyrrolo[1,2-d]pyrazin-5-one (70 mg, yield: 85%). ESI-MI m/z [M+H]⁺ 323.0.

Step 8a

To generate the acid chloride: to a chilled suspension of 3-methylisoxazole-4-carboxylic acid (60 mg, 0.47 mmol) in dry CH₂Cl₂ (1 mL) was added oxalyl chloride (0.15 mL, 1.8 mmol) followed by DMF (1 drop, catalytic). The mixture was stirred at 0° C. for 10 minutes and then at room temperature for 1 hour. The resulting solution was concentrated in vacuo at ambient temperature to give a liquid that was diluted in CH₂Cl₂ and concentrated to give the acid chloride as an oil.

To a chilled suspension of the acid chloride (generated as above, 0.47 mmol) in pyridine (2.5 mL) was added a suspension of 10a-[5-(trifluoromethyl)pyridin-2-yl]-2,3,10,10a-tetrahydro-1H,5H-imidazo[1,2-a]pyrrolo[1,2-d]pyrazin-5-one (50 mg, 0.16 mmol) in pyridine (1 mL). The suspension was stirred at 0° C. for 5 minutes and then at room temperature for 1.5 hour. When complete (reaction monitored by LCMS) the suspension was diluted with water (5 mL) and extracted with CH₂Cl₂ (3×2.5 mL). The extracts were combined, dried (MgSO₄), filtered and concentrated in vacuo to give a residue that was purified by flash chromatography (silica gel, 30% to 40% acetone in hexanes) the resultant residue was dissolved in CH₂Cl₂ and washed with a saturated aqueous solution of NaHCO₃ and by water. The organic layer was dried (MgSO₄), filtered and the filtrate azeotroped with hexanes in vacuo to give 1-[(3-methyl-1,2-oxazol-4-yl)carbonyl]-10a-[5-(trifluoromethyl)pyridin-2-yl]-2,3,10,10a-tetrahydro-1H,5H-imidazo[1,2-a]pyrrolo[1,2-d]-pyrazin-5-one (116) as a yellow solid (33 mg, yield 47%).

The following compounds were similarly prepared using General Method P Route (a).

| Cpd. No. | Structure | ESI-MI m/z [M + H]⁺/¹H-NMR |
|---|---|---|
| 114 | 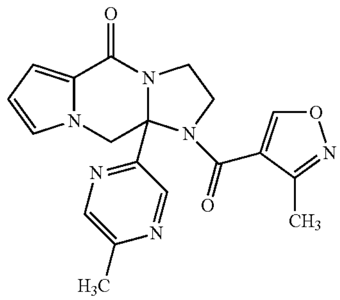 | ESI-MI m/z [M + H]⁺ 379.0. ¹H NMR (400 MHz, CDCl₃): δ 2.34 (s, 3H), 2.51 (s, 3H), 3.95-4.13 (m, 2H), 4.18 (td, 1H, J 8.4, 2.6 Hz), 4.38-4.43 (m, 1H), 4.46 (d, 1H, J 13.1 Hz), 5.81 (d, 1H, J 13.1 Hz), 6.26-6.31 (m, 1H), 6.90 (d, 2H, J 3.2 Hz), 8.27 (d, 1H, J 1.5 Hz), 8.31 (d, 1H, J 1.0 Hz), 8.65 (br s, 1H, J 0.4 Hz). |
| 115 | 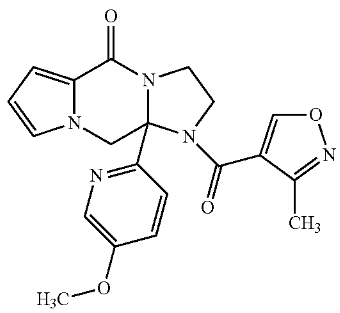 [SMILES: COc1ccc(C23Cn4cccc4C(=O)N2CCN3C(=O)c2conc2C)nc1] | ESI-MI m/z [M + H]⁺ 394.4. ¹H NMR (400 MHz, CDCl₃): δ 2.36 (s, 3H), 3.79 (s, 3H), 3.97-4.09 (m, 2H), 4.15 (dt, 1H, J 8.6, 7.6 Hz), 4.33-4.40 (m, 1H), 4.47 (d, 1H, J 13.0 Hz), 5.73 (d, 1H, J 13.0 Hz), 6.28 (dd, 1H, J 3.9, 2.6 Hz), 6.84-6.91 (m, 2H), 6.99 (dd, 1H, J 8.8, 0.7 Hz), 7.04 (dd, 1H, J 8.8, 2.9 Hz), 8.15 (dd, 1H, J 2.8, 0.7 Hz), 8.61 (s, 1H). |
| 118 | 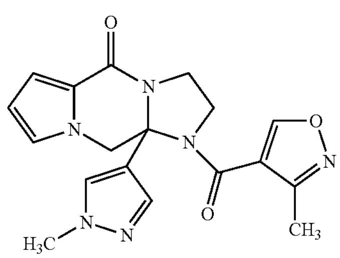 [SMILES: Cc1nocc1C(=O)N1CCN2C(=O)c3cccn3CC12c1cnn(C)c1] | ESI-MI m/z [M + H]⁺ 367.1. ¹H NMR (400 MHz, CDCl₃): δ 2.46 (s, 3H), 3.65-3.73 (m, 1H), 3.77 (s, 3H), 3.90-4.06 (m, 2H), 4.34 (d, 1H, J 12.3 Hz), 4.40 (ddd, 1H, J 11.5, 8.2, 3.2 Hz), 5.47 (d, 1H, J 12.3 Hz), 6.23 (dd, 1H, J 3.9, 2.6 Hz), 6.74 (dd, 1H, J 2.4, 1.6 Hz), 6.94 (dd, 1H, J 3.9, 1.5 Hz), 7.10 (s, 1H), 7.36 (d, 1H, J 0.7 Hz), 8.61 (br s, 1H). |
| 119 | 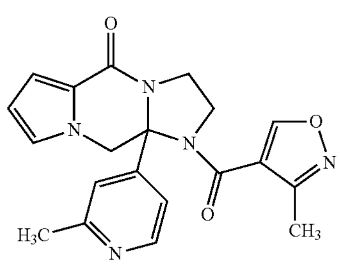 [SMILES: Cc1cc(C23Cn4cccc4C(=O)N2CCN3C(=O)c2conc2C)ccn1] | ESI-MI m/z [M + H]⁺ 378.1. ¹H NMR (400 MHz, CDCl₃): δ 2.43 (s, 3H), 2.48 (s, 3H), 3.74 (ddd, 1H, J 11.6, 8.2, 7.0 Hz), 3.83-3.90 (m, 1H), 4.07 (td, 1H, J 8.9, 7.0 Hz), 4.40 (ddd, 1H, J 11.6, 8.7, 4.3 Hz), 4.53 (d, 1H, J 13.0 Hz), 5.64 (d, 1H, J 13.0 Hz), 6.22 (dd, 1H, J 3.9, 2.6 Hz), 6.73 (dd, 1H, J 2.4, 1.6 Hz), 6.93 (dd, 1H, J 3.9, 1.4 Hz), 7.03-7.07 (m, 2H), 8.40-8.45 (m, 1H), 8.60 (br s, 1H). |

Example of General Method P

Route (b)

1-[(3-methyl-1,2-oxazol-4-yl)carbonyl]-10a-(5-methylpyrazin-2-yl)-7-(pyridin-3-yl)-2,3,10,10a-tetrahydro-1H,5H-imidazo[1,2-a]pyrrolo[1,2-d]pyrazin-5-one (121)

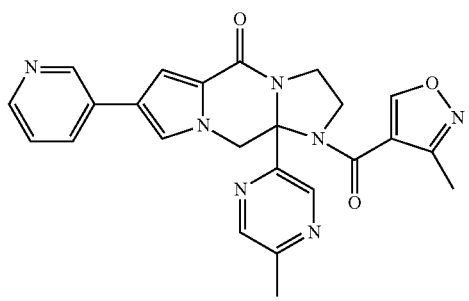 [SMILES: Cc1cnc(C23Cn4cc(-c5cccnc5)cc4C(=O)N2CCN3C(=O)c2conc2C)cn1]

$^1$H-NMR (400 MHz, CDCl$_3$): δ 2.36 (s, 3H), 2.52 (s, 3H), 4.01-4.23 (m, 3H), 4.30-4.49 (m, 1H), 4.52 (d, 1H, J 13.1 Hz), 5.88 (d, 1H, J 13.1 Hz), 7.21 (dd, 2H, J 11.0, 7.2 Hz), 7.29 ddd, 1H, J 7.8. 4.8, 0.7 Hz), 7.76 (ddd, 1H, J 7.9, 2.2, 1.7 Hz), 8.33-8.34 (dd, 1H, J 4.8, 1.6 Hz), 8.41 (d, 1H, J 1.5 Hz), 8.47 (dd, 1H, J 4.8, 1.6 Hz), 8.66 (br s, 1H), 8.68-8.80 (m, 1H).
ESI-MI m/z [M+H]$^+$ 456.6.

Step 4

To a solution of 2-bromo-5-methyl-pyrazine (865 mg, 5.0 mmol) in dry THF (35 mL) was added n-BuLi (1.6 M solution in hexanes, 3.2 mL, 5.1 mmol) dropwise, at −78° C. and under nitrogen. The dark red-brown solution was stirred at −78° C. for 20 minutes before a solution of the Weinreb amide N-methoxy-N-methyl-2-(1H-pyrrol-1-yl)acetamide (900 mg, 5.35 mmol) in THF (26 mL) was added. The solution was stirred at −78° C. for 2 hours before being quenched with a saturated aqueous solution of NH$_4$Cl (40 mL) at −78° C. and extracted with CH$_2$Cl$_2$ (3×30 mL). The organic extracts were combined, dried (Na$_2$SO$_4$), filtrated and concentrated in vacuo to give a residue that was purified by flash chromatography (Biotage SP4, 40 g cartridge, gradient hexanes 1 CV, 0-60% EtOAc in hexanes 15 CV) to give 1-(5-methylpyrazin-2-yl)-2-(1H-pyrrol-1-yl)ethanone (318 mg, yield 32%). $^1$H-NMR (400 MHz, CDCl$_3$): δ 2.69 (s, 3H), 5.51 (s, 2H), 6.25 (t, 2H, J 2.1 Hz), 6.69 (t, 2H, J 2.1 Hz), 8.52-8.53 (m, 1H), 9.13 (d, 1H, J 1.3 Hz).

Step 5

To a chilled (0° C.) solution of 1-(5-methylpyrazin-2-yl)-2-(1H-pyrrol-1-yl)ethanone (318 mg, 1.58 mmol) in CH$_2$Cl$_2$ (21 mL) was added 2,2,2-trichloroacetyl chloride (400 μL, 3.56 mmol). The solution was allowed at room temperature and stirred until complete (overnight, monitored by LCMS). A chilled saturated solution of NaHCO$_3$ (15 mL) was then added and the mixture extracted with CH$_2$Cl$_2$ (3×15 mL). The organic were dried (Na$_2$SO$_4$), filtrated and concentrated in vacuo to give a residue that is purified by flash chromatography (Biotage SP4, 4 g cartridge, gradient 1 CV hexane, 0-50% EtOAc in hexanes 10 CV; 50-100% 3CV). The compound 2,2,2-Trichloro-1-{1-[2-(5-methylpyrazin-2-yl)-2-oxoethyl]-1H-pyrrol-2-yl}ethanone was isolated as a crystalline solid (260 mg, yield 38%). $^1$H-NMR (400 MHz, CDCl$_3$): δ 2.70 (s, 3H), 5.91 (2H, s), 6.45 (dd, 1H, J 4.4, 2.5, Hz), 7.02 (dd, 1H, J 2.4, 1.6 Hz), 7.64 (dd, 1H, J 4.4, 1.5 Hz), 8.53-8.55 (m, 1H), 9.15 (d, 1H, J 1.3 Hz).

Step 6b

To a solution of 2,2,2-trichloro-1-{1-[2-(5-methylpyrazin-2-yl)-2-oxoethyl]-1H-pyrrol-2-yl}ethanone (260 mg, 0.75 mmol) in THF (4.4 mL) was added N-bromosuccinimide (144 mg, 0.81 mmol) at −15° C. The mixture was allowed at room temperature overnight. A saturated aqueous solution of NH$_4$Cl (5 mL) was added and the mixture extracted with CH$_2$Cl$_2$ (3×5 mL). The organics were dried (Na$_2$SO$_4$), filtrated and concentrated in vacuo to give a residue that was purified by chromatography (Biotage SP4, gradient 1 CV hexanes, 0-40% EtOAc in hexanes 15 CV, 40-60% 5CV) to give 1-{4-bromo-1-[2-(5-methylpyrazin-2-yl)-2-oxoethyl]-1H-pyrrol-2-yl}-2,2,2-trichloroethanone as a yellow solid (157 mg, yield: 49%).
ESI-MI m/z [M+H]$^+$: 425.9.

Step 7b

A solution of 1-{4-bromo-1-[2-(5-methylpyrazin-2-yl)-2-oxoethyl]-1H-pyrrol-2-yl}-2,2,2-trichloroethanone (157 mg, 0.37 mmol) in methanol (7 mL) was treated with sodium hydroxide (15 mg, 0.37 mmol) in water (0.4 mL) at 0° C. and the mixture stirred at room temperature. After one hour the reaction was complete (monitored by LCMS). The mixture was acidified with a aqueous solution of HCl (1 M) and then extracted with CH$_2$Cl$_2$ (3 times). The organic were then dried (Na$_2$SO$_4$), filtrated and concentrated in vacuo to give methyl 4-bromo-1-[2-(5-methylpyrazin-2-yl)-2-oxoethyl]-1H-pyrrole-2-carboxylate (140 mg). The crude was used in the next step without purification. $^1$H-NMR (400 MHz, CDCl$_3$): δ 2.69 (s, 3H), 3.71 (s, 3H), 5.86 (s, 2H), 6.83 (d, 1H, 1.9 Hz), 7.01 (d, 1H, J 1.9 Hz), 8.53 (s, 1H), 9.13 (s, 1H)

Step 8b

To a solution of methyl 4-bromo-1-[2-(5-methylpyrazin-2-yl)-2-oxoethyl]-1H-pyrrole-2-carboxylate (111 mg, 0.33 mmol) in 1,4-dioxane (2 mL) was added ethane-1,2-diamine (0.6 mL, 9.0 mmol). The solution was heated at reflux. After 2 days the reaction was complete (monitored by LCMS). The mixture was then concentrated in vacuo to give a oily solid. The material was purified by flash chromatography (Biotage SP4, 12 g cartridge, gradient CH$_2$Cl$_2$ 1 CV, 0-10% MeOH in CH$_2$Cl$_2$ 15 CV and hold 10% MeOH 5 CV) to give 7-bromo-10a-(5-methylpyrazin-2-yl)-2,3,10,10a-tetrahydro-1H,5H-imidazo[1,2-a]pyrrolo[1,2-d]pyrazin-5-one (33 mg, yield 29%). $^1$H-NMR (400 MHz, CDCl$_3$): δ 2.53 (s, 3H), 2.95 (dt, 1H, J 10.8, 7.9 Hz), 3.31 (ddd, 1H, J 11.0, 7.6, 3.8 Hz), 3.37 (ddd, 1H, J 11.3, 7.7, 3.8 Hz), 3.94 (dt, 1H, J 11.2, 7.8 Hz), 4.16 (d, 1H, J 12.0 Hz), 4.77 (d, 1H, J 12.0 Hz), 6.51 (d, 1H, J 1.6 Hz), 6.87 (d, 1H, J 1.7 Hz), 8.34 (d, 1H, J 1.4 Hz), 8.40-8.41 (m, 1H).

Step 9b

To a mixture of 7-bromo-10a-(5-methylpyrazin-2-yl)-2,3,10,10a-tetrahydro-1H,5H-imidazo[1,2-a]pyrrolo[1,2-d]pyrazin-5-one (20 mg, 0.057 mmol), 3-pyridylboronic acid (9 mg, 0.073 mg) in 1,2-dimethoxyethane (0.5 mL) was added a solution of sodium carbonate (16 mg, 0.19 mmol) in water (0.15 mL) and ethanol (0.1 mL). The mixture was flushed with argon and dichlorobis(triphenylphosphine)palladium (II) (3.5 mg, 5×10⁻³ mmol) was added. The mixture was further degassed with argon, sealed and heated at 100° C. overnight. The following day an additional batch of 3-pyridylboronic acid (20 mg, 0.16 mmol) and dichlorobis(triphenylphosphine)palladium(II) (4 mg, 5.7×10⁻³ mmol) were added. The mixture was degassed, sealed and heated at 100° C. After 3 hours the reaction was complete. The mixture was then concentrated and purified by flash chromatography (Biotage SP4, gradient 1CV CH₂Cl₂, 0-10% MeOH in CH₂Cl₂ and hold 10% MeOH) to give 10a-(5-methylpyrazinby LCMS) the suspension was diluted with water (4 mL) and extracted with CH₂Cl₂ (3×3 mL). The extracts were combined, dried (Na₂SO₄), filtered and concentrated in vacuo to give a residue that was purified by flash chromatography (Biotage SP4, 4 g cartridge, gradient 1CV dichloromethane, 0-8% methanol in CH₂Cl₂ and then hold 8% MeOH 8CV) to give 1-[(3-methyl-1,2-oxazol-4-yl)carbonyl]-10a-(5-methylpyrazin-2-yl)-7-(pyridin-3-yl)-2,3,10,10a-tetrahydro-1H,5H-imidazo[1,2-a]pyrrolo[1,2-d]pyrazin-5-one (121) as a off-white solid (3.74 mg, yield 19%).

The following compounds were similarly prepared using General Method P: Route (b).

| Cpd. No. | Structure | ESI-MI m/z [M + H]⁺/¹H-NMR |
|---|---|---|
| 117 | 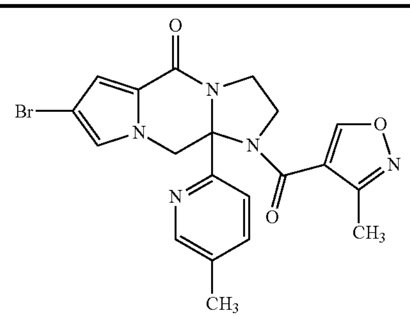 | ESI-MI m/z [M + H]⁺ 456.0. ¹H NMR (400 MHz, CDCl₃): δ 2.28 (s, 3H). 2.35 (s, 3H), 4.01-4.18 (m, 3H), 4.31-4.38 (m, 1H), 4.44 (d, 1H, J 13.0 Hz), 5.73 (d, 1H, J 13.0 Hz), 6.86 (dd, 2H, J 5.9, 1.7 Hz), 7.02 (br d, 1H, J 8.1 Hz), 7.41 (ddd, 1H, J 8.1, 2.2, 0.7 Hz), 8.29-8.31 (m, 1H), 8.61 (s, 1H). |
| 120 | 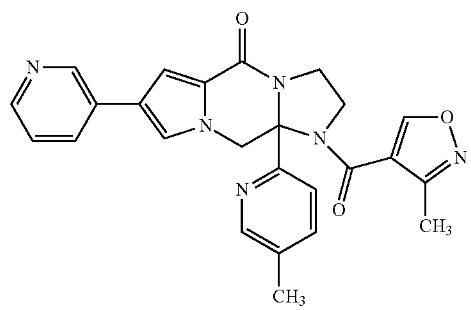 [SMILES: Cc1ccc(C23Cn4cc(-c5cccnc5)cc4C(=O)N2CCN3C(=O)c2conc2C)nc1] | ESI-MI m/z [M + H]⁺ 455.2. ¹H NMR (400 MHz, CDCl₃): δ 2.27 (s, 3H). 2.37 (s, 3H), 4.00-4.21 (m, 3H), 4.40 (t, 1H, J 11.3 Hz), 4.53 (d, 1H, J 13.0 Hz), 5.82 (d, 1H, J 13.0 Hz), 7.07 (d, 1H, J 8.1 Hz), 7.28-7.34 (m, 1H), 7.20 (s, 2H), 7.40 (br d, 1H, J 6.9 Hz), 7.78 (br d, 1H, J 8.0 Hz), 8.31 (br s, 1H), 8.46 (br d, 1H, J 3.8 Hz), 8.63 (s, 1H), 8.81 (br s, 1H). |

2-yl)-7-(pyridin-3-yl)-2,3,10,10a-tetrahydro-1H,5H-imidazo[1,2-a]pyrrolo[1,2-d]-pyrazin-5-one (15 mg, yield: 76%). ¹H-NMR (400 MHz, CDCl₃): δ 2.53 (s, 3H), 2.99 (dt, 1H, J 7.9 Hz), 3.35 (ddd, 1H, J 10.9, 7.5, 3.7 Hz), 3.77 (ddd, 1H, J 11.2, 7.6, 3.8 Hz), 4.00 (dt, 1H, J 11.1, 7.8 Hz), 4.26 (d, 1H, J 12.0 Hz), 4.87 (d, 1H, J 12.0 Hz), 6.87 (d, 1H, J 1.7 Hz), 7.20-7.25 (m, 2H), 7.66-7.70 (m, 1H), 8.37-8.44 (m, 3H), 8.68 (d, 1H, J 1.8 Hz).

Step 10b

To generate the acid chloride: to a chilled suspension of 3-methylisoxazole-4-carboxylic acid (46 mg, 0.36 mmol) in dry CH₂Cl₂ (0.5 mL) was added oxalyl chloride (75 μL, 0.89 mmol) followed by DMF (1 drop, catalytic). The mixture was stirred at 0° C. for 10 minutes and then at room temperature for 1 hour. The resulting solution was concentrated in vacuo at ambient temperature to give a liquid that was diluted in CH₂Cl₂ and re-concentrated to give the acid chloride as a oil. To a chilled suspension of the acid chloride (generated as above, 0.36 mmol) in pyridine (0.5 mL) was added a suspension of 10a-(5-methylpyrazin-2-yl)-7-(pyridin-3-yl)-2,3,10,10a-tetrahydro-1H,5H-imidazo[1,2-a]pyrrolo[1,2-d]pyrazin-5-one (15 mg, 0.043 mmol) in pyridine (1.2 mL). The suspension was stirred at 0° C. for 5 minutes and then at room temperature for 1 hour. When complete (reaction monitored Example of General Method Q 1-[(3-methyl-1,2-oxazol-4-yl)carbonyl]-10a-(pyridin-4-yl)-2,3,10,10a-tetrahydro-1H,5H-imidazo[1,2-a]pyrrolo[1,2-d]pyrazin-5-one (122)

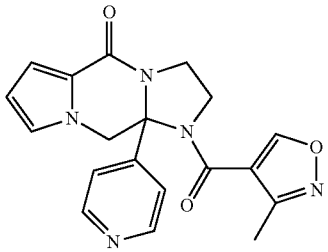 [SMILES: Cc1nocc1C(=O)N1CCN2C(=O)c3cccn3CC12c1ccncc1]

¹H-NMR (400 MHz, CDCl₃): δ 2.44 (s, 3H), 3.74 (ddd, 1H, J 15.4, 8.2, 7.3 Hz), 3.89 (ddd, 1H, J 12.2, 11.1, 2.8 Hz), 4.04-4.13 (m, 1H), 4.44 (ddd, 1H, J 11.8, 8.6, 4.2 Hz), 4.55 (d, 1H, J 13.0 Hz), 5.66 (d, 1H, J 13.0 Hz), 6.23 (dd, 1H, J 3.9, 1.4 Hz), 6.74 (dd, 1H, J 2.4, 1.6 Hz), 6.95 (dd, 1H, J 3.9, 1.4 Hz), 7.23 (dd, 2H, J 4.6, 1.7 Hz), 8.56 (dd, 2H, J 4.7, 1.5 Hz), 8.60 (br s, 1H). ESI-MI m/z [M+H]⁺ 364.1.

Step 1

To a suspension of N-(tert-butoxycarbonyl)glycine (4.0 g, 23 mmol), N,O-dimethylhydroxylamine hydrochloride (3.0 g, 31 mmol) and N,N-dimethylpyridin-4-amine (300 mg, 2.5 mmol) in dry $CH_2Cl_2$ (100 mL) was added N-(3-dimethylaminopropyl)-W-ethylcarbodiimide hydrochloride (5.2 g, 27 mmol) followed by triethylamine (5.4 mL, 39 mmol) at 0° C. The mixture was stirred at that temperature 30 minutes and then at room temperature over 3 days. The suspension was washed with aqueous HCl (1 M, 2×40 mL) followed by a saturated aqueous solution of $NaHCO_3$ (2×40 mL). The organic layer was dried ($Na_2SO_4$), filtered and concentrated in vacuo to yield tert-butyl {2-[methoxy(methyl)amino]-2-oxoethyl}carbamate as a white solid (4.5 g, yield 90%). $^1$H-NMR (400 MHz, $CDCl_3$): δ 1.45 (s, 9H), 3.20 (s, 3H), 3.71 (s, 3H), 4.08 (br s, 2H), 5.26 (br s, 2H).

Step 2

4-Bromopyridine hydrochloride (1.1 g, 5.7 mmol) was treated with 5% $Na_2CO_3$ (aq, 35 mL) and the solution extracted with $CH_2Cl_2$ (3×15 mL). The extracts were combined, dried ($Na_2SO_4$), filtered and concentrated in vacuo to yield a oil. The oil was dried under high vacuum before the flask was flushed with nitrogen and then immediately dissolved in dry THF (15 mL). To this solution was added isopropylmagnesium chloride (2.6 M solution in ether, 2.2 mL, 5.7 mmol) dropwise under nitrogen. The resulting dark solution was stirred at room temperature for 1.5 h during which time a precipitate formed. Meanwhile, to a chilled (ice/acetone bath) suspension of tert-butyl {2-[methoxy(methyl) amino]-2-oxoethyl}carbamate (1.0 g, 4.6 mmol) in THF (10 mL) was added isopropylmagnesium chloride (2.6 M solution in ether, 1.8 mL, 4.7 mmol) dropwise. The resulting solution was stirred for 10 minutes before being added to the aryl Grignard initially generated. The mixture was stirred at room temperature overnight, diluted with water (25 mL) and brine (25 mL) and extracted with ethyl acetate (3×35 mL). The organic layers were dried ($MgSO_4$), filtered and concentrated in vacuo to yield a yellow residue. The material was purified by flash chromatography (Biotage SP4, 40 g cartridge, 1 gradient CV hexanes, 0-100% EtOAc in hexanes 10 CV, hold for 5 CV) to give tert-butyl [2-oxo-2-(pyridin-4-yl) ethyl]carbamate as a yellow oil (785 mg yield 52%). $^1$H-NMR (400 MHz, $CDCl_3$): δ 1.47 (s, 9H), 4.65 (d, 2H, J 4.6 Hz), 7.71-7.74 (m, 2H), 8.83-8.86 (m, 2H).

Step 3

Dry MeOH (10 mL) was treated with acetyl chloride (1.8 mL, 25 mmol) at 0° C. under nitrogen. The solution was allowed at room temperature and stirred for 15 minutes before being added to a chilled (ice bath) solution of tert-butyl [2-oxo-2-(pyridin-4-yl)ethyl]carbamate (785 mg, 3.0 mmol) in dry MeOH (10 mL). The resulting yellow solution was allowed at room temperature and stirred for 4 hours and then concentrated in vacuo to give the crude 4-(ammonioacetyl) pyridinium dichloride as a yellow solid (600 mg, yield 96%). The material was carried through without purification. $^1$H-NMR (400 MHz, d6-DMSO): δ 7.35 (t, 1H, 50.8 Hz), 8.01-8.05 (m, 2H), 8.60 (br s, 2H), 8.93-8.97 (m, 2H).

Step 4

4-(ammonioacetyl)pyridinium dichloride (crude, 100 mg, 0.48 mmol), methyl 2,5-dimethoxytetrahydrofuran-2-carboxylate (99 mg, 0.52 mmol) and sodium acetate (157 mg, 1.9 mmol) were suspended in glacial acetic acid (1.5 mL) and the mixture heated at 100° C. After 4.5 hours the dark mixture was allowed to cool to room temperature and ice (5 g) was added. The mixture was neutralised with solid $NaHCO_3$ and allowed at room temperature. The resulting suspension was diluted with $CH_2Cl_2$ (5 mL), filtered and the aqueous layer extracted with $CH_2Cl_2$ (3×5 mL). The organic layers were dried ($MgSO_4$), filtered and concentrated in vacuo to yield a brown oil that was purified by flash chromatography (Biotage SP4 (4 g cartridge, gradient hexanes 3 CV, 0-100% EtOAc in hexanes 15 CV, hold for 5 CV) to give methyl 1-[2-oxo-2-(pyridin-4-yl)ethyl]-1H-pyrrole-2-carboxylate (13 mg, yield 11%). ESI-MI m/z $[M+H]^+$ 245.1.

Step 5

To a solution of methyl 1-[2-oxo-2-(pyridin-4-yl)ethyl]-1H-pyrrole-2-carboxylate (55 mg, 0.23 mmol) in 1,4-dioxane (10 mL) was added ethane-1,2-diamine (0.6 mL, 9.0 mmol). The mixture was heated at reflux for 64 hours and then concentrated in vacuo to give a residue that was purified by flash chromatography (Biotage SP4, gradient $CH_2Cl_2$ 3 CV, 0 to 10% methanol in $CH_2Cl_2$ 10 CV, hold 10% MeOH 10 CV) to give 10a-(pyridin-4-yl)-2,3,10,10a-tetrahydro-1H,5H-imidazo[1,2-a]pyrrolo[1,2-d]pyrazin-5-one as an off-white solid (35 mg, yield: 60%). $^1$H-NMR (400 MHz, $CDCl_3$): δ 2.84 (dt, 1H, J 15.2, 4.4 Hz), 3.30-3.37 (m, 1H), 3.49 (ddd, 1H, J 11.3, 7.1, 3.5 Hz), 3.79 (dt, 1H, J 11.2, 8.0 Hz), 4.26 (d, 1H, J 12.2 Hz), 4.39 (d, 1H, J 12.3 Hz), 4.48 (dd, 1H, J 2.5, 1.6 Hz), 6.12 (dd, 1H, J 3.8, 2.6 Hz), 6.92 (dd, 1H, J 3.9, 1.5 Hz), 7.25-7.28 (m, 2H), 8.47-8.50 (m, 2H).

Step 6

To generate the acid chloride, 3-methyl-1,2-oxazole-4-carboxylic acid (55 mg, 0.43 mmol) was dissolved in $CH_2Cl_2$ (1.0 mL). Oxalyl chloride (0.12 mL, 1.4 mmol) was added followed by a drop of DMF at 0° C. The ice bath was removed after 10 minutes and the mixture stirred for 1 hour at room temperature before the solvent and the excess of oxalyl chloride were removed in vacuo. $CH_2Cl_2$ was added and the mixture concentrated in vacuo to give the acid chloride as a oil. 10a-(pyridin-4-yl)-2,3,10,10a-tetrahydro-1H,5H-imidazo[1,2-a]pyrrolo[1,2-d]pyrazin-5-one (35 mg, 0.14 mmol) was dissolved in pyridine (1.0 mL) and the solution added to the previously generated acid chloride in pyridine (0.5 mL) at 0° C. The ice bath was removed after 5 minutes and the mixture stirred at room temperature for 1.5 hour. The suspension was then diluted with water (5 mL) and extracted with $CH_2Cl_2$ (3×2 mL). The extracts were combined, dried ($MgSO_4$), filtered and concentrated in vacuo to give a residue that was purified by flash chromatography (silica gel, 40 then 70-80% acetone in hexanes) to give 1-[(3-methyl-1,2-oxazol-4-yl)carbonyl]-10a-(pyridin-4-yl)-2,3,10,10a-tetrahydro-1H,5H-imidazo[1,2-a]pyrrolo[1,2-d]pyrazin-5-one (122) as a white solid (24 mg, yield 47%).

Example of General Method R 10a-(4-fluorophenyl)-8-methyl-1-[(3-methyl-1,2-oxazol-4-yl)carbonyl]-2,3,10,10a-tetrahydro-1H,5H-imidazo[1,2-a]pyrrolo[1,2-d]pyrazin-5-one (154)

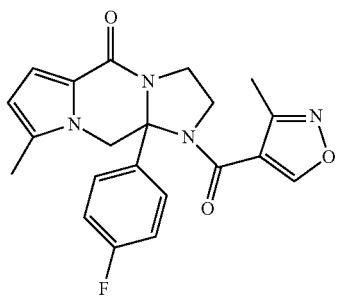 [SMILES: Cc1nocc1C(=O)N1CCN2C(=O)c3ccc(C)n3CC12c1ccc(F)cc1]

$^1$H NMR (400 MHz, CDCl$_3$): δ 2.21 (s, 3H), 2.44 (d, 3H, J 0.5 Hz), 3.67-3.87 (m, 2H), 3.99-4.09 (m, 1H), 4.30 (d, 1H, J 13.0 Hz), 4.37 (ddd, 1H, J 11.3, 8.8, 4.1 Hz), 5.64 (d, 1H, J 13.0 Hz), 5.94 (dd, 1H, J 3.8, 0.7 Hz), 6.86 (d, 1H, J 3.8 Hz), 6.93-7.04 (m, 2H), 7.38 (dd, 2H, J 9.1, 5.1 Hz), 8.56 (s, 1H). ESI-MI m/z [M+H]$^+$ 395.10.

Step 1

Ethyl 5-methyl-1H-pyrrole-2-carboxylate (400 mg, 2.6 mmol), 2-(4-fluorophenyl)oxirane (400 mg, 2.9 mmol) and potassium carbonate (200 mg, 1 mmol) were suspended in DMF (5 mL) and heated at 100° C. for 18 h. The reaction mixture was partitioned between brine (10 mL) and EtOAc (20 mL) and the organic layer separated. The aqueous layer was extracted further with EtOAc (3×20 mL) and the combined organic layers were dried (MgSO$_4$), filtered and concentrated in vacuo to give a yellow gum, which was purified by flash column chromatography (Biotage SP4, 12 g cartridge, 10-60% EtOAc/hexanes 10 CV) to give 3-(4-fluorophenyl)-6-methyl-3,4-dihydro-1H-pyrrolo[2,1-c][1,4]oxazin-1-one as an off-white solid (210 mg, 32% based on reacted starting material).

$^1$H NMR (400 MHz, CDCl$_3$): δ 2.28 (s, 3H), 3.98 (dd, 1H, J 13.2, 11.0 Hz), 4.16 (dd, 1H, J 13.2, 3.4 Hz), 5.62 (dd, 1H, J 11.0, 3.4 Hz), 6.11 (dd, 1H, J 4.0, 0.7 Hz), 7.08-7.16 (m, 3H), 7.47 (dd, 2H, J 8.5, 5.2 Hz). ESI-MI m/z [M+H]$^+$ 246.01.

Step 2

A solution of lithium hydroxide hydrate (103 mg, 2.4 mmol) in water (1 mL) was added to a solution of 3-(4-fluorophenyl)-6-methyl-3,4-dihydro-1H-pyrrolo[2,1-c][1,4]oxazin-1-one (200 mg, 0.8 mmol) in THF (9 mL) at room temperature. The reaction was stirred at room temperature for 2 days. The reaction mixture was then diluted with EtOAc (20 mL) and acidified to approx. pH 2 with 1 M HCl (aq). The organic layer was separated and the aqueous layer extracted further with EtOAc (2×20 mL). The combined organic layers were washed with water, dried (MgSO$_4$), filtered and concentrated in vacuo to give 1-[2-(4-fluorophenyl)-2-hydroxyethyl]-5-methyl-1H-pyrrole-2-carboxylic acid as an off-white solid (211 mg, 98%). $^1$H NMR (400 MHz, CD$_3$OD): δ 2.07 (s, 3H), 4.31 (dd, 1H, J 13.7, 7.9 Hz), 4.42 (dd, 1H, J 13.7, 4.9 Hz), 4.99 (dd, 1H, J 7.7, 5.1 Hz), 5.85 (dd, 1H, J 3.9, 0.7 Hz), 6.92 (d, 1H, J 3.9 Hz), 6.97-7.06 (m, 2H), 7.34 (dd, 2H, J 8.5, 5.5 Hz).

Step 3

A solution of oxalyl chloride (0.3 mL, 3.5 mmol) in CH$_2$Cl$_2$ (0.5 mL) was added drop-wise to a solution of DMSO (0.34 mL, 4.8 mmol) in CH$_2$Cl$_2$ (1.5 mL) at −65° C. and stirred for 10 min. The resultant solution was added to a suspension of 1-[2-(4-fluorophenyl)-2-hydroxyethyl]-5-methyl-1H-pyrrole-2-carboxylic acid (211 mg, 0.8 mmol) in CH$_2$Cl$_2$ (10 mL) at −65° C. The resultant suspension was stirred at −65° C. for 15 min, then triethylamine (1.12 mL, 8.0 mmol) was added drop-wise. Once the addition was complete the reaction mixture was allowed to warm to room temperature and stirred for 2 hours. The reaction was then quenched by the addition of CH$_2$Cl$_2$ (50 mL) and water (10 mL), the organic layer was separated and the aqueous extracted with further CH$_2$Cl$_2$ (10 mL). The organic layers were combined and washed with brine, dried (MgSO$_4$), filtered and concentrated in vacuo to give a brown solid. The solid was purified by flash column chromatography (Biotage SP4, 40 g cartridge, hexane 1 CV, 0-50% EtOAc/hexanes 10 CV) to give (methylsulfanyl)methyl 1-[2-(4-fluorophenyl)-2-oxoethyl]-5-methyl-1H-pyrrole-2-carboxylate as a off-white solid (162 mg, 62%). $^1$H NMR (400 MHz, CDCl$_3$): δ 2.19 (s, 3H), 2.22 (s, 3H), 5.19 (s, 2H), 5.76 (s, 2H), 6.06 (dd, 1H, J 3.9, 0.7 Hz), 7.06 (d, 1H, J 3.9 Hz), 7.13-7.24 (m, 2H), 8.06 (dd, 2H, J 9.0, 5.3 Hz). ESI-MI m/z [M+H]$^+$ 321.80.

Step 4

To a solution of (methylsulfanyl)methyl 1-[2-(4-fluorophenyl)-2-oxoethyl]-5-methyl-1H-pyrrole-2-carboxylate (120 mg, 0.37 mmol) in chloroform (2 mL) was added ethane-1,2-diamine (0.05 mL, 0.7 mmol) and acetic acid (0.002 mL, 0.04 mmol). The mixture was stirred at 60° C. for 18 h. LCMS indicated approx. 50% conversion to desired product, so a further equivalent of ethane-1,2-diamine (0.025 mL) was added and the reaction stirred at 60° C. for 2 days. Sat. aq. NaHCO$_3$ (1 mL) and CH$_2$Cl$_2$ (2 mL) were then added. The organic layer was separated and the aqueous extracted with further CH$_2$Cl$_2$ (2×5 mL). The organic layers were combined and dried (MgSO$_4$), filtered and concentrated in vacuo to give 10a-(4-fluorophenyl)-8-methyl-2,3,10,10a-tetrahydro-1H,5H-imidazo[1,2-a]pyrrolo[1,2-d]pyrazin-5-one as a yellow solid (100 mg, 93%). $^1$H NMR (400 MHz, CDCl$_3$): δ 2.03 (s, 3H), 2.83-3.03 (m, 1H), 3.30 (ddd, 1H, J 12.0, 7.6, 4.3 Hz), 3.38-3.58 (m, 1H), 3.85-3.94 (m, 1H), 3.97 (d, 1H, J 12.0 Hz), 4.43 (d, 1H, J 12.0 Hz), 5.87 (dd, 1H, J 3.7, 0.6 Hz), 6.85 (d, 1H, J 3.7 Hz), 6.96 (t, 2H, J 8.7 Hz), 7.34 (dd, 2H, J 8.9, 5.2 Hz). ESI-MI m/z [M+H]$^+$ 285.99.

Step 5

To generate the acid chloride, oxalyl chloride (0.42 mL, 5.0 mmol) and DMF (1 drop) were added to a suspension of 3-methyl-1,2-oxazole-4-carboxylic acid (261 mg, 2.05 mmol) in dry CH$_2$Cl$_2$ (3 mL) at 0° C. The suspension was then stirred at room temperature until the acid was fully converted to the acid chloride. The resulting solution was concentrated in vacuo to yield an oily solid which was further dried under nitrogen.

To a chilled (ice bath) suspension of the acid chloride (generated as above, 2.05 mmol) in pyridine (4.5 mL) was added 10a-(4-fluorophenyl)-8-methyl-2,3,10,10a-tetrahydro-1H,5H-imidazo[1,2-a]pyrrolo[1,2-d]pyrazin-5-one (117 mg, 0.41 mmol) in pyridine (5.0 mL). The suspension was then stirred at room temperature until completion (2 h, monitored by LCMS). Water was added and the mixture extracted with EtOAc (3 times). The organic layers were combined, dried (MgSO$_4$), filtered and concentrated in vacuo to give a residue that was purified by flash chromatography using the Biotage SP4 (0-5% methanol in CH$_2$Cl$_2$ 10 CV, 5-10% methanol in CH$_2$Cl$_2$ 5 CV). The material was then triturated with acetone and the resulting white solid dissolved in EtOAc and washed with sat. aq. NaHCO$_3$. The organic layers were combined, dried (MgSO$_4$), filtered, concentrated in vacuo and then freeze-dried to give 10a-(4-fluorophenyl)-8-methyl-1-[(3-methyl-1,2-oxazol-4-yl)carbonyl]-2,3,10,10a-tetrahydro-1H,5H-imidazo[1,2-a]pyrrolo[1,2-d]pyrazin-5-one (154) as white solid (35 mg, 22%).

Example of General Method S 10a-(4-methoxyphenyl)-1-[(3-methyl-1,2-oxazol-4-yl)carbonyl]-2,3,10,10a-tetrahydro-1H,5H-imidazo[1,2-a]pyrazolo[1,5-d]pyrazine-5,7(8H)-dione (155)

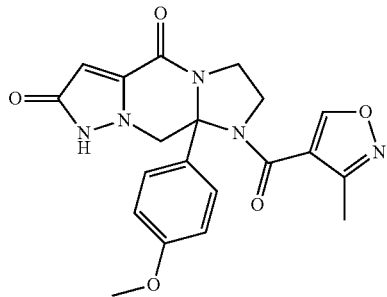 [SMILES: COc1ccc(C23Cn4[nH]c(=O)cc4C(=O)N2CCN3C(=O)c2conc2C)cc1]

$^1$H NMR (400 MHz, d6-acetone): δ 2.34 (s, 3H), 3.77 (s, 3H), 3.73-3.84 (m, 1H), 4.14-4.24 (m, 1H), 4.24-4.35 (m, 2H), 4.68 (d, 1H, J 13.2 Hz), 5.60 (d, 1H, J 13.2 Hz), 5.99 (s, 1H), 6.88 (d, 2H, J 9.0 Hz), 7.37 (d, 2H, J 8.9 Hz), 9.14 (s, 1H). ESI-MI m/z [M+H]$^+$ 409.93.

Step 1

Potassium carbonate (3 equivalents) was added to a solution of tert-butyl carbazate (500 mg, 3.8 mmol) in DMF at 0° C. After 10 minutes, 2-bromo-1-(4-methoxyphenyl)ethanone (1 equivalent) was added and the reaction stirred at 0° C. for 1 hour. After this time, the reaction was worked-up to give crude tert-butyl 2-[2-(4-methoxyphenyl)-2-oxoethyl]hydrazinecarboxylate. The material was carried through without purification. ESI-MI m/z [M+Na]$^+$ 303.2.

Step 2

Diethyl but-2-ynedioate (1.6 equivalents) was added to a stirred solution of crude tert-butyl 2-[2-(4-methoxyphenyl)-2-oxoethyl]hydrazinecarboxylate (2 g) in ethanol at 0° C. The reaction was monitored by LCMS. Upon completion, the reaction mixture was concentrated in vacuo to give crude diethyl 2-{2-(tert-butoxycarbonyl)-1-[2-(4-methoxyphenyl)-2-oxoethyl]hydrazinyl}but-2-enedioate (1.3 g). The material was carried through without purification. ESI-MI m/z [M+H]$^+$ 451.

Step 3

A solution of crude diethyl 2-{2-(tert-butoxycarbonyl)-1-[2-(4-methoxyphenyl)-2-oxoethyl]hydrazinyl}but-2-enedioate (1.3 g) in toluene was added to polyphosphoric acid at 85° C. The reaction was heated at 85° C. for 1 hour after which time it was worked-up to give crude ethyl 2-[2-(4-methoxyphenyl)-2-oxoethyl]-5-oxo-2,5-dihydro-1H-pyrazole-3-carboxylate (800 mg). ESI-MI m/z [M+H]$^+$ 305.3.

Step 4

To a stirred solution of crude ethyl 2-[2-(4-methoxyphenyl)-2-oxoethyl]-5-oxo-2,5-dihydro-1H-pyrazole-3-carboxylate (400 mg) in dioxane was added ethane-1,2-diamine (35 equivalents) and the mixture heated at reflux. After 5 hours the mixture was concentrated in vacuo and the residue partitioned between ethyl acetate and water. The work-up was completed and the resulting residue purified by flash chromatography to give a solid (100 mg). The solid was triturated with diethyl ether hexanes to give 10a-(4-methoxyphenyl)-2,3,10,10a-tetrahydro-1H,5H-imidazo[1,2-a]pyrazolo[1,5-d]pyrazine-5,7(8I-1)-dione as a brown solid. $^1$H NMR (400 MHz, DMSO): δ 2.52-2.65 (m, 1H), 3.18-3.26 (m, 1H), 3.50-3.61 (m, 1H), 3.71 (s, 3H), 3.74-3.83 (m, 1H), 4.35 (d, 1H, J 12.5 Hz), 4.46 (d, 1H, J 12.4 Hz), 5.90 (s, 1H), 6.87 (d, 2H, J 8.8 Hz), 7.21 (d, 2H, J 8.8 Hz). ESI-MI m/z [M+H]$^+$ 300.90

Step 5

To generate the acid chloride, oxalyl chloride (0.48 mL, 5.7 mmol) and DMF (1 drop) were added to a suspension of 3-methyl-1,2-oxazole-4-carboxylic acid (296 mg, 2.3 mmol) in dry CH$_2$Cl$_2$ (7 mL) at 0° C. The suspension was then stirred at room temperature until the acid was fully converted to the acid chloride. The resulting solution was concentrated in vacuo to yield an oily solid which was further dried under nitrogen.

To a chilled (ice bath) suspension of the acid chloride (generated as above, 2.3 mmol) in pyridine (4.5 mL) was added 10a-(4-methoxyphenyl)-2,3,10,10a-tetrahydro-1H,5H-imidazo[1,2-a]pyrazolo[1,5-d]pyrazine-5,7(8M-dione (70 mg, 0.23 mmol) in pyridine (5.0 mL). The suspension was stirred at room temperature until completion (2 h, monitored by LCMS). Water (30 mL) was added and the mixture extracted with EtOAc (3×20 mL). The organic layers were combined, dried (Na$_2$SO$_4$), filtered and concentrated in vacuo. The residue was purified by flash chromatography using the Biotage SP4 (0-10% methanol in EtOAc, 12 CV) to give 10a-(4-methoxyphenyl)-1-[(3-methyl-1,2-oxazol-4-yl)carbonyl]-5-oxo-2,3,10,10a-tetrahydro-1H,5H-imidazo[1,2-a]pyrazolo[1,5-d]pyrazin-7-yl 3-methyl-1,2-oxazole-4-carboxylate (120 mg, 100%). $^1$H NMR (400 MHz, CDCl$_3$): δ 2.41 (s, 3H), 2.54 (s, 3H), 3.76 (s, 3H), 3.80-3.96 (m, 2H), 4.04-4.12 (m, 1H), 4.26-4.41 (m, 1H), 4.72 (d, 1H, J 13.5 Hz), 5.90 (d, 1H, J 13.4 Hz), 6.80 (s, 1H), 6.84 (d, 2H, J 9.0 Hz), 7.34 (d, 2H, J 9.0 Hz), 8.51 (s, 1H), 9.02 (s, 1H). ESI-MI m/z [M+H]$^+$ 519.00.

Step 6

To a solution of 10a-(4-methoxyphenyl)-1-[(3-methyl-1,2-oxazol-4-yl)carbonyl]-5-oxo-2,3,10,10a-tetrahydro-1H,5H-imidazo[1,2-a]pyrazolo[1,5-d]pyrazin-7-yl 3-methyl-1,2-oxazole-4-carboxylate (120 mg, 0.23 mmol) in THF (1 mL) and methanol (1 mL) was added an aqueous solution of lithium hydroxide (0.1 M, 0.3 mL, 0.3 mmol). The mixture was stirred at room temperature until completion (2 h, monitored by LCMS). The solution was concentrated in vacuo and the residue partitioned between CH$_2$Cl$_2$ and 5% HCl (aq). The organic layer was separated and the aqueous layer further extracted with CH$_2$Cl$_2$. The organic layers were combined, dried (Na$_2$SO$_4$), filtered and concentrated in vacuo. The residue was purified by flash chromatography using the Biotage SP4 (12 g cartridge, 0-10% methanol in $CH_2Cl_2$, 15 CV) to give 10a-(4-methoxyphenyl)-1-[(3-methyl-1,2-oxazol-4-yl)carbonyl]-2,3,10,10a-tetrahydro-1H,5H-imidazo[1,2-a]pyrazolo[1,5-d]-pyrazine-5,7(8H)-dione (155) (36 mg, 38%).

Compound 156 was similarly prepared using general method S.

10a-(4-methylphenyl)-2,3,10,10a-tetrahydro-1H,5H-imidazo[1,2-a]pyrazolo[1,5-d]pyrazine-5,7(8H)-dione (156)

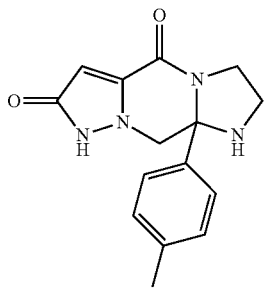 [SMILES: Cc1ccc(C23Cn4[nH]c(=O)cc4C(=O)N2CCN3)cc1]

$^1$H NMR (400 MHz, $CD_3OD$): δ 2.29 (s, 3H), 2.74-2.80 (m, 1H), 3.25-3.36 (m, 1H), 3.48-3.54 (m, 1H), 3.69-3.76 (m, 1H), 4.29 (d, 1H, J 12 Hz), 4.52 (d, 1H, J 12 Hz), 6.00 (s, 1H), 7.14 (d, 2H, J 8 Hz), 7.22 (d, 2H, J 8 Hz). ESI-MI m/z [M+H]$^+$ 285.25.

Example

Separation of Enantiomers Using Chiracel OD-H Column

An intermediate compound of Formula II was separated into its enantiomers using the following column conditions.

Column: Chiracel OD-H (250 mm×4.6 mm) 5 uM; Isocratic Elution: Hexane:Ethanol (90:10 v/v); Detector wavelength: 220 nm; Flow rate: 1.2 ml/min; Concentration: 1.0 mg/mL; Injection Volume: 10 μL; Column Temperature: 25° C.

| Compound Number | Structure | Retention Time of Enantiomer A (mins) | Retention Time of Enantiomer B (mins) |
|---|---|---|---|
| Intermediate core of Compound 77 | (structure) | 15.4 | 35.2 |

Example

Acylation of Enantiomers of Intermediate Compound of Formula II

The purified enantiomeric intermediate cores (enantiomer A and enantiomer B) of compound 77 may be acylated to give enantiomers (10aS)-1-[(3-methyl-1,2-oxazol-4-yl)carbonyl]-10a-(6-methylpyridin-3-yl)-2,3,10,10a-tetrahydro-1H,5H-imidazo[1,2-a]pyrrolo[1,2-d]pyrazin-5-one (77A) and (10aR)-1-[(3-methyl-1,2-oxazol-4-yl)carbonyl]-10a-(6-methylpyridin-3-yl)-2,3,10,10a-tetrahydro-1H,5H-imidazo[1,2-a]pyrrolo[1,2-d]pyrazin-5-one (77B).

| Cpd. No. | Structure | ESI-MI m/z [M + H]$^+$/$^1$H-NMR |
|---|---|---|
| 77A | (structure) | ESI-MI m/z [M + H]$^+$ 378.10. $^1$H NMR (400 MHz, $CDCl_3$): δ 2.43 (s, 3H), 2.50 (s, 3H), 3.63-3.80 (m, 1H), 3.90 (ddd, 1H, J 9.4, 8.3, 4.1 Hz), 3.99-4.13 (m, 1H), 4.43 (ddd, 1H, J 11.8, 8.6, 4.1 Hz), 4.51 (d, 1H, J 13.0 Hz), 5.65 (d, 1H, J 13.0 Hz), 6.22 (dd, 1H, J 3.9, 2.6 Hz), 6.74 (dd, 1H, J 2.4, 1.6 Hz), 6.93 (dd, 1H, J 3.9, 1.4 Hz), 7.07 (d, 1H, J 8.3 Hz), 7.46 (dd, 1H, J 8.3, 2.6 Hz), 8.52 (d, 1H, J 2.4 Hz), 8.60 (s, 1H). |
| 77B | (structure) | ESI-MI m/z [M + H]$^+$ 378.11. $^1$H NMR (400 MHz, $CDCl_3$): δ 2.43 (s, 3H), 2.50 (s, 3H), 3.65-3.82 (m, 1H), 3.90 (ddd, 1H, J 9.4, 8.3, 4.1 Hz), 4.01-4.16 (m, 1H), 4.43 (ddd, 1H, J 11.8, 8.6, 4.1 Hz), 4.50 (d, 1H, J 13.0 Hz), 5.64 (d, 1H, J 13.0 Hz), 6.21 (dd, 1H, J 3.9, 2.6 Hz), 6.73 (dd, 1H, J 2.4, 1.6 Hz), 6.93 (dd, 1H, J 3.9, 1.5 Hz), 7.07 (d, 1H, J 8.3 Hz), 7.45 (dd, 1H, J 8.3, 2.7 Hz), 8.52 (d, 1H, J 2.4 Hz), 8.60 (s, 1H). |

Biological Data

The in vivo and in vitro antiviral activity of the compounds of the invention may be determined using the following methods.

RSV Antiviral Assay Protocol

Compounds of the invention were tested for their antiviral activity against respiratory syncytial virus. Cytopathic effect (CPE) assays were performed essentially as described in the literature (see for example Watanabe et al, 1994, J. Virological Methods, 48:257). Serial dilutions of the test compounds were made in 96 well plates. HEp2 cells ($1.0 \times 10^4$ cells/well) were infected with RSV at a low multiplicity of infection (e.g. RSV A2 at an moi of ~0.01) and added to plates to assess antiviral activity. Uninfected HEp2 cells were used to assess compound cytotoxicity. Assays were incubated for 5 days at 37° C. in a 5% $CO_2$ atmosphere. The extent of CPE was determined via metabolism of the vital dye 3-(4,5-dimethylthiaxol-2-yl)-2,5-diphenyltetrazolium bromide (MTT). MTT (1 mg/ml) was added to each well and plates incubated for 2 hours incubation at 37° C. Wells were aspirated, isopropanol (200 µL) was added and absorbance values read at 540/650 nm. Compound concentrations that inhibited CPE by 50% ($EC_{50}$) and developed cytotoxicity ($CC_{50}$) were calculated using non-linear regression analysis.

Representative activity ranges for compounds of the invention against RSV A2 are shown in Table 1 where RSV A2 $EC_{50}$ values lie in the ranges A: <0.049 µM, B: 0.05-0.099 µM, C, 0.10-0.499 µM, D: 0.5-10.0 µM and E: >10.0 µM. Representative mean $EC_{50}$ values obtained are also provided. In the inventors' experience, replicate $EC_{50}$ values usually fall within three standard deviations of the mean.

TABLE 1

RSV A2 Antiviral Data for Compounds

| No. | Activity Range | RSV A2 $EC_{50}$ (µM) | No. | Activity Range | RSV A2 $EC_{50}$ (µM) | No. | Activity Range | RSV A2 $EC_{50}$ (µM) |
|---|---|---|---|---|---|---|---|---|
| 1 | B | 0.089 | 2 | A | 0.021 | 3 | C | 0.14 |
| 4 | A | 0.019 | 5 | A | 0.034 | 6 | B | 0.052 |
| 7 | C | 0.41 | 8 | D | 1.8 | 9 | A | 0.013 |
| 10 | E | ND | 11 | C | 0.17 | 12 | D | 7.5 |
| 13 | D | 1.2 | 14 | B | 0.094 | 15 | B | 0.056 |
| 16 | D | 0.98 | 17 | D | 0.86 | 18 | D | 4.1 |
| 19 | B | 0.065 | 20 | D | 6.7 | 21 | E | ND |
| 22 | A | 0.0022 | 23 | A | 0.0080 | 24 | E | ND |
| 25 | B | 0.065 | 26 | E | ND | 27 | D | 9.5 |
| 28 | B | 0.088 | 29 | D | 1.0 | 30 | A | 0.036 |
| 31 | A | 0.0076 | 32 | D | 0.69 | 33 | D | 3.1 |
| 34 | C | 0.38 | 35 | B | 0.054 | 36 | C | 0.48 |
| 37 | C | 0.12 | 38 | E | ND | 39 | A | 0.015 |
| 40 | C | 0.21 | 41 | E | ND | 42 | E | ND |
| 43 | D | 3.4 | 44 | E | ND | 45 | E | ND |
| 46 | E | ND | 47 | E | ND | 48 | D | 1.3 |
| 49 | A | 0.0079 | 50 | D | 1.42 | 51 | D | 0.70 |
| 52 | A | 0.024 | 53 | C | 0.26 | 54 | D | 0.60 |
| 55 | D | 2.5 | 56 | C | 0.37 | 57 | A | 0.014 |
| 58 | A | 0.049 | 59 | C | 0.18 | 60 | D | 4.7 |
| 61 | D | 0.98 | 62 | A | 0.048 | 63 | A | 0.021 |
| 64 | D | 8.6 | 65 | B | 0.066 | 66 | A | 0.015 |
| 67 | A | 0.017 | 68 | B | 0.053 | 69 | C | 0.16 |
| 70 | A | 0.0036 | 71 | E | 11 | 72 | A | 0.048 |
| 73 | C | 0.25 | 74 | C | 0.22 | 75 | E | ND |
| 76 | B | 0.067 | 77 | B | 0.056 | 78 | D | 5.8 |
|  |  |  | 77A | D | 7.3 |  |  |  |
|  |  |  | 77B | A | 0.019 |  |  |  |
| 79 | B | 0.056 | 80 | A | 0.0031 | 81 | B | 0.067 |
| 82 | A | 0.048 | 83 | B | 0.12 | 84 | A | 0.018 |
| 85 | E | ND | 86 | E | ND | 87 | B | 0.50 |
| 88 | B | 0.065 | 89 | D | 1.6 | 90 | D | 1.3 |
| 91 | C | 0.14 | 92 | E | ND | 93 | A | 0.0082 |
| 94 | ND | ND | 95 | C | 0.16 | 96 | C | 0.15 |
| 97 | C | 0.46 | 98 | B | 0.069 | 99 | C | 0.19 |
| 100 | D | 8.0 | 101 | D | 0.73 | 102 | E | ND |
| 103 | C | 0.38 | 104 | A | 0.027 | 105 | C | 0.13 |
| 106 | A | 0.0041 | 107 | A | 0.014 | 108 | A | 0.017 |
| 109 | C | 0.30 | 110 | D | 0.68 | 111 | E | 16 |
| 112 | E | ND | 113 | C | 0.32 | 114 | A | 0.039 |
| 115 | C | 0.23 | 116 | B | 0.059 | 117 | D | 0.88 |
| 118 | C | 0.32 | 119 | B | 0.096 | 120 | B | 0.087 |
| 121 | A | 0.042 | 122 | C | 0.43 | 123 | ND | ND |
| 124 | ND | ND | 125 | ND | ND | 126 | A | 0.0078 |
| 127 | A | 0.027 | 128 | B | 0.064 | 129 | C | 0.13 |
| 130 | E | ND | 131 | E | ND | 132 | A | 0.031 |
| 133 | A | 0.0070 | 134 | A | 0.031 | 135 | A | 0.0091 |
| 136 | D | 0.89 | 137 | D | 6.6 | 138 | D | 4.2 |
| 139 | B | 0.066 | 140 | D | 0.55 | 141 | A | 0.039 |
| 142 | D | 6.7 | 143 | D | 0.75 | 144 | B | 0.079 |
| 145 | D | 3.7 | 146 | A | 0.046 | 147 | C | 0.39 |
| 148 | A | 0.038 | 149 | C | 0.13 | 150 | A | 0.011 |
| 151 | A | 0.0087 | 152 | A | 0.0058 | 153 | A | 0.0062 |

TABLE 1-continued

RSV A2 Antiviral Data for Compounds

| No. | Activity Range | RSV A2 EC$_{50}$ (µM) | No. | Activity Range | RSV A2 EC$_{50}$ (µM) | No. | Activity Range | RSV A2 EC$_{50}$ (µM) |
|---|---|---|---|---|---|---|---|---|
| 154 | A | 0.0023 | 155 | ND | ND | 156 | ND | ND |
| 157 | C | 0.36 | | | | | | |

ND is "Exact value not determined"

RSV Fusion Assay

Selected compounds of the invention can be tested for their ability to inhibit the essential fusion processes of the respiratory syncytial virus.

Generation of RSV-F Constructs

Single-stranded synthetic DNA oligonucleotides encoding the portions of RSV A2 F glycoprotein incorporating optimal codons and without potential poly(A) addition or splice sites were generated synthetically (Mason et al, WO0242326). A membrane-anchored full-length F was generated essentially according to the method described therein and in Morton et al.

Syncytium Formation Assay

Fusion activity of the RSV-F constructs was measured in 293 cells essentially according to the method described in Morton et al, 2003, Virology, 311:275. For example: cells in six well plates at approximately 80% confluency were transfected by adding plasmid DNA (0.5-1.5 µg/well) carrying the constructs of interest in CaPO$_4$ solution for 2 hours. After glycerol shock and wash, the transfected cells were trypsinized and 4-10×10$^4$ cells/well added to 96-well plates containing 2-fold or 3-fold serial dilutions of the test compound. Syncytium formation was evaluated by visual inspection and quantified at 42 hours post-transfection by addition of 20 µL of CellTiter 96 One Solution (Promega) followed by incubation for 2 hours at 37° C. The absorbance values read at 490/690 nm. The compound concentration that reduced absorbance relative to untreated control cultures by 50% (EC$_{50}$) was calculated using non-linear regression analysis.

RSV Cotton Rat Model

The cotton rat model may be performed essentially as described in the literature (Wyde et al, 2003, Antiviral Res., 60:221). Briefly, cotton rats weighing 50-100 g are lightly anesthetized with isoflurane and dosed orally with 100 mg/kg/day of compound or vehicle control. Viral infection follows 2 hours post-treatment in similarly anesthetized rats by intranasal instillation with approximately 1000 TCID$_{50}$ of RSV A2 per animal. Four days after virus inoculation, each cotton rat is sacrificed and their lungs removed and RSV titres determined by plaque assay.

RSV Balb/c Mouse Model

The mouse model may be performed essentially as described by Clanci et al, 2004, Antimicrobial Agents and Chemotherapy., 48:413. Briefly, eight week old female Balb/c mice are weighed, anesthetized intraperitoneally with Avertin™ and compound or vehicle administered orally pre-infection and subsequently on a daily or twice daily basis. Mice are inoculated intranasally with approximately 10000 TCID$_{50}$ RSV A2 per animal. Three days after virus inoculation, each mouse is sacrificed and their lungs removed and RSV titres determined by plaque assay. Body weights, spleen and liver weights can also be assessed. In addition, the ability of a test compound to reduce total and differential (macrophages, neutrophils and lymphocytes) inflammatory cell counts in bronchoalveolar lavage fluid (BALF) can also be measured. This allows a study of the ability of the test compound to ameliorate the inflammatory response to RSV infection in animals treated with compound compared with those only inoculated with RSV.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication, or information derived from it, or to any matter which is know, is not, and should not be taken as an acknowledgement or admission or any form of suggestion that that prior publication, or information derived from it, or known matter forms part of the common general knowledge in the field of endeavour to which this specification relates.

It will be understood to persons skilled in the art of the invention that many modifications may be made without departing from the spirit and scope of the invention.

The invention claimed is:

1. A method for modulating respiratory syncytial viral activity in a subject, comprising the step of administering to said subject a compound of formula (I):

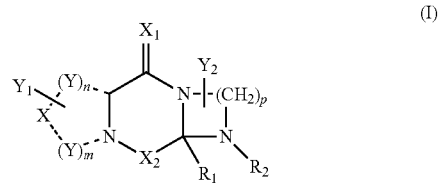

wherein

-------- represents single or double bonds depending on the required valencies of the ring atoms;

each Y is CH;

X is CH;

X$_1$ is selected from O, S, NR$_6$, and C(R$_6$)$_2$ wherein each R$_6$ is independently selected from H, optionally substituted C$_{1-6}$alkyl, optionally substituted C$_{2-6}$alkenyl, optionally substituted C$_{2-6}$alkynyl, optionally substituted C$_{3-8}$cycloalkyl, optionally substituted heterocyclyl and optionally substituted aryl;

X$_2$ is C(R$_3$R$_4$) wherein R$_3$ and R$_4$ are each independently selected from H, optionally substituted C$_{1-6}$alkyl, optionally substituted C$_{2-6}$alkenyl, optionally substituted C$_{2-6}$alkynyl, optionally substituted C$_{3-8}$cycloalkyl, optionally substituted heterocyclyl and optionally substituted aryl;

R$_1$ is optionally substituted C$_{1-6}$alkyl, optionally substituted C$_{2-6}$alkenyl, optionally substituted C$_{2-6}$alkynyl, optionally substituted C$_{3-8}$cycloalkyl, optionally substituted heterocyclyl or optionally substituted aryl;

R₂ is H, R₈, C(=O)R₈, C(=S)R₈ or S(O₂)R₈ wherein R₈ is selected from optionally substituted $C_{1-6}$alkyl, optionally substituted $C_{2-6}$alkenyl, optionally substituted $C_{2-6}$alkynyl, $N(R_6)_2$, optionally substituted —$N(R_6)_q$ $(R_7)_q$cycloalkyl, optionally substituted —$N(R_6)_q$ $(R_7)_q$heterocyclyl and optionally substituted —$N(R_6)_q$ $(R_7)_q$aryl wherein each $R_7$ is independently selected from optionally substituted $C_{1-6}$alkyl, optionally substituted $C_{2-6}$alkenyl, optionally substituted $C_{2-6}$alkynyl, optionally substituted $C_{3-8}$cycloalkyl, optionally substituted heterocyclyl or optionally substituted aryl and each q is independently 0 or 1;

$Y_1$ is one or more optional substituents, or is absent;
$Y_2$ is H or one or more optionally substituted $R_7$;
m and n are both 1;
p is 2; and
wherein the optional substituents are independently selected from the group consisting of $R_7$, $R_7$-$R_7$, $(R_7)_q$halo, $(R_7)_q$CN, =O, $(R_7)_q$OR$_6$, $(R_7)_q$OCHF$_2$, $(R_7)_q$OCF$_3$, $(R_7)_q$CHF$_2$, $(R_7)_q$CF$_3$, =S, $(R_7)_q$SR$_6$, $(R_7)_q$SO$_3$H, $(R_7)_q$SO$_2$—$R_7$, $(R_7)_q$SO$_2$N(R$_6$)$_2$, $(R_7)_q$NO$_2$, $(R_7)_q$N(R$_6$)$_2$, $(R_7)_q$OC(=O)—$R_7$, $(R_7)_q$C(=O)OR$_6$, $(R_7)_q$C(=O)R$_6$, $(R_7)_q$C(=O)N(R$_6$)$_2$, $(R_7)_q$NR$_6$C(=O)—$R_7$, $(R_7)_q$NR$_6$SO$_2$R$_7$, $(R_7)_q$Si(R$_7$)$_3$ and $(R_7)_q$O—Si(R$_7$)$_3$;

or a pharmaceutically acceptable salt, stereoisomer, or tautomer thereof.

2. The method according to claim 1 wherein the compound is a compound of formula (Ia):

or a pharmaceutically acceptable salt, stereoisomer, or tautomer thereof.

3. The method according to claim 2 wherein the compound is a compound of formula (Ia-iii):

or a pharmaceutically acceptable salt, stereoisomer, or tautomer thereof.

4. The method according to claim 1 wherein the compound is a compound selected from the group consisting of:
10a-[4-(difluoromethoxy)phenyl]-1-[(3-methyl-1,2-oxazol-4-yl)carbonyl]-2,3,10,10a-tetrahydro-1H,5H-imidazo[1,2-a]pyrrolo[1,2-d]pyrazin-5-one (1);
10a-(4-fluorophenyl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (2);
10a-(4-chlorophenyl)-1-[(5-methyl-1,3-oxazol-4-yl)carbonyl]-2,3,10,10a-tetrahydro-1H,5H-imidazo[1,2-a]pyrrolo[1,2-d]pyrazin-5-one (3);
10a-(4-chlorophenyl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (4);
10a-(3-fluorophenyl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (5);
10a-(4-methoxyphenyl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (6);
10a-(4-fluorophenyl)-1-(1,3-oxazol-4-ylcarbonyl)-2,3,10,10a-tetrahydro-1H,5H-imidazo[1,2-a]pyrrolo[1,2-d]pyrazin-5-one (7);
10a-(4-methoxyphenyl)-1-(1,3-oxazol-4-ylcarbonyl)-2,3,10,10a-tetrahydro-1H,5H-imidazo[1,2-a]pyrrolo[1,2-d]pyrazin-5-one (8);
1-[(3-methyl-1,2-oxazol-4-yl)carbonyl]-10a-(4-methylphenyl)-2,3,10,10a-tetrahydro-1H,5H-imidazo[1,2-a]pyrrolo[1,2-d]pyrazin-5-one (9);
N,N-diethyl-4-{1-[(3-methyl-1,2-oxazol-4-yl)carbonyl]-5-oxo-2,3-dihydro-1H,5H-imidazo[1,2-a]pyrrolo[1,2-d]pyrazin-10a(10H)-yl}benzenesulfonamide (10);
10a-(3-fluoro-4-methylphenyl)-1-[(5-methyl-1,2-oxazol-4-yl)carbonyl]-2,3,10,10a-tetrahydro-1H,5H-imidazo[1,2-a]pyrrolo[1,2-d]pyrazin-5-one (14);
10a-(4-chlorophenyl)-1-(furan-3-ylcarbonyl)-2,3,10,10a-tetrahydro-1H,5H-imidazo[1,2-a]pyrrolo[1,2-d]pyrazin-5-one (15);
10a-(4-chlorophenyl)-1-(1,2-oxazol-3-ylcarbonyl)-2,3,10,10a-tetrahydro-1H,5H-imidazo[1,2-a]pyrrolo[1,2-d]pyrazin-5-one (16);
10a-(4-chlorophenyl)-1-{[1-methyl-3-(trifluoromethyl)-1H-pyrazol-4-yl]carbonyl}-2,3,10,10a-tetrahydro-1H,5H-imidazo[1,2-a]pyrrolo[1,2-d]pyrazin-5-one (17);
10a-(4-chlorophenyl)-1-(cyclopropylcarbonyl)-2,3,10,10a-tetrahydro-1H,5H-imidazo[1,2-a]pyrrolo[1,2-d]pyrazin-5-one (18);
10a-cyclohexyl-1-[(3-methyl-1,2-oxazol-4-yl)carbonyl]-2,3,10,10a-tetrahydro-1H,5H-imidazo[1,2-a]pyrrolo[1,2-d]pyrazin-5-one (19);
10a-ethyl-1-[(3-methyl-1,2-oxazol-4-yl)carbonyl]-2,3,10,10a-tetrahydro-1H,5H-imidazo[1,2-a]pyrrolo[1,2-d]pyrazin-5-one (20);
10a-tert-butyl-1-[(3-methyl-1,2-oxazol-4-yl)carbonyl]-2,3,10,10a-tetrahydro-1H,5H-imidazo[1,2-a]pyrrolo[1,2-d]pyrazin-5-one (21);
8-chloro-10a-(4-chlorophenyl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (22);
8-chloro-10a-(4-methoxyphenyl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (23);
7-acetyl-10a-(4-chlorophenyl)-1-[(5-methyl-1,2-oxazol-4-yl)carbonyl]-2,3,10,10a-tetrahydro-1H,5H-imidazo[1,2-a]pyrrolo[1,2-d]pyrazin-5-one (24);
10a-(4-chlorophenyl)-1-[(3-methyl-1,2-oxazol-4-yl)carbonyl]-8-(morpholin-4-ylmethyl)-2,3,10,10a-tetrahydro-1H,5H-imidazo[1,2-a]pyrrolo[1,2-d]pyrazin-5-one (25);
10a-(4-chlorophenyl)-1-[(3-methyl-1,2-oxazol-4-yl)carbonyl]-7-(morpholin-4-ylmethyl)-2,3,10,10a-tetrahydro-1H,5H-imidazo[1,2-a]pyrrolo[1,2-d]pyrazin-5-one (26);

10a-(4-chlorophenyl)-7-[(dimethylamino)methyl]-1-[(3-methyl-1,2-oxazol-4-yl)carbonyl]-2,3,10,10a-tetrahydro-1H,5H-imidazo[1,2-a]pyrrolo[1,2-d]pyrazin-5-one (27);

10a-(4-chlorophenyl)-8-(hydroxymethyl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (28);

10a-(4-chlorophenyl)-7-(hydroxymethyl)-1-[(3-methyl-1,2-oxazol-4-yl-)carbonyl]-2,3,10,10a-tetrahydro-1H,5H-imidazo[1,2-a]pyrrolo[1,2-d]pyrazin-5-one (29);

10a-(4-chlorophenyl)-1-[(3-methyl-1,2-oxazol-4-yl)carbonyl]-7-(pyridin-3-yl)-2,3,10,10a-tetrahydro-1H,5H-imidazo[1,2-a]pyrrolo[1,2-d]pyrazin-5-one (30);

10a-(4-chlorophenyl)-1-[(3-methyl-1,2-oxazol-4-yl)carbonyl]-7-(1-methyl-1H-pyrazol-4-yl)-2,3,10,10a-tetrahydro-1H,5H-imidazo[1,2-a]pyrrolo[1,2-d]pyrazin-5-one (31);

10a-(4-chlorophenyl)-1-[(5-methyl-1,2-oxazol-4-yl)carbonyl]-8-(pyridin-4-yl)-2,3,10,10a-tetrahydro-1H,5H-imidazo[1,2-a]pyrrolo[1,2-d]pyrazin-5-one (32);

10a-(4-chlorophenyl)-1-[(3-methyl-1,2-oxazol-4-yl)carbonyl]-8-(pyridin-3-yl)-2,3,10,10a-tetrahydro-1H,5H-imidazo[1,2-a]pyrrolo[1,2-d]pyrazin-5-one (33);

10a-(4-methoxyphenyl)-1-[(3-methyl-1,2-oxazol-4-yl)carbonyl]-8-(1-methyl-1H-pyrazol-4-yl)-2,3,10,10a-tetrahydro-1H,5H-imidazo[1,2-a]pyrrolo[1,2-d]pyrazin-5-one (34);

1-[(3-methyl-1,2-oxazol-4-yl)carbonyl]-10a-phenyl-2,3,10,10a-tetrahydro-1H,5H-imidazo[1,2-a]pyrrolo[1,2-d]pyrazin-5-one (35);

1-[(3-methyl-1,2-oxazol-4-yl)carbonyl]-10a-[4-(pyrrolidin-1-yl)phenyl]-2,-3,10,10a-tetrahydro-1H,5H-imidazo[1,2-a]pyrrolo[1,2-d]pyrazin-5-one (36);

4-{1-[(3-methyl-1,2-oxazol-4-yl)carbonyl]-5-oxo-2,3-dihydro-1H,5H-imidazo[1,2-a]pyrrolo[1,2-d]pyrazin-10a(10H)-yl}benzonitrile (37);

10a-(4-chlorophenyl)-N,N-dimethyl-1-[(3-methyl-1,2-oxazol-4-yl)carbonyl]-5-oxo-2,3,10,10a-tetrahydro-1H,5H-imidazo[1,2-a]pyrrolo[1,2-d]pyrazine-7-carboxamide (38);

10a-(4-chlorophenyl)-5-oxo-N-(2-phenylethyl)-2,3,10,10a-tetrahydro-1H,5H-imidazo[1,2a]pyrrolo[1,2-d]pyrazine-1-carboxamide (48);

10a-(4-chlorophenyl)-1-{[3-(trifluoromethyl)-1,2-oxazol-4-yl]carbonyl}-2,-3,10,10a-tetrahydro-1H,5H-imidazo[1,2-a]pyrrolo[1,2-d]pyrazin-5-one (49);

1-[(3-methyl-1,2-oxazol-4-yl)carbonyl]-10a-(tetrahydro-2H-pyran-4-yl)-2,3,10,10a-tetrahydro-1H,5H-imidazo[1,2-a]pyrrolo[1,2-d]pyrazin-5-one (50);

10a-(4-methoxyphenyl)-1-(1,2-oxazol-4-ylcarbonyl)-2,3,10,10a-tetrahydro-1H,5H-imidazo[1,2-a]pyrrolo[1,2-d]pyrazin-5-one (51);

10a-(4-methoxyphenyl)-1-{[3-(trifluoromethyl)-1,2-oxazol-4-yl]carbonyl}-2,3,10,10a-tetrahydro-1H,5H-imidazo[1,2-a]pyrrolo[1,2-d]pyrazin-5-one (52);

1-[(3,5-dimethyl-1,2-oxazol-4-yl)carbonyl]-10a-(4-methoxyphenyl)-2,3,10,10a-tetrahydro-1H,5H-imidazo[1,2-a]pyrrolo[1,2-d]pyrazin-5-one (53);

1-(furan-3-ylcarbonyl)-10a-(4-methoxyphenyl)-2,3,10,10a-tetrahydro-1H,5H-imidazo[1,2-a]pyrrolo[1,2-d]pyrazin-5-one (54);

10a-(4-methoxyphenyl)-1-[(4-methyl-1,3-oxazol-5-yl)carbonyl]-2,3,10,10a-tetrahydro-1H,5H-imidazo[1,2-a]pyrrolo[1,2-d]pyrazin-5-one (55);

10a-(4-methoxyphenyl)-1-[(4-methyl-1,2,3-thiadiazol-5-yl)carbonyl]-2,3,10,10a-tetrahydro-1H,5H-imidazo[1,2-a]pyrrolo[1,2-d]pyrazin-5-one (56);

10a-(2,3-dihydro-1-benzofuran-5-yl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (57);

10a-(6-methoxypyridin-3-yl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (58);

1-[(5-cyclopropyl-1,3-oxazol-4-yl)carbonyl]-10a-(4-methoxyphenyl)-2-3,10,10a-tetrahydro-1H,5H-imidazo[1,2-a]pyrrolo[1,2-d]pyrazin-5-one (59);

10a-(4-methoxyphenyl)-1-[(1-methyl-1H-pyrrol-2-yl)carbonyl]-2,3,10,10a-tetrahydro-1H,5H-imidazo[1,2-a]pyrrolo[1,2-d]pyrazin-5-one (60);

10a-(4-methoxyphenyl)-1-[(1-methyl-1H-pyrazol-5-yl)carbonyl]-2,3,10,10a-tetrahydro-1H,5H-imidazo[1,2-a]pyrrolo[1,2-d]pyrazin-5-one (61);

4-{1-[(3-methyl-1,2-oxazol-4-yl)carbonyl]-5-oxo-2,3-dihydro-1H,5H-imidazo-[1,2-a]pyrrolo[1,2-d]pyrazin-10a(10H)-yl}benzyl-3-methyl-1,2-oxazole-4-carboxylate (62);

7-fluoro-10a-(4-methoxyphenyl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (65);

7-fluoro-10a-(4-methoxyphenyl)-1-{[3-(trifluoromethyl)-1,2-oxazol-4-yl]carbonyl}-2,3,10,10a-tetrahydro-1H,5H-imidazo[1,2-a]pyrrolo[1,2-d]pyrazin-5-one (66);

1-[(3-ethyl-1,2-oxazol-4-yl)carbonyl]-10a-(4-methoxyphenyl)-2,3,10,10a-tetrahydro-1H,5H-imidazo[1,2-a]pyrrolo[1,2-d]pyrazin-5-one (67);

10a-(4-methoxyphenyl)-1-{[3-(propan-2-yl)-1,2-oxazol-4-yl]carbonyl}-2,3,10,10a-tetrahydro-1H,5H-imidazo[1,2-a]pyrrolo[1,2-d]pyrazin-5-one (68);

10a-(4-hydroxyphenyl)-1-[(3-methyl-1,2-oxazol-4-yl)carbonyl]-2,3,10,10a-tetrahydro-1H,5H-imidazo[1,2-a]pyrrolo[1,2-d]-pyrazin-5-one (69);

10a-(4-methoxyphenyl)-1-(pyridin-2-ylcarbonyl)-2,3,10,10a-tetrahydro-1H,5H-imidazo[1,2-a]pyrrolo[1,2-d]pyrazin-5-one (71);

1-[(3-methyl-1,2-oxazol-4-yl)carbonyl]-10a-(thiophen-3-yl)-2,3,10,10a-tetrahydro-1H,5H-imidazo[1,2-a]pyrrolo[1,2-d]pyrazin-5-one (73);

1-[(3-methyl-1,2-oxazol-4-yl)carbonyl]-10a-(thiophen-2-yl)-2,3,10,10a-tetrahydro-1H,5H-imidazo[1,2-a]pyrrolo[1,2-d]pyrazin-5-one (74);

10a-(4-methoxyphenyl)-1-[(3-methyl-1,2-oxazol-4-yl)carbonyl]-7-(1H-tetrazol-5-yl)-2,3,10,10a-tetrahydro-1H,5H-imidazo[1,2-a]pyrrolo[1,2-d]pyrazin-5-one (75);

10a-[4-(methoxymethyl)phenyl]-1-[(3-methyl-1,2-oxazol-4-yl)carbonyl]-2,3,10,10a-tetrahydro-1H,5H-imidazo[1,2-a]pyrrolo[1,2-d]pyrazin-5-one (76);

1-[(3-methyl-1,2-oxazol-4-yl)carbonyl]-10a-(6-methylpyridin-3-yl)-2,3,10,10a-tetrahydro-1H,5H-imidazo[1,2-a]pyrrolo[1,2-d]pyrazin-5-one (77);

1-[(3-methyl-1,2-oxazol-4-yl)carbonyl]-10a-(1-oxidopyridin-3-yl)-2,-3,10,10a-tetrahydro-1H,5H-imidazo[1,2-a]pyrrolo[1,2-d]pyrazin-5-one (78);

10a-[4-(hydroxymethyl)phenyl]-1-[(3-methyl-1,2-oxazol-4-yl)carbonyl]-2,3,10,10a-tetrahydro-1H,5H-imidazo[1,2-a]pyrrolo[1,2-d]pyrazin-5-one (79);

8-chloro-10a-(4-fluorophenyl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (80);

8-chloro-1-[(3-methyl-1,2-oxazol-4-yl)carbonyl]-10a-(tetrahydro-2H-pyran-4-yl)-2,3,10,10a-tetrahydro-1H,5H-imidazo[1,2-a]pyrrolo[1,2-d]pyrazin-5-one (81);

10a-(4-methoxyphenyl)-1-[(3-methyl-1,2-oxazol-4-yl)carbonyl]-7-(1-methyl-1H-pyrazol-4-yl)-2,3,10,10a-tetrahydro-1H,5H-imidazo[1,2-a]pyrrolo[1,2-d]pyrazin-5-one (82);

10a-(4-methoxyphenyl)-1-[(3-methyl-1,2-oxazol-4-yl)carbonyl]-7-(pyridin-3-yl)-2,3,10,10a-tetrahydro-1H,5H-imidazo[1,2-a]pyrrolo[1,2-d]pyrazin-5-one (83);

10a-(4-methoxyphenyl)-1-[(3-methyl-1,2-oxazol-4-yl)carbonyl]-7-(pyridin-4-yl)-2,3,10,10a-tetrahydro-1H,5H-imidazo[1,2-a]pyrrolo[1,2-d]pyrazin-5-one (84);

7-bromo-10a-(4-fluorophenyl)-2,3,10,10a-tetrahydro-1H,5H-imidazo[1,2-a]pyrrolo[1,2-d]pyrazin-5-one (85);

7-bromo-10a-(4-methylphenyl)-2,3,10,10a-tetrahydro-1H,5H-imidazo[1,2-a]pyrrolo[1,2-d]pyrazin-5-one (86);

10a-(4-methoxyphenyl)-1-[(3-methyl-1,2-oxazol-4-yl)carbonyl]-7-(1-methyl-1H-pyrazol-5-yl)-2,3,10,10a-tetrahydro-1H,5H-imidazo[1,2-a]pyrrolo[1,2-d]pyrazin-5-one (87);

10a-(4-methoxyphenyl)-1-[(3-methyl-1,2-oxazol-4-yl)carbonyl]-7-[1-(propan-2-yl)-1H-pyrazol-4-yl]-2,3,10,10a-tetrahydro-1H,5H-imidazo[1,2-a]pyrrolo[1,2-d]pyrazin-5-one (88);

10a-(4-methoxyphenyl)-1-[(3-methyl-1,2-oxazol-4-yl)carbonyl]-5-oxo-2,3,10,10a-tetrahydro-1H,5H-imidazo[1,2-a]pyrrolo[1,2-d]pyrazine-7-carbonitrile (89);

10a-(4-methoxyphenyl)-1-[(3-methyl-1,2-oxazol-4-yl)carbonyl]-7-(pyrimidin-5-yl)-2,3,10,10a-tetrahydro-1H,5H-imidazo[1,2-a]pyrrolo[1,2-d]pyrazin-5-one (90);

7-(1,3-dimethyl-1H-pyrazol-4-yl)-10a-(4-methoxyphenyl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (91);

10a-(4-methoxyphenyl)-1-[(3-methyl-1,2-oxazol-4-yl)carbonyl]-7-(4-methylpyridin-3-yl)-2,3,10,10a-tetrahydro-1H,5H-imidazo[1,2-a]pyrrolo[1,2-d]pyrazin-5-one (92);

1-[(3-methyl-1,2-oxazol-4-yl)carbonyl]-10a-(4-methylphenyl)-7-(pyridin-2-yl)-2,3,10,10a-tetrahydro-1H,5H-imidazo[1,2-a]pyrrolo[1,2-d]pyrazin-5-one (93);

7-bromo-10a-(4-methoxyphenyl)-2,3,10,10a-tetrahydro-1H,5H-imidazo[1,2-a]pyrrolo[1,2-d]pyrazin-5-one (94);

10a-[4-(hydroxymethyl)phenyl]-1-[(3-methyl-1,2-oxazol-4-yl)carbonyl]-7-(pyridin-3-yl)-2,3,10,10a-tetrahydro-1H,5H-imidazo[1,2-a]pyrrolo[1,2-d]pyrazin-5-one (95);

10a-(4-fluorophenyl)-1-[(3-methyl-1,2-oxazol-4-yl)carbonyl]-8-(1-methyl-1H-pyrazol-4-yl)-2,3,10,10a-tetrahydro-1H,5H-imidazo[1,2-a]pyrrolo[1,2-d]pyrazin-5-one (96);

10a-(4-fluorophenyl)-1-[(3-methyl-1,2-oxazol-4-yl)carbonyl]-8-(pyridin-3-yl)-2,3,10,10a-tetrahydro-1H,5H-imidazo[1,2-a]pyrrolo[1,2-d]pyrazin-5-one (97);

10a-(4-fluorophenyl)-1-[(3-methyl-1,2-oxazol-4-yl)carbonyl]-7-(pyridin-3-yl)-2,3,10,10a-tetrahydro-1H,5H-imidazo[1,2-a]pyrrolo[1,2-d]pyrazin-5-one (98);

10a-(4-fluorophenyl)-1-[(3-methyl-1,2-oxazol-4-yl)carbonyl]-8-(pyridin-4-yl)-2,3,10,10a-tetrahydro-1H,5H-imidazo[1,2-a]pyrrolo[1,2-d]pyrazin-5-one (99);

4-{10a-(4-methoxyphenyl)-1-[(3-methyl-1,2-oxazol-4-yl)carbonyl]-5-oxo-2,3,10,10a-tetrahydro-1H,5H-imidazo[1,2-a]pyrrolo[1,2-d]pyrazin-7-yl}benzoic acid (100);

1-[(3-methyl-1,2-oxazol-4-yl)carbonyl]-10a-(pyridin-3-yl)-2,3,10,10a-tetrahydro-1H,5H-imidazo[1,2-a]pyrrolo[1,2-d]pyrazin-5-one (101);

10a-(pyridin-3-yl)-2,3,10,10a-tetrahydro-1H,5H-imidazo[1,2-a]pyrrolo[1,2-d]pyrazin-5-one (102);

1-[(3-methyl-1,2-oxazol-4-yl)carbonyl]-10a-(pyridin-2-yl)-2,3,10,10a-tetrahydro-1H,5H-imidazo[1,2-a]pyrrolo[1,2-d]pyrazin-5-one (103);

1-[(3-methyl-1,2-oxazol-4-yl)carbonyl]-10a-(5-methylpyridin-2-yl)-2,3,10,10a-tetrahydro-1H,5H-imidazo[1,2-a]pyrrolo[1,2-d]pyrazin-5-one (104);

1-[(3-methyl-1,2-oxazol-4-yl)carbonyl]-10a-[6-(trifluoromethyl)pyridin-3-yl]-2,3,10,10a-tetrahydro-1H,5H-imidazo[1,2-a]pyrrolo[1,2-d]pyrazin-5-one (105);

10a-(4-methoxyphenyl)-1-[(3-methyl-1,2-oxazol-4-yl)carbonyl]-5-oxo-2,3,10,10a-tetrahydro-1H,5H-imidazo[1,2-a]pyrrolo[1,2-d]pyrazine-8-carbonitrile (106);

10a-(4-methoxyphenyl)-8-methyl-1-[(3-methyl-1,2-oxazol-4-yl)carbonyl]-2,3,10,10a-tetrahydro-1H,5H-imidazo[1,2-a]pyrrolo[1,2-d]pyrazin-5-one (107);

8-ethynyl-10a-(4-methoxyphenyl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (108);

10a-[4-(2-hydroxyethoxyl)phenyl]-1-[(3-methyl-1,2-oxazol-4-yl)carbonyl]-2,3,10,10a-tetrahydro-1H,5H-imidazo[1,2-a]pyrrolo[1,2-d]pyrazin-5-one (109);

1-[(3-methyl-1,2-oxazol-4-yl)carbonyl]-10a-{4-[2-(morpholin-4-yl)ethoxy]phenyl}-2,3,10,10a-tetrahydro-1H,5H-imidazo[1,2-a]pyrrolo[1,2-d]pyrazin-5-one (110);

7-amino-10a-(4-methoxyphenyl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (111);

7-(cyclohexylamino)-10a-(4-methoxyphenyl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (112);

10a-(4-methoxyphenyl)-1-[(3-methyl-1,2-oxazol-4-yl)carbonyl]-7-(1H-1,2,3-triazol-1-yl)-2,3,10,10a-tetrahydro-1H,5H-imidazo[1,2-a]pyrrolo[1,2-d]pyrazin-5-one (113);

1-[(3-methyl-1,2-oxazol-4-yl)carbonyl]-10a-(5-methylpyrazin-2-yl)-2,3,10,10a-tetrahydro-1H,5H-imidazo[1,2-a]pyrrolo[1,2-d]pyrazin-5-one (114);

10a-(5-methoxypyridin-2-yl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (115);

1-[(3-methyl-1,2-oxazol-4-yl)carbonyl]-10a-[5-(trifluoromethyl)pyridin-2-yl]-2,3,10,10a-tetrahydro-1H,5H-imidazo[1,2-a]pyrrolo[1,2-d]pyrazin-5-one (116);

7-bromo-1-[(3-methyl-1,2-oxazol-4-yl)carbonyl]-10a-(5-methylpyridin-2-yl)-2,3,10,10a-tetrahydro-1H,5H-imidazo[1,2-a]pyrrolo[1,2-d]pyrazin-5-one (117);

1-[(3-methyl-1,2-oxazol-4-yl)carbonyl]-10a-(1-methyl-1H-pyrazol-4-yl)-2,3,10,10a-tetrahydro-1H,5H-imidazo[1,2-a]pyrrolo[1,2-d]pyrazin-5-one (118);

1-[(3-methyl-1,2-oxazol-4-yl)carbonyl]-10a-(2-methylpyridin-4-yl)-2,3,10,10a-tetrahydro-1H,5H-imidazo[1,2-a]pyrrolo[1,2-d]pyrazin-5-one (119);

1-[(3-methyl-1,2-oxazol-4-yl)carbonyl]-10a-(5-methylpyridin-2-yl)-7-(pyridin-3-yl)-2,3,10,10a-tetrahydro-1H,5H-imidazo[1,2-a]pyrrolo[1,2-d]pyrazin-5-one (120);

1-[(3-methyl-1,2-oxazol-4-yl)carbonyl]-10a-(5-methylpyrazin-2-yl)-7-(pyridin-3-yl)-2,3,10,10a-tetrahydro-1H,5H-imidazo[1,2-a]pyrrolo[1,2-d]pyrazin-5-one (121);

1-[(3-methyl-1,2-oxazol-4-yl)carbonyl]-10a-(pyridin-4-yl)-2,3,10,10a-tetrahydro-1H,5H-imidazo[1,2-a]pyrrolo[1,2-d]pyrazin-5-one (122);

10a-(4-methoxyphenyl)-1-[(3-methyl-1,2-oxazol-4-yl)carbonyl]-7-nitro-2,3,10,10a-tetrahydro-1H,5H-imidazo[1,2-a]pyrrolo[1,2-d]pyrazin-5-one (124);

10a-(4-chlorophenyl)-10-methyl-2,3,10,10a-tetrahydro-1H,5H-imidazo[1,2-a]pyrrolo[1,2-d]pyrazin-5-one (125);

1-[(3-methyl-1,2-oxazol-4-yl)carbonyl]-10a-(6-methylpyridin-3-yl)-5-oxo-2,3,10,10a-tetrahydro-1H,5H-imidazo[1,2-a]pyrrolo[1,2-d]pyrazine-8-carbonitrile (126);

1-[(3-methyl-1,2-oxazol-4-yl)carbonyl]-10a-(6-methylpyridin-3-yl)-7-(pyridin-2-yl)-2,3,10,10a-tetrahydro-1H,5H-imidazo[1,2-a]pyrrolo[1,2-d]pyrazin-5-one (127);

10a-(6-methoxypyridin-3-yl)-1-[(3-methyl-1,2-oxazol-4-yl)carbonyl]-7-(pyridin-2-yl)-2,3,10,10a-tetrahydro-1H,5H-imidazo[1,2-a]pyrrolo[1,2-d]pyrazin-5-one (128);

N-(furan-2-ylmethyl)-10a-(4-methoxyphenyl)-5-oxo-2,3,10,10a-tetrahydro-1H,5H-imidazo[1,2-a]pyrrolo[1,2-d]pyrazine-1-carboxamide (130);

10a-(4-methoxyphenyl)-1-(phenylsulfonyl)-2,3,10,10a-tetrahydro-1H,5H-imidazo[1,2-a]pyrrolo[1,2-d]pyrazin-5-one (131);

1-[(3-methyl-1,2-oxazol-4-yl)carbonyl]-7-(1-methyl-1H-pyrazol-4-yl)-10a-(6-methylpyridin-3-yl)-2,3,10,10a-tetrahydro-1H,5H-imidazo[1,2-a]pyrrolo[1,2-d]pyrazin-5-one (132);

10a-(6-methoxypyridin-3-yl)-1-[3-methyl-1,2-oxazol-4-yl)carbonyl]-5-oxo-2,3,10,10a-tetrahydro-1H,5H-imidazo[1,2-a]pyrrolo[1,2-d]pyrazine-8-carbonitrile (133);

1-[(3-methyl-1,2-oxazol-4-yl)carbonyl]-7-(1-methyl-1H-pyrazol-4-yl)-10a-(5-methylpyridin-2-yl)-2,3,10,10a-tetrahydro-1H,5H-imidazo[1,2-a]pyrrolo[1,2-d]pyrazin-5-one (134);

1-[(3-methyl-1,2-oxazol-4-yl)carbonyl]-10a-(6-methylpyridin-3-yl)-7-(pyridin-4-yl)-2,3,10,10a-tetrahydro-1H,5H-imidazo[1,2-a]pyrrolo[1,2-d]pyrazin-5-one (135);

10a-(4-methoxyphenyl)-1-[(4-methyl-1,2,5-oxadiazol-3-yl)carbonyl]-2,3,10,10a-tetrahydro-1H,5H-imidazo[1,2-a]pyrrolo[1,2-d]pyrazin-5-one (136);

10a-(4-methoxyphenyl)-1-(thiophen-3-ylcarbonyl)-2,3,10,10a-tetrahydro-1H,-5H-imidazo[1,2-a]pyrrolo[1,2-d]pyrazin-5-one (137);

10a-(6-hydroxypyridin-3-yl)-1-[(3-methyl-1,2-oxazol-4-yl)carbonyl-]-2,3,10,10a-tetrahydro-1H,5H-imidazo[1,2-a]pyrrolo[1,2-d]pyrazin-5-one (142);

1-[(3-methyl-1,2-oxazol-4-yl)carbonyl]-10a-(1-methyl-6-oxo-1,6-dihydropyridin-3-yl)-2,3,10,10a-tetrahydro-1H,5H-imidazo[1,2-a]pyrrolo[1,2-d]pyrazin-5-one (143);

10a-[4-(hydroxymethyl)phenyl]-1-[(3-methyl-1,2-oxazol-4-yl)carbonyl]-7-(1-methyl-1H-pyrazol-4-yl)-2,3,10,10a-tetrahydro-1H,5H-imidazo[1,2-a]pyrrolo[1,2-d]pyrazin-5-one (144);

10a-(4-methoxyphenyl)-1-[(3-methyl-1,2-oxazol-4-yl)carbonyl]-7-(1-methyl-1H-tetrazol-5-yl)-2,3,10,10a-tetrahydro-1H,5H-imidazo[1,2-a]pyrrolo[1,2-d]pyrazin-5-one (145);

10a-(4-methoxyphenyl)-1-[(3-methyl-1,2-oxazol-4-yl)carbonyl]-7-(2-methyl-2H-tetrazol-5-yl)-2,3,10,10a-tetrahydro-1H,5H-imidazo[1,2-a]pyrrolo[1,2-d]pyrazin-5-one (146);

7-(aminomethyl)-10a-(4-methoxyphenyl)-1-[(3-methyl-1,2-oxazol-4-yl)carbonyl]-2,3,10,10a-tetrahydro-1H,5H-imidazo[1,2-a]pyrrolo[1,2-d]pyrazin-5-one trifluoroacetate salt (147);

8-methyl-1-[(3-methyl-1,2-oxazol-4-yl)carbonyl]-10a-(6-methylpyridin-3-yl-)-2,3,10,10a-tetrahydro-1H,5H-imidazo[1,2-a]pyrrolo[1,2-d]pyrazin-5-one (151);

10a-(6-methoxypyridin-3-yl)-8-methyl-1-[(3-methyl-1,2-oxazol-4-yl)-carbonyl]-2,3,10,10a-tetrahydro-1H,5H-imidazo[1,2-a]pyrrolo[1,2-d]pyrazin-5-one (152);

10a-[4-(hydroxymethyl)phenyl]-8-methyl-1-[(3-methyl-1,2-oxazol-4-yl)carbonyl]-2,3,10,10a-tetrahydro-1H,5H-imidazo[1,2-a]pyrrolo[1,2-d]pyrazin-5-one (153);

10a-(4-fluorophenyl)-8-methyl-1-[(3-methyl-1,2-oxazol-4-yl)carbonyl]-2,3,10,10a-tetrahydro-1H,5H-imidazo[1,2-a]pyrrolo[1,2-d]pyrazin-5-one (154);

or a pharmaceutically acceptable salt, stereoisomer, or tautomer thereof.

5. A method for inhibiting respiratory syncytial virus in a subject, comprising the step of administering to said subject a compound of formula (I):

wherein
-------- represents single or double bonds depending on the required valencies of the ring atoms;
each Y is CH;
X is CH;
$X_1$ is selected from O, S, $NR_6$, and $C(R_6)_2$ wherein each $R_6$ is independently selected from H, optionally substituted $C_{1-6}$alkyl, optionally substituted $C_{2-6}$alkenyl, optionally substituted $C_{2-6}$alkynyl, optionally substituted $C_{3-8}$cycloalkyl, optionally substituted heterocyclyl and optionally substituted aryl;
$X_2$ is $C(R_3R_4)$ wherein $R_3$ and $R_4$ are each independently selected from H, optionally substituted $C_{1-6}$alkyl, optionally substituted $C_{2-6}$alkenyl, optionally substituted $C_{2-6}$alkynyl, optionally substituted $C_{3-8}$cycloalkyl, optionally substituted heterocyclyl and optionally substituted aryl;
$R_1$ is optionally substituted $C_{1-6}$alkyl, optionally substituted $C_{2-6}$alkenyl, optionally substituted $C_{2-6}$alkynyl, optionally substituted $C_{3-8}$cycloalkyl, optionally substituted heterocyclyl or optionally substituted aryl;
$R_2$ is H, $R_8$, C(=O)$R_8$, C(=S)$R_8$ or S(O$_2$)$R_8$ wherein $R_8$ is selected from optionally substituted $C_{1-6}$alkyl, optionally substituted $C_{2-6}$alkenyl, optionally substituted $C_{2-6}$alkynyl, $N(R_6)_2$, optionally substituted —$N(R_6)_q$$(R_7)_q$cycloalkyl, optionally substituted —$N(R_6)_q$$(R_7)_q$heterocyclyl and optionally substituted —$N(R_6)_q$$(R_7)_q$aryl wherein each $R_7$ is independently selected from optionally substituted $C_{1-6}$alkyl, optionally substituted $C_{2-6}$alkenyl, optionally substituted $C_{2-6}$alkynyl, optionally substituted $C_{3-8}$cycloalkyl, optionally substituted heterocyclyl or optionally substituted aryl and each q is independently 0 or 1;
$Y_1$ is one or more optional substituents, or is absent;
$Y_2$ is H or one or more optionally substituted $R_7$;
m and n are both 1;
p is 2; and
wherein the optional substituents are independently selected from the group consisting Of $R_7$, $R_7$-$R_7$, $(R_7)_q$halo, $(R_7)_q$CN, =O, $(R_7)_q$OR_6$, $(R_7)_q$OCHF$_2$, $(R_7)_q$OCF$_3$, $(R_7)_q$CHF$_2$, $(R_7)_q$CF$_3$, =S, $(R_7)_q$SR$_6$, $(R_7)_q$SO$_3$H, $(R_7)_q$SO$_2$—$R_7$, $(R_7)_q$SO$_2$N(R$_6$)$_2$, $(R_7)_q$NO$_2$, $(R_7)_q$N(R$_6$)$_2$, $(R_7)_q$OC(=O)—$R_7$, $(R_7)_q$C(=O)OR$_6$, $(R_7)_q$C(=O)R$_6$, $(R_7)_q$C(=O)N(R$_6$)$_2$, $(R_7)_q$NR$_6$C(=O)—$R_7$, $(R_7)_q$NR$_6$SO$_2$R$_7$, $(R_7)_q$Si(R$_7$)$_3$ and $(R_7)_q$O—Si(R$_7$)$_3$;
or a pharmaceutically acceptable salt, stereoisomer, or tautomer thereof.

6. The method according to claim 5 wherein the compound is administered along with a pharmaceutically acceptable carrier.

7. The method according to claim 5 wherein the compound is a compound of formula (Ia):

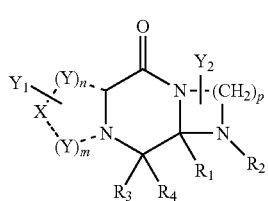

(Ia)

or a pharmaceutically acceptable salt, stereoisomer, or tautomer thereof.

8. The method according to claim 7 wherein the compound is a compound of formula (Ia-iii):

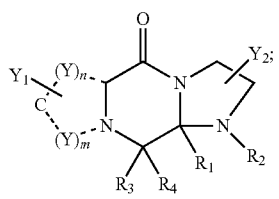

(Ia-iii)

or a pharmaceutically acceptable salt, stereoisomer, or tautomer thereof.

9. The method according to claim 5 wherein the compound is a compound selected from the group consisting of:
10a-[4-(difluoromethoxy)phenyl]-1-[(3-methyl-1,2-oxazol-4-yl)carbonyl]-2,3,10,10a-tetrahydro-1H,5H-imidazo[1,2-a]pyrrolo[1,2-d]pyrazin-5-one (1);
10a-(4-fluorophenyl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (2);
10a-(4-chlorophenyl)-1-[(5-methyl-1,3-oxazol-4-yl)carbonyl]-2,3,10,10a-tetrahydro-1H,5H-imidazo[1,2-a]pyrrolo[1,2-d]pyrazin-5-one (3);
10a-(4-chlorophenyl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (4);
10a-(3-fluorophenyl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (5);
10a-(4-methoxyphenyl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (6);
10a-(4-fluorophenyl)-1-(1,3-oxazol-4-ylcarbonyl)-2,3,10,10a-tetrahydro-1H,5H-imidazo[1,2-a]pyrrolo[1,2-d]pyrazin-5-one (7);
10a-(4-methoxyphenyl)-1-(1,3-oxazol-4-ylcarbonyl)-2,3,10,10a-tetrahydro-1H,5H-imidazo[1,2-a]pyrrolo[1,2-d]pyrazin-5-one (8);
1-[(3-methyl-1,2-oxazol-4-yl)carbonyl]-10a-(4-methylphenyl)-2,3,10,10a-tetrahydro-1H,5H-imidazo[1,2-a]pyrrolo[1,2-d]pyrazin-5-one (9);
N,N-diethyl-4-{1-[(3-methyl-1,2-oxazol-4-yl)carbonyl]-5-oxo-2,3-dihydro-1H,5H-imidazo[1,2-a]pyrrolo[1,2-d]pyrazin-10a(10H)-yl}benzenesulfonamide (10);
10a-(3-fluoro-4-methylphenyl)-1-[(5-methyl-1,2-oxazol-4-yl)carbonyl]-2,3,10,10a-tetrahydro-1H,5H-imidazo[1,2-a]pyrrolo[1,2-d]pyrazin-5-one (14);
10a-(4-chlorophenyl)-1-(furan-3-ylcarbonyl)-2,3,10,10a-tetrahydro-1H,5H-imidazo[1,2-a]pyrrolo[1,2-d]pyrazin-5-one (15);
10a-(4-chlorophenyl)-1-(1,2-oxazol-3-ylcarbonyl)-2,3,10,10a-tetrahydro-1H,5H-imidazo[1,2-a]pyrrolo[1,2-d]pyrazin-5-one (16);
10a-(4-chlorophenyl)-1-{[1-methyl-3-(trifluoromethyl)-1H-pyrazol-4-yl]carbonyl}-2,3,10,10a-tetrahydro-1H,5H-imidazo[1,2-a]pyrrolo[1,2-d]pyrazin-5-one (17);
10a-(4-chlorophenyl)-1-(cyclopropylcarbonyl)-2,3,10,10a-tetrahydro-1H,5H-imidazo[1,2-a]pyrrolo[1,2-d]pyrazin-5-one (18);
10a-cyclohexyl-1-[(3-methyl-1,2-oxazol-4-yl)carbonyl]-2,3,10,10a-tetrahydro-1H,5H-imidazo[1,2-a]pyrrolo[1,2-d]pyrazin-5-one (19);
10a-ethyl-1-[(3-methyl-1,2-oxazol-4-yl)carbonyl]-2,3,10,10a-tetrahydro-1H,5H-imidazo[1,2-a]pyrrolo[1,2-d]pyrazin-5-one (20);
10a-tert-butyl-1-[(3-methyl-1,2-oxazol-4-yl)carbonyl]-2,3,10,10a-tetrahydro-1H,5H-imidazo[1,2-a]pyrrolo[1,2-d]pyrazin-5-one (21);
8-chloro-10a-(4-chlorophenyl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (22);
8-chloro-10a-(4-methoxyphenyl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (23);
7-acetyl-10a-(4-chlorophenyl)-1-[(5-methyl-1,2-oxazol-4-yl)carbonyl]-2,3,10,10a-tetrahydro-1H,5H-imidazo[1,2-a]pyrrolo[1,2-d]pyrazin-5-one (24);
10a-(4-chlorophenyl)-1-[(3-methyl-1,2-oxazol-4-yl)carbonyl]-8-(morpholin-4-ylmethyl)-2,3,10,10a-tetrahydro-1H,5H-imidazo[1,2-a]pyrrolo[1,2-d]pyrazin-5-one (25);
10a-(4-chlorophenyl)-1-[(3-methyl-1,2-oxazol-4-yl)carbonyl]-7-(morpholin-4-ylmethyl)-2,3,10,10a-tetrahydro-1H,5H-imidazo[1,2-a]pyrrolo[1,2-d]pyrazin-5-one (26);
10a-(4-chlorophenyl)-7-[(dimethylamino)methyl]-1-[(3-methyl-1,2-oxazol-4-yl)carbonyl]-2,3,10,10a-tetrahydro-1H,5H-imidazo[1,2-a]pyrrolo[1,2-d]pyrazin-5-one (27);
10a-(4-chlorophenyl)-8-(hydroxymethyl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (28);
10a-(4-chlorophenyl)-7-(hydroxymethyl)-1-[(3-methyl-1,2-oxazol-4-yl-)carbonyl]-2,3,10,10a-tetrahydro-1H,5H-imidazo[1,2-a]pyrrolo[1,2-d]pyrazin-5-one (29);

10a-(4-chlorophenyl)-1-[(3-methyl-1,2-oxazol-4-yl)carbonyl]-7-(pyridin-3-yl)-2,3,10,10a-tetrahydro-1H,5H-imidazo[1,2-a]pyrrolo[1,2-d]pyrazin-5-one (30);

10a-(4-chlorophenyl)-1-[(3-methyl-1,2-oxazol-4-yl)carbonyl]-7-(1-methyl-1H-pyrazol-4-yl)-2,3,10,10a-tetrahydro-1H,5H-imidazo[1,2-a]pyrrolo[1,2-d]pyrazin-5-one (31);

10a-(4-chlorophenyl)-1-[(5-methyl-1,2-oxazol-4-yl)carbonyl]-8-(pyridin-4-yl)-2,3,10,10a-tetrahydro-1H,5H-imidazo[1,2-a]pyrrolo[1,2-d]pyrazin-5-one (32);

10a-(4-chlorophenyl)-1-[(3-methyl-1,2-oxazol-4-yl)carbonyl]-8-(pyridin-3-yl)-2,3,10,10a-tetrahydro-1H,5H-imidazo[1,2-a]pyrrolo[1,2-d]pyrazin-5-one (33);

10a-(4-methoxyphenyl)-1-[(3-methyl-1,2-oxazol-4-yl)carbonyl]-8-(1-methyl-1H-pyrazol-4-yl)-2,3,10,10a-tetrahydro-1H,5H-imidazo[1,2-a]pyrrolo[1,2-d]pyrazin-5-one (34);

1-[(3-methyl-1,2-oxazol-4-yl)carbonyl]-10a-phenyl-2,3,10,10a-tetrahydro-1H,5H-imidazo[1,2-a]pyrrolo[1,2-d]pyrazin-5-one (35);

1-[(3-methyl-1,2-oxazol-4-yl)carbonyl]-10a-[4-(pyrrolidin-1-yl)phenyl]-2,-3,10,10a-tetrahydro-1H,5H-imidazo[1,2-a]pyrrolo[1,2-d]pyrazin-5-one (36);

4-{1-[(3-methyl-1,2-oxazol-4-yl)carbonyl]-5-oxo-2,3-dihydro-1H,5H-imidazo[1,2-a]pyrrolo[1,2-d]pyrazin-10a(10H)-yl}benzonitrile (37);

10a-(4-chlorophenyl)-N,N-dimethyl-1-[(3-methyl-1,2-oxazol-4-yl)carbonyl]-5-oxo-2,3,10,10a-tetrahydro-1H,5H-imidazo[1,2-a]pyrrolo[1,2-d]pyrazine-7-carboxamide (38);

10a-(4-chlorophenyl)-5-oxo-N-(2-phenylethyl)-2,3,10,10a-tetrahydro-1H,5H-imidazo[1,2a]pyrrolo[1,2-d]pyrazine-1-carboxamide (48);

10a-(4-chlorophenyl)-1-{[3-(trifluoromethyl)-1,2-oxazol-4-yl]carbonyl}-2,-3,10,10a-tetrahydro-1H,5H-imidazo[1,2-a]pyrrolo[1,2-d]pyrazin-5-one (49);

1-[(3-methyl-1,2-oxazol-4-yl)carbonyl]-10a-(tetrahydro-2H-pyran-4-yl)-2,3,10,10a-tetrahydro-1H,5H-imidazo[1,2-a]pyrrolo[1,2-d]pyrazin-5-one (50);

10a-(4-methoxyphenyl)-1-(1,2-oxazol-4-ylcarbonyl)-2,3,10,10a-tetrahydro-1H,5H-imidazo[1,2-a]pyrrolo[1,2-d]pyrazin-5-one (51);

10a-(4-methoxyphenyl)-1-{[3-(trifluoromethyl)-1,2-oxazol-4-yl]carbonyl}-2,3,10,10a-tetrahydro-1H,5H-imidazo[1,2-a]pyrrolo[1,2-d]pyrazin-5-one (52);

1-[(3,5-dimethyl-1,2-oxazol-4-yl)carbonyl]-10a-(4-methoxyphenyl)-2,3,10,10a-tetrahydro-1H,5H-imidazo[1,2-a]pyrrolo[1,2-d]pyrazin-5-one (53);

1-(furan-3-ylcarbonyl)-10a-(4-methoxyphenyl)-2,3,10,10a-tetrahydro-1H,5H-imidazo[1,2-a]pyrrolo[1,2-d]pyrazin-5-one (54);

10a-(4-methoxyphenyl)-1-[(4-methyl-1,3-oxazol-5-yl)carbonyl]-2,3,10,10a-tetrahydro-1H,5H-imidazo[1,2-a]pyrrolo[1,2-d]pyrazin-5-one (55);

10a-(4-methoxyphenyl)-1-[(4-methyl-1,2,3-thiadiazol-5-yl)carbonyl]-2,3,10,10a-tetrahydro-1H,5H-imidazo[1,2-a]pyrrolo[1,2-d]pyrazin-5-one (56);

10a-(2,3-dihydro-1-benzofuran-5-yl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (57);

10a-(6-methoxypyridin-3-yl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (58);

1-[(5-cyclopropyl-1,3-oxazol-4-yl)carbonyl]-10a-(4-methoxyphenyl)-2-3,10,10a-tetrahydro-1H,5H-imidazo[1,2-a]pyrrolo[1,2-d]pyrazin-5-one (59);

10a-(4-methoxyphenyl)-1-[(1-methyl-1H-pyrrol-2-yl)carbonyl]-2,3,10,10a-tetrahydro-1H,5H-imidazo[1,2-a]pyrrolo[1,2-d]pyrazin-5-one (60);

10a-(4-methoxyphenyl)-1-[(1-methyl-1H-pyrazol-5-yl)carbonyl]-2,3,10,10a-tetrahydro-1H,5H-imidazo[1,2-a]pyrrolo[1,2-d]pyrazin-5-one (61);

4-{1-[(3-methyl-1,2-oxazol-4-yl)carbonyl]-5-oxo-2,3-dihydro-1H,5H-imidazo-[1,2-a]pyrrolo[1,2-d]pyrazin-10a(10H)-yl}benzyl-3-methyl-1,2-oxazole-4-carboxylate (62);

7-fluoro-10a-(4-methoxyphenyl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (65);

7-fluoro-10a-(4-methoxyphenyl)-1-{[3-(trifluoromethyl)-1,2-oxazol-4-yl]carbonyl}-2,3,10,10a-tetrahydro-1H,5H-imidazo[1,2-a]pyrrolo[1,2-d]pyrazin-5-one (66);

1-[(3-ethyl-1,2-oxazol-4-yl)carbonyl]-10a-(4-methoxyphenyl)-2,3,10,10a-tetrahydro-1H,5H-imidazo[1,2-a]pyrrolo[1,2-d]pyrazin-5-one (67);

10a-(4-methoxyphenyl)-1-{[3-(propan-2-yl)-1,2-oxazol-4-yl]carbonyl}-2,3,10,10a-tetrahydro-1H,5H-imidazo[1,2-a]pyrrolo[1,2-d]pyrazin-5-one (68);

10a-(4-hydroxyphenyl)-1-[(3-methyl-1,2-oxazol-4-yl)carbonyl]-2,3,10,10a-tetrahydro-1H,5H-imidazo[1,2-a]pyrrolo[1,2-d]-pyrazin-5-one (69);

10a-(4-methoxyphenyl)-1-(pyridin-2-ylcarbonyl)-2,3,10,10a-tetrahydro-1H,5H-imidazo[1,2-a]pyrrolo[1,2-d]pyrazin-5-one (71);

1-[(3-methyl-1,2-oxazol-4-yl)carbonyl]-10a-(thiophen-3-yl)-2,3,10,10a-tetrahydro-1H,5H-imidazo[1,2-a]pyrrolo[1,2-d]pyrazin-5-one (73);

1-[(3-methyl-1,2-oxazol-4-yl)carbonyl]-10a-(thiophen-2-yl)-2,3,10,10a-tetrahydro-1H,5H-imidazo[1,2-a]pyrrolo[1,2-d]pyrazin-5-one (74);

10a-(4-methoxyphenyl)-1-[(3-methyl-1,2-oxazol-4-yl)carbonyl]-7-(1H-tetrazol-5-yl)-2,3,10,10a-tetrahydro-1H,5H-imidazo[1,2-a]pyrrolo[1,2-d]pyrazin-5-one (75);

10a-[4-(methoxymethyl)phenyl]-1-[(3-methyl-1,2-oxazol-4-yl)carbonyl]-2,3,10,10a-tetrahydro-1H,5H-imidazo[1,2-a]pyrrolo[1,2-d]pyrazin-5-one (76);

1-[(3-methyl-1,2-oxazol-4-yl)carbonyl]-10a-(6-methylpyridin-3-yl)-2,3,10,10a-tetrahydro-1H,5H-imidazo[1,2-a]pyrrolo[1,2-d]pyrazin-5-one (77);

1-[(3-methyl-1,2-oxazol-4-yl)carbonyl]-10a-(1-oxidopyridin-3-yl)-2,-3,10,10a-tetrahydro-1H,5H-imidazo[1,2-a]pyrrolo[1,2-d]pyrazin-5-one (78);

10a-[4-(hydroxymethyl)phenyl]-1-[(3-methyl-1,2-oxazol-4-yl)carbonyl]-2,3,10,10a-tetrahydro-1H,5H-imidazo[1,2-a]pyrrolo[1,2-d]pyrazin-5-one (79);

8-chloro-10a-(4-fluorophenyl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (80);

8-chloro-1-[(3-methyl-1,2-oxazol-4-yl)carbonyl]-10a-(tetrahydro-2H-pyran-4-yl)-2,3,10,10a-tetrahydro-1H,5H-imidazo[1,2-a]pyrrolo[1,2-d]pyrazin-5-one (81);

10a-(4-methoxyphenyl)-1-[(3-methyl-1,2-oxazol-4-yl)carbonyl]-7-(1-methyl-1H-pyrazol-4-yl)-2,3,10,10a-tetrahydro-1H,5H-imidazo[1,2-a]pyrrolo[1,2-d]pyrazin-5-one (82);

10a-(4-methoxyphenyl)-1-[(3-methyl-1,2-oxazol-4-yl)carbonyl]-7-(pyridin-3-yl)-2,3,10,10a-tetrahydro-1H,5H-imidazo[1,2-a]pyrrolo[1,2-d]pyrazin-5-one (83);

10a-(4-methoxyphenyl)-1-[(3-methyl-1,2-oxazol-4-yl)carbonyl]-7-(pyridin-4-yl)-2,3,10,10a-tetrahydro-1H,5H-imidazo[1,2-a]pyrrolo[1,2-d]pyrazin-5-one (84);

7-bromo-10a-(4-fluorophenyl)-2,3,10,10a-tetrahydro-1H, 5H-imidazo[1,2-a]pyrrolo[1,2-d]pyrazin-5-one (85);

7-bromo-10a-(4-methylphenyl)-2,3,10,10a-tetrahydro-1H,5H-imidazo[1,2-a]pyrrolo[1,2-d]pyrazin-5-one (86);

10a-(4-methoxyphenyl)-1-[(3-methyl-1,2-oxazol-4-yl)carbonyl]-7-(1-methyl-1H-pyrazol-5-yl)-2,3,10,10a-tetrahydro-1H,5H-imidazo[1,2-a]pyrrolo[1,2-d]pyrazin-5-one (87);

10a-(4-methoxyphenyl)-1-[(3-methyl-1,2-oxazol-4-yl)carbonyl]-7-[1-(propan-2-yl)-1H-pyrazol-4-yl]-2,3,10,10a-tetrahydro-1H,5H-imidazo[1,2-a]pyrrolo[1,2-d]pyrazin-5-one (88);

10a-(4-methoxyphenyl)-1-[(3-methyl-1,2-oxazol-4-yl)carbonyl]-5-oxo-2,3,10,10a-tetrahydro-1H,5H-imidazo[1,2-a]pyrrolo[1,2-d]pyrazine-7-carbonitrile (89);

10a-(4-methoxyphenyl)-1-[(3-methyl-1,2-oxazol-4-yl)carbonyl]-7-(pyrimidin-5-yl)-2,3,10,10a-tetrahydro-1H,5H-imidazo[1,2-a]pyrrolo[1,2-d]pyrazin-5-one (90);

7-(1,3-dimethyl-1H-pyrazol-4-yl)-10a-(4-methoxyphenyl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (91);

10a-(4-methoxyphenyl)-1-[(3-methyl-1,2-oxazol-4-yl)carbonyl]-7-(4-methylpyridin-3-yl)-2,3,10,10a-tetrahydro-1H,5H-imidazo[1,2-a]pyrrolo[1,2-d]pyrazin-5-one (92);

1-[(3-methyl-1,2-oxazol-4-yl)carbonyl]-10a-(4-methylphenyl)-7-(pyridin-2-yl)-2,3,10,10a-tetrahydro-1H,5H-imidazo[1,2-a]pyrrolo[1,2-d]pyrazin-5-one (93);

7-bromo-10a-(4-methoxyphenyl)-2,3,10,10a-tetrahydro-1H,5H-imidazo[1,2-a]pyrrolo[1,2-d]pyrazin-5-one (94);

10a-[4-(hydroxymethyl)phenyl]-1-[(3-methyl-1,2-oxazol-4-yl)carbonyl]-7-(pyridin-3-yl)-2,3,10,10a-tetrahydro-1H,5H-imidazo[1,2-a]pyrrolo[1,2-d]pyrazin-5-one (95);

10a-(4-fluorophenyl)-1-[(3-methyl-1,2-oxazol-4-yl)carbonyl]-8-(1-methyl-1H-pyrazol-4-yl)-2,3,10,10a-tetrahydro-1H,5H-imidazo[1,2-a]pyrrolo[1,2-d]pyrazin-5-one (96);

10a-(4-fluorophenyl)-1-[(3-methyl-1,2-oxazol-4-yl)carbonyl]-8-(pyridin-3-yl)-2,3,10,10a-tetrahydro-1H,5H-imidazo[1,2-a]pyrrolo[1,2-d]pyrazin-5-one (97);

10a-(4-fluorophenyl)-1-[(3-methyl-1,2-oxazol-4-yl)carbonyl]-7-(pyridin-3-yl)-2,3,10,10a-tetrahydro-1H,5H-imidazo[1,2-a]pyrrolo[1,2-d]pyrazin-5-one (98);

10a-(4-fluorophenyl)-1-[(3-methyl-1,2-oxazol-4-yl)carbonyl]-8-(pyridin-4-yl)-2,3,10,10a-tetrahydro-1H,5H-imidazo[1,2-a]pyrrolo[1,2-d]pyrazin-5-one (99);

4-{10a-(4-methoxyphenyl)-1-[(3-methyl-1,2-oxazol-4-yl)carbonyl]-5-oxo-2,3,10,10a-tetrahydro-1H,5H-imidazo[1,2-a]pyrrolo[1,2-d]pyrazin-7-yl}benzoic acid (100);

1-[(3-methyl-1,2-oxazol-4-yl)carbonyl]-10a-(pyridin-3-yl)-2,3,10,10a-tetrahydro-1H,5H-imidazo[1,2-a]pyrrolo[1,2-d]pyrazin-5-one (101);

10a-(pyridin-3-yl)-2,3,10,10a-tetrahydro-1H,5H-imidazo[1,2-a]pyrrolo[1,2-d]pyrazin-5-one (102);

1-[(3-methyl-1,2-oxazol-4-yl)carbonyl]-10a-(pyridin-2-yl)-2,3,10,10a-tetrahydro-1H,5H-imidazo[1,2-a]pyrrolo[1,2-d]pyrazin-5-one (103);

1-[(3-methyl-1,2-oxazol-4-yl)carbonyl]-10a-(5-methylpyridin-2-yl)-2,3,10,10a-tetrahydro-1H,5H-imidazo[1,2-a]pyrrolo[1,2-d]pyrazin-5-one (104);

1-[(3-methyl-1,2-oxazol-4-yl)carbonyl]-10a-[6-(trifluoromethyl)pyridin-3-yl]-2,3,10,10a-tetrahydro-1H,5H-imidazo[1,2-a]pyrrolo[1,2-d]pyrazin-5-one (105);

10a-(4-methoxyphenyl)-1-[(3-methyl-1,2-oxazol-4-yl)carbonyl]-5-oxo-2,3,10,10a-tetrahydro-1H,5H-imidazo[1,2-a]pyrrolo[1,2-d]pyrazine-8-carbonitrile (106);

10a-(4-methoxyphenyl)-8-methyl-1-[(3-methyl-1,2-oxazol-4-yl)carbonyl]-2,3,10,10a-tetrahydro-1H,5H-imidazo[1,2-a]pyrrolo[1,2-d]pyrazin-5-one (107);

8-ethynyl-10a-(4-methoxyphenyl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (108);

10a-[4-(2-hydroxyethoxyl)phenyl]-1-[(3-methyl-1,2-oxazol-4-yl)carbonyl]-2,3,10,10a-tetrahydro-1H,5H-imidazo[1,2-a]pyrrolo[1,2-d]pyrazin-5-one (109);

1-[(3-methyl-1,2-oxazol-4-yl)carbonyl]-10a-{4-[2-(morpholin-4-yl)ethoxy]phenyl}-2,3,10,10a-tetrahydro-1H,5H-imidazo[1,2-a]pyrrolo[1,2-d]pyrazin-5-one (110);

7-amino-10a-(4-methoxyphenyl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (111);

7-(cyclohexylamino)-10a-(4-methoxyphenyl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (112);

10a-(4-methoxyphenyl)-1-[(3-methyl-1,2-oxazol-4-yl)carbonyl]-7-(1H-1,2,3-triazol-1-yl)-2,3,10,10a-tetrahydro-1H,5H-imidazo[1,2-a]pyrrolo[1,2-d]pyrazin-5-one (113);

1-[(3-methyl-1,2-oxazol-4-yl)carbonyl]-10a-(5-methylpyrazin-2-yl)-2,3,10,10a-tetrahydro-1H,5H-imidazo[1,2-a]pyrrolo[1,2-d]pyrazin-5-one (114);

10a-(5-methoxypyridin-2-yl)-1-[(3-methyl-1,2-oxazol-4-yl)carbonyl]-2,3,10,10a-tetrahydro-1H,5H-imidazo[1,2-a]pyrrolo[1,2-d]pyrazin-5-one (115);

1-[(3-methyl-1,2-oxazol-4-yl)carbonyl]-10a-[5-(trifluoromethyl)pyridin-2-yl]-2,3,10,10a-tetrahydro-1H,5H-imidazo[1,2-a]pyrrolo[1,2-d]pyrazin-5-one (116);

7-bromo-1-[(3-methyl-1,2-oxazol-4-yl)carbonyl]-10a-(5-methylpyridin-2-yl)-2,3,10,10a-tetrahydro-1H,5H-imidazo[1,2-a]pyrrolo[1,2-d]pyrazin-5-one (117);

1-[(3-methyl-1,2-oxazol-4-yl)carbonyl]-10a-(1-methyl-1H-pyrazol-4-yl)-2,3,10,10a-tetrahydro-1H,5H-imidazo[1,2-a]pyrrolo[1,2-d]pyrazin-5-one (118);

1-[(3-methyl-1,2-oxazol-4-yl)carbonyl]-10a-(2-methylpyridin-4-yl)-2,3,10,10a-tetrahydro-1H,5H-imidazo[1,2-a]pyrrolo[1,2-d]pyrazin-5-one (119);

1-[(3-methyl-1,2-oxazol-4-yl)carbonyl]-10a-(5-methylpyridin-2-yl)-7-(pyridin-3-yl)-2,3,10,10a-tetrahydro-1H,5H-imidazo[1,2-a]pyrrolo[1,2-d]pyrazin-5-one (120);

1-[(3-methyl-1,2-oxazol-4-yl)carbonyl]-10a-(5-methylpyrazin-2-yl)-7-(pyridin-3-yl)-2,3,10,10a-tetrahydro-1H,5H-imidazo[1,2-a]pyrrolo[1,2-d]pyrazin-5-one (121);

1-[(3-methyl-1,2-oxazol-4-yl)carbonyl]-10a-(pyridin-4-yl)-2,3,10,10a-tetrahydro-1H,5H-imidazo[1,2-a]pyrrolo[1,2-d]pyrazin-5-one (122);

10a-(4-methoxyphenyl)-1-[(3-methyl-1,2-oxazol-4-yl)carbonyl]-7-nitro-2,3,10,10a-tetrahydro-1H,5H-imidazo[1,2-a]pyrrolo[1,2-d]pyrazin-5-one (124);

10a-(4-chlorophenyl)-10-methyl-2,3,10,10a-tetrahydro-1H,5H-imidazo[1,2-a]pyrrolo[1,2-d]pyrazin-5-one (125);

1-[(3-methyl-1,2-oxazol-4-yl)carbonyl]-10a-(6-methylpyridin-3-yl)-5-oxo-2,3,10,10a-tetrahydro-1H,5H-imidazo[1,2-a]pyrrolo[1,2-d]pyrazine-8-carbonitrile (126);

1-[(3-methyl-1,2-oxazol-4-yl)carbonyl]-10a-(6-methylpyridin-3-yl)-7-(pyridin-2-yl)-2,3,10,10a-tetrahydro-1H,5H-imidazo[1,2-a]pyrrolo[1,2-d]pyrazin-5-one (127);

10a-(6-methoxypyridin-3-yl)-1-[(3-methyl-1,2-oxazol-4-yl)carbonyl]-7-(pyridin-2-yl)-2,3,10,10a-tetrahydro-1H,5H-imidazo[1,2-a]pyrrolo[1,2-d]pyrazin-5-one (128);

N-(furan-2-ylmethyl)-10a-(4-methoxyphenyl)-5-oxo-2,3,10,10a-tetrahydro-1H,5H-imidazo[1,2-a]pyrrolo[1,2-d]pyrazine-1-carboxamide (130);

10a-(4-methoxyphenyl)-1-(phenylsulfonyl)-2,3,10,10a-tetrahydro-1H,5H-imidazo[1,2-a]pyrrolo[1,2-d]pyrazin-5-one (131);

1-[(3-methyl-1,2-oxazol-4-yl)carbonyl]-7-(1-methyl-1H-pyrazol-4-yl)-10a-(6-methylpyridin-3-yl)-2,3,10,10a-tetrahydro-1H,5H-imidazo[1,2-a]pyrrolo[1,2-d]pyrazin-5-one (132);

10a-(6-methoxypyridin-3-yl)-1-[3-methyl-1,2-oxazol-4-yl)carbonyl]-5-oxo-2,3,10,10a-tetrahydro-1H,5H-imidazo[1,2-a]pyrrolo[1,2-d]pyrazine-8-carbonitrile (133);

1-[(3-methyl-1,2-oxazol-4-yl)carbonyl]-7-(1-methyl-1H-pyrazol-4-yl)-10a-(5-methylpyridin-2-yl)-2,3,10,10a-tetrahydro-1H,5H-imidazo[1,2-a]pyrrolo[1,2-d]pyrazin-5-one (134);

1-[(3-methyl-1,2-oxazol-4-yl)carbonyl]-10a-(6-methylpyridin-3-yl)-7-(pyridin-4-yl)-2,3,10,10a-tetrahydro-1H,5H-imidazo[1,2-a]pyrrolo[1,2-d]pyrazin-5-one (135);

10a-(4-methoxyphenyl)-1-[(4-methyl-1,2,5-oxadiazol-3-yl)carbonyl]-2,3,10,10a-tetrahydro-1H,5H-imidazo[1,2-a]pyrrolo[1,2-d]pyrazin-5-one (136);

10a-(4-methoxyphenyl)-1-(thiophen-3-ylcarbonyl)-2,3,10,10a-tetrahydro-1H,-5H-imidazo[1,2-a]pyrrolo[1,2-d]pyrazin-5-one (137);

10a-(6-hydroxypyridin-3-yl)-1-[(3-methyl-1,2-oxazol-4-yl)carbonyl-]-2,3,10,10a-tetrahydro-1H,5H-imidazo[1,2-a]pyrrolo[1,2-d]pyrazin-5-one (142);

1-[(3-methyl-1,2-oxazol-4-yl)carbonyl]-10a-(1-methyl-6-oxo-1,6-dihydropyridin-3-yl)-2,3,10,10a-tetrahydro-1H,5H-imidazo[1,2-a]pyrrolo[1,2-d]pyrazin-5-one (143);

10a-[4-(hydroxymethyl)phenyl]-1-[(3-methyl-1,2-oxazol-4-yl)carbonyl]-7-(1-methyl-1H-pyrazol-4-yl)-2,3,10,10a-tetrahydro-1H,5H-imidazo[1,2-a]pyrrolo[1,2-d]pyrazin-5-one (144);

10a-(4-methoxyphenyl)-1-[(3-methyl-1,2-oxazol-4-yl)carbonyl]-7-(1-methyl-1H-tetrazol-5-yl)-2,3,10,10a-tetrahydro-1H,5H-imidazo[1,2-a]pyrrolo[1,2-d]pyrazin-5-one (145);

10a-(4-methoxyphenyl)-1-[(3-methyl-1,2-oxazol-4-yl)carbonyl]-7-(2-methyl-2H-tetrazol-5-yl)-2,3,10,10a-tetrahydro-1H,5H-imidazo[1,2-a]pyrrolo[1,2-d]pyrazin-5-one (146);

7-(aminomethyl)-10a-(4-methoxyphenyl)-1-[(3-methyl-1,2-oxazol-4-yl)carbonyl]-2,3,10,10a-tetrahydro-1H,5H-imidazo[1,2-a]pyrrolo[1,2-d]pyrazin-5-one trifluoroacetate salt (147);

8-methyl-1-[(3-methyl-1,2-oxazol-4-yl)carbonyl]-10a-(6-methylpyridin-3-yl-)-2,3,10,10a-tetrahydro-1H,5H-imidazo[1,2-a]pyrrolo[1,2-d]pyrazin-5-one (151);

10a-(6-methoxypyridin-3-yl)-8-methyl-1-[(3-methyl-1,2-oxazol-4-yl)-carbonyl]-2,3,10,10a-tetrahydro-1H,5H-imidazo[1,2-a]pyrrolo[1,2-d]pyrazin-5-one (152);

10a-[4-(hydroxymethyl)phenyl]-8-methyl-1-[(3-methyl-1,2-oxazol-4-yl)carbonyl]-2,3,10,10a-tetrahydro-1H,5H-imidazo[1,2-a]pyrrolo[1,2-d]pyrazin-5-one (153);

10a-(4-fluorophenyl)-8-methyl-1-[(3-methyl-1,2-oxazol-4-yl)carbonyl]-2,3,10,10a-tetrahydro-1H,5H-imidazo[1,2-a]pyrrolo[1,2-d]pyrazin-5-one (154);

or a pharmaceutically acceptable salt, stereoisomer, or tautomer thereof.

\* \* \* \* \*